US010631871B2

(12) United States Patent
Goldfarb et al.

(10) Patent No.: US 10,631,871 B2
(45) Date of Patent: *Apr. 28, 2020

(54) FIXATION DEVICES, SYSTEMS AND METHODS FOR ENGAGING TISSUE

(71) Applicant: EVALVE, INC., Santa Clara, CA (US)

(72) Inventors: Eric A. Goldfarb, Belmont, CA (US); Alfred H. Raschdorf, Saint James, NY (US); Jaime E. Sarabia, Mableton, GA (US); Sylvia Wen-Chin Erickson, San Carlos, CA (US); Kent D. Dell, Redwood City, CA (US); Jan Komtebedde, Los Gatos, CA (US); Ferolyn T. Powell, San Francisco, CA (US)

(73) Assignee: EVALVE, INC., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/406,583

(22) Filed: May 8, 2019

(65) Prior Publication Data

US 2019/0261997 A1    Aug. 29, 2019

Related U.S. Application Data

(60) Continuation of application No. 15/483,523, filed on Apr. 10, 2017, which is a continuation of application
(Continued)

(51) Int. Cl.
*A61B 17/04* (2006.01)
*A61M 25/01* (2006.01)
(Continued)

(52) U.S. Cl.
CPC ...... *A61B 17/122* (2013.01); *A61B 17/00234* (2013.01); *A61B 17/04* (2013.01);
(Continued)

(58) Field of Classification Search
CPC ... A61B 17/122; A61B 17/0487; A61B 17/08; A61B 17/10; A61B 17/1227; A61B 17/128; A61B 17/1285; A61D 2/2442
See application file for complete search history.

(56) References Cited

U.S. PATENT DOCUMENTS 2,097,018 A    10/1937   Chamberlain
2,108,206 A     2/1938   Meeker
(Continued)

FOREIGN PATENT DOCUMENTS

CA    2296317 C    1/2009
CN    1142351 A    2/1997
(Continued)

OTHER PUBLICATIONS

Abe et al., "De Vega's Annuloplasty for Acquired Tricuspid Disease: Early and Late Results in 110 Patients," Ann. Thorac. Surg., Jan. 1989, pp. 670-676, vol. 48.
(Continued)

*Primary Examiner* — Gregory A Anderson
(74) *Attorney, Agent, or Firm* — Baker Botts L.L.P.

(57) ABSTRACT

System for fixation of leaflets of a heart valve including a delivery catheter having an elongated shaft, a proximal end portion and a distal end portion configured to be positioned proximate native leaflets of a heart valve from a remote vascular access point, and a fixation device releasably coupled to the delivery catheter. The fixation device includes a first arm moveable between a closed position and an open position, and a second arm moveable between a closed position and an open position. The fixation device further includes a first gripping element movable relative to the first arm in the open position, the first gripping element biased toward the first arm to capture a first leaflet of the heart valve therebetween, and a second gripping element movable relative to the second arm in the open position, the second
(Continued)

gripping element biased toward the second arm to capture a second leaflet of the heart valve therebetween. The first gripping element and the second gripping element each include a plurality of barbs extending therefrom, the plurality of barbs of each of the first gripping element and the second gripping element being aligned transversely in at least one row. The fixation device further includes a covering disposed on each of the first gripping element and the second gripping element, wherein the plurality of barbs of the first gripping element and the second gripping element, respectively, protrude through the covering.

18 Claims, 68 Drawing Sheets

Related U.S. Application Data

No. 15/334,992, filed on Oct. 26, 2016, now abandoned, which is a continuation of application No. 14/259,826, filed on Apr. 23, 2014, now Pat. No. 9,510,829, which is a division of application No. 13/899,901, filed on May 22, 2013, now Pat. No. 8,740,820, which is a continuation of application No. 12/636,471, filed on Dec. 11, 2009, now Pat. No. 8,500,761, which is a continuation of application No. 11/962,654, filed on Dec. 21, 2007, now Pat. No. 7,655,015, which is a division of application No. 10/441,531, filed on May 19, 2003, now Pat. No. 7,563,267.

(51) Int. Cl.
```
A61F 2/24        (2006.01)
A61B 17/08       (2006.01)
A61B 17/122      (2006.01)
A61B 17/062      (2006.01)
A61B 17/068      (2006.01)
A61B 17/064      (2006.01)
A61B 50/30       (2016.01)
A61B 18/14       (2006.01)
A61B 17/128      (2006.01)
A61B 17/00       (2006.01)
A61B 17/10       (2006.01)
A61M 25/00       (2006.01)
A61B 8/10        (2006.01)
A61B 17/06       (2006.01)
A61B 17/29       (2006.01)
A61B 18/18       (2006.01)
A61B 17/072      (2006.01)
A61B 18/20       (2006.01)
A61M 25/04       (2006.01)
```
(52) U.S. Cl.
CPC ...... *A61B 17/0401* (2013.01); *A61B 17/0469* (2013.01); *A61B 17/0482* (2013.01); *A61B 17/0487* (2013.01); *A61B 17/064* (2013.01); *A61B 17/068* (2013.01); *A61B 17/0625* (2013.01); *A61B 17/0643* (2013.01); *A61B 17/0644* (2013.01); *A61B 17/08* (2013.01); *A61B 17/10* (2013.01); *A61B 17/1227* (2013.01); *A61B 17/1285* (2013.01); *A61B 18/1492* (2013.01); *A61B 50/30* (2016.02); *A61F 2/246* (2013.01); *A61F 2/2442* (2013.01); *A61F 2/2445* (2013.01); *A61F 2/2463* (2013.01); *A61F 2/2466* (2013.01); *A61M 25/00* (2013.01); *A61M 25/0136* (2013.01); *A61M 25/0138* (2013.01); *A61M 25/0147* (2013.01); *A61B 8/10* (2013.01); *A61B 17/07207* (2013.01); *A61B 17/29* (2013.01); *A61B 18/18* (2013.01); *A61B 18/20* (2013.01); *A61B 2017/00243* (2013.01); *A61B 2017/00314* (2013.01); *A61B 2017/00318* (2013.01); *A61B 2017/00327* (2013.01); *A61B 2017/00407* (2013.01); *A61B 2017/00473* (2013.01); *A61B 2017/00477* (2013.01); *A61B 2017/00575* (2013.01); *A61B 2017/00579* (2013.01); *A61B 2017/00588* (2013.01); *A61B 2017/00592* (2013.01); *A61B 2017/00606* (2013.01); *A61B 2017/00615* (2013.01); *A61B 2017/00619* (2013.01); *A61B 2017/00623* (2013.01); *A61B 2017/00783* (2013.01); *A61B 2017/00867* (2013.01); *A61B 2017/0406* (2013.01); *A61B 2017/047* (2013.01); *A61B 2017/0409* (2013.01); *A61B 2017/0417* (2013.01); *A61B 2017/0419* (2013.01); *A61B 2017/0429* (2013.01); *A61B 2017/0435* (2013.01); *A61B 2017/0458* (2013.01); *A61B 2017/0464* (2013.01); *A61B 2017/0472* (2013.01); *A61B 2017/0474* (2013.01); *A61B 2017/0488* (2013.01); *A61B 2017/0496* (2013.01); *A61B 2017/061* (2013.01); *A61B 2017/0641* (2013.01); *A61B 2017/06052* (2013.01); *A61B 2017/06057* (2013.01); *A61B 2017/06076* (2013.01); *A61B 2017/06171* (2013.01); *A61B 2017/088* (2013.01); *A61B 2017/2908* (2013.01); *A61B 2017/2926* (2013.01); *A61B 2050/314* (2016.02); *A61F 2/24* (2013.01); *A61M 25/04* (2013.01); *A61M 2025/0161* (2013.01)

(56) References Cited

U.S. PATENT DOCUMENTS

| | | |
|---|---|---|
| 3,296,668 A | 1/1967 | Aiken |
| 3,378,010 A | 4/1968 | Codling et al. |
| 3,557,780 A | 1/1971 | Sato |
| 3,671,979 A | 6/1972 | Mouloupoulos |
| 3,675,639 A | 7/1972 | Cimber |
| 3,874,338 A | 4/1975 | Happel |
| 3,874,388 A | 4/1975 | King et al. |
| 4,007,743 A | 2/1977 | Blake |
| 4,055,861 A | 11/1977 | Carpentier et al. |
| 4,056,854 A | 11/1977 | Boretos et al. |
| 4,064,881 A | 12/1977 | Meredith |
| 4,091,815 A | 5/1978 | Larsen |
| 4,112,951 A | 9/1978 | Hulka et al. |
| 4,235,238 A | 11/1980 | Ogiu et al. |
| 4,297,749 A | 11/1981 | Davis et al. |
| 4,327,736 A | 5/1982 | Inoue |
| 4,340,091 A | 7/1982 | Skelton et al. |
| 4,458,682 A | 7/1984 | Cerwin |
| 4,425,908 A | 11/1984 | Simon |
| 4,484,579 A | 11/1984 | Meno et al. |
| 4,487,205 A | 12/1984 | Di Giovanni et al. |
| 4,498,476 A | 2/1985 | Cerwin et al. |
| 4,510,934 A | 4/1985 | Batra |
| 4,531,522 A | 7/1985 | Bedi et al. |
| 4,578,061 A | 3/1986 | Lemelson |
| 4,641,366 A | 2/1987 | Yokoyama et al. |
| 4,657,024 A | 4/1987 | Coneys |
| 4,686,963 A | 8/1987 | Cohen et al. |
| 4,686,965 A | 8/1987 | Bonnet et al. |
| 4,693,248 A | 9/1987 | Failla |
| 4,716,886 A | 1/1988 | Schulman et al. |
| 4,742,817 A | 5/1988 | Kawashima et al. |
| 4,777,951 A | 10/1988 | Cribier et al. |
| 4,795,458 A | 1/1989 | Regan |
| 4,809,695 A | 3/1989 | Gwathmey et al. |

(56) References Cited

U.S. PATENT DOCUMENTS

| | | |
|---|---|---|
| 4,887,601 A * | 12/1989 | Richards ............ A61B 17/0644 606/219 |
| 4,917,089 A | 4/1990 | Sideris |
| 4,930,674 A | 6/1990 | Barak |
| 4,944,295 A | 7/1990 | Gwathmey et al. |
| 4,969,890 A | 11/1990 | Sugita et al. |
| 4,994,077 A | 2/1991 | Dobben |
| 5,002,562 A | 3/1991 | Oberlander |
| 5,015,249 A | 5/1991 | Nakao et al. |
| 5,019,096 A | 5/1991 | Fox, Jr. et al. |
| 5,042,707 A | 8/1991 | Taheri |
| 5,047,041 A | 9/1991 | Samuels |
| 5,049,153 A | 9/1991 | Nakao et al. |
| 5,061,277 A | 10/1991 | Carpentier et al. |
| 5,069,679 A | 12/1991 | Taheri |
| 5,098,440 A | 3/1992 | Hillstead |
| 5,108,368 A | 4/1992 | Hammerslag et al. |
| 5,125,758 A | 6/1992 | DeWan |
| 5,125,895 A | 6/1992 | Buchbinder et al. |
| 5,147,370 A | 9/1992 | McNamara et al. |
| 5,171,252 A | 12/1992 | Friedland |
| 5,171,259 A | 12/1992 | Inoue |
| 5,190,554 A | 3/1993 | Coddington et al. |
| 5,195,968 A | 3/1993 | Lundquist et al. |
| 5,209,756 A | 5/1993 | Seedhom et al. |
| 5,222,963 A | 6/1993 | Brinkerhoff et al. |
| 5,226,429 A | 7/1993 | Kuzmak |
| 5,226,911 A | 7/1993 | Chee et al. |
| 5,234,437 A | 8/1993 | Sepetka |
| 5,242,456 A | 9/1993 | Nash et al. |
| 5,250,071 A | 10/1993 | Palermo |
| 5,251,611 A | 10/1993 | Zehel et al. |
| 5,254,130 A | 10/1993 | Poncet et al. |
| 5,261,916 A | 11/1993 | Engelson |
| 5,271,381 A | 12/1993 | Ailinger et al. |
| 5,271,544 A | 12/1993 | Fox et al. |
| 5,275,578 A | 1/1994 | Adams |
| 5,282,845 A | 2/1994 | Bush et al. |
| 5,304,131 A | 4/1994 | Paskar |
| 5,306,283 A | 4/1994 | Conners |
| 5,306,286 A | 4/1994 | Stack et al. |
| 5,312,415 A | 5/1994 | Palermo |
| 5,314,424 A | 5/1994 | Nicholas |
| 5,318,525 A | 6/1994 | West et al. |
| 5,320,632 A | 6/1994 | Heidmueller |
| 5,325,845 A | 7/1994 | Adair |
| 5,327,905 A | 7/1994 | Avitall |
| 5,330,442 A | 7/1994 | Green et al. |
| 5,330,501 A | 7/1994 | Tovey et al. |
| 5,332,402 A | 7/1994 | Teitelbaum |
| 5,334,217 A | 8/1994 | Das |
| 5,342,393 A | 8/1994 | Stack |
| 5,350,397 A | 9/1994 | Palermo et al. |
| 5,350,399 A | 9/1994 | Erlebacher et al. |
| 5,359,994 A | 11/1994 | Kreuter et al. |
| 5,363,861 A | 11/1994 | Edwards et al. |
| 5,368,564 A | 11/1994 | Savage |
| 5,368,601 A | 11/1994 | Sauer et al. |
| 5,383,886 A | 1/1995 | Kensey et al. |
| 5,389,077 A | 2/1995 | Melinyshyn et al. |
| 5,391,182 A | 2/1995 | Chin |
| 5,403,312 A | 4/1995 | Yates et al. |
| 5,403,326 A | 4/1995 | Harrison et al. |
| 5,411,552 A | 5/1995 | Andersen et al. |
| 5,413,584 A | 5/1995 | Schulze |
| 5,417,699 A | 5/1995 | Klein et al. |
| 5,417,700 A | 5/1995 | Egan |
| 5,423,857 A | 6/1995 | Rosenman et al. |
| 5,423,858 A | 6/1995 | Bolanos et al. |
| 5,423,882 A | 6/1995 | Jackman et al. |
| 5,425,744 A | 6/1995 | Fagan et al. |
| 5,431,666 A | 7/1995 | Sauer et al. |
| 5,437,551 A | 8/1995 | Chalifoux |
| 5,437,681 A | 8/1995 | Meade et al. |
| 5,447,966 A | 9/1995 | Hermes et al. |
| 5,450,860 A | 9/1995 | O'Connor |
| 5,452,837 A | 9/1995 | Williamson, IV et al. |
| 5,456,400 A | 10/1995 | Schichman et al. |
| 5,456,674 A | 10/1995 | Bos et al. |
| 5,456,684 A | 10/1995 | Schmidt et al. |
| 5,462,527 A | 10/1995 | Stevens-Wright et al. |
| 5,472,044 A | 12/1995 | Hall et al. |
| 5,476,470 A | 12/1995 | Fitzgibbons, Jr. |
| 5,477,856 A | 12/1995 | Lundquist |
| 5,478,309 A | 12/1995 | Sweezer et al. |
| 5,478,353 A | 12/1995 | Yoon |
| 5,487,746 A | 1/1996 | Yu et al. |
| 5,496,332 A | 3/1996 | Sierra et al. |
| 5,507,725 A | 4/1996 | Savage et al. |
| 5,507,755 A | 4/1996 | Gresl et al. |
| 5,507,757 A | 4/1996 | Sauer et al. |
| 5,520,701 A | 5/1996 | Lerch |
| 5,522,873 A | 6/1996 | Jackman et al. |
| 5,527,313 A | 6/1996 | Scott et al. |
| 5,527,321 A | 6/1996 | Hinchliffe |
| 5,527,322 A | 6/1996 | Klein et al. |
| 5,536,251 A | 7/1996 | Evard et al. |
| 5,540,705 A | 7/1996 | Meade et al. |
| 5,542,949 A | 8/1996 | Yoon |
| 5,554,185 A | 9/1996 | Block et al. |
| 5,562,678 A | 10/1996 | Booker |
| 5,569,274 A | 10/1996 | Rapacki et al. |
| 5,571,085 A | 11/1996 | Accisano, III |
| 5,571,137 A | 11/1996 | Marlow et al. |
| 5,571,215 A | 11/1996 | Sterman et al. |
| 5,575,802 A | 11/1996 | McQuilkin et al. |
| 5,582,611 A | 12/1996 | Tsuruta et al. |
| 5,593,424 A | 1/1997 | Northrup, III |
| 5,593,435 A | 1/1997 | Carpentier et al. |
| 5,601,224 A | 2/1997 | Bishop et al. |
| 5,601,574 A | 2/1997 | Stefanchik et al. |
| 5,607,462 A | 3/1997 | Imran |
| 5,607,471 A | 3/1997 | Seguin et al. |
| 5,609,598 A | 3/1997 | Laufer et al. |
| 5,611,794 A | 3/1997 | Sauer et al. |
| 5,618,306 A | 4/1997 | Roth et al. |
| 5,620,452 A | 4/1997 | Yoon |
| 5,620,461 A | 4/1997 | Muijs Van De Moer et al. |
| 5,626,588 A | 5/1997 | Sauer et al. |
| 5,634,932 A | 6/1997 | Schmidt |
| 5,636,634 A | 6/1997 | Kordis et al. |
| 5,639,277 A | 6/1997 | Mariant et al. |
| 5,640,955 A | 6/1997 | Ockuly et al. |
| 5,649,937 A | 7/1997 | Bito et al. |
| 5,662,681 A | 9/1997 | Nash et al. |
| 5,669,917 A | 9/1997 | Sauer et al. |
| 5,690,671 A | 11/1997 | McGurk et al. |
| 5,695,504 A | 12/1997 | Gifford, III et al. |
| 5,695,505 A | 12/1997 | Yoon |
| 5,702,825 A | 12/1997 | Keita et al. |
| 5,706,824 A | 1/1998 | Whittier |
| 5,709,707 A | 1/1998 | Lock et al. |
| 5,713,910 A | 2/1998 | Gordon et al. |
| 5,713,911 A | 2/1998 | Racenet et al. |
| 5,715,817 A | 2/1998 | Stevens-Wright et al. |
| 5,716,367 A | 2/1998 | Koike et al. |
| 5,716,417 A | 2/1998 | Girard et al. |
| 5,718,725 A | 2/1998 | Sterman et al. |
| 5,719,725 A | 2/1998 | Nakao |
| 5,722,421 A | 3/1998 | Francese et al. |
| 5,725,542 A | 3/1998 | Yoon |
| 5,725,556 A | 3/1998 | Moser et al. |
| 5,738,649 A | 4/1998 | Macoviak |
| 5,741,280 A | 4/1998 | Fleenor |
| 5,741,297 A | 4/1998 | Simon |
| 5,749,828 A | 5/1998 | Solomon et al. |
| 5,755,778 A | 5/1998 | Kleshinski |
| 5,759,193 A | 6/1998 | Burbank et al. |
| 5,769,812 A | 6/1998 | Stevens et al. |
| 5,769,863 A | 6/1998 | Garrison |
| 5,772,578 A | 6/1998 | Heimberger et al. |
| 5,782,239 A | 7/1998 | Webster, Jr. |
| 5,782,845 A | 7/1998 | Shewchuk |
| 5,797,927 A | 8/1998 | Yoon |

(56) References Cited

U.S. PATENT DOCUMENTS

| | | |
|---|---|---|
| 5,797,960 A | 8/1998 | Stevens et al. |
| 5,810,847 A | 9/1998 | Laufer et al. |
| 5,810,849 A | 9/1998 | Kontos |
| 5,810,853 A | 9/1998 | Yoon |
| 5,810,876 A | 9/1998 | Kelleher |
| 5,814,029 A | 9/1998 | Hassett |
| 5,814,097 A | 9/1998 | Sterman et al. |
| 5,820,592 A | 10/1998 | Hammerslag |
| 5,820,631 A | 10/1998 | Nobles |
| 5,823,955 A | 10/1998 | Kuck et al. |
| 5,823,956 A | 10/1998 | Roth et al. |
| 5,824,065 A | 10/1998 | Gross |
| 5,827,237 A | 10/1998 | Macoviak et al. |
| 5,829,447 A | 11/1998 | Stevens et al. |
| 5,833,671 A | 11/1998 | Macoviak et al. |
| 5,836,955 A | 11/1998 | Buelna et al. |
| 5,840,081 A | 11/1998 | Andersen et al. |
| 5,843,031 A | 12/1998 | Hermann et al. |
| 5,843,178 A | 12/1998 | Vanney et al. |
| 5,849,019 A | 12/1998 | Yoon |
| 5,853,422 A | 12/1998 | Huebsch et al. |
| 5,855,271 A | 1/1999 | Eubanks et al. |
| 5,855,590 A | 1/1999 | Malecki et al. |
| 5,855,601 A | 1/1999 | Bessler et al. |
| 5,855,614 A | 1/1999 | Stevens et al. |
| 5,860,990 A | 1/1999 | Nobles et al. |
| 5,861,003 A | 1/1999 | Latson et al. |
| 5,868,733 A | 2/1999 | Ockuly et al. |
| 5,876,399 A | 3/1999 | Chia et al. |
| 5,879,307 A | 3/1999 | Chio et al. |
| 5,885,258 A | 3/1999 | Sachdeva et al. |
| 5,885,271 A | 3/1999 | Hamilton et al. |
| 5,891,160 A | 4/1999 | Williamson, IV et al. |
| 5,916,147 A | 6/1999 | Boury |
| 5,928,224 A | 7/1999 | Laufer |
| 5,944,733 A | 8/1999 | Engelson |
| 5,947,363 A | 9/1999 | Bolduc et al. |
| 5,954,732 A | 9/1999 | Hart et al. |
| 5,957,949 A | 9/1999 | Leonhard et al. |
| 5,972,020 A | 10/1999 | Carpentier et al. |
| 5,972,030 A | 10/1999 | Garrison et al. |
| 5,976,159 A | 11/1999 | Bolduc et al. |
| 5,980,455 A | 11/1999 | Daniel et al. |
| 5,989,284 A | 11/1999 | Laufer |
| 6,007,552 A | 12/1999 | Fogarty et al. |
| 6,015,417 A | 1/2000 | Reynolds, Jr. |
| 6,017,358 A | 1/2000 | Yoon et al. |
| 6,019,722 A | 2/2000 | Spence et al. |
| 6,022,360 A | 2/2000 | Reimels et al. |
| 6,033,378 A | 3/2000 | Lundquist et al. |
| 6,036,699 A | 3/2000 | Andreas et al. |
| 6,048,351 A | 4/2000 | Gordon et al. |
| 6,056,769 A | 5/2000 | Epstein et al. |
| 6,059,757 A | 5/2000 | Macoviak et al. |
| 6,060,628 A | 5/2000 | Aoyama et al. |
| 6,060,629 A | 5/2000 | Pham et al. |
| 6,063,106 A | 5/2000 | Gibson |
| 6,066,146 A | 5/2000 | Carroll et al. |
| 6,068,628 A | 5/2000 | Fanton et al. |
| 6,068,629 A | 5/2000 | Haissaguerre et al. |
| 6,077,214 A | 6/2000 | Mortier et al. |
| 6,079,414 A | 6/2000 | Roth |
| 6,086,600 A | 7/2000 | Kortenbach |
| 6,088,889 A | 7/2000 | Luther et al. |
| 6,099,505 A | 8/2000 | Ryan et al. |
| 6,099,553 A | 8/2000 | Hart et al. |
| 6,110,145 A | 8/2000 | Macoviak |
| 6,117,144 A | 9/2000 | Nobles et al. |
| 6,117,159 A | 9/2000 | Huebsch et al. |
| 6,120,496 A | 9/2000 | Whayne et al. |
| 6,123,699 A | 9/2000 | Webster, Jr. |
| 6,126,658 A | 10/2000 | Baker |
| 6,132,447 A | 10/2000 | Dorsey |
| 6,136,010 A | 10/2000 | Modesitt et al. |
| 6,143,024 A | 11/2000 | Campbell et al. |
| 6,149,658 A | 11/2000 | Gardiner et al. |
| 6,156,055 A | 12/2000 | Ravenscroft |
| 6,159,240 A | 12/2000 | Sparer et al. |
| 6,162,233 A | 12/2000 | Williamson, IV et al. |
| 6,165,164 A | 12/2000 | Hill et al. |
| 6,165,183 A | 12/2000 | Kuehn et al. |
| 6,165,204 A | 12/2000 | Levinson et al. |
| 6,168,614 B1 | 1/2001 | Andersen et al. |
| 6,171,320 B1 | 1/2001 | Monassevitch |
| 6,182,664 B1 | 2/2001 | Cosgrove |
| 6,187,003 B1 | 2/2001 | Buysse et al. |
| 6,190,408 B1 | 2/2001 | Melvin |
| 6,193,734 B1 | 2/2001 | Bolduc et al. |
| 6,200,315 B1 | 3/2001 | Gaiser et al. |
| 6,203,531 B1 | 3/2001 | Ockuly et al. |
| 6,203,553 B1 | 3/2001 | Robertson et al. |
| 6,206,893 B1 | 3/2001 | Klein et al. |
| 6,206,907 B1 | 3/2001 | Marino et al. |
| 6,210,337 B1 | 4/2001 | Dunham et al. |
| 6,210,419 B1 | 4/2001 | Mayenberger et al. |
| 6,210,432 B1 | 4/2001 | Solem et al. |
| 6,217,528 B1 | 4/2001 | Koblish et al. |
| 6,245,079 B1 | 6/2001 | Nobles et al. |
| 6,267,746 B1 | 7/2001 | Bumbalough |
| 6,267,781 B1 | 7/2001 | Tu |
| 6,269,819 B1 | 8/2001 | Oz et al. |
| 6,277,555 B1 | 8/2001 | Duran et al. |
| 6,283,127 B1 | 9/2001 | Sterman et al. |
| 6,283,962 B1 | 9/2001 | Tu et al. |
| 6,290,674 B1 | 9/2001 | Roue et al. |
| 6,299,637 B1 | 10/2001 | Shaolian et al. |
| 6,306,133 B1 | 10/2001 | Tu et al. |
| 6,312,447 B1 | 11/2001 | Grimes |
| 6,319,250 B1 | 11/2001 | Falwell et al. |
| 6,322,559 B1 | 11/2001 | Daulton et al. |
| 6,332,880 B1 | 12/2001 | Yang et al. |
| 6,332,893 B1 | 12/2001 | Mortier et al. |
| 6,346,074 B1 | 2/2002 | Roth |
| 6,352,708 B1 | 3/2002 | Duran et al. |
| 6,355,030 B1 | 3/2002 | Aldrich et al. |
| 6,358,277 B1 | 3/2002 | Duran |
| 6,368,326 B1 | 4/2002 | Dakin et al. |
| 6,387,104 B1 | 5/2002 | Pugsley, Jr. et al. |
| 6,402,780 B2 | 6/2002 | Williamson et al. |
| 6,402,781 B1 | 6/2002 | Langberg et al. |
| 6,419,669 B1 | 7/2002 | Frazier et al. |
| 6,419,696 B1 | 7/2002 | Ortiz et al. |
| 6,461,366 B1 | 10/2002 | Seguin |
| 6,464,707 B1 | 10/2002 | Bjerken |
| 6,482,224 B1 | 11/2002 | Michler et al. |
| 6,485,489 B2 | 11/2002 | Teirstein et al. |
| 6,406,420 B1 | 12/2002 | McCarthy |
| 6,508,828 B1 | 1/2003 | Akerfeldt et al. |
| 6,533,796 B1 | 3/2003 | Sauer et al. |
| 6,537,314 B2 | 3/2003 | Langberg et al. |
| 6,540,755 B2 | 4/2003 | Ockuly et al. |
| 6,544,215 B1 | 4/2003 | Bencini et al. |
| 6,551,303 B1 | 4/2003 | Van Tassel et al. |
| 6,551,331 B2 | 4/2003 | Nobles et al. |
| 6,562,037 B2 | 5/2003 | Paton et al. |
| 6,562,052 B2 | 5/2003 | Nobles et al. |
| 6,575,971 B2 | 6/2003 | Hauck et al. |
| 6,585,761 B2 | 7/2003 | Taheri |
| 6,599,311 B1 | 7/2003 | Biggs et al. |
| 6,616,684 B1 | 9/2003 | Vidlund et al. |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,641,592 B1 | 11/2003 | Sauer et al. |
| 6,656,221 B2 | 12/2003 | Taylor et al. |
| 6,669,687 B1 | 12/2003 | Saadat |
| 6,685,648 B2 | 2/2004 | Flaherty et al. |
| 6,689,164 B1 | 2/2004 | Seguin |
| 6,695,866 B1 | 2/2004 | Kuehn et al. |
| 6,701,929 B2 | 3/2004 | Hussein |
| 6,702,825 B2 | 3/2004 | Frazier et al. |
| 6,702,826 B2 | 3/2004 | Liddicoat et al. |
| 6,709,382 B1 | 3/2004 | Horner |

(56) References Cited

U.S. PATENT DOCUMENTS

| | | |
|---|---|---|
| 6,709,456 B2 | 3/2004 | Langberg et al. |
| 6,718,985 B2 | 4/2004 | Hlavka et al. |
| 6,719,767 B1 | 4/2004 | Kimblad |
| 6,723,038 B1 | 4/2004 | Schroeder et al. |
| 6,726,716 B2 | 4/2004 | Marquez |
| 6,740,107 B2 | 5/2004 | Loeb et al. |
| 6,746,471 B2 | 6/2004 | Mortier et al. |
| 6,752,813 B2 | 6/2004 | Goldfarb et al. |
| 6,755,777 B2 | 6/2004 | Schweich et al. |
| 6,764,510 B2 | 7/2004 | Vidlund et al. |
| 6,767,349 B2 | 7/2004 | Ouchi |
| 6,770,083 B2 | 8/2004 | Seguin |
| 6,797,001 B2 | 9/2004 | Mathis et al. |
| 6,797,002 B2 | 9/2004 | Spence et al. |
| 6,837,867 B2 | 1/2005 | Kortelling |
| 6,855,137 B2 | 2/2005 | Bon |
| 6,860,179 B2 | 3/2005 | Hopper et al. |
| 6,875,224 B2 | 4/2005 | Grimes |
| 6,908,481 B2 | 6/2005 | Cribier |
| 6,926,715 B1 | 8/2005 | Hauck et al. |
| 6,926,730 B1 | 8/2005 | Nguyen et al. |
| 6,945,978 B1 | 9/2005 | Hyde |
| 6,949,122 B2 | 9/2005 | Adams et al. |
| 6,966,914 B2 | 11/2005 | Abe |
| 6,986,775 B2 | 1/2006 | Morales et al. |
| 7,004,970 B2 | 2/2006 | Cauthen, III et al. |
| 7,011,669 B2 | 3/2006 | Kimblad |
| 7,048,754 B2 | 5/2006 | Martin et al. |
| 7,101,395 B2 | 9/2006 | Tremulis et al. |
| 7,112,207 B2 | 9/2006 | Allen et al. |
| 7,226,467 B2 | 6/2007 | Lucatero et al. |
| 7,288,097 B2 | 10/2007 | Seguin |
| 7,381,210 B2 | 6/2008 | Zarbatany et al. |
| 7,464,712 B2 | 12/2008 | Oz et al. |
| 7,497,822 B1 | 3/2009 | Kugler et al. |
| 7,513,908 B2 | 4/2009 | Lattouf |
| 7,533,790 B1 | 5/2009 | Knodel et al. |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,604,646 B2 | 10/2009 | Goldfarb et al. |
| 7,608,091 B2 | 10/2009 | Goldfarb et al. |
| 7,635,329 B2 | 12/2009 | Goldfarb et al. |
| 7,651,502 B2 | 1/2010 | Jackson |
| 7,655,015 B2 | 2/2010 | Goldfarb et al. |
| 7,655,040 B2 | 2/2010 | Douk et al. |
| 7,666,204 B2 | 2/2010 | Thornton et al. |
| 7,704,269 B2 | 4/2010 | St. Goar et al. |
| 7,798,953 B1 | 9/2010 | Wilk |
| 7,811,296 B2 | 10/2010 | Goldfarb et al. |
| 7,914,544 B2 | 3/2011 | Nguyen et al. |
| 7,972,323 B1 | 7/2011 | Bencini et al. |
| 7,972,330 B2 | 7/2011 | Alejandro et al. |
| 8,029,565 B2 | 10/2011 | Lattouf |
| 8,062,313 B2 | 11/2011 | Kimblad |
| 8,118,822 B2 | 2/2012 | Schaller et al. |
| 8,216,256 B2 | 7/2012 | Raschdorf, Jr. et al. |
| 8,348,963 B2 | 1/2013 | Wilson et al. |
| 2001/0004715 A1 | 6/2001 | Duran et al. |
| 2001/0005787 A1 | 6/2001 | Oz et al. |
| 2001/0010005 A1 | 7/2001 | Kammerer et al. |
| 2001/0018611 A1 | 8/2001 | Solem et al. |
| 2001/0022872 A1 | 9/2001 | Marui |
| 2001/0037084 A1 | 11/2001 | Nardeo |
| 2001/0039411 A1 | 11/2001 | Johansson et al. |
| 2001/0044568 A1 | 11/2001 | Langberg et al. |
| 2002/0013571 A1 | 1/2002 | Goldfarb et al. |
| 2002/0022848 A1 | 2/2002 | Garrison et al. |
| 2002/0026233 A1 | 2/2002 | Shaknovich |
| 2002/0035361 A1 | 3/2002 | Houser et al. |
| 2002/0035381 A1 | 3/2002 | Bardy et al. |
| 2002/0042651 A1 | 4/2002 | Liddicoat et al. |
| 2002/0055767 A1 | 5/2002 | Forde et al. |
| 2002/0055774 A1 | 5/2002 | Liddicoat |
| 2002/0055775 A1 | 5/2002 | Carpentier et al. |
| 2002/0058858 A1 | 5/2002 | Ogura et al. |
| 2002/0058910 A1 | 5/2002 | Hermann et al. |
| 2002/0058995 A1 | 5/2002 | Stevens |
| 2002/0077687 A1 | 6/2002 | Ahn |
| 2002/0082621 A1 | 6/2002 | Schurr et al. |
| 2002/0087148 A1 | 7/2002 | Brock et al. |
| 2002/0087169 A1 | 7/2002 | Brock et al. |
| 2002/0087173 A1 | 7/2002 | Alferness et al. |
| 2002/0103532 A1 | 8/2002 | Langberg et al. |
| 2002/0107534 A1 | 8/2002 | Schaefer et al. |
| 2002/0133178 A1 | 9/2002 | Muramatsu et al. |
| 2002/0147456 A1 | 10/2002 | Diduch et al. |
| 2002/0156526 A1 | 10/2002 | Hilavka et al. |
| 2002/0158528 A1 | 10/2002 | Tsuzaki et al. |
| 2002/0161378 A1 | 10/2002 | Downing |
| 2002/0169360 A1 | 11/2002 | Taylor et al. |
| 2002/0183766 A1 | 12/2002 | Seguin |
| 2002/0183787 A1 | 12/2002 | Wahr et al. |
| 2002/0183835 A1 | 12/2002 | Taylor et al. |
| 2003/0005797 A1 | 1/2003 | Hopper et al. |
| 2003/0018358 A1 | 1/2003 | Saadat |
| 2003/0045778 A1 | 3/2003 | Ohline et al. |
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0069636 A1 | 4/2003 | Solem et al. |
| 2003/0074012 A1 | 4/2003 | Nguyen et al. |
| 2003/0078654 A1 | 4/2003 | Taylor et al. |
| 2003/0083742 A1 | 5/2003 | Spence et al. |
| 2003/0105519 A1 | 6/2003 | Fasol et al. |
| 2003/0105520 A1 | 6/2003 | Alferness et al. |
| 2003/0120340 A1 | 6/2003 | Lisk et al. |
| 2003/0120341 A1 | 6/2003 | Shennib et al. |
| 2003/0130669 A1 | 7/2003 | Damarati |
| 2003/0130730 A1 | 7/2003 | Cohn et al. |
| 2003/0144697 A1 | 7/2003 | Mathis et al. |
| 2003/0167071 A1 | 9/2003 | Martin et al. |
| 2003/0171776 A1 | 9/2003 | Adams et al. |
| 2003/0187467 A1 | 10/2003 | Schreck |
| 2003/0195562 A1 | 10/2003 | Collier et al. |
| 2003/0208231 A1 | 11/2003 | Williamson, IV et al. |
| 2003/0225423 A1 | 12/2003 | Huitema |
| 2003/0229395 A1 | 12/2003 | Cox |
| 2003/0233038 A1 | 12/2003 | Hassett |
| 2004/0002719 A1 | 1/2004 | Oz et al. |
| 2004/0003819 A1 | 1/2004 | St. Goar et al. |
| 2004/0019377 A1 | 1/2004 | Taylor et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0034365 A1 | 2/2004 | Lentz et al. |
| 2004/0039442 A1 | 2/2004 | St. Goar et al. |
| 2004/0039443 A1 | 2/2004 | Solem et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0049211 A1 | 3/2004 | Tremulis et al. |
| 2004/0073302 A1 | 4/2004 | Rourke et al. |
| 2004/0078053 A1 | 4/2004 | Berg et al. |
| 2004/0087975 A1 | 5/2004 | Lucatero et al. |
| 2004/0088047 A1 | 5/2004 | Spence et al. |
| 2004/0092962 A1 | 5/2004 | Thorton et al. |
| 2004/0093023 A1 | 5/2004 | Allen et al. |
| 2004/0097878 A1 | 5/2004 | Anderson et al. |
| 2004/0097979 A1 | 5/2004 | Svanidze et al. |
| 2004/0106989 A1 | 6/2004 | Wilson et al. |
| 2004/0111099 A1 | 6/2004 | Nguyen et al. |
| 2004/0122448 A1 | 6/2004 | Levine |
| 2004/0127981 A1 | 7/2004 | Randert et al. |
| 2004/0127982 A1 | 7/2004 | Machold et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0133082 A1 | 7/2004 | Abraham-Fuchs et al. |
| 2004/0133192 A1 | 7/2004 | Houser et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138744 A1 | 7/2004 | Lashinski et al. |

(56) References Cited

U.S. PATENT DOCUMENTS

| | | |
|---|---|---|
| 2004/0138745 A1 | 7/2004 | Macoviak et al. |
| 2004/0148021 A1 | 7/2004 | Cartledge et al. |
| 2004/0152847 A1 | 8/2004 | Emri et al. |
| 2004/0152947 A1 | 8/2004 | Schroeder et al. |
| 2004/0153144 A1 | 8/2004 | Seguin |
| 2004/0158123 A1 | 8/2004 | Jayaraman |
| 2004/0162610 A1 | 8/2004 | Laiska et al. |
| 2004/0167539 A1 | 8/2004 | Kuehn et al. |
| 2004/0186486 A1 | 9/2004 | Roue et al. |
| 2004/0186566 A1 | 9/2004 | Hindrichs et al. |
| 2004/0193191 A1 | 9/2004 | Starksen et al. |
| 2004/0215339 A1 | 10/2004 | Drasler et al. |
| 2004/0220593 A1 | 11/2004 | Greenhalgh |
| 2004/0220657 A1 | 11/2004 | Nieminen et al. |
| 2004/0225300 A1 | 11/2004 | Goldfarb et al. |
| 2004/0236354 A1 | 11/2004 | Seguin |
| 2004/0243229 A1 | 12/2004 | Vidlund et al. |
| 2004/0249452 A1 | 12/2004 | Adams et al. |
| 2004/0249453 A1 | 12/2004 | Cartledge et al. |
| 2004/0260393 A1 | 12/2004 | Randert et al. |
| 2005/0004583 A1 | 1/2005 | Oz et al. |
| 2005/0004665 A1 | 1/2005 | Aklog |
| 2005/0004668 A1 | 1/2005 | Aklog et al. |
| 2005/0021056 A1 | 1/2005 | St. Goer et al. |
| 2005/0021057 A1 | 1/2005 | St. Goer et al. |
| 2005/0021058 A1 | 1/2005 | Negro |
| 2005/0033446 A1 | 2/2005 | Deem et al. |
| 2005/0038508 A1 | 2/2005 | Gabbay |
| 2005/0049698 A1 | 3/2005 | Bolling et al. |
| 2005/0055089 A1 | 3/2005 | Macoviak et al. |
| 2005/0059351 A1 | 3/2005 | Cauwels et al. |
| 2005/0149014 A1 | 7/2005 | Hauck et al. |
| 2005/0159810 A1 | 7/2005 | Filsoufi |
| 2005/0197694 A1 | 9/2005 | Pai et al. |
| 2005/0197695 A1 | 9/2005 | Stacchino et al. |
| 2005/0216039 A1 | 9/2005 | Lederman |
| 2005/0228422 A1 | 10/2005 | Machold et al. |
| 2005/0228495 A1 | 10/2005 | Macoviak |
| 2005/0251001 A1 | 11/2005 | Hassett |
| 2005/0267493 A1 | 12/2005 | Schreck et al. |
| 2005/0273160 A1 | 12/2005 | Lashinski et al. |
| 2005/0287493 A1 | 12/2005 | Novak et al. |
| 2006/0004247 A1 | 1/2006 | Kute et al. |
| 2006/0015003 A1 | 1/2006 | Moaddes et al. |
| 2006/0020275 A1 | 1/2006 | Goldfarb et al. |
| 2006/0030866 A1 | 2/2006 | Schreck |
| 2006/0030867 A1 | 2/2006 | Zadno |
| 2006/0030885 A1 | 2/2006 | Hyde |
| 2006/0058871 A1 | 3/2006 | Zakay et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0089671 A1 | 4/2006 | Goldfarb et al. |
| 2006/0089711 A1 | 4/2006 | Dolan |
| 2006/0135993 A1 | 6/2006 | Seguin |
| 2006/0184203 A1 | 8/2006 | Martin et al. |
| 2006/0190036 A1 | 8/2006 | Wendel et al. |
| 2006/0195012 A1 | 8/2006 | Mortier et al. |
| 2006/0229708 A1 | 10/2006 | Powell et al. |
| 2006/0252984 A1 | 11/2006 | Randert et al. |
| 2006/0293701 A1 | 12/2006 | Ainsworth et al. |
| 2007/0038293 A1 | 2/2007 | St. Goar et al. |
| 2007/0100356 A1 | 5/2007 | Lucatero et al. |
| 2007/0118155 A1 | 5/2007 | Goldfarb et al. |
| 2007/0129737 A1 | 6/2007 | Goldfarb et al. |
| 2007/0135826 A1 | 6/2007 | Zaver et al. |
| 2007/0198082 A1 | 8/2007 | Kapadia et al. |
| 2007/0282373 A1 | 12/2007 | Ashby et al. |
| 2008/0039935 A1 | 2/2008 | Buch et al. |
| 2008/0045997 A1 | 2/2008 | Balgobin et al. |
| 2008/0051703 A1 | 2/2008 | Thorton et al. |
| 2008/0051807 A1 | 2/2008 | St. Goar et al. |
| 2008/0097489 A1 | 4/2008 | Goldfarb et al. |
| 2008/0167714 A1 | 7/2008 | St. Goer et al. |
| 2008/0183194 A1 | 7/2008 | Goldfarb et al. |
| 2009/0156995 A1 | 6/2009 | Martin et al. |
| 2009/0163934 A1 | 6/2009 | Raschdorf, Jr. et al. |
| 2009/0177266 A1 | 7/2009 | Powell et al. |
| 2009/0198322 A1 | 8/2009 | Deem et al. |
| 2009/0270858 A1 | 10/2009 | Hauck et al. |
| 2009/0326567 A1 | 12/2009 | Goldfarb et al. |
| 2010/0016958 A1 | 1/2010 | St. Goer et al. |
| 2010/0022823 A1 | 1/2010 | Goldfarb et al. |
| 2010/0324585 A1 | 12/2010 | Miles et al. |
| 2013/0138121 A1 | 5/2013 | Allen et al. |
| 2015/0223793 A1 | 8/2015 | Goldfarb et al. |

FOREIGN PATENT DOCUMENTS

| | | |
|---|---|---|
| DE | 3504292 C1 | 7/1986 |
| DE | 19810696 C1 | 5/1999 |
| DE | 101 16 168 A1 | 11/2001 |
| EP | 0 179 562 B1 | 7/1989 |
| EP | 0 558 031 B1 | 2/1993 |
| EP | 0 558 031 A2 | 9/1993 |
| EP | 0 684 012 A2 | 11/1995 |
| EP | 0 727 239 A2 | 8/1996 |
| EP | 0 752 235 A1 | 1/1997 |
| EP | 0 782 836 A1 | 7/1997 |
| EP | 1 199 037 A2 | 4/2002 |
| EP | 1 230 899 A1 | 8/2002 |
| EP | 1383448 A2 | 1/2004 |
| EP | 1 674 040 A2 | 6/2006 |
| FR | 2 768 324 A1 | 3/1999 |
| FR | 2768324 A1 | 3/1999 |
| GB | 1 598 111 A | 9/1981 |
| GB | 2 151 142 A | 7/1985 |
| JP | 9-192137 A | 7/1997 |
| JP | 09-253030 A | 9/1997 |
| JP | 11-089937 A | 4/1999 |
| JP | 2000-283130 A | 10/2000 |
| JP | 2002-540878 A | 12/2002 |
| JP | 2006-528911 A | 12/2006 |
| JP | 59-85653 B2 | 9/2016 |
| WO | WO 81/00668 A1 | 3/1981 |
| WO | WO 91/01689 A1 | 2/1991 |
| WO | WO 91/18881 A1 | 12/1991 |
| WO | WO 92/12690 A1 | 8/1992 |
| WO | WO 94/18881 A1 | 9/1994 |
| WO | WO 94/18893 A1 | 9/1994 |
| WO | WO 95/11620 A2 | 5/1995 |
| WO | WO 95/15715 A1 | 6/1995 |
| WO | WO 96/14032 A1 | 5/1996 |
| WO | WO 96/20655 A1 | 7/1996 |
| WO | WO 96/22735 A1 | 8/1996 |
| WO | WO 96/30072 A1 | 10/1996 |
| WO | WO 96/32882 A1 | 10/1996 |
| WO | WO 97/18746 A2 | 5/1997 |
| WO | WO 97/25927 A1 | 7/1997 |
| WO | WO 97/26034 A1 | 7/1997 |
| WO | WO 97/27807 A1 | 8/1997 |
| WO | WO 97/38748 A2 | 10/1997 |
| WO | WO 97/39688 A2 | 10/1997 |
| WO | WO 97/48436 A2 | 12/1997 |
| WO | WO 98/07375 A1 | 2/1998 |
| WO | WO 98/24372 A1 | 6/1998 |
| WO | WO 98/30153 A1 | 7/1998 |
| WO | WO 98/32382 A1 | 7/1998 |
| WO | WO 98/35638 A1 | 8/1998 |
| WO | WO 99/00059 A1 | 1/1999 |
| WO | WO 99/01377 A1 | 1/1999 |
| WO | WO 99/07354 A2 | 2/1999 |
| WO | WO 99/13777 A1 | 3/1999 |
| WO | WO 99/15223 A1 | 4/1999 |
| WO | WO 99/66967 A1 | 12/1999 |
| WO | WO 00/02489 A1 | 1/2000 |
| WO | WO 00/03651 A1 | 1/2000 |
| WO | WO 00/03759 A2 | 1/2000 |
| WO | WO 00/12168 A1 | 3/2000 |
| WO | WO 00/44313 A1 | 8/2000 |
| WO | WO 00/59382 A1 | 10/2000 |
| WO | WO 00/60995 A2 | 10/2000 |
| WO | WO 01/00111 A1 | 1/2001 |
| WO | WO 01/00114 A1 | 1/2001 |

(56) References Cited

FOREIGN PATENT DOCUMENTS

| | | |
|---|---|---|
| WO | WO 01/03651 A2 | 1/2001 |
| WO | WO 01/26557 A1 | 4/2001 |
| WO | WO 01/26586 A1 | 4/2001 |
| WO | WO 01/26587 A1 | 4/2001 |
| WO | WO 01/26588 A2 | 4/2001 |
| WO | WO 01/26703 A1 | 4/2001 |
| WO | WO 01/28432 A1 | 4/2001 |
| WO | WO 01/28455 A1 | 4/2001 |
| WO | WO 01/35832 A2 | 5/2001 |
| WO | WO 01/47438 A1 | 7/2001 |
| WO | WO 01/49213 A2 | 7/2001 |
| WO | WO 01/50985 A1 | 7/2001 |
| WO | WO 01/54618 A1 | 8/2001 |
| WO | WO 01/56512 A1 | 8/2001 |
| WO | WO 01/66001 A2 | 9/2001 |
| WO | WO 01/70320 A1 | 9/2001 |
| WO | WO 01/89440 A2 | 11/2001 |
| WO | WO 01/95831 A2 | 12/2001 |
| WO | WO 01/95832 A2 | 12/2001 |
| WO | WO 01/97741 A2 | 12/2001 |
| WO | WO 02/00099 A2 | 1/2002 |
| WO | WO 02/01999 A2 | 1/2002 |
| WO | WO 02/03892 A1 | 1/2002 |
| WO | WO 02/34167 A2 | 5/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 03/001893 A2 | 1/2003 |
| WO | WO 03/003930 A1 | 1/2003 |
| WO | WO 03/020179 A1 | 3/2003 |
| WO | WO 03/028558 A2 | 4/2003 |
| WO | WO 03/037171 A2 | 5/2003 |
| WO | WO 03/047467 A1 | 6/2003 |
| WO | WO 03/049619 A2 | 6/2003 |
| WO | WO 03/073910 A2 | 9/2003 |
| WO | WO 03/073913 A2 | 9/2003 |
| WO | WO 03/082129 A2 | 10/2003 |
| WO | WO 03/105667 A2 | 12/2003 |
| WO | WO 2004/004607 A1 | 1/2004 |
| WO | WO 2004/012583 A2 | 2/2004 |
| WO | WO 2004/012789 A2 | 2/2004 |
| WO | WO 2004/014282 A2 | 2/2004 |
| WO | WO 2004/019811 A2 | 3/2004 |
| WO | WO 2004/030570 A2 | 4/2004 |
| WO | WO 2004/037317 A2 | 5/2004 |
| WO | WO 2004/045370 A2 | 6/2004 |
| WO | WO 2004/045378 A2 | 6/2004 |
| WO | WO 2004/045463 A2 | 6/2004 |
| WO | WO 2004/047679 A1 | 6/2004 |
| WO | WO 2004/062725 A1 | 7/2004 |
| WO | WO 2004/082523 A2 | 9/2004 |
| WO | WO 2004/082538 A2 | 9/2004 |
| WO | WO 2004/093730 A2 | 11/2004 |
| WO | WO 04/103162 A2 | 12/2004 |
| WO | WO 2004/103162 A2 | 12/2004 |
| WO | WO 2004/112585 A2 | 12/2004 |
| WO | WO 2004/112651 A2 | 12/2004 |
| WO | WO 2005/002424 A2 | 1/2005 |
| WO | WO 2005/018507 A2 | 3/2005 |
| WO | WO 2005/027797 A1 | 3/2005 |
| WO | WO 2005/032421 A2 | 4/2005 |
| WO | WO 2005/062931 A2 | 7/2005 |
| WO | WO 2005/112792 A2 | 12/2005 |
| WO | WO 2006/105008 A1 | 10/2006 |
| WO | WO 2006/105009 A1 | 10/2006 |
| WO | WO 2006/115875 A2 | 11/2006 |
| WO | WO 2006/115876 A2 | 11/2006 |
| WO | WO 2007/106495 A2 | 9/2007 |
| WO | WO 2008/109394 A2 | 9/2008 |
| WO | WO 2010/128502 A1 | 11/2010 |

OTHER PUBLICATIONS

Abe et al., "Updated: De Vega's Annuloplasty for Acquired Tricuspid Disease: Early and Late Results in 110 Patients," Ann. Thorac. Surg. 62:1876-1877 (1996).
Agricola et al., "Mitral Valve Reserve in Double Orifice Technique: an Exercise Echocardiographic Study," Journal of Heart Valve Disease, 11(5):637-643 (2002).
Alfieri et al., "An Effective Technique to Correct Anterior Mitral Leaflet Prolapse," J. Card Surg., 14:468-470 (1999).
Alfieri et al., "Novel Suture Device for Beating Heart Mitral Leaflet Approximation," Annals of Thoracic Surgery, 74:1488-1493 (2002).
Alfieri et al., "The double orifice technique in mitral valve repair: a simple solution for complex problems," Journal of Thoracic and Cardiovascular Surgery, 122:674-681 (2001).
Alfieri et al., "The Edge to Edge Technique," The European Association for Cardio-Thoracic Surgery, 14th Annual Meeting, Frankfurt / Germany, Oct. 7-11, 2000, Post Graduate Courses, Book of Proceedings.
Alfieri, "The Edge-to-Edge Repair of the Mitral Valve," [Abstract] 6th Annual New Era Cardiac Care: Innovation & Technology, Heart Surgery Forum, (Jan. 2003) pp. 103.
Alvarez et al., "Repairing the Degenerative Mitral Valve: Ten to Fifteen-year Follow-up," J. Thorac. Cardiovasc. Surg., Aug. 1996, pp. 238-247, vol. 112.
Arisi et al., "Mitral Valve Repair with Alfieri Technique in Mitral Regurgitation of Diverse Etiology: Early Echocardiographic Results," Circulation Supplement II, 104(17):3240 (2001).
Bach et al., "Early Improvement in Congestive Heart Failure After Correction of Secondary Mitral Regurgitation in End-stage Cardiomyopathy," Am. Heart J., Jun. 1995, pp. 1165-1170, vol. 129.
Bach et al., "Improvement Following Correction of Secondary Mitral Regurgitation in End-stage Cardiomyopathy with Mitral Annuloplasty," Am. J. Cardiol., Oct. 15, 1996, pp. 966-969, vol. 78.
Bailey, "Mitral Regurgitation" in Surgery of the Heart, Chapter 20, pp. 686-737 (1955).
Bernal et al., "The Valve Racket: a new and different concept of atrioventricular valve repair," Eur. J. Cardio-thoracic Surgery 29:1026-1029 (2006).
Bhudia et al., "Edge-to-Edge (Alfieri) Mitral Repair: Results in Diverse Clinical Settings," Ann Thorac Surg, 77:1598-1606 (2004).
Bhudia et al., "Edge-to-edge Mitral Repair: A Versatile Mitral Repair," http://www.sts.org/doc/7007 accessed on Sep. 24, 2008.
Bolling et al., "Surgery for Acquired Heart Disease: Early Outcome of Mitral Valve Reconstruction in Patients with End-stage Cardiomyopathy," J. Thor. and Cardiovasc. Surg., Apr. 1995, pp. 676-683, vol. 109.
Borghetti et al., "Preliminary observations on haemodynamics during physiological stress conditions following 'double-orifice' mitral valve repair," European Journal of Cardiothoracic Surgery, 20:262-269 (2001).
Castedo, "Edge-to-Edge Tricuspid Repair for Redeveloped Valve Incompetence after DeVega's Annuloplasty," Ann Thora Surg., 75:605-606 (2003).
Chinese Office Action dated Sep. 9, 2013 in Application No. 200980158707.2 (with English translation).
Communication dated Apr. 16, 2018 from the European Patent Office in counterpart European application No. 04752603.3.
Communication dated Apr. 28, 2017 issued by the European Patent Office in counterpart application No. 16196023.2.
Communication dated Jan. 26, 2017, from the European Patent Office in counterpart European application No. 16196023.2.
Communication dated May 8, 2017, from the European Patent Office in counterpart European Application No. 04752714.8.
Derwent citing Japanese language patent, JP 11089937 published Jun 4, 1999, for: "Catheter for mitral regurgitation test—includes jet nozzles provided on rear side of large diametered spindle shaped portion attached to end of narrow diametered tube".
Dottori et al., "Echocardiographic imaging of the Alfieri type mitral valve repair," Ital. Heart J., 2(4):319-320 (2001).
Downing et al., "Beating heart mitral valve surgery: Preliminary model and methodology," Journal of Thoracic and Cardiovascular Surgery, 123(6):1141-1146 (2002).

(56) References Cited

OTHER PUBLICATIONS

Extended European Search Report dated Jul. 19, 2018 in EP 18177999.2.
Extended European Search Report, dated Oct. 17, 2014, issued in European Patent Application No. 06751584.1.
Falk et al., "Computer-Enhanced Mitral Valve Surgery: Toward a Total Endoscopic Procedure," Seminars in Thoracic and Cardiovascular Surgery, 11(3):244-249 (1999).
Filsoufi et al., "Restoring Optimal Surface of Coaptation With a Mini Leaflet Prosthesis: A New Surgical Concept for the Correction of Mitral Valve Prolapse," Intl. Soc. for Minimally Invasive Cardiothoracic Surgery 1(4):186-87 (2006).
Frazier et al., "Early Clinical Experience with an Implantable, Intracardiac Circulatory Support Device: Operative Considerations and Physiologic Implications," http://www.sts.org/doc/7007 accessed on Sep. 24, 2008.
Fucci et al., "Improved Results with Mitral Valve Repair Using New Surgical Techniques," Eur. J. Cardiothorac. Surg., Nov. 1995, pp. 621-627, vol. 9.
Fundaro et al., "Chordal Plication and Free Edge Remodeling for Mitral Anterior Leaflet Prolapse Repair: 8-Year Follow-up," Annals of Thoracic Surgery, 72:1515-1519 (2001).
Garcia-Rinaldi et al., "Left Ventricular Volume Reduction and Reconstruction is Ischemic Cardiomyopathy," Journal of Cardiac Surgery, 14:199-210 (1999).
Gateliene et al., "Early and late postoperative results of mitral and tricuspid valve insufficiency surgical treatment using edge-to-edge central coaptation procedure," Medicina (Kaunas) 38(Suppl. 2):172-175 (2002).
Gatti et al., "The edge to edge technique as a trick to rescue an imperfect mitral valve repair," Eur. J. Cardiothorac Surg, 22:817-820 (2002).
Gillinov et al., "Is Minimally Invasive Heart Valve Surgery a Paradigm for the Future?" Current Cardiology Reports, 1:318-322 (1999).
Gundry et al., "Facile Mitral Valve Repair Utilizing Leaflet Edge Approximation: Midterm Results of the Alfieri Figure of Eight Repair," The Western Thoracic Surgical Association, Scientific Session (May 1999).
Gupta et al., "Influence of Older Donor Grafts on Heart Transplant Survival: Lack of Recipient Effects," http://www.sts.org/doc/7007 accessed on Sep. 24, 2008.
Ikeda et al., "Batista's Operation with Coronary Artery Bypass Grafting and Mitral Valve Plasty for Ischemic Dilated Cardiomyopathy," The Japanese Journal of Thoracic and Cardiovascular Surgery, 48:746-749 (2000).
International Search Report and Written Opinion of PCT Application No. PCT/US2009/068023, dated Mar. 2, 2010, 10 pages total.
Izzat et al., "Early Experience with Partial Left Ventriculectomy in the Asia-Pacific Region," Annals of Thoracic Surgery, 67:1703-1707 (1999).
Kallner et al., "Transaortic Approach for the Alfieri Stitch," Ann Thorac Surg, 71:378-380 (2001).
Kameda et al., "Annuloplasty for Severe Mitral Regurgitation Due to Dilated Cardiomyopathy," Ann. Thorac. Surg., 1996, pp. 1829-1832, vol. 61.
Kavarana et al., "Transaortic Repair of Mitral Regurgitation," The Heart Surgery Forum, #2000-2389, 3(1):24-28 (2000).
Kaza et al., "Ventricular Reconstruction Results in Improved Left Ventricular Function and Amelioration of Mitral Insufficiency," Annals of Surgery, 235(6):828-832 (2002).
Khan et al., "Blade Atrial Septostomy: Experience with the First 50 Procedures," Cathet. Cardiovasc. Diagn., Aug. 1991, pp. 257-262, vol. 23.
Kherani et al., "The Edge-To-Edge Mitral Valve Repair: The Columbia Presbyterian Experience," Ann. Thorac. Surg., 78:73-76 (2004).
Konertz et al., "Results After Partial Left Ventriculectomy in a European Heart Failure Population," Journal of Cardiac Surgery, 14:129-135 (1999).
Kron et al., "Surgical Relocation of the Posterior Papillary Muscle in Chronic Ischemic Mitral Regurgitation," Annals. of Thoracic Surgery, 74:600-601 (2002).
Kruger et al., "P73—Edge to Edge Technique in Complex Mitral Valve Repair," Thorac Cardiovasc Surg., 48(Suppl. 1):106 (2000).
Langer et al., "Posterier mitral leaflet extensions: An adjunctive repair option for ischemic mitral regurgitation?" J Thorac Cardiovasc Surg, 131:868-877 (2006).
Lorusso et al., "'Double-Orifice' Technique to Repair Extensive Mitral Valve Excision Following Acute Endocarditis," J. Card Surg, 13:24-26 (1998).
Lorusso et al., "The double-orifice technique for mitral valve reconstruction: predictors of postoperative outcome," Eur J. Cardiothorac Surg, 20:583-589 (2001).
Maisano et al., "The Double Orifice Repair for Barlow Disease: A Simple Solution for Complex Repair," Circulation 100(18)1-94 (1999).
Maisano et al., "The double orifice technique as a standardized approach to treat mitral regurgitation due to severe myxomatous disease: surgical technique," European Journal of Cardio-thoracic Surgery, 17:201-205 (2000).
Maisano et al., "The Edge-to-edge Technique: A Simplified Method to Correct Mitral Insufficiency," Eur. J. Cardiothorac. Surg., Jan. 14, 1998, pp. 240-246, vol. 13.
Maisano et al., "The hemodynamic effects of double-orifice valve repair for mitral regurgitation: a 3D computational model," European Journal of Cardio-thoracic Surgery, 15:419-425 (1999).
Maisano et al., "Valve repair for traumatic tricuspid regurgitation," Eur. J. Cardio-thorac Surg, 10:867-873 (1996).
Mantovani et al., "Edge-to-edge Repair of Congenital Familiar Tricuspid Regurgitation: Case Report," J. Heart Valve Dis., 9:641-643 (2000).
McCarthy et al., "Partial left ventriculectomy and mitral valve repair for end-stage congestive heart failure," European Journal of Cardio-thoracic Surgery, 13:337-343 (1998).
McCarthy et al., "Tricuspid Valve Repair with the Cosgrove-Edwards Annuloplasty System," Ann. Thorac. Surg., Jan. 16, 1997, pp. 267-268, vol. 64.
Moainie et al., "Correction of Traumatic Tricuspid Regurgitation Using the Double Orifice Technique," Annals of Thoracic Surgery, 73:963-965 (2002).
Morales et al., "Development of an Off Bypass Mitral Valve Repair," The Heart Surgery Forum #1999-4693, 2(2):115-120 (1999).
Nakanishi et al., "Early Outcome with the Alfieri Mitral Valve Repair," J. Cardiol., 37:263-266 (2001) [Abstract in English; Article in Japanese].
Nielsen et al., "Edge-to-Edge Mitral Repair: Tension of the Approximating Suture and Leaflet Deformation During Acute Ischemic Mitral Regurgitation in the Ovine Heart," Circulation, 104(Suppl. I):I-29-1-35 (2001).
Noera et al., "Tricuspid Valve Incompetence Caused by Nonpenetrating Thoracic Trauma", Annals of Thoracic Surgery, 51:320-322 (1991).
Osawa et al., "Partial Left Ventriculectomy in a 3-Year Old Boy with Dilated Cardiomyopathy," Japanese Journal of Thoracic and Cardiovascular Surg, 48:590-593 (2000).
Park et al., "Clinical Use of Blade Atrial Septostomy," Circulation, 1978, pp. 600-608, vol. 58.
Patel et al., "Epicardial Atrial Defibrillation: Novel Treatment of Postoperative Atrial Fibrillation," http://www.sts.org/doc/7007 accessed on Sep. 23, 2008.
Privitera et al., "Alfieri Mitral Valve Repair: Clinical Outcome and Pathology," Circulation, 106:e173-e174 (2002).
Redaelli et al., "A Computational Study of the Hemodynamics After 'Edge-To-Edge' Mitral Valve Repair," Journal of Biomechanical Engineering, 123:565-570 (2001).
Reul et al., "Mitral Valve Reconstruction for Mitral Insufficiency," Progress in Cardiovascular Diseases, XXXIX(6):567-599 (1997).
Ricchi et al., "Linear Segmental Annuloplasty for Mitral Valve Repair," Ann. Thorac. Surg., Jan. 7, 1997, pp. 1805-1806, vol. 63.
Robicsek et al., "The Bicuspid Aortic Valve. How Does It Function? Why Does It Fail," http://www.sts.org/doc/7007 accessed on Sep. 24, 2008.

(56) References Cited

OTHER PUBLICATIONS

Supplemental European Search Report of EP Application No. 02746781, dated May 13, 2008, 3 pages total.
Supplementary European Search Report issued in European Application No. 05753261.6 dated Jun. 9, 2011, 3 pages total.
Tager et al., "Long-Term Follow-Up of Rheumatic Patients Undergoing Left-Sided Valve Replacement with Tricuspid Annuloplasty—Validity of Preoperative Echocardiographic Criteria in the Decision to Perform Tricuspid Annuloplasty," Am. J. Cardiol., Apr. 15, 1998, pp. 1013-1016, vol. 81.
Tamura et al., "Edge to Edge Repair for Mitral Regurgitation in a Patient with Chronic Hemodialysis: Report of a Case," Kyobu Geka. The Japanese Journal of Thoracic Surgery, 54(9):788-790 (2001).
Tibayan et al., "Annular Geometric Remodeling in Chronic Ischemic Mitral Regurgitation," http://www.sts.org/doc/7007 accessed on Sep. 24, 2008.
Timek et al., "Edge-to-edge mitral repair: gradients and three-dimensional annular dynamics in vivo during inotropic stimulation," Eur J. of Cardiothoracic Surg., 19:431-437 (2001).
Timek, "Edge-to-Edge Mitral Valve Repair without Annuloplasty Ring in Acute Ischemic Mitral Regurgitation," [Abstract] Clinical Science, Abstracts from Scientific Sessions, 106(19):2281 (2002).
Totaro, "Mitral valve repair for isolated prolapse of the anterior leaflet: an 11-year follow-up," European Journal of Cardio-thoracic Surgery, 15:119-126 (1999).
Uchida et al., "Percutaneous Cardiomyotomy and Valvulotomy with Angioscopic Guidance," Am. Heart J., Apr. 1991, pp. 1221-1224, vol. 121.
Umana et al., "'Bow-tie' Mitral Valve Repair Successfully Addresses Subvalvular Dysfunction in Ischemic Mitral Regurgitation," Surgical Forum, XLVIII:279-280 (1997).
Umana et al., "Bow-Tie Mitral Valve Repair: An Adjuvant Technique for Ischemic Mitral Regurgitation," Ann. Thorac. Surg., May 12, 1998, pp. 1640-1646, vol. 66.
Votta et al., "3-D Computational Analysis of the Stress Distribution on the Leaflets after Edge-to-Edge Repair of Mitral Regurgitation," Journal of Heart Valve Disease, 11:810-822 (2002).
Dec et al., "Idiopathic Dilated Cardiomyopathy," N. Engl. J. Med., Dec. 8, 1994, pp. 1564-1575, vol. 331.
Derwent citing German language patent, EP 684012 published Nov. 12, 1995, for: "Thread for constructing surgical seam—has flexible section with two ends, with lower fastening part on thread first end having hollow cylinder with continuous hole through which surgical needle threads".
Vismara et al., "Transcatheter Edge-to-Edge Treatment of Functional Tricuspid Regurgitation in an Ex Vivo Pulsatile Heart Model," JACC 68(10):1024-1033 (2016).
Petition for Inter Partes Review of Claims 1-9, 12, and 17 of U.S. Pat. No. 7,563,267 filed May 29, 2019 in Inter Partes Review of U.S. Pat. No. 7,563,267, Case No. IPR2019-01132, 101 pages.
Exhibit 1001—U.S. Pat. No. 7,563,267 filed May 29, 2019 in Inter Partes Review of U.S. Pat. No. 7,563,267, Case No. IPR2019-01132, 103 pages.
Exhibit 1002—Vesely Declaration filed May 29, 2019 in Inter Partes Review of U.S. Pat. No. 7,563,267, Case No. IPR2019-01132, 97 pages.
Exhibit 1003—Vesely Curriculum Vitae filed May 29, 2019 in Inter Partes Review of U.S. Pat. No. 7,563,267, Case No. IPR2019-01132, 8 pages.
Exhibit 1004—File History of U.S. Pat. No. 7,563,267 (Excerpts) filed May 29, 2019 in Inter Partes Review of U.S. Pat. No. 7,563,267, Case No. IPR2019-01132, 616 pages.
Exhibit 1005—U.S. Pat. No. 6,165,183 (Kuehn) filed May 29, 2019 in Inter Partes Review of U.S. Pat. No. 7,563,267, Case No. IPR2019-01132, 21 pages.
Exhibit 1006—U.S. Pat. No. 6,346,074 (Roth) filed May 29, 2019 in Inter Partes Review of U.S. Pat. No. 7,563,267, Case No. IPR2019-01132, 64 pages.

Exhibit 1007—U.S. Pat. No. 4,340,091 (Skelton) filed May 29, 2019 in Inter Partes Review of U.S. Pat. No. 7,563,267, Case No. IPR2019-01132, 12 pages.
Exhibit 1008—US 2002-0013571 filed May 29, 2019 in Inter Partes Review of U.S. Pat. No. 7,563,267, Case No. IPR2019-01132, 69 pages.
Exhibit 1009—U.S. Appl. No. 60/128,690 Provisional filed May 29, 2019 in Inter Partes Review of U.S. Pat. No. 7,563,267, Case No. IPR2019-01132, 100 pages.
Exhibit 1010—Batista, Partial Left Ventriculectomy filed May 29, 2019 in Inter Partes Review of U.S. Pat. No. 7,563,267, Case No. IPR2019-01132, 5 pages.
Exhibit 1011—Fucci, Improved Results filed May 29, 2019 in Inter Partes Review of U.S. Pat. No. 7,563,267, Case No. IPR2019-01132, 7 pages.
Exhibit 1012—Webster's New World College Dictionary (Excerpts) filed May 29, 2019 in Inter Partes Review of U.S. Pat. No. 7,563,267, Case No. IPR2019-01132, 7 pages.
Exhibit 1013—Oxford Dictionary (Excerpts) filed May 29, 2019 in Inter Partes Review of U.S. Pat. No. 7,563,267, Case No. IPR2019-01132, 10 pages.
Exhibit 1014—Random House Dictionary (Excerpts) filed May 29, 2019 in Inter Partes Review of U.S. Pat. No. 7,563,267, Case No. IPR2019-01132, 6 pages.
Exhibit 1015—Netter, Ciba Collection of Medical Illustrations filed May 29, 2019 in Inter Partes Review of U.S. Pat. No. 7,563,267, Case No. IPR2019-01132, 4 pages.
Exhibit 1016—Stone, Clinical Trial Design Principles filed May 29, 2019 in Inter Partes Review of U.S. Pat. No. 7,563,267, Case No. IPR2019-01132, 30 pages.
Exhibit 1017—WO 2003-020179 (Tremulis) filed May 29, 2019 in Inter Partes Review of U.S. Pat. No. 7,563,267, Case No. IPR2019-01132, 56 pages.
Exhibit 1018—U.S. Pat. No. 5,741,297 (Simon) filed May 29, 2019 in Inter Partes Review of U.S. Pat. No. 7,563,267, Case No. IPR2019-01132, 11 pages.
Exhibit 1019—U.S. Pat. No. 3,874,388 (King) filed May 29, 2019 in Inter Partes Review of U.S. Pat. No. 7,563,267, Case No. IPR2019-01132, 20 pages.
Exhibit 1020—U.S. Pat. No. 5,716,417 (Girard) filed May 29, 2019 in Inter Partes Review of U.S. Pat. No. 7,563,267, Case No. IPR2019-01132, 12 pages.
Exhibit 1021—Beall, Clinical Experience filed May 29, 2019 in Inter Partes Review of U.S. Pat. No. 7,563,267, Case No. IPR2019-01132, 9 pages.
Exhibit 1022—Complaint (Excerpts) in Abbott v. Edwards, 19-cv-00149 filed May 29, 2019 in Inter Partes Review of U.S. Pat. No. 7,563,267, Case No. IPR2019-01132, 9 pages.
Exhibit 1023—Abbott MitraClip IFU (Excerpts) filed May 29, 2019 in Inter Partes Review of U.S. Pat. No. 7,563,267, Case No. IPR2019-01132, 3 pages.
Exhibit 1024—Preliminary Injunction Opening Brief (Excerpts) in Abbott v. Edwards, 19-cv-00149 filed May 29, 2019 in Inter Partes Review of U.S. Pat. No. 7,563,267, Case No. IPR2019-01132, 5 pages.
Exhibit 1025—Preliminary Injunction Transcript (Excerpts) in Abbott v. Edwards, 19-cv-00149 filed May 29, 2019 in Inter Partes Review of U.S. Pat. No. 7,563,267, Case No. IPR2019-01132, 4 pages.
Exhibit 1026—Yoganathan Declaration (Excerpts) in Abbott v. Edwards, 19-cv-00149 filed May 29, 2019 in Inter Partes Review of U.S. Pat. No. 7,563,267, Case No. IPR2019-01132, 9 pages.
Exhibit 1027—Keller Letter (Excerpts) in Abbott v. Edwards, 19-cv-00149 filed May 29, 2019 in Inter Partes Review of U.S. Pat. No. 7,563,267, Case No. IPR2019-01132, 3 pages.
Exhibit 1028—Kolata, Tiny Device (NY Times) filed May 29, 2019 in Inter Partes Review of U.S. Pat. No. 7,563,267, Case No. IPR2019-01132, 4 pages.
Petition for Inter Partes Review of Claims 1-12, 15, 20-31, and 34 of U.S. Pat. No. 8,057,493 filed Jul. 3, 2019 in Inter Partes Review of U.S. Pat. No. 8,057,493, Case No. IPR2019-01301, 106 pages.
Exhibit 1001—U.S. Pat. No. 8,057,493 filed Jul. 3, 2019 in Inter Partes Review of U.S. Pat. No. 8,057,493, Case No. IPR2019-01301, 103 pages.

(56) References Cited

OTHER PUBLICATIONS

Exhibit 1002—Vesely Declaration filed Jul. 3, 2019 in Inter Partes Review of U.S. Pat. No. 8,057,493, Case No. IPR2019-01301, 111 pages.
Exhibit 1003—Vesely Curriculum Vitae filed Jul. 3, 2019 in Inter Partes Review of U.S. Pat. No. 8,057,493, Case No. IPR2019-01301, 8 pages.
Exhibit 1004—File History of U.S. Pat. No. 8.057,493 (Excerpts) filed Jul. 3, 2019 in Inter Partes Review of U.S. Pat. No. 8,057,493, Case No. IPR2019-01301, 352 pages.
Exhibit 1005—U.S. Pat. No. 6,165,183 (Kuehn) filed Jul. 3, 2019 in Inter Partes Review of U.S. Pat. No. 8,057,493, Case No. IPR2019-01301, 21 pages.
Exhibit 1006—U.S. Pat. No. 6,346,074 (Roth) filed Jul. 3, 2019 in Inter Partes Review of U.S. Pat. No. 8,057,493, Case No. IPR2019-01301, 64 pages.
Exhibit 1007—U.S. Pat. No. 4,340,091 (Skelton) filed Jul. 3, 2019 in Inter Partes Review of U.S. Pat. No. 8,057,493, Case No. IPR2019-01301, 12 pages.
Exhibit 1008—US 2002-0013571 filed Jul. 3, 2019 in Inter Partes Review of U.S. Pat. No. 8,057,493, Case No. IPR2019-01301, 69 pages.
Exhibit 1009—60-128,690 Provisional filed Jul. 3, 2019 in Inter Partes Review of U.S. Pat. No. 8,057,493, Case No. IPR2019-01301, 100 pages.
Exhibit 1010—Batista, Partial Left Ventriculectomy filed Jul. 3, 2019 in Inter Partes Review of U.S. Pat. No. 8,057,493, Case No. IPR2019-01301, 5 pages.
Exhibit 1011—Fucci, Improved Results filed Jul. 3, 2019 in Inter Partes Review of U.S. Pat. No. 8,057,493, Case No. IPR2019-01301, 7 pages.
Exhibit 1012—Webster's New World College Dictionary filed Jul. 3, 2019 in Inter Partes Review of U.S. Pat. No. 8,057,493, Case No. IPR2019-01301, 7 pages.
Exhibit 1013—Oxford Dictionary filed Jul. 3, 2019 in Inter Partes Review of U.S. Pat. No. 8,057,493, Case No. IPR2019-01301, 10 pages.
Exhibit 1014—Random House Dictionary filed Jul. 3, 2019 in Inter Partes Review of U.S. Pat. No. 8,057,493, Case No. IPR2019-01301, 6 pages.
Exhibit 1015—Netter, Ciba Collection of Medical Illustrations filed Jul. 3, 2019 in Inter Partes Review of U.S. Pat. No. 8,057,493, Case No. IPR2019-01301, 4 pages.
Exhibit 1016—Stone, Clinical Trial Design Principles filed Jul. 3, 2019 in Inter Partes Review of U.S. Pat. No. 8,057,493, Case No. IPR2019-01301, 30 pages.
Exhibit 1017—WO 2003-020179 (Tremulis) filed Jul. 3, 2019 in Inter Partes Review of U.S. Pat. No. 8,057,493, Case No. IPR2019-01301, 56 pages.
Exhibit 1018—U.S. Pat. No. 5,741,297 (Simon) filed Jul. 3, 2019 in Inter Partes Review of U.S. Pat. No. 8,057,493, Case No. IPR2019-01301, 11 pages.
Exhibit 1019—U.S. Pat. No. 3,874,388 (King) filed Jul. 3, 2019 in Inter Partes Review of U.S. Pat. No. 8,057,493, Case No. IPR2019-01301, 20 pages.
Exhibit 1020—U.S. Pat. No. 5,716,417 (Girard) filed Jul. 3, 2019 in Inter Partes Review of U.S. Pat. No. 8,057,493, Case No. IPR2019-01301, 12 pages.
Exhibit 1021—Beall, Clinical Experience filed Jul. 3, 2019 in Inter Partes Review of U.S. Pat. No. 8,057,493, Case No. IPR2019-01301, 9 pages.
Exhibit 1022—Complaint (Excerpts) in *Abbott* v. *Edwards*, 19-cv-00149 filed Jul. 3, 2019 in Inter Partes Review of U.S. Pat. No. 8,057,493, Case No. IPR2019-01301, 9 pages.
Exhibit 1023—MitraClip IFU (Excerpts) filed Jul. 3, 2019 in Inter Partes Review of U.S. Pat. No. 8,057,493, Case No. IPR2019-01301, 3 pages.
Exhibit 1024—Preliminary Injunction Opening Brief (Excerpts) in *Abbott* v. *Edwards*, 19-cv-00149 filed Jul. 3, 2019 in Inter Partes Review of U.S. Pat. No. 8,057,493, Case No. IPR2019-01301, 5 pages.
Exhibit 1025—Preliminary Injunction Transcript (Excerpts) in *Abbott* v. *Edwards*, 19-cv-00149 filed Jul. 3, 2019 in Inter Partes Review of U.S. Pat. No. 8,057,493, Case No. IPR2019-01301, 4 pages.
Exhibit 1026—Yoganathan Declaration in *Abbott* v. *Edwards*, 19-cv-00149 filed Jul. 3, 2019 in Inter Partes Review of U.S. Pat. No. 8,057,493, Case No. IPR2019-01301, 9 pages.
Exhibit 1027—Keller Letter (Excerpts) in *Abbott* v. *Edwards*, 19-cv-00149 filed Jul. 3, 2019 in Inter Partes Review of U.S. Pat. No. 8,057,493, Case No. IPR2019-01301, 3 pages.
Exhibit 1028—Kolata, Tiny Device (NY Times) filed Jul. 3, 2019 in Inter Partes Review of U.S. Pat. No. 8,057,493, Case No. IPR2019-01301, 4 pages.
Exhibit 1029—U.S. Pat. No. 7,736,388 filed Jul. 3, 2019 in Inter Partes Review of U.S. Pat. No. 8,057,493, Case No. IPR2019-01301, 103 pages.
Exhibit 1030—U.S. Pat. No. 7,563,267 filed Jul. 3, 2019 in Inter Partes Review of U.S. Pat. No. 8,057,493, Case No. IPR2019-01301, 103 pages.
Notice of Opposition dated Apr. 5, 2018 in Opposition of EP1624810, 38 pages.
Proprietor Reply to Opposition dated Aug. 25, 2018 in Opposition of EP1624810, 22 pages.
Opponent's Further Submissions dated Dec. 24, 2018 in Opposition of EP1624810, 3 pages.
EPO Summons to Oral Proceedings dated Mar. 11, 2019 in Opposition of EP1624810, 10 pages.
Notice of Intervention dated Mar. 27, 2019 in Opposition of EP1624810, 32 pages.
Annex to Notice of Intervention (German Infrigement Complaint) dated Mar. 27, 2019 in Opposition of EP 1624810, 56 pages (submitted in foreign language in full with sections directed to cited art translated to English, wherein this Infrigement Complaint resulted in Edwards Nullity Complaint, which alleges invalidity of the patents-in-suit in this Infrigement Complaint and is submitted in another Information Disclosure Statement filed concurrently herewith).
Intervener's Further Submissions dated Apr. 29, 2019 in Opposition of EP1624810, 9 pages.
Opponent's Written Submissions dated Jul. 30, 2019 in Opposition of EP1624810, 11 pages.
EPO consolidated references listing for EPB1624810 dated Jul. 31, 2019 in Opposition of EP1624810, 1 page.
Extended European Search report dated Jul. 24, 2019 in EP Application No. 19171888.
POPR dated Oct. 11, 2019 in Inter Partes Review of U.S. Pat. No. 6,461,366, Case No. IPR2019-01285, 41 pages.
Ex. 2001—USPTO Response for Certificate of Correction filed Oct. 11, 2019 in Inter Partes Review of U.S. Pat. No. 6,461,366, Case No. IPR2019-01285, 2 pages.
Ex. 2002—Excerpts of '097 File History filed Oct. 11, 2019 in Inter Partes Review of U.S. Pat. No. 6,461,366, Case No. IPR2019-01285, 2 pages.
Ex. 2003—MPEP 200 7th Rev 1 filed Oct. 11, 2019 in Inter Partes Review of U.S. Pat. No. 6,461,366, Case No. IPR2019-01285, 78 pages.
Ex. 2004—Parsons Petition Paper 3 filed Oct. 11, 2019 in Inter Partes Review of U.S. Pat. No. 6,461,366, Case No. IPR2019-01285, 85 pages.
Ex. 2005—Complaint filed Oct. 11, 2019 in Inter Partes Review of U.S. Pat. No. 6,461,366, Case No. IPR2019-01285, 32 pages.
Ex. 2006—Answer and Counterclaims filed Oct. 11, 2019 in Inter Partes Review of U.S. Pat. No. 6,461,366, Case No. IPR2019-01285, 29 pages.
Ex. 2007—Amended Answer and Counterclaims filed Oct. 11, 2019 in Inter Partes Review of U.S. Pat. No. 6,461,366, Case No. IPR2019-01285, 39 pages.
Ex. 2008—Edwards' Initial Invalidity Contentions filed Oct. 11, 2019 in Inter Partes Review of U.S. Pat. No. 6,461,366, Case No. IPR2019-01285, 249 pages.

(56) References Cited

OTHER PUBLICATIONS

Ex. 2009—Scheduling Order filed Oct. 11, 2019 in Inter Partes Review of U.S. Pat. No. 6,461,366, Case No. IPR2019-01285, 16 pages.
Ex. 2010—WIPO Handbook filed Oct. 11, 2019 in Inter Partes Review of U.S. Pat. No. 6,461,366, Case No. IPR2019-01285, 30 pages.
Ex. 2011—U.S. Pat. No. 7,288,097 filed Oct. 11, 2019 in Inter Partes Review of U.S. Pat. No. 6,461,366, Case No. IPR2019-01285, 12 pages.
Ex. 2012—MPEP 1800 7th Rev 1 filed Oct. 11, 2019 in Inter Partes Review of U.S. Pat. No. 6,461,366, Case No. IPR2019-01285, 126 pages.
Ex. 2013—MPEP 900 3rd Rev 35 filed Oct. 11, 2019 in Inter Partes Review of U.S. Pat. No. 6,461,366, Case No. IPR2019-01285, 27 pages.
Ex. 2014—MPEP 900 7th Rev 1 filed Oct. 11, 2019 in Inter Partes Review of U.S. Pat. No. 6,461,366, Case No. IPR2019-01285, 48 pages.
Ex. 2015—U.S. Pat. No. 6,463,476 filed Oct. 11, 2019 in Inter Partes Review of U.S. Pat. No. 6,461,366, Case No. IPR2019-01285, 13 pages.
Ex. 2016—U.S. Pat. No. 7,643,168 filed Oct. 11, 2019 in Inter Partes Review of U.S. Pat. No. 6,461,366, Case No. IPR2019-01285, 89 pages.
Ex. 2017—Request for Certificate of Correction filed Oct. 11, 2019 in Inter Partes Review of U.S. Pat. No. 6,461,366, Case No. IPR2019-01285, 31 pages.
Petitioners' Motion on Procedural Issues dated Oct. 22, 2019 in Inter Partes Review of U.S. Pat. No. 6,461,366, Case No. IPR2019-01285, 16 pages.
Exhibit 1021—Excerpts of File History of 097 dated Oct. 22, 2019 in Inter Partes Review of U.S. Pat. No. 6,461,366, Case No. IPR2019-01285, 5 pages.
U.S. Appl. No. 14/698470 (US 2015/0223793), filed Apr. 28, 2015 (Aug. 13, 2015).
U.S. Appl. No. 15/483,523 (US 2017/0239048), filed Apr. 10, 2017 (Aug. 24, 2017).
U.S. Appl. No. 16/276,357 (US 2019/0175182), filed Feb. 14, 2019 (Jun. 13, 2019).
U.S. Appl. No. 16/406,476, filed May 8, 2019.
U.S. Appl. No. 16/406,530, filed May 8, 2019.
U.S. Appl. No. 16/408,018, filed May 9, 2019.
U.S. Appl. No. 14/698,470, Jun. 7, 2019 Notice of Allowance.
U.S. Appl. No. 14/698,470, May 13, 2019 Amendment and Request for Continued Examination (RCE).
U.S. Appl. No. 14/698,470, Feb. 15, 2019 Final Office Action.
U.S. Appl. No. 14/698,470, Jan. 23, 2019 Response to Non-Final Office Action.
U.S. Appl. No. 14/698,470, Oct. 23, 2018 Non-Final Office Action.
U.S. Appl. No. 14/698,470, Oct. 5, 2018 Amendment and Request for Continued Examination (RCE).
U.S. Appl. No. 14/698,470, Apr. 6, 2018 Final Office Action.
U.S. Appl. No. 14/698,470, Feb. 26, 2018 Response to Non-Final Office Action.
U.S. Appl. No. 14/698,470, Aug. 31, 2017 Non-Final Office Action.
U.S. Appl. No. 14/698,470, Jul. 19, 2017 Response to Restriction Requirement.
U.S. Appl. No. 14/698,470, Apr. 20, 2017 Restriction Requirement.
U.S. Appl. No. 15/483,523, Mar. 20, 2019 Non-Final Office Action.
U.S. Appl. No. 16/406,476, Jun. 20, 2019 Non-Final Office Action.
U.S. Appl. No. 16/406,530, Jul. 5, 2019 Non-Final Office Action.
U.S. Appl. No. 16/408,018, Aug. 6, 2019 Non-Final Office Action.
EP '850 DE nullity—Response English translation, dated Sep. 12, 2019, 48 pages in *Abbott Medical GmbH v. Edwards Lifesciences Corporation et al.*, Ref. No. 4b O 8/19(Germany).
EP '850 DE nullity—Response in German, dated Sep. 12, 2019, 50 pages in *Abbott Medical GmbH v. Edwards Lifesciences Corporation et al.*, Ref. No. 4b O 8/19 (Germany).
Judgement English translation, dated Aug. 20, 2019, 67 pages in *Evalve, Inc. et al. v. Edwards Lifesciences SA et al.*, Docket No. S2019_002 (Switzerland).
Judgement, dated Aug. 20, 2019, 68 pages in *Evalve, Inc. et al. v. Edwards Lifesciences SA et al.*, Docket No. S2019_002 (Switzerland).
Transcript PI Hearing, dated Aug. 20, 2019, 67 pages in *Evalve, Inc. et al. v. Edwards Lifesciences SA et al.*, Docket No. S2019_002 (Switzerland).
Statement of Claim, dated Oct. 4, 2019, 187 pages in *Evalve, Inc. et al. v. Edwards Lifesciences SA et al.*, Docket No. S2019_002 (Switzerland).
Amended Grounds of Invalidity, dated Oct. 2, 2019, 3 pages in *Evalve, Inc. et al. v. Edwards Lifesciences Limited*, Claim No. HP-2019-000003 (United Kingdom).
Appeal in civil matters dated Sep. 13, 2019, 48 pages in *Evalve, Inc. et al. v. Edwards Lifesciences SA et al.*, Docket No. S2019_002 (Switzerland).
Appeal in civil matters Translation dated Sep. 13, 2019, 47 pages in *Evalve, Inc. et al. v. Edwards Lifesciences SA et al.*, Docket No. S2019_002 (Switzerland).
Supplement to Request of Suspensive Effect dated Sep. 27, 2019, 3 pages in *Evalve, Inc. et al. v. Edwards Lifesciences SA et al.*, Docket No. S2019_002.
Supplement to Request of Suspensive Effect Translation dated Sep. 27, 2019, 3 pages in *Evalve, Inc. et al. v. Edwards Lifesciences SA et al.*, Docket No. S2019_002 (Switzerland).
Supplement of Appeal Grounds dated Sep. 20, 2019, 3 pages in *Evalve, Inc. et al. v. Edwards Lifesciences SA et al.*, Docket No. S2019_002 (Switzerland).
Supplement of Appeal Grounds Translation dated Sep. 20, 2019, 3 pages in *Evalve, Inc. et al. v. Edwards Lifesciences SA et al.*, Docket No. S2019_002 (Switzerland).
Application to Amend dated Oct. 4, 2019, 3 pages in *Evalve, Inc. et al. v. Edwards Lifesciences Limited*, Claim No. HP-2019-000003 (United Kingdom).
Statement of Grounds dated Oct. 4, 2019, 3 pages in *Evalve, Inc. et al. v. Edwards Lifesciences Limited*, Claim No. HP-2019-000003 (United Kingdom).
Abbott Hearing Slides—Redacted dated Apr. 15, 2019, 189 pages in *Abbott Cardiovascular Systems, Inc. et al. v. Edwards Lifesciences Corp. et al.*, Case No. 19-149 (MN) (District of Delaware).
Edwards Ltr re 4-22 Abbott Ltr re Claim Construction dated Apr. 22, 2019, 2 pages in *Abbott Cardiovascular Systems, Inc. et al. v. Edwards Lifesciences Corp. et al.*, Case No. 19-149 (MN) (District of Delaware).
Edwards Ltr re Additional Citations to Patents dated Apr. 22, 2019, 2 pages in *Abbott Cardiovascular Systems, Inc. et al. v. Edwards Lifesciences Corp. et al.*, Case No. 19-149 (MN) (District of Delaware).
Abbott Ltr re Claim Construction Redacted dated May 3, 2019, 10 pages in *Abbott Cardiovascular Systems, Inc. et al. v. dwards Lifesciences Corp. et al.*, Case No. 19-149 (MN) (District of Delaware).
Abbott's Objections and Responses to Edwards Second Set of ROGs (Nos. 16-17) (Redacted) dated Aug. 2, 2019, 67 pages in Abbott Ltr re Claim Construction Redacted dated May 3, 2019, 10 pages in *Abbott Cardiovascular Systems, Inc. et al. v. Edwards Lifesciences Corp. et al.*, Case No. 19-149 (MN) (District of Delaware).
Amended Answer dated Aug. 21, 2019, 39 pages in *Abbott Cardiovascular Systems, Inc. et al. v. Edwards Lifesciences Corp. et al.*, Case No. 19-149 (MN) (District of Delaware).
Joint Claim Construction Brief dated Sep. 10, 2019, 94 pages in *Abbott Cardiovascular Systems, Inc. et al. v. Edwards Lifesciences Corp. et al.*, Case No. 19-149 (MN) (District of Delaware).
Amended Joint Claim Construction Chart dated Oct. 16, 2019, 23 pages in *Abbott Cardiovascular Systems, Inc. et al. v. Edwards Lifesciences Corp. et al.*, Case No. 19-149 (MN) (District of Delaware).

(56) References Cited

OTHER PUBLICATIONS

Abbott Markman Demonstratives Redacted dated Oct. 17, 2019, 127 pages in *Abbott Cardiovascular Systems, Inc. et al. v. Edwards Lifesciences Corp. et al.*, Case No. 19-149 (MN) (District of Delaware).
Edwards Markman Demonstratives dated Oct. 17, 2019, 127 pages in *Abbott Cardiovascular Systems, Inc. et al. v. Edwards Lifesciences Corp. et al.*, Case No. 19-149 (MN) (District of Delaware).
Markman Memorandum Order dated Oct. 22, 2019, 19 pages in *Abbott Cardiovascular Systems, Inc. et al. v. Edwards Lifesciences Corp. et al.*, Case No. 19-149 (MN) (District of Delaware).
Petition for Inter Partes Review of Claim 1 of U.S. Pat. No. 6,461,366 filed Jun. 28, 2019 in Inter Partes Review of U.S. Pat. No. 6,461,366, Case No. IPR2019-01285, 76 pages.
Exhibit 1001—U.S. Pat. No. 6,461,366 filed Jun. 28, 2019 in Inter Partes Review of U.S. Pat. No. 6,461,366, Case No. IPR2019-01285, 8 pages.
Exhibit 1002—Vesely Declaration filed Jun. 28, 2019 in Inter Partes Review of U.S. Pat. No. 6,461,366, Case No. IPR2019-01285, 78 pages.
Exhibit 1003—Vesely Curriculum Vitae filed Jun. 28, 2019 in Inter Partes Review of U.S. Pat. No. 6,461,366, Case No. IPR2019-01285, 8 pages.
Exhibit 1004—Materials Considered filed Jun. 28, 2019 in Inter Partes Review of U.S. Pat. No. 6,461,366, Case No. IPR2019-01285, 1 page.
Exhibit 1005—WO 99-13777 (Publication of PCT-FR98-01960) (with Cover translated to English) filed Jun. 28, 2019 in Inter Partes Review of U.S. Pat. No. 6,461,366, Case No. IPR2019-01285, 26 pages.
Exhibit 1006—Certified Copy of French Appl. No. 97-11600 filed Jun. 28, 2019 in Inter Partes Review of U.S. Pat. No. 6,461,366, Case No. IPR2019-01285, 23 pages.
Exhibit 1007—U.S. Pat. No. 6,165,183 (Kuehn) filed Jun. 28, 2019 in Inter Partes Review of U.S. Pat. No. 6,461,366, Case No. IPR2019-01285, 21 pages.
Exhibit 1008—U.S. Pat. No. 6,629,534 (St. Goar) filed Jun. 28, 2019 in Inter Partes Review of U.S. Pat. No. 6,461,366, Case No. IPR2019-01285, 111 pages.
Exhibit 1009—U.S. Appl. No. 60/128,690 (St. Goar Provisional) filed Jun. 28, 2019 in Inter Partes Review of U.S. Pat. No. 6,461,366, Case No. IPR2019-01285, 100 pages.
Exhibit 1010—U.S. Pat. No. 6,461,366 File History filed Jun. 28, 2019 in Inter Partes Review of U.S. Pat. No. 6,461,366, Case No. IPR2019-01285, 98 pages.
Exhibit 1011—U.S. Pat. No. 5,450,860 (O'Connor) filed Jun. 28, 2019 in Inter Partes Review of U.S. Pat. No. 6,461,366, Case No. IPR2019-01285, 18 pages.
Exhibit 1012—U.S. Pat. No. 5,389,077 (Melinyshyn) filed Jun. 28, 2019 in Inter Partes Review of U.S. Pat. No. 6,461,366, Case No. IPR2019-01285, 6 pages.
Exhibit 1013—WO 94-18893 (Fitton) filed Jun. 28, 2019 in Inter Partes Review of U.S. Pat. No. 6,461,366, Case No. IPR2019-01285, 27 pages.
Exhibit 1014—EP 0558031 A2 (Green) filed Jun. 28, 2019 in Inter Partes Review of U.S. Pat. No. 6,461,366, Case No. IPR2019-01285, 49 pages.
Exhibit 1015—Fucci (1995), Improved Results filed Jun. 28, 2019 in Inter Partes Review of U.S. Pat. No. 6,461,366, Case No. IPR2019-01285, 7 pages.
Exhibit 1016—Reul (1997), Mitral Valve Reconstruction filed Jun. 28, 2019 in Inter Partes Review of U.S. Pat. No. 6,461,366, Case No. IPR2019-01285, 33 pages.
Exhibit 1017—Maisano (1998), The Edge-to-Edge Technique filed Jun. 28, 2019 in Inter Partes Review of U.S. Pat. No. 6,461,366, Case No. IPR2019-01285, 7 pages.
Exhibit 1018—Umana (1998), Bow-Tie Mitral Valve Repair filed Jun. 28, 2019 in Inter Partes Review of U.S. Pat. No. 6,461,366, Case No. IPR2019-01285, 6 pages.
Exhibit 1019—U.S. Pat. No. 6,770,083 (083 Patent) filed Jun. 28, 2019 in Inter Partes Review of U.S. Pat. No. 6,461,366, Case No. IPR2019-01285, 9 pages.
Exhibit 1020—Misc Communication re U.S. Pat. No. 7,288,097 filed Jun. 28, 2019 in Inter Partes Review of U.S. Pat. No. 6,461,366, Case No. IPR2019-01285, 26 pages.
Petition for Inter Partes Review of Claims 1-2 of U.S. Pat. No. 7,288,097 dated Aug. 8, 2019 from Inter Partes Review of U.S. Pat. No. 7,288,097, Case No. IPR2019-01479, 107 pages.
Exhibit 1001—U.S. Pat. No. 7,288,097 dated Aug. 8, 2019 from Inter Partes Review of U.S. Pat. No. 7,288,097, Case No. IPR2019-01479, 11 pages.
Exhibit 1002—Vesely Declaration dated Aug. 8, 2019 from Inter Partes Review of U.S. Pat. No. 7,288,097, Case No. IPR2019-01479, 106 pages.
Exhibit 1003—Vesely Curriculum Vitae dated Aug. 8, 2019 from Inter Partes Review of U.S. Pat. No. 7,288,097, Case No. IPR2019-01479, 8 pages.
Exhibit 1004—Materials Considered dated Aug. 8, 2019 from Inter Partes Review of U.S. Pat. No. 7,288,097, Case No. IPR2019-01479, 1 page.
Exhibit 1005—Certified French App. No. 97-11600 dated Aug. 8, 2019 from Inter Partes Review of U.S. Pat. No. 7,288,097, Case No. IPR2019-01479, 23 pages.
Exhibit 1006—WO 99-13777 (with Cover translated to English) dated Aug. 8, 2019 from Inter Partes Review of U.S. Pat. No. 7,288,097, Case No. IPR2019-01479, 26 pages.
Exhibit 1007—U.S. Pat. No. 6,461,366 dated Aug. 8, 2019 from Inter Partes Review of U.S. Pat. No. 7,288,097, Case No. IPR2019-01479, 8 pages.
Exhibit 1008—File History of U.S. Pat. No. 6,461,366 dated Aug. 8, 2019 from Inter Partes Review of U.S. Pat. No. 7,288,097, Case No. IPR2019-01479, 98 pages.
Exhibit 1009—U.S. Pat. No. 6,770,083 dated Aug. 8, 2019 from Inter Partes Review of U.S. Pat. No. 7,288,097, Case No. IPR2019-01479, 9 pages.
Exhibit 1010—File History of U.S. Pat. No. 6,770,083 dated Aug. 8, 2019 from Inter Partes Review of U.S. Pat. No. 7,288,097, Case No. IPR2019-01479, 80 pages.
Exhibit 1011—Misc Communication re U.S. Pat. No. 7,288,097 dated Aug. 8, 2019 from Inter Partes Review of U.S. Pat. No. 7,288,097, Case No. IPR2019-01479, 26 pages.
Exhibit 1012—U.S. Pat. No. 6,165,183 (Kuehn) dated Aug. 8, 2019 from Inter Partes Review of U.S. Pat. No. 7,288,097, Case No. IPR2019-01479, 21 pages.
Exhibit 1013—U.S. Pat. No. 3,874,388 (King) dated Aug. 8, 2019 from Inter Partes Review of U.S. Pat. No. 7,288,097, Case No. IPR2019-01479, 20 pages.
Exhibit 1014—U.S. Pat. No. 5,478,353 (Yoon) dated Aug. 8, 2019 from Inter Partes Review of U.S. Pat. No. 7,288,097, Case No. IPR2019-01479, 15 pages.
Exhibit 1016—File History of U.S. Pat. No. 7,188,097 (Excerpts) dated Aug. 8, 2019 from Inter Partes Review of U.S. Pat. No. 7,288,097, Case No. IPR2019-01479, 372 pages.
Exhibit 1017—U.S. Pat. No. 6,269,819 (Oz) dated Aug. 8, 2019 from Inter Partes Review of U.S. Pat. No. 7,288,097, Case No. IPR2019-01479, 22 pages.
Exhibit 1018—U.S. Pat. No. 5,695,504 (Gifford) dated Aug. 8, 2019 from Inter Partes Review of U.S. Pat. No. 7,288,097, Case No. IPR2019-01479, 108 pages.
Exhibit 1019—U.S. Pat. No. 5,389,077 (Melinyshyn) dated Aug. 8, 2019 from Inter Partes Review of U.S. Pat. No. 7,288,097, Case No. IPR2019-01479, 6 pages.
Exhibit 1020—WO 94-18893 (Fitton) dated Aug. 8, 2019 from Inter Partes Review of U.S. Pat. No. 7,288,097, Case No. IPR2019-01479, 27 pages.
Exhibit 1021—EP 0558031 A2 (Green) dated Aug. 8, 2019 from Inter Partes Review of U.S. Pat. No. 7,288,097, Case No. IPR2019-01479, 49 pages.
Exhibit 1022—Fucci (1995), Improved Results dated Aug. 8, 2019 from Inter Partes Review of U.S. Pat. No. 7,288,097, Case No. IPR2019-01479, 7 pages.

(56) References Cited

OTHER PUBLICATIONS

Exhibit 1023—Reul (1997), Mitral Valve Reconstruction dated Aug. 8, 2019 from Inter Partes Review of U.S. Pat. No. 7,288,097, Case No. IPR2019-01479, 33 pages.
Exhibit 1024—Maisano (1998), the Edge-to-Edge Technique dated Aug. 8, 2019 from Inter Partes Review of U.S. Pat. No. 7,288,097, Case No. IPR2019-01479, 7 pages.
Exhibit 1025—Umana (1998), Bow-Tie Mitral Valve Repair dated Aug. 8, 2019 from Inter Partes Review of U.S. Pat. No. 7,288,097, Case No. IPR2019-01479, 6 pages.
Exhibit 1026—U.S. Pat. No. 5,411,552 (Andersen) dated Aug. 8, 2019 from Inter Partes Review of U.S. Pat. No. 7,288,097, Case No. IPR2019-01479, 26 pages.
Exhibit 1027—Opinion re PI dated Aug. 8, 2019 from Inter Partes Review of U.S. Pat. No. 7,288,097, Case No. IPR2019-01479, 61 pages.
Exhibit 1028—Order re TRO dated Aug. 8, 2019 from Inter Partes Review of U.S. Pat. No. 7,288,097, Case No. IPR2019-01479, 5 pages.
Exhibit 1029—Revised List of Asserted Claims dated Aug. 8, 2019 from Inter Partes Review of U.S. Pat. No. 7,288,097, Case No. IPR2019-01479, 1 page.
Exhibit 1030—Scheduling Order (Excerpt) dated Aug. 8, 2019 from Inter Partes Review of U.S. Pat. No. 7,288,097, Case No. IPR2019-01479, 4 pages.
Exhibit 1031—Complaint (Excerpt) dated Aug. 8, 2019 from Inter Partes Review of U.S. Pat. No. 7,288,097, Case No. IPR2019-01479, 9 pages.
Exhibit 1032—MitraClip IFU (Excerpt) dated Aug. 8, 2019 from Inter Partes Review of U.S. Pat. No. 7,288,097, Case No. IPR2019-01479, 3 pages.
Exhibit 1033—PI Opening Brief (Excerpt) dated Aug. 8, 2019 from Inter Partes Review of U.S. Pat. No. 7,288,097, Case No. IPR2019-01479, 5 pages.
Exhibit 1034—PI Transcript (Excerpt) dated Aug. 8, 2019 from Inter Partes Review of U.S. Pat. No. 7,288,097, Case No. IPR2019-01479, 4 pages.
Exhibit 1035—Kolata, Tiny Device (NY Times Article) dated Aug. 8, 2019 from Inter Partes Review of U.S. Pat. No. 7,288,097, Case No. IPR2019-01479, 4 pages.
Notice of Opposition dated Jan. 11, 2019 in Opposition of EP2755573, 60 pages.
Proprietor's Reply to Opposition dated Jul. 22, 2019 in Opposition of EP2755573, 21 pages.
U.S. Appl. No. 60/051,078, filed Jun. 27, 1997, Oz, et al.
Alfieri, O., et al., "Novel Suture Device for Beating-Heart Mitral Leaflet Approximation," Ann Thorac Surg 74:1488-93 (2002).
Alfieri, O., et al., "The Double-orifice Technique in Mitral Valve Repair: A Simple Solution for Complex Problems," Journal of Thoracic and Cardiovascular Surgery 122(4):674-681 (2001).
Cribier, A., et al., "Percutaneous Mitral Valvotomy with a Metal Dilatator," The Lancet 349:1667 (1997).
Feldman, T., et al., "Technique of Percutaneous Transvenous Mitral Commissurotomy Using the Inoue Balloon Catheter," Catheterization and Cardiovascular Diagnosis Supplement 2:26-34 (1994).
Glazier, J. and Turi, Z., "Percutaneous Balloon Mitral Valvuloplasty," Progress in Cardiovascular Diseases 40(1):5-26 (1997).
Hung et al., "Atrial Septal Puncture Technique in Percutaneous Transvenous Mitral Commissurotomy : Mitral Valvuloplasty Using the Inoue Balloon Catheter Technique," Catheterization and Cardiovascular Diagnosis 26: 275-284 (1992).
Hung et al., "Pitfalls and Tips in Inoue Balloon Mitral Commissurotomy," Catheterization and Cardiovascular Diagnosis, 37:188-199 (1996).
Inoue, K. and Feldman, T., "Percutaneous Transvenous Mitral Commissurotomy Using the Inoue Balloon Catheter," Catheterization and Cardiovascular Diagnosis 28:119-125 (1993).
Inoue, K., et al., "Clinical Application of Transvenous Mitral Commissurotomy by a New Balloon Catheter," J Thorac Cardiovasc Surg 87:394-402 (1984).
Lau, K. and Hung, J., "'Balloon Impasse'; A Marker for Severe Mitral Subvalvular Disease and a Predictor of Mitral Regurgitation in Inoue-Balloon Percutaneous Transvenous Mitral Commissurotomy," Catheterization and Cardiovascular Diagnosis 35:310-319 (1995).
Lock et al., "Transcatheter Closure of Atrial Septal Defects: Experimental Studies," Circulation 79:1091-1099 (1989).
McCarthy, P., et al., "Early Results with Partial Left Ventriculectomy," J Thorac Cardiovasc Surg 114(5):755-765 (1997).
Morales et al., "Development of an Off Bypass Mitral Valve Repair," The Heart Surgery Forum, 2(2):115-120 (1999).
O'Rourke, R. and Crawford, M., "Mitral Valve Regurgitation," Year Book Medical Publishers, Inc. 1-52 (1984).
Otto, Catherine M., "Timing of Surgery in Mitral Regurgitation," Heart 89:100-105 (2003).
Werker, P. and Kon M., "Review of Facilitated Approaches to Vascular Anastomosis Surgery," Ann Thorac Surg 63:122-7 (1997).
Complaint dated Jan. 28, 2019 in *Abbott Cardiovascular Systems, Inc. et al.* v. *Edwards Lifesciences Corp. et al.*, Case No. 19-149 (MN) (District of Delaware), 32 pages.
Plaintiffs' Opening PI Brief dated Jan. 29, 2019 in *Abbott Cardiovascular Systems, Inc. et al.* v. *Edwards Lifesciences Corp. et al.*, Case No. 19-149 (MN) (District of Delaware), 30 pages.
Declaration and Expert Report of Yoganathan dated Jan. 24, 2019 in *Abbott Cardiovascular Systems, Inc. et al.* v. *Edwards Lifesciences Corp. et al.*, Case No. 19-149 (MN) (District of Delaware), 452 pages.
Plaintiffs' Brief in Support of TRO dated Feb. 18, 2019 in *Abbott Cardiovascular Systems, Inc. et al.* v. *Edwards Lifesciences Corp. et al.*, Case No. 19-149 (MN) (District of Delaware), 27 pages.
Answer and Counterclaims dated Feb. 19, 2019 in *Abbott Cardiovascular Systems, Inc. et al.* v. *Edwards Lifesciences Corp. et al.*, Case No. 19-149 (MN) (District of Delaware), 29 pages.
Edwards' Answering Brief in Opposition of TRO dated Feb. 25, 2019 in *Abbott Cardiovascular Systems, Inc. et al.* v. *Edwards Lifesciences Corp. et al.*, Case No. 19-149 (MN) (District of Delaware), 32 pages.
Plaintiffs' Reply Brief in Support of TRO dated Feb. 26, 2019 in *Abbott Cardiovascular Systems, Inc. et al.* v. *Edwards Lifesciences Corp. et al.*, Case No. 19-149 (MN) (District of Delaware), 22 pages.
Memorandum Order re TRO dated Mar. 5, 2019 in *Abbott Cardiovascular Systems, Inc. et al.* v. *Edwards Lifesciences Corp. et al.*, Case No. 19-149 (MN) (District of Delaware), 5 pages.
First Amended Complaint dated Mar. 8, 2019 in *Abbott Cardiovascular Systems, Inc. et al.* v. *Edwards Lifesciences Corp. et al.*, Case No. 19-149 (MN) (District of Delaware), 32 pages.
Answer and Counterclaims to the First Amended Complaint dated Mar. 22, 2019 in *Abbott Cardiovascular Systems, Inc. et al.* v. *Edwards Lifesciences Corp. et al.*, Case No. 19-149 (MN) (District of Delaware), 30 pages.
Edwards' Answering Brief in Opposition to PI dated Apr. 5, 2019 in *Abbott Cardiovascular Systems, Inc. et al.* v. *Edwards Lifesciences Corp. et al.*, Case No. 19-149 (MN) (District of Delaware), 32 pages.
Declaration of Jensen dated Apr. 5, 2019 in *Abbott Cardiovascular Systems, Inc. et al.* v. *Edwards Lifesciences Corp. et al.*, Case No. 19-149 (MN) (District of Delaware), 184 pages.
Exhibits to Declaration of Jensen dated Apr. 5, 2019 in *Abbott Cardiovascular Systems, Inc. et al.* v. *Edwards Lifesciences Corp. et al.*, Case No. 19-149 (MN) (District of Delaware), 33 pages.
Reply to Counterclaims dated Apr. 12, 2019 in *Abbott Cardiovascular Systems, Inc. et al.* v. *Edwards Lifesciences Corp. et al.*, Case No. 19-149 (MN) (District of Delaware), 9 pages.
Plaintiffs' Reply PI Brief dated Apr. 16, 2019 in *Abbott Cardiovascular Systems, Inc. et al.* v. *Edwards Lifesciences Corp. et al.*, Case No. 19-149 (MN) (District of Delaware), 22 pages.
Reply Declaration and Expert Report of Yoganathan dated Apr. 16, 2019 in *Abbott Cardiovascular Systems, Inc. et al.* v. *Edwards Lifesciences Corp. et al.*, Case No. 19-149 (MN) (District of Delaware), 156 pages.

(56) References Cited

OTHER PUBLICATIONS

Memorandum Opinion re PI dated Jun. 6, 2019 in *Abbott Cardiovascular Systems, Inc. et al. v. Edwards Lifesciences Corp. et al.*, Case No. 19-149 (MN) (District of Delaware), 61 pages.
Edwards' Initial Invalidity Contentions dated Jul. 3, 2019 in *Abbott Cardiovascular Systems, Inc. et al. v. Edwards Lifesciences Corp. et al.*, Case No. 19-149 (MN) (District of Delaware), 249 pages.
Joint Claim Construction Chart dated Jul. 23, 2019 in *Abbott Cardiovascular Systems, Inc. et al. v. Edwards Lifesciences Corp. et al.*, Case No. 19-149 (MN) (District of Delaware), 26 pages.
Request for a Preliminary Injunction dated Jan. 28, 2019 from *Evalve, Inc. et al. v. Edwards Lifesciences SA et al.*, Docket No. S2019_002 (Switzerland).
Response to the Request for a Preliminary Injunction dated Mar. 5, 2019 from *Evalve, Inc. et al. v. Edwards Lifesciences SA et al.*, Docket No. S2019_002 (Switzerland).
Entry of New Evidence dated Mar. 15, 2019 from *Evalve, Inc. et al. v. Edwards Lifesciences SA et al.*, Docket No. S2019_002 (Switzerland).
Declaration of Professor Stephen Brecker dated Mar. 29, 2019 from *Evalve, Inc. et al. v. Edwards Lifesciences SA et al.*, Docket No. S2019_002 (Switzerland).
Reply Regarding the Objection of Invalidity dated Apr. 2, 2019 from *Evalve, Inc. et al. v. Edwards Lifesciences SA et al.*, Docket No. S2019_002 (Switzerland).
Response to Abbott's Submission dated Apr. 16, 2019 from *Evalve, Inc. et al. v. Edwards Lifesciences SA et al.*, Docket No. S2019_002 (Switzerland).
Technical Opinion dated May 20, 2019 from *Evalve, Inc. et al. v. Edwards Lifesciences SA et al.*, Docket No. S2019_002 (Switzerland).
Hearing slides for Evalve dated Jul. 3, 2019 from *Evalve, Inc. et al. v. Edwards Lifesciences SA et al.*, Docket No. S2019_002 (Switzerland).
Hearing slides re EP 810 non-infringement dated Jul. 3, 2019 from *Evalve, Inc. et al. v. Edwards Lifesciences SA et al.*, Docket No. S2019_002 (Switzerland).
Hearing slides re Oral Pleadings of the Defendants dated Jul. 3, 2019 from *Evalve, Inc. et al. v. Edwards Lifesciences SA et al.*, Docket No. S2019_002 (Switzerland).
Hearing slides re Invalidity of EP 1 408 850 dated Jul. 5, 2019 from *Evalve, Inc. et al. v. Edwards Lifesciences SA et al.*, Docket No. S2019_002 (Switzerland).
Claim Form dated Jan. 28, 2019 from *Evalve, Inc. et al. v. Edwards Lifesciences Limited*, Claim No. HP-2019-000003 (United Kingdom).
Particulars of Claim dated Jan. 28, 2019 from *Evalve, Inc. et al. v. Edwards Lifesciences Limited*, Claim No. HP-2019-000003 (United Kingdom).
Particulars of Infringement dated Jan. 28, 2019 from *Evalve, Inc. et al. v. Edwards Lifesciences Limited*, Claim No. HP-2019-000003 (United Kingdom).
Grounds of Invalidity dated Mar. 13, 2019 from *Evalve, Inc. et al. v. Edwards Lifesciences Limited*, Claim No. HP-2019-000003 (United Kingdom).
Reply and Defence to Counterclaim dated Apr. 3, 2019 from *Evalve, Inc. et al. v. Edwards Lifesciences Limited*, Claim No. HP-2019-000003 (United Kingdom).
Amended Defence and Counterclaim dated Jul. 25, 2019 from *Evalve, Inc. et al. v. Edwards Lifesciences Limited*, Claim No. HP-2019-000003 (United Kingdom).
Infringement Complaint dated Jan. 28, 2019 from *Abbott Medical GmbH v. Edwards Lifesciences Corporation et al.*, Ref. No. 4b O 8/19 (Germany) (submitted in foreign language in full with sections directed to cited art translated to English, wherein this Infringement Complaint resulted in Edwards Nullity Complaint, which alleges invalidity of the patents-in-suits in this Infringement Complaint and is submitted concurrently herewith).
Edwards Nullity Complaint dated Mar. 15, 2019 from *Abbott Medical GmbH v. Edwards Lifesciences Corporation et al.*, Ref. No. 4b O 8/19 (Germany) (with translation to English).
PI Application dated Jan. 28, 2019 from *Abbott Cardiovascular Systems Inc. et al. v. Edwards Lifesciences LLC et al.*, Docket No. 4251/2019/CC (Italy) (submitted in foreign language in full, wherein this document requests a Preliminary Injunction that resulted in Edwards Statement of Defense, which asserts invalidity of the patent-in-suit and is submitted concurrently herewith).
Burriesci Declaration dated Jan. 22, 2019 from *Abbott Cardiovascular Systems Inc. et al. v. Edwards Lifesciences LLC et al.*, Docket No. 4251/2019/CC (Italy) (submitted in foreign language in full, wherein this document supports the request for a Preliminary Injunction that resulted in Edwards Statement of Defense, which asserts invalidity of the patent-in-suit and is submitted concurrently herewith).
Statement of Defense dated Apr. 10, 2019 from *Abbott Cardiovascular Systems Inc. et al. v. Edwards Lifesciences LLC et al.*, Docket No. 4251/2019/CC (Italy) (with translation to English).
Technical Opinion dated Apr. 10, 2019 from *Abbott Cardiovascular Systems Inc. et al. v. Edwards Lifesciences LLC et al.*, Docket No. 4251/2019/CC (Italy) (with translation to English).
Authorized Brief dated May 2, 2019 from *Abbott Cardiovascular Systems Inc. et al. v. Edwards Lifesciences LLC et al.*, Docket No. 4251/2019/CC (Italy) (with translation to English).
Authorized Brief dated May 13, 2019 from *Abbott Cardiovascular Systems Inc. et al. v. Edwards Lifesciences LLC et al.*, Docket No. 4251/2019/CC (Italy) (with translation to English).
U.S. Appl. No. 60/128,690, filed Apr. 9, 1999, Deem et al.
Arthur C. Beall et al., Clinical Experience with a Dacron Velour-Covered Teflon-Disc Mitral Valve Prosthesis, 5 Ann. Thorac. Surg. 402-10 (1968).
C. Fucci et al., Improved Results with Mitral Valve Repair Using New Surgical Techniques, 9 Eur. J. Cardiothorac. Surg. 621-27 (1995).
F. Maisano et al., The Edge-to-Edge Technique: A Simplified Method to Correct Mitral Insufficiency, 13 J. Cardio-thoracic Surgery 240-46 (1998).
Gregg W. Stone et al., Clinical Trial Design Principles and Endpoint Definitions for Transcatheter Mitral Valve Repair and Replacement: Part 1: Clinical Trial Design Principles: A Consensus Document from the Mitral Valve Academic Research Consortium, 66 J. Am. Coll. Cardiol. 278-307 (2015).
Juan P. Umaña et al., "Bow-Tie" Mitral Valve Repair: An Adjuvant Technique for Ischemic Mitral Regurgitation, 66 Annals of Thoracic Surgery 1640-46 (1998).
Netter, F. H., et al., "The Ciba Collection of Medical Illustrations," vol. 5. Royal Victorian Institute for the Blind Tertiary Resource Service, Melbourne (1969).
Randas J. V. Batista et al., Partial Left Ventriculectomy to Treat End-Stage Heart Disease, 64 Ann. Thorac. Surg. 634-38 (1997).
Ross M. Reul et al., Mitral Valve Reconstruction for Mitral Insufficiency, 39 Progress in Cardiovascular Diseases 567-99 (1997).
Patent Owner Preliminary Response POPR, filed Sep. 5, 2019, in Inter Partes Review of U.S. Pat. No. 7,563,267, Case No. IPR2019-01132, 87 pages.
Exhibit 2001—Christopher Quinn Declaration, filed Sep. 5, 2019, in Inter Partes Review of U.S. Pat. No. 7,563,267, Case No. IPR2019-01132, 59 pages.
Exhibit 2002—Christopher Quinn CV, filed Sep. 5, 2019, in Inter Partes Review of U.S. Pat. No. 7,563,267, Case No. IPR2019-01132, 3 pages.
Exhibit 2003—Dr. Joshua Rovin Declaration, filed Sep. 5, 2019, in Inter Partes Review of U.S. Pat. No. 7,563,267, Case No. IPR2019-01132, 51 pages.
Exhibit 2004—Dr. Joshua Rovin CV, filed Sep. 5, 2019, in Inter Partes Review of U.S. Pat. No. 7,563,267, Case No. IPR2019-01132, 10 pages.
Exhibit 2005—U.S. Pat. No. 5,823,956 to Roth, filed Sep. 5, 2019, in Inter Partes Review of U.S. Pat. No. 7,563,267, Case No. IPR2019-01132, 54 pages.

(56) References Cited

OTHER PUBLICATIONS

Exhibit 2006—FDA Letter, filed Sep. 5, 2019, in Inter Partes Review of U.S. Pat. No. 7,563,267, Case No. IPR2019-01132, 16 pages.
Exhibit 2007—NYTimes Article, filed Sep. 5, 2019, in Inter Partes Review of U.S. Pat. No. 7,563,267, Case No. IPR2019-01132, 5 pages.
Exhibit 2008—Yoganathan Report, filed Sep. 5, 2019, in Inter Partes Review of U.S. Pat. No. 7,563,267, Case No. IPR2019-01132, 449 pages.
Exhibit 2009—Complaint, filed Sep. 5, 2019, in Inter Partes Review of U.S. Pat. No. 7,563,267, Case No. IPR2019-01132, 32 pages.
Exhibit 2010—Answer and Counterclaims, filed Sep. 5, 2019, in Inter Partes Review of U.S. Pat. No. 7,563,267, Case No. IPR2019-01132, 29 pages.
Exhibit 2011—Scheduling Order, filed Sep. 5, 2019, in Inter Partes Review of U.S. Pat. No. 7,563,267, Case No. IPR2019-01132, 16 pages.
Exhibit 2012—COAPT MitraClip, filed Sep. 5, 2019, in Inter Partes Review of U.S. Pat. No. 7,563,267, Case No. IPR2019-01132, 9 pages.
Exhibit 2013—Demonstrative re Petition same as Litigation, filed Sep. 5, 2019, in Inter Partes Review of U.S. Pat. No. 7,563,267, Case No. IPR2019-01132, 8 pages.
Exhibit 2014—Amended Answer and Counterclaims, filed Sep. 5, 2019, in Inter Partes Review of U.S. Pat. No. 7,563,267, Case No. IPR2019-01132, 39 pages.
Exhibit 2015—Edwards' Initial Invalidity Contentions, filed Sep. 5, 2019, in Inter Partes Review of U.S. Pat. No. 7,563,267, Case No. IPR2019-01132, 249 pages.
Exhibit 2016—US20040167539 to Kuehn, filed Sep. 5, 2019, in Inter Partes Review of U.S. Pat. No. 7,563,267, Case No. IPR2019-01132, 21 pages.
Exhibit 2017—U.S. Pat. No. 6,695,866 to Kuehn, filed Sep. 5, 2019, in Inter Partes Review of U.S. Pat. No. 7,563,267, Case No. IPR2019-01132, 21 pages.
Exhibit 2018—U.S. Pat. No. 6,346,074 to Roth, filed Sep. 5, 2019, in Inter Partes Review of U.S. Pat. No. 7,563,267, Case No. IPR2019-01132, 64 pages.
Exhibit 2019—U.S. Pat. No. 5,823,956 to Roth, filed Sep. 5, 2019, in Inter Partes Review of U.S. Pat. No. 7,563,267, Case No. IPR2019-01132, 54 pages.
Exhibit 2020—U.S. Pat. No. 5,855,614 to Stevens and Roth, filed Sep. 5, 2019, in Inter Partes Review of U.S. Pat. No. 7,563,267, Case No. IPR2019-01132, 55 pages.
Exhibit 2021—Perlowski Pt1, filed Sep. 5, 2019, in Inter Partes Review of U.S. Pat. No. 7,563,267, Case No. IPR2019-01132, 100 pages.
Exhibit 2021—Perlowski Pt2, filed Sep. 5, 2019, in Inter Partes Review of U.S. Pat. No. 7,563,267, Case No. IPR2019-01132, 98 pages.
Exhibit 2022—Transcatheter Mitral Valve Repair with MitraClip, filed Sep. 5, 2019, in Inter Partes Review of U.S. Pat. No. 7,563,267, Case No. IPR2019-01132, 20 pages.
Exhibit 2023—Feldman 2005, filed Sep. 5, 2019, in Inter Partes Review of U.S. Pat. No. 7,563,267, Case No. IPR2019-01132, 7 pages.
Exhibit 2024—Excerpts Oxford Dictionary, filed Sep. 5, 2019, in Inter Partes Review of U.S. Pat. No. 7,563,267, Case No. IPR2019-01132, 3 pages.
Exhibit 2025—Excerpts Webster's New World Dictionary, filed Sep. 5, 2019, in Inter Partes Review of U.S. Pat. No. 7,563,267, Case No. IPR2019-01132, 4 pages.
Exhibit 2026—Excerpts Webster's Dictionary of American English, filed Sep. 5, 2019, in Inter Partes Review of U.S. Pat. No. 7,563,267, Case No. IPR2019-01132, 3 pages.
Exhibit 2027—Excerpts Illustrated Oxford Dictionary, filed Sep. 5, 2019, in Inter Partes Review of U.S. Pat. No. 7,563,267, Case No. IPR2019-01132, 3 pages.
Exhibit 2028—U.S. Appl. No. 10/383,596 File History, filed Sep. 5, 2019, in Inter Partes Review of U.S. Pat. No. 7,563,267, Case No. IPR2019-01132, 196 pages.
Exhibit 2029—Maisano, filed Sep. 5, 2019, in Inter Partes Review of U.S. Pat. No. 7,563,267, Case No. IPR2019-01132, 10 pages.
Exhibit 2030—Alfieri, filed Sep. 5, 2019, in Inter Partes Review of U.S. Pat. No. 7,563,267, Case No. IPR2019-01132, 8 pages.
Exhibit 2031—MitraClip Instructions for Use, filed Sep. 5, 2019, in Inter Partes Review of U.S. Pat. No. 7,563,267, Case No. IPR2019-01132, 54 pages.
Exhibit 2032—Transcript Feldman re Everest, filed Sep. 5, 2019, in Inter Partes Review of U.S. Pat. No. 7,563,267, Case No. IPR2019-01132, 3 pages.
Exhibit 2033—Joint Claim Construction Chart, filed Sep. 5, 2019, in Inter Partes Review of U.S. Pat. No. 7,563,267, Case No. IPR2019-01132, 26 pages.
Exhibit 2034—Edwards Analyst Investor Day, filed Sep. 5, 2019, in Inter Partes Review of U.S. Pat. No. 7,563,267, Case No. IPR2019-01132, 49 pages.
Exhibit 2035—Mack, filed Sep. 5, 2019, in Inter Partes Review of U.S. Pat. No. 7,563,267, Case No. IPR2019-01132, 3 pages.
Exhibit 2036—Rogoski, filed Sep. 5, 2019, in Inter Partes Review of U.S. Pat. No. 7,563,267, Case No. IPR2019-01132, 3 pages.
Exhibit 2037—Piazza, filed Sep. 5, 2019, in Inter Partes Review of U.S. Pat. No. 7,563,267, Case No. IPR2019-01132, 15 pages.
Exhibit 2040—Kheradvar, filed Sep. 5, 2019, in Inter Partes Review of U.S. Pat. No. 7,563,267, Case No. IPR2019-01132, 11 pages.
Exhibit 2041—FDA re MitraClip, filed Sep. 5, 2019, in Inter Partes Review of U.S. Pat. No. 7,563,267, Case No. IPR2019-01132, 3 pages.
Exhibit 2042—Gossl, filed Sep. 5, 2019, in Inter Partes Review of U.S. Pat. No. 7,563,267, Case No. IPR2019-01132, 8 pages.
Exhibit 2043—Business Monitor Online, filed Sep. 5, 2019, in Inter Partes Review of U.S. Pat. No. 7,563,267, Case No. IPR2019-01132, 2 pages.
Exhibit 2044—Excerpts MitraClip Physician Site, filed Sep. 5, 2019, in Inter Partes Review of U.S. Pat. No. 7,563,267, Case No. IPR2019-01132, 6 pages.
Exhibit 2045—Feldman 2009, filed Sep. 5, 2019, in Inter Partes Review of U.S. Pat. No. 7,563,267, Case No. IPR2019-01132, 9 pages.
Exhibit 2046—LexMachina Case Timing for Delaware, filed Sep. 5, 2019, in Inter Partes Review of U.S. Pat. No. 7,563,267, Case No. IPR2019-01132, 1 page.
Exhibit 2047—Wood TCT 2018, filed Sep. 5, 2019, in Inter Partes Review of U.S. Pat. No. 7,563,267, Case No. IPR2019-01132, 5 pages.
Exhibit 2048—Excerpts MitraClip FAQ Physician, filed Sep. 5, 2019, in Inter Partes Review of U.S. Pat. No. 7,563,267, Case No. IPR2019-01132, 4 pages.
Exhibit 2049—U.S. Pat. No. 8,172,856 to Eigler, filed Sep. 5, 2019, in Inter Partes Review of U.S. Pat. No. 7,563,267, Case No. IPR2019-01132, 26 pages.
Exhibit 2050—U.S. Pat. No. 9,76,3658 to Eigler, filed Sep. 5, 2019, in Inter Partes Review of U.S. Pat. No. 7,563,267, Case No. IPR2019-01132, 27 pages.
Exhibit 2052—*Belden Technologies Inc* v *Superior Essex Communications LP*, filed Sep. 5, 2019, in Inter Partes Review of U.S. Pat. No. 7,563,267, Case No. IPR2019-01132, 3 pages.
Exhibit 2053—Wood TCTMD, filed Sep. 5, 2019, in Inter Partes Review of U.S. Pat. No. 7,563,267, Case No. IPR2019-01132, 11 pages.
Exhibit 2054—D. Del. Docket Sheet, filed Sep. 5, 2019, in Inter Partes Review of U.S. Pat. No. 7,563,267, Case No. IPR2019-01132, 27 pages.
Exhibit 2055—Letter re Markman Hearing, filed Sep. 5, 2019, in Inter Partes Review of U.S. Pat. No. 7,563,267, Case No. IPR2019-01132, 2 pages.
Edwards Petition for Inter Partes Review of '388 Patent, filed Aug. 23, 2019, in Inter Partes Review of U.S. Pat. No. 7,736,388; Case No. IPR2019-01546, 105 pages.

(56) References Cited

OTHER PUBLICATIONS

Exhibit 1001—U.S. Pat. No. 7,736,388, filed Aug. 23, 2019, in Inter Partes Review of U.S. Pat. No. 7,736,388; Case No. IPR2019-01546, 103 pages.
Exhibit 1002—Vesely Declaration, filed Aug. 23, 2019, in Inter Partes Review of U.S. Pat. No. 7,736,388; Case No. IPR2019-01546, 101 pages.
Exhibit 1003—Vesely Curriculum Vitae, filed Aug. 23, 2019, in Inter Partes Review of U.S. Pat. No. 7,736,388; Case No. IPR2019-01546, 8 pages.
Exhibit 1004—File History of U.S. Pat. No. 7,736,388 (Excerpts), filed Aug. 23, 2019, in Inter Partes Review of U.S. Pat. No. 7,736,388; Case No. IPR2019-01546, 353 pages.
Exhibit 1005—U.S. Pat. No. 6,165,183 (Kuehn), filed Aug. 23, 2019, in Inter Partes Review of U.S. Pat. No. 7,736,388; Case No. IPR2019-01546, 21 pages.
Exhibit 1006—U.S. Pat. No. 6,346,074 (Roth), filed Aug. 23, 2019, in Inter Partes Review of U.S. Pat. No. 7,736,388; Case No. IPR2019-01546, 64 pages.
Exhibit 1007—U.S. Pat. No. 4,340,091 (Skelton), filed Aug. 23, 2019, in Inter Partes Review of U.S. Pat. No. 7,736,388; Case No. IPR2019-01546, 12 pages.
Exhibit 1008—US 2002-0013571 (Goldfarb), filed Aug. 23, 2019, in Inter Partes Review of U.S. Pat. No. 7,736,388; Case No. IPR2019-01546, 69 pages.
Exhibit 1009—U.S. Appl. No. 60/128,690, filed Aug. 23, 2019, in Inter Partes Review of U.S. Pat. No. 7,736,388; Case No. IPR2019-01546, 100 pages.
Exhibit 1010—Batista, Partial Left Ventriculectomy, filed Aug. 23, 2019, in Inter Partes Review of U.S. Pat. No. 7,736,388; Case No. IPR2019-01546, 5 pages.
Exhibit 1011—Fucci, Improved Results, filed Aug. 23, 2019, in Inter Partes Review of U.S. Pat. No. 7,736,388; Case No. IPR2019-01546, 7 pages.
Exhibit 1012—Webster's New World College Dictionary (Excerpt), filed Aug. 23, 2019, in Inter Partes Review of U.S. Pat. No. 7,736,388; Case No. IPR2019-01546, 7 pages.
Exhibit 1013—Oxford Dictionary (Excerpt), filed Aug. 23, 2019, in Inter Partes Review of U.S. Pat. No. 7,736,388; Case No. IPR2019-01546, 10 pages.
Exhibit 1014—Random House Dictionary (Excerpt), filed Aug. 23, 2019, in Inter Partes Review of U.S. Pat. No. 7,736,388; Case No. IPR2019-01546, 6 pages.
Exhibit 1015—Netter, Ciba Collection of Medical Illustrations (Excerpt), filed Aug. 23, 2019, in Inter Partes Review of U.S. Pat. No. 7,736,388; Case No. IPR2019-01546, 4 pages.
Exhibit 1017—WO 2003-020179 (Tremulis), filed Aug. 23, 2019, in Inter Partes Review of U.S. Pat. No. 7,736,388; Case No. IPR2019-01546, 56 pages.
Exhibit 1018—U.S. Pat. No. 5,741,297 (Simon), filed Aug. 23, 2019, in Inter Partes Review of U.S. Pat. No. 7,736,388; Case No. IPR2019-01546, 11 pages.
Exhibit 1019—U.S. Pat. No. 3,874,388 (King), filed Aug. 23, 2019, in Inter Partes Review of U.S. Pat. No. 7,736,388; Case No. IPR2019-01546, 20 pages.
Exhibit 1020—U.S. Pat. No. 5,716,417 (Girard), filed Aug. 23, 2019, in Inter Partes Review of U.S. Pat. No. 7,736,388; Case No. IPR2019-01546, 12 pages.
Exhibit 1021—Beall, Clinical Experience, filed Aug. 23, 2019, in Inter Partes Review of U.S. Pat. No. 7,736,388; Case No. IPR2019-01546, 9 pages.
Exhibit 1022—Complaint (Excerpt) in *Abbott v. Edwards*, 19-cv-00149, filed Aug. 23, 2019, in Inter Partes Review of U.S. Pat. No. 7,736,388; Case No. IPR2019-01546, 9 pages.
Exhibit 1023—MitraClip IFU (Excerpt), filed Aug. 23, 2019, in Inter Partes Review of U.S. Pat. No. 7,736,388; Case No. IPR2019-01546, 3 pages.
Exhibit 1024—PI Opening Brief (Excerpt) in *Abbott v. Edwards*, 19-cv-00149, filed Aug. 23, 2019, in Inter Partes Review of U.S. Pat. No. 7,736,388; Case No. IPR2019-01546, 5 pages.
Exhibit 1025—PI Transcript (Excerpt) in *Abbott v. Edwards*, 19-cv-00149, filed Aug. 23, 2019, in Inter Partes Review of U.S. Pat. No. 7,736,388; Case No. IPR2019-01546, 4 pages.
Exhibit 1026—Yoganathan Declaration (Excerpt) in *Abbott v. Edwards*, 19-cv-00149, filed Aug. 23, 2019, in Inter Partes Review of U.S. Pat. No. 7,736,388; Case No. IPR2019-01546, 9 pages.
Exhibit 1027—Keller Letter (Excerpt) in *Abbott v. Edwards*, 19-cv-00149, filed Aug. 23, 2019, in Inter Partes Review of U.S. Pat. No. 7,736,388; Case No. IPR2019-01546, 3 pages.
Exhibit 1028—Kolata, Tiny Device (NY Times), filed Aug. 23, 2019, in Inter Partes Review of U.S. Pat. No. 7,736,388; Case No. IPR2019-01546, 4 pages.
Exhibit 1030—U.S. Pat. No. 7,563,267, filed Aug. 23, 2019, in Inter Partes Review of U.S. Pat. No. 7,736,388; Case No. IPR2019-01546, 103 pages.
Exhibit 1032—Opinion (Excerpts), filed Aug. 23, 2019, in Inter Partes Review of U.S. Pat. No. 7,736,388; Case No. IPR2019-01546, 6 pages.
Exhibit 1033—Abbott Claim Construction Email, filed Aug. 23, 2019, in Inter Partes Review of U.S. Pat. No. 7,736,388; Case No. IPR2019-01546, 2 pages.
Exhibit 1034—Joint Claim Construction Chart (Excerpts), filed Aug. 23, 2019, in Inter Partes Review of U.S. Pat. No. 7,736,388; Case No. IPR2019-01546, 3 pages.
Final Written Submissions of Evalve dated Sep. 4, 2019 in Opposition of EP1624810, 39 pages.
Written Submissions from Edwards dated Sep. 4, 2019 in Opposition of EP1624810, 9 pages.
Written Submissions from Edwards dated Sep. 18, 2019 in Opposition of EP1624810, 29 pages.
Final POPR dated Oct. 18, 2019 in Inter Partes Review of U.S. Pat. No. 8,057,493, Case No. IPR2019-01301, 90 pages.
Exhibit 2001—Quinn Declaration filed Oct. 18, 2019 in Inter Partes Review of U.S. Pat. No. 8,057,493, Case No. IPR2019-01301, 63 pages.
Exhibit 2002—Quinn CV filed Oct. 18, 2019 in Inter Partes Review of U.S. Pat. No. 8,057,493, Case No. IPR2019-01301, 3 pages.
Exhibit 2003—Rovin Decl. 493 Patent filed Oct. 18, 2019 in Inter Partes Review of U.S. Pat. No. 8,057,493, Case No. IPR2019-01301, 57 pages.
Exhibit 2004—Rovin CV filed Oct. 18, 2019 in Inter Partes Review of U.S. Pat. No. 8,057,493, Case No. IPR2019-01301, 10 pages.
Exhibit 2005—U.S. Pat. No. 5,823,956 filed Oct. 18, 2019 in Inter Partes Review of U.S. Pat. No. 8,057,493, Case No. IPR2019-01301, 54 pages.
Exhibit 2006—FDA Letter filed Oct. 18, 2019 in Inter Partes Review of U.S. Pat. No. 8,057,493, Case No. IPR2019-01301, 16 pages.
Exhibit 2007—NYTimes Article filed Oct. 18, 2019 in Inter Partes Review of U.S. Pat. No. 8,057,493, Case No. IPR2019-01301, 5 pages.
Exhibit 2008—Yoganathan Report filed Oct. 18, 2019 in Inter Partes Review of U.S. Pat. No. 8,057,493, Case No. IPR2019-01301, 449 pages.
Exhibit 2009—Complaint filed Oct. 18, 2019 in Inter Partes Review of U.S. Pat. No. 8,057,493, Case No. IPR2019-01301, 32 pages.
Exhibit 2010—Answer and Counterclaims filed Oct. 18, 2019 in Inter Partes Review of U.S. Pat. No. 8,057,493, Case No. IPR2019-01301, 29 pages.
Exhibit 2011—Scheduling Order filed Oct. 18, 2019 in Inter Partes Review of U.S. Pat. No. 8,057,493, Case No. IPR2019-01301, 16 pages.
Exhibit 2012—COAPT MitraClip filed Oct. 18, 2019 in Inter Partes Review of U.S. Pat. No. 8,057,493, Case No. IPR2019-01301, 9 pages.
Exhibit 2013 Demonstrative Comparing POPR to Invalidity Contentions filed Oct. 18, 2019 in Inter Partes Review of U.S. Pat. No. 8,057,493, Case No. IPR2019-01301, 8 pages.
Exhibit 2014—Amended Answer and Counterclaims filed Oct. 18, 2019 in Inter Partes Review of U.S. Pat. No. 8,057,493, Case No. IPR2019-01301, 39 pages.

(56) References Cited

OTHER PUBLICATIONS

Exhibit 2015—Edwards' Initial Invalidity Contentions filed Oct. 18, 2019 in Inter Partes Review of U.S. Pat. No. 8,057,493, Case No. IPR2019-01301, 249 pages.
Exhibit 2016—US 20040167539 filed Oct. 18, 2019 in Inter Partes Review of U.S. Pat. No. 8,057,493, Case No. IPR2019-01301, 21 pages.
Exhibit 2017—U.S. Pat. No. 6,695,866 filed Oct. 18, 2019 in Inter Partes Review of U.S. Pat. No. 8,057,493, Case No. IPR2019-01301, 21 pages.
Exhibit 2018—U.S. Pat. No. 6,346,074 (Roth) Highlighted filed Oct. 18, 2019 in Inter Partes Review of U.S. Pat. No. 8,057,493, Case No. IPR2019-01301, 64 pages.
Exhibit 2019—U.S. Pat. No. 5,823,956 filed Oct. 18, 2019 in Inter Partes Review of U.S. Pat. No. 8,057,493, Case No. IPR2019-01301, 54 pages.
Exhibit 2021—Perlowski Pt1 filed Oct. 18, 2019 in Inter Partes Review of U.S. Pat. No. 8,057,493, Case No. IPR2019-01301, 100 pages.
Exhibit 2021—Perlowski Pt2 filed Oct. 18, 2019 in Inter Partes Review of U.S. Pat. No. 8,057,493, Case No. IPR2019-01301, 98 pages.
Exhibit 2022—Transcather Mitral Valve Repair with MitraClip filed Oct. 18, 2019 in Inter Partes Review of U.S. Pat. No. 8,057,493, Case No. IPR2019-01301, 20 pages.
Exhibit 2023—Feldman 2005 filed Oct. 18, 2019 in Inter Partes Review of U.S. Pat. No. 8,057,493, Case No. IPR2019-01301, 7 pages.
Exhibit 2024—Excerpts Oxford Dictionary filed Oct. 18, 2019 in Inter Partes Review of U.S. Pat. No. 8,057,493, Case No. IPR2019-01301, 3 pages.
Exhibit 2025—Excerpts Webster's New World Dictionary filed Oct. 18, 2019 in Inter Partes Review of U.S. Pat. No. 8,057,493, Case No. IPR2019-01301, 4 pages.
Exhibit 2026—Excerpts Webster's Dictionary of American English filed Oct. 18, 2019 in Inter Partes Review of U.S. Pat. No. 8,057,493, Case No. IPR2019-01301, 3 pages.
Exhibit 2027—Excerpts Illustrated Oxford Dictionary filed Oct. 18, 2019 in Inter Partes Review of U.S. Pat. No. 8,057,493, Case No. IPR2019-01301, 3 pages.
Exhibit 2028—U.S. Pat. No. 10,383,596 File History filed Oct. 18, 2019 in Inter Partes Review of U.S. Pat. No. 8,057,493, Case No. IPR2019-01301, 196 pages.
Exhibit 2029—Maisano filed Oct. 18, 2019 in Inter Partes Review of U.S. Pat. No. 8,057,493, Case No. IPR2019-01301, 10 pages.
Exhibit 2030—Alfieri filed Oct. 18, 2019 in Inter Partes Review of U.S. Pat. No. 8,057,493, Case No. IPR2019-01301, 8 pages.
Exhibit 2031—MitraClip Instructions for Use filed Oct. 18, 2019 in Inter Partes Review of U.S. Pat. No. 8,057,493, Case No. IPR2019-01301, 54 pages.
Exhibit 2032—Transcript Feldman re Everest filed Oct. 18, 2019 in Inter Partes Review of U.S. Pat. No. 8,057,493, Case No. IPR2019-01301, 3 pages.
Exhibit 2034—Edwards Analyst Investor Day filed Oct. 18, 2019 in Inter Partes Review of U.S. Pat. No. 8,057,493, Case No. IPR2019-01301, 49 pages.
Exhibit 2035—Mack filed Oct. 18, 2019 in Inter Partes Review of U.S. Pat. No. 8,057,493, Case No. IPR2019-01301, 3 pages.
Exhibit 2036—Rogoski filed Oct. 18, 2019 in Inter Partes Review of U.S. Pat. No. 8,057,493, Case No. IPR2019-01301, 3 pages.
Exhibit 2037—Piazza filed Oct. 18, 2019 in Inter Partes Review of U.S. Pat. No. 8,057,493, Case No. IPR2019-01301, 15 pages.
Exhibit 2040—Kheradvar filed Oct. 18, 2019 in Inter Partes Review of U.S. Pat. No. 8,057,493, Case No. IPR2019-01301, 11 pages.
Exhibit 2041—FDA re MitraClip filed Oct. 18, 2019 in Inter Partes Review of U.S. Pat. No. 8,057,493, Case No. IPR2019-01301, 3 pages.
Exhibit 2042—Gossl filed Oct. 18, 2019 in Inter Partes Review of U.S. Pat. No. 8,057,493, Case No. IPR2019-01301, 8 pages.
Exhibit 2043—Business Monitor Online filed Oct. 18, 2019 in Inter Partes Review of U.S. Pat. No. 8,057,493, Case No. IPR2019-01301, 2 pages.
Exhibit 2044—Excerpts MitraClip Physician Site filed Oct. 18, 2019 in Inter Partes Review of U.S. Pat. No. 8,057,493, Case No. IPR2019-01301, 6 pages.
Exhibit 2045—Feldman 2009 filed Oct. 18, 2019 in Inter Partes Review of U.S. Pat. No. 8,057,493, Case No. IPR2019-01301, 9 pages.
Exhibit 2046—LexMachina Case Timing for Delaware filed Oct. 18, 2019 in Inter Partes Review of U.S. Pat. No. 8,057,493, Case No. IPR2019-01301, 1 page.
Exhibit 2047—Wood TCT 2018 filed Oct. 18, 2019 in Inter Partes Review of U.S. Pat. No. 8,057,493, Case No. IPR2019-01301, 5 pages.
Exhibit 2048—Excerpts MitraClip FAQ Physician filed Oct. 18, 2019 in Inter Partes Review of U.S. Pat. No. 8,057,493, Case No. IPR2019-01301, 4 pages.
Exhibit 2049—U.S. Pat. No. 8,172,856 to Eigler filed Oct. 18, 2019 in Inter Partes Review of U.S. Pat. No. 8,057,493, Case No. IPR2019-01301, 26 pages.
Exhibit 2050—U.S. Pat. No. 9,763,658 to Eigler filed Oct. 18, 2019 in Inter Partes Review of U.S. Pat. No. 8,057,493, Case No. IPR2019-01301, 27 pages.
Exhibit 2052—*Belden Technologies Inc* v *Superior Essex Communications LP* filed Oct. 18, 2019 in Inter Partes Review of U.S. Pat. No. 8,057,493, Case No. IPR2019-01301, 3 pages.
Exhibit 2053—Wood TCTMD filed Oct. 18, 2019 in Inter Partes Review of U.S. Pat. No. 8,057,493, Case No. IPR2019-01301, 11 pages.
Exhibit 2054—Docket Oct. 10, 2019 filed Oct. 18, 2019 in Inter Partes Review of U.S. Pat. No. 8,057,493, Case No. IPR2019-01301, 40 pages.
Exhibit 2056—WO0003759A2 to Kuehn filed Oct. 18, 2019 in Inter Partes Review of U.S. Pat. No. 8,057,493, Case No. IPR2019-01301, 47 pages.
Exhibit 2057—U.S. Pat. No. 6,773,440B2 filed Oct. 18, 2019 in Inter Partes Review of U.S. Pat. No. 8,057,493, Case No. IPR2019-01301, 38 pages.
Exhibit 2058—Joint Claim Construction Brief filed Oct. 18, 2019 in Inter Partes Review of U.S. Pat. No. 8,057,493, Case No. IPR2019-01301, 94 pages.
Exhibit 2059—Email from B Lasky filed Oct. 18, 2019 in Inter Partes Review of U.S. Pat. No. 8,057,493, Case No. IPR2019-01301, 1 page.
Petitioners' Authorized Reply dated Oct. 14, 2019 in Inter Partes Review of U.S. Pat. No. 7,563,267, Case No. IPR2019-01132, 8 pages.
PO Sur Reply dated Oct. 21, 2019 in Inter Partes Review of U.S. Pat. No. 7,563,267, Case No. IPR2019-01132, 11 pages.
Patent Owner Briefing Re Claim Construction, filed Nov. 26, 2019, in *Inter Partes* Review of U.S. Pat. No. 7,563,267, Case No. IPR2019-01132, 14 pages.
Petitioner's Response Re Claim Construction, filed Dec. 2, 2019, in *Inter Partes* Review of U.S. Pat. No. 7,563,267, Case No. IPR2019-01132, 8 pages.
Decision Denying Institution, filed Dec. 4, 2019, in *Inter Partes* Review of U.S. Pat. No. 7,563,267, Case No. IPR2019-01132, 34 pages.
Patent Owner Briefing Re Claim Construction, filed Nov. 26, 2019 in *Inter Partes* Review of U.S. Pat. No. 8,057,493, Case No. IPR2019-01301, 14 pages.
Petitioner's Response Re Claim Construction, filed Dec. 2, 2019 in *Inter Partes* Review of U.S. Pat. No. 8,057,493, Case No. IPR2019-01301, 8 pages.
Petitioner's Reply to POPR, filed Dec. 3, 2019 in *Inter Partes* Review of U.S. Pat. No. 8,057,493, Case No. IPR2019-01301, 10 pages.
Patent Owner Surreply, filed Dec. 12, 2019 in *Inter Partes* Review of U.S. Pat. No. 8,057,493, Case No. IPR2019-01301, 12 pages.
EP810 Amended Specification, filed Jan. 3, 2020 in Opposition of EP1624810, 107 pages.

(56) References Cited

OTHER PUBLICATIONS

EP810 Decision, filed Jan. 3, 2020 in Opposition of EP1624810, 37 pages.
EP810 Minutes filed Jan. 3, 2020 in Opposition of EP1624810, 23 pages.
'388 POPR, filed Dec. 23, 2019 in *Inter Partes* Review of U.S. Pat. No. 7,736,388; Case No. IPR2019-01546, 90 pages.
Exhibit 2001—Dr. Quinn Declaration filed Dec. 23, 2019 in *Inter Partes* Review of U.S. Pat. No. 7,736,388; Case No. IPR2019-01546, 71 pages.
Exhibit 2002—Quinn CV filed Dec. 23, 2019 in *Inter Partes* Review of U.S. Pat. No. 7,736,388; Case No. IPR2019-01546, 3 pages.
Exhibit 2003—Dr. Rovin Declaration filed Dec. 23, 2019 in *Inter Partes* Review of U.S. Pat. No. 7,736,388; Case No. IPR2019-01546, 51 pages.
Exhibit 2004—Rovin CV filed Dec. 23, 2019 in *Inter Partes* Review of U.S. Pat. No. 7,736,388; Case No. IPR2019-01546, 10 pages.
Exhibit 2005—U.S. Pat. No. 5823956 filed Dec. 23, 2019 in *Inter Partes* Review of U.S. Pat. No. 7,736,388; Case No. IPR2019-01546, 54 pages.
Exhibit 2006—FDA Letter filed Dec. 23, 2019 in *Inter Partes* Review of U.S. Pat. No. 7,736,388; Case No. IPR2019-01546, 16 pages.
Exhibit 2007—NY Times Article filed Dec. 23, 2019 in *Inter Partes* Review of U.S. Pat. No. 7,736,388; Case No. IPR2019-01546, 5 pages.
Exhibit 2008—Yoganathan Report filed Dec. 23, 2019 in *Inter Partes* Review of U.S. Pat. No. 7,736,388; Case No. IPR2019-01546, 449 pages.
Exhibit 2009 — Complaint filed Dec. 23, 2019 in *Inter Partes* Review of U.S. Pat. No. 7,736,388; Case No. IPR2019-01546, 32 pages.
Exhibit 2011—Scheduling Order filed Dec. 23, 2019 in *Inter Partes* Review of U.S. Pat. No. 7,736,388; Case No. IPR2019-01546, 16 pages.
Exhibit 2012—COAPT MitraClip filed Dec. 23, 2019 in *Inter Partes* Review of U.S. Pat. No. 7,736,388; Case No. IPR2019-01546, 9 pages.
Exhibit 2013—Demonstrative re copied arguments filed Dec. 23, 2019 in *Inter Partes* Review of U.S. Pat. No. 7,736,388; Case No. IPR2019-01546, 5 pages.
Exhibit 2016—US20040167539 filed Dec. 23, 2019 in *Inter Partes* Review of U.S. Pat. No. 7,736,388; Case No. IPR2019-01546, 21 pages.
Exhibit 2017—U.S. Pat. No.6695866 filed Dec. 23, 2019 in *Inter Partes* Review of U.S. Pat. No. 7,736,388; Case No. IPR2019-01546, 21 pages.
Exhibit 2018—U.S. Pat. No. 6346074 (Roth) Highlighted filed Dec. 23, 2019 in *Inter Partes* Review of U.S. Pat. No. 7,736,388; Case No. IPR2019-01546, 64 pages.
Exhibit 2019—Roth '956 Highlighted filed Dec. 23, 2019 in *Inter Partes* Review of U.S. Pat. No. 7,736,388; Case No. IPR2019-01546, 54 pages.
Exhibit 2020—U.S. Pat. No.5855614 filed Dec. 23, 2019 in *Inter Partes* Review of U.S. Pat. No. 7,736,388; Case No. IPR2019-01546, 55 pages.
Exhibit 2021 — Perlowski Part 1 filed Dec. 23, 2019 in *Inter Partes* Review of U.S. Pat. No. 7,736,388; Case no. IPR2019-01546, 100 pages.
Exhibit 2021 — Perlowski Part 2 filed Dec. 23, 2019 in *Inter Partes* Review of U.S. Pat. No. 7,736,388; Case no. IPR2019-01546, 98 pages.
Exhibit 2022—Transcather Mitral Valve Repair with MitraClip filed Dec. 23, 2019 in *Inter Partes* Review of U.S. Pat. No. 7,736,388; Case No. IPR2019-01546, 20 pages.
Exhibit 2023—Feldman 2005 filed Dec. 23, 2019 in *Inter Partes* Review of U.S. Pat. No. 7,736,388; Case No. IPR2019-01546, 7 pages.
Exhibit 2024—Excerpts Oxford Dictionary filed Dec. 23, 2019 in *Inter Partes* Review of U.S. Pat. No. 7,736,388; Case No. IPR2019-01546, 3 pages.
Exhibit 2025—Webster's New World Dictionary filed Dec. 23, 2019 in *Inter Partes* Review of U.S. Pat. No. 7,736,388; Case No. IPR2019-01546, 4 pages.
Exhibit 2026—Excerpts Webster's Dictionary of American English filed Dec. 23, 2019 in *Inter Partes* Review of U.S. Pat. No. 7,736,388; Case No. IPR2019-01546, 3 pages.
Exhibit 2027—Excerpts Illustrated Oxford Dictionary filed Dec. 23, 2019 in *Inter Partes* Review of U.S. Pat. No. 7,736,388; Case No. IPR2019-01546, 3 pages.
Exhibit 2029 — Maisano filed Dec. 23, 2019 in *Inter Partes* Review of U.S. Pat. No. 7,736,388; Case No. IPR2019-01546, 10 pages.
Exhibit 2030 — Alfieri filed Dec. 23, 2019 in *Inter Partes* Review of U.S. Pat. No. 7,736,388; Case No. IPR2019-01546, 8 pages.
Exhibit 2031—MitraClip IFU filed Dec. 23, 2019 in *Inter Partes* Review of U.S. Pat. No. 7,736,388; Case No. IPR2019-01546, 54 pages.
Exhibit 2032—Transcript Feldman re Everest filed Dec. 23, 2019 in *Inter Partes* Review of U.S. Pat. No. 7,736,388; Case No. IPR2019-01546, 3 pages.
Exhibit 2034—Edwards Analyst Investor Day filed Dec. 23, 2019 in *Inter Partes* Review of U.S. Pat. No. 7,736,388; Case No. IPR2019-01546, 49 pages.
Exhibit 2035 — Mack filed Dec. 23, 2019 in *Inter Partes* Review of U.S. Pat. No. 7,736,388; Case No. IPR2019-01546, 3 pages.
Exhibit 2036 — Rogoski filed Dec. 23, 2019 in *Inter Partes* Review of U.S. Pat. No. 7,736,388; Case No. IPR2019-01546, 3 pages.
Exhibit 2037 — Piazza filed Dec. 23, 2019 in *Inter Partes* Review of U.S. Pat. No. 7,736,388; Case No. IPR2019-01546, 15 pages.
Exhibit 2040 — Kheradvar filed Dec. 23, 2019 in *Inter Partes* Review of U.S. Pat. No. 7,736,388; Case No. IPR2019-01546, 11 pages.
Exhibit 2041—FDA re MitraClip filed Dec. 23, 2019 in *Inter Partes* Review of U.S. Pat. No. 7,736,388; Case No. IPR2019-01546, 3 pages.
Exhibit 2042 — Gossl filed Dec. 23, 2019 in *Inter Partes* Review of U.S. Pat. No. 7,736,388; Case No. IPR2019-01546, 8 pages.
Exhibit 2043—Business Monitor Online filed Dec. 23, 2019 in *Inter Partes* Review of U.S. Pat. No. 7,736,388; Case No. IPR2019-01546, 2 pages.
Exhibit 2044—Excerpts MitraClip Physician Site filed Dec. 23, 2019 in *Inter Partes* Review of U.S. Pat. No. 7,736,388; Case No. IPR2019-01546, 6 pages.
Exhibit 2045—Feldman 2009 filed Dec. 23, 2019 in *Inter Partes* Review of U.S. Pat. No. 7,736,388; Case No. IPR2019-01546, 9 pages.
Exhibit 2046—LexMachina Case Timing for Delaware filed Dec. 23, 2019 in *Inter Partes* Review of U.S. Pat. No. 7,736,388; Case No. IPR2019-01546, 1 page.
Exhibit 2047—Wood TCT 2018 filed Dec. 23, 2019 in *Inter Partes* Review of U.S. Pat. No. 7,736,388; Case No. IPR2019-01546, 5 pages.
Exhibit 2048—Excerpts MitraClip FAQ Physician filed Dec. 23, 2019 in *Inter Partes* Review of U.S. Pat. No. 7,736,388; Case No. IPR2019-01546, 4 pages.
Exhibit 2049—U.S. Pat. No. 8172856 to Eigler filed Dec. 23, 2019 in *Inter Partes* Review of U.S. Pat. No. 7,736,388; Case No. IPR2019-01546, 26 pages.
Exhibit 2050—U.S. Pat. No.9763658 to Eigler filed Dec. 23, 2019 in *Inter Partes* Review of U.S. Pat. No. 7,736,388; Case No. IPR2019-01546, 27 pages.
Exhibit 2052—Belden Technologies Inc v Superior Essex Communications LP filed Dec. 23, 2019 in *Inter Partes* Review of U.S. Pat. No. 7,736,388; Case No. IPR2019-01546, 3 pages.
Exhibit 2053—Wood TCTMD filed Dec. 23, 2019 in *Inter Partes* Review of U.S. Pat. No. 7,736,388; Case No. IPR2019-01546, 11 pages.
Exhibit 2054—Docket Nov. 21, 2019 filed Dec. 23, 2019 in *Inter Partes* Review of U.S. Pat. No. 7,736,388; Case No. IPR2019-01546, 44 pages.

(56) References Cited

OTHER PUBLICATIONS

Exhibit 2056—WO0003759A2 to Kuehn filed Dec. 23, 2019 in *Inter Partes* Review of U.S. Pat. No. 7,736,388; Case No. IPR2019-01546, 47 pages.
Exhibit 2061—Markman Order filed Dec. 23, 2019 in *Inter Partes* Review of U.S. Pat. No. 7,736,388; Case No. IPR2019-01546, 19 pages.
Exhibit 2062—Claim Construction Stipulation filed Dec. 23, 2019 in *Inter Partes* Review of U.S. Pat. No. 7,736,388; Case No. IPR2019-01546, 2 pages.
Exhibit 2063—Edwards Final Invalidity Contentions filed Dec. 23, 2019 in *Inter Partes* Review of U.S. Pat. No. 7,736,388; Case No. IPR2019-01546, 262 pages.
Exhibit 2066—Tremulis filed Dec. 23, 2019 in *Inter Partes* Review of U.S. Pat. No. 7,736,388; Case No. IPR2019-01546, 37 pages.
Exhibit 2067 — Decision Denying Institution filed Dec. 23, 2019 in *Inter Partes* Review of U.S. Pat. No. 7,736,388; Case No. IPR2019-01546, 34 pages.
Patent Owner Preliminary Response filed Nov. 27, 2019 in *Inter Partes* Review of U.S. Pat. No. 7,288,097, Case No. IPR2019-01479, 86 pages.
Exhibit 2001—Quinn Declaration filed Nov. 27, 2019 in *Inter Partes* Review of U.S. Pat. No. 7,288,097, Case No. IPR2019-01479, 52 pages.
Exhibit 2002—Quinn CV filed Nov. 27, 2019 in *Inter Partes* Review of U.S. Pat. No. 7,288,097, Case No. IPR2019-01479, 3 pages.
Exhibit 2003—Rovin Declaration filed Nov. 27, 2019 in *Inter Partes* Review of U.S. Pat. No. 7,288,097, Case No. IPR2019-01479, 42 pages.
Exhibit 2004—Rovin CV filed Nov. 27, 2019 in *Inter Partes* Review of U.S. Pat. No. 7,288,097, Case No. IPR2019-01479, 10 pages.
Exhibit 2005—U.S. Pat. No. 5,823,956 filed Nov. 27, 2019 in *Inter Partes* Review of U.S. Pat. No. 7,288,097, Case No. IPR2019-01479, 54 pages.
Exhibit 2006—FDA Letter filed Nov. 27, 2019 in *Inter Partes* Review of U.S. Pat. No. 7,288,097, Case No. IPR2019-01479, 16 pages.
Exhibit 2007 — NY Times Article filed Nov. 27, 2019 in *Inter Partes* Review of U.S. Pat. No. 7,288,097, Case no. IPR2019-01479, 5 pages.
Exhibit 2008—Yoganathan Report filed Nov. 27, 2019 in *Inter Partes* Review of U.S. Pat. No. 7,288,097, Case No. IPR2019-01479, 449 pages.
Exhibit 2009 — Complaint filed Nov. 27, 2019 in *Inter Partes* Review of U.S. Pat. No. 7,288,097, Case No. IPR2019-01479, 32 pages.
Exhibit 2011—Scheduling Order filed Nov. 27, 2019 in *Inter Partes* Review of U.S. Pat. No. 7,288,097, Case No. IPR2019-01479, 16 pages.
Exhibit 2012—Coapt MitraClip filed Nov. 27, 2019 in *Inter Partes* Review of U.S. Pat. No. 7,288,097, Case No. IPR2019-01479, 9 pages.
Exhibit 2013—Demonstrative Comparing POPR to Invalidity Contentions filed Nov. 27, 2019 in *Inter Partes* Review of U.S. Pat. No. 7,288,097, Case No. IPR2019-01479, 1 page.
Exhibit 2016—US20040167539 filed Nov. 27, 2019 in *Inter Partes* Review of U.S. Pat. No. 7,288,097, Case No. IPR2019-01479, 21 pages.
Exhibit 2021 — Perlowski Pt. 1 filed Nov. 27, 2019 in *Inter Partes* Review of U.S. Pat. No. 7,288,097, Case No. IPR2019-01479, 100 pages.
Exhibit 2021 — Perlowski Pt. 2 filed Nov. 27, 2019 in *Inter Partes* Review of U.S. Pat. No. 7,288,097, Case No. IPR2019-01479, 98 pages.
Exhibit 2022—Transcatheter Mitral Valve Repair with MitraClip filed Nov. 27, 2019 in *Inter Partes* Review of U.S. Pat. No. 7,288,097, Case No. IPR2019-01479, 20 pages.
Exhibit 2023—Feldman 2005 filed Nov. 27, 2019 in *Inter Partes* Review of U.S. Pat. No. 7,288,097, Case No. IPR2019-01479, 7 pages.
Exhibit 2029 — Maisano 2013 filed Nov. 27, 2019 in *Inter Partes* Review of U.S. Pat. No. 7,288,097, Case No. IPR2019-01479, 10 pages.
Exhibit 2030 — Alfieri filed Nov. 27, 2019 in *Inter Partes* Review of U.S. Pat. No. 7,288,097, Case No. IPR2019-01479, 8 pages.
Exhibit 2031—MitraClip Instructions for Use filed Nov. 27, 2019 in *Inter Partes* Review of U.S. Pat. No. 7,288,097, Case No. IPR2019-01479, 54 pages.
Exhibit 2032—Transcript Feldman re Everest filed Nov. 27, 2019 in *Inter Partes* Review of U.S. Pat. No. 7,288,097, Case No. IPR2019-01479, 3 pages.
Exhibit 2034—Edwards Analyst Investor Day filed Nov. 27, 2019 in *Inter Partes* Review of U.S. Pat. No. 7,288,097, Case No. IPR2019-01479, 49 pages.
Exhibit 2035 — Mack filed Nov. 27, 2019 in *Inter Partes* Review of U.S. Pat. No. 7,288,097, Case No. IPR2019-01479, 3 pages.
Exhibit 2036 — Rogoski filed Nov. 27, 2019 in Inter *Partes Review* of U.S. Pat. No. 7,288,097, Case No. IPR2019-01479, 3 pages.
Exhibit 2037 — Piazza filed Nov. 27, 2019 in *Inter Partes* Review of U.S. Pat. No. 7,288,097, Case No. IPR2019-01479, 15 pages.
Exhibit 2040 — Kheradvar filed Nov. 27, 2019 in *Inter Partes* Review of U.S. Pat. No. 7,288,097, Case No. IPR2019-01479, 11 pages.
Exhibit 2042 — Gossl filed Nov. 27, 2019 in *Inter Partes* Review of U.S. Pat. No. 7,288,097, Case No. IPR2019-01479, 8 pages.
Exhibit 2043—Business Monitor Online filed Nov. 27, 2019 in *Inter Partes* Review of U.S. Pat. No. 7,288,097, Case No. IPR2019-01479, 2 pages.
Exhibit 2044—Excerpts MitraClip Physician Site filed Nov. 27, 2019 in *Inter Partes* Review of U.S. Pat. No. 7,288,097, Case No. IPR2019-01479, 6 pages.
Exhibit 2045—Feldman 2009 filed Nov. 27, 2019 in *Inter Partes* Review of U.S. Pat. No. 7,288,097, Case No. IPR2019-01479, 9 pages.
Exhibit 2046—LexMachina Case Timing for Delaware filed Nov. 27, 2019 in *Inter Partes* Review of U.S. Pat. No. 7,288,097, Case No. IPR2019-01479, 1 page.
Exhibit 2047—Wood TCT 2018 filed Nov. 27, 2019 in *Inter Partes* Review of U.S. Pat. No. 7,288,097, Case No. IPR2019-01479, 5 pages.
Exhibit 2048—Excerpts MitraClip FAQ Physician filed Nov. 27, 2019 in *Inter Partes* Review of U.S. Pat. No. 7,288,097, Case No. IPR2019-01479, 4 pages.
Exhibit 2052—Belden Technologies Inc v. Superior Essex Communications LP filed Nov. 27, 2019 in *Inter Partes* Review of U.S. Pat. No. 7,288,097, Case No. IPR2019-01479, 3 pages.
Exhibit 2055—Letter re Markman Hearing filed Nov. 27, 2019 in *Inter Partes* Review of U.S. Pat. No. 7,288,097, Case No. IPR2019-01479, 2 pages.
Exhibit 2056—WO0003759A2 to Kuehn filed Nov. 27, 2019 in *Inter Partes* Review of U.S. Pat. No. 7,288,097, Case No. IPR2019-01479, 47 pages.
Exhibit 2060—Docket Nov. 21, 2019 filed Nov. 27, 2019 in *Inter Partes* Review of U.S. Pat. No. 7,288,097, Case No. IPR2019-01479, 44 pages.
Exhibit 2061—Markman Order filed Nov. 27, 2019 in *Inter Partes* Review of U.S. Pat. No. 7,288,097, Case No. IPR2019-01479, 19 pages.
Exhibit 2062—Claim Construction Stipulation filed Nov. 27, 2019 in *Inter Partes* Review of U.S. Pat. No. 7,288,097, Case No. IPR2019-01479, 2 pages.
Exhibit 2063—Edwards Final Invalidity Contentions filed Nov. 27, 2019 in *Inter Partes* Review of U.S. Pat. No. 7,288,097, Case No. IPR2019-01479, 262 pages.
Exhibit 2064—'097 File History Part 1 filed Nov. 27, 2019 in *Inter Partes* Review of U.S. Pat. No. 7,288,097, Case No. IPR2019-01479, 408 pages.
Exhibit 2064—'097 File History Part 2 filed Nov. 27, 2019 in *Inter Partes* Review of U.S. Pat. No. 7,288,097, Case No. IPR2019-01479, 592 pages.

(56) References Cited

OTHER PUBLICATIONS

Exhibit 2064—'097 File History Part 3 filed Nov. 27, 2019 in *Inter Partes* Review of U.S. Pat. No. 7,288,097, Case No. IPR2019-01479, 386 pages.
Exhibit 2064—'097 File History Part 4 filed Nov. 27, 2019 in *Inter Partes* Review of U.S. Pat. No. 7,288,097, Case No. IPR2019-01479, 291 pages.
Exhibit 2065 — Gunnai filed Nov. 27, 2019 in *Inter Partes* Review of U.S. Pat. No. 7,288,097, Case No. IPR2019-01479, 5 pages.
Certificate of Correction Exhibit 2018 filed Oct. 28, 2019 in *Inter Partes* Review of U.S. Pat. No. 6,461,366, Case No. IPR2019-01285, 1 page.
Patent Owner Opposing Brief and Conditional Motion for Leave filed Oct. 28, 2019 in *Inter Partes* Review of U.S. Pat. No. 6,461,366, Case No. IPR2019-01285, 17 pages.
Petitioners' Reply re CoC filed Nov. 1, 2019 in *Inter Partes* Review of U.S. Pat. No. 6,461,366, Case No. IPR2019-01285, 10 pages.
Patent Owner's Surreply re CoC filed Nov. 8, 2019 in *Inter Partes* Review of U.S. Pat. No. 6,461,366, Case No. IPR2019-01285, 10 pages.
Petitioners' Reply to POPR filed Dec. 3, 2019 in *Inter Partes* Review of U.S. Pat. No. 6,461,366, Case No. IPR2019-01285, 17 pages.
Patent Owner's Surreply to POPR filed Dec. 12, 2019 in *Inter Partes* Review of U.S. Pat. No. 6,461,366, Case No. IPR2019-01285, 16 pages.
Decision Denying Institution filed Jan. 9, 2020 in *Inter Partes* Review of U.S. Pat. No. 6,461,366, Case No. IPR2019-01285, 9 pages.
Edwards Final Invalidity Contentions dated Nov. 6, 2019, 262 pages in *Abbott Cardiovascular Systems, Inc. et al.* v. *Edwards Lifesciences Corp. et al.*, Case No. 19-149 (MN) (District of Delaware).
Opening Expert Report of Morten Olgaard Jensen Redacted dated Nov. 11, 2019, 615 pages in *Abbott Cardiovascular Systems, Inc. et al.* v. *Edwards Lifesciences Corp. et al.*, Case No. 19-149 (MN) (District of Delaware).
Rebuttal Expert Report of Robert Chang Redacted dated Dec. 6, 2019, 497 pages in *Abbott Cardiovascular Systems, Inc. et al.* v. *Edwards Lifesciences Corp. et al.*, Case No. 19-149 (MN) (District of Delaware).
Reply Expert Report of Morten Olgaard Jensen Redacted dated Dec. 20, 2019, 283 pages in *Abbott Cardiovascular Systems, Inc. et al.* v. *Edwards Lifesciences Corp. et al.*, Case No. 19-149 (MN) (District of Delaware).
Statement of Opposition dated Oct. 25, 2019, 2 pages in *Evalve, Inc. et al.* v. *Edwards Lifesciences Limited*, Claim No. HP-2019-000003 (United Kingdom).
Intellectual Property Office Letter dated Nov. 18, 2019, 4 pages in *Evalve, Inc. et al.* v. *Edwards Lifesciences Limited*, Claim No. HP-2019-000003 (United Kingdom).
Re-Amended Grounds of Invalidity dated Nov. 29, 2019, 4 pages in *Evalve, Inc. et al.* v. *Edwards Lifesciences Limited*, Claim No. HP-2019-000003 (United Kingdom).
Copelan, "How Dr. Oz Kick-Started a Groundbreaking Device for Patients with Heart Failure," Parade (Sep. 26, 2018).
Cribier et al., "Percutaneous Mechanical Mitral Commissurotomy With a Newly Designed Metallic Valvulotome: Immediate Results of the Initial Experience in 153 Patients," Circulation 99:793-799 (1999).
Dias de Azeredo Bastos et al., "Percutaneous Mechanical Mitral Commissurotomy Performed With a Cribier's Metallic Valvulotome. Initial Results," Arq Bras Cardiol, 77:126-131 (2001).
Freeny et al., "Subselective Diagnostic and Interventional Arteriography Using a Simple Coaxial Catheter System," Cardiovasc. Intervent. Radiol. 7:209-213 (1984).
Ing et al., "The Snare-Assisted Technique for Transcatheter Coil Occlusion of Moderate to Large Patent Ductus Arteriosus: Immediate and Intermediate Results," J. Am. Col. Cardiol. 33(6):1710-1718 (1999).
Rahhal, "Tiny device to 'zip up' leaky hearts invented by Dr Oz 20 years ago could save millions, study finds," Daily Mail (Sep. 26, 2018).
U.S. Appl. No. 60/316,892 to Tremulis et al., filed Aug. 31, 2001.
Waller et al., "Anatomic Basis for and Morphologic Results from Catheter Balloon Valvuloplasty of Stenotic Mitral Valves," Clin. Cardiol. 13:655-661 (1990).
Decision Denying Institution dated Jan. 9, 2020 in Inter Partes Review of U.S. Pat. No. 6,461,366, Case No. IPR2019-01285, 9 pages.
Abbott's Opening Skeleton Argument dated Dec. 4, 2019 in *Evalve, Inc. et al.* v. *Edwards Lifesciences Limited*, Claim No. HP-2019-000003 (United Kingdom), 105 pages.
Edwards' Skeleton Argument dated Dec. 4, 2019 in *Evalve, Inc. et al.* v *Edwards Lifesciences Limited*, Claim No. HP-2019-000003 (United Kingdom), 59 pages.
Abbott's Closing Skeleton Argument dated Dec. 16, 2019 in *Evalve, Inc. et al.* v. *Edwards Lifesciences Limited*, Claim No. HP-2019-000003 (United Kingdom), 88 pages.
Edwards' Closing Submissions dated Dec. 16, 2019 in *Evalve, Inc. et al.* v. *Edwards Lifesciences Limited*, Claim No. HP-2019-000003 (United Kingdom), 73 pages.
Statement of Defense dated Jan. 27, 2020 in *Evalve, Inc. et al.* v. *Edwards Lifesciences SA et al.*, (Switzerland), 179 pages.
List of Evidence to the Statement of Defense dated Jan. 27, 2020 in *Evalve, Inc. et al.* v. *Edwards Lifesciences SA et al.*, (Switzerland), 2 pages.
Exhibit 01 to the Statement of Defense dated Jan. 27, 2020 in *Evalve, Inc. et al.* v. *Edwards Lifesciences SA et al.*, (Switzerland), 1 page.
Exhibit 02 to the Statement of Defense dated Jan. 27, 2020 in *Evalve, Inc. et al.* v. *Edwards Lifesciences SA et al.*, (Switzerland), 1 page.
Exhibit 03 to the Statement of Defense dated Jan. 27, 2020 in *Evalve, Inc. et al.* v. *Edwards Lifesciences SA et al.*, (Switzerland), 2 pages.
Exhibit 04 to the Statement of Defense dated Jan. 27, 2020 in *Evalve, Inc. et al.* v. *Edwards Lifesciences SA et al.*, (Switzerland), 2 pages.
Exhibit 05 to the Statement of Defense dated Jan. 27, 2020 in *Evalve, Inc. et al.* v. *Edwards Lifesciences SA et al.*, (Switzerland), 1 page.
Exhibit 06 to the Statement of Defense dated Jan. 27, 2020 in *Evalve, Inc. et al.* v. *Edwards Lifesciences SA et al.*, (Switzerland), 7 pages.
Exhibit 07 to the Statement of Defense dated Jan. 27, 2020 in *Evalve, Inc. et al.* v. *Edwards Lifesciences SA et al.*, (Switzerland), 15 pages.
Exhibit 08 to the Statement of Defense dated Jan. 27, 2020 in *Evalve, Inc. et al.* v. *Edwards Lifesciences SA et al.*, (Switzerland), 3 pages.
Exhibit 09 to the Statement of Defense dated Jan. 27, 2020 in *Evalve, Inc. et al.* v. *Edwards Lifesciences SA et al.*, (Switzerland), 6 pages.
Exhibit 10 to the Statement of Defense dated Jan. 27, 2020 in *Evalve, Inc. et al.* v.*Edwards Lifesciences SA et al.*, (Switzerland), 28 pages.
Exhibit 11 to the Statement of Defense dated Jan. 27, 2020 in *Evalve, Inc. et al.* v. *Edwards Lifesciences SA et al.*, (Switzerland), 4 pages.
Exhibit 12 to the Statement of Defense dated Jan. 27, 2020 in *Evalve, Inc. et al.* v. *Edwards Lifesciences SA et al.*, (Switzerland), 156 pages.
Exhibit 13 to the Statement of Defense dated Jan. 27, 2020 in *Evalve, Inc. et al.* v. *Edwards Lifesciences SA et al.*, (Switzerland), 95 pages.
Exhibit 14 to the Statement of Defense dated Jan. 27, 2020 in *Evalve, Inc. et al.* v. *Edwards Lifesciences SA et al.*, (Switzerland), 14 pages.
Exhibit 15 to the Statement of Defense dated Jan. 27, 2020 in *Evalve, Inc. et al.* v. *Edwards Lifesciences SA et al.*, (Switzerland), 3 pages.

(56) References Cited

OTHER PUBLICATIONS

Exhibit 16 to the Statement of Defense dated Jan. 27, 2020 in *Evalve, Inc. et al.* v. *Edwards Lifesciences SA et al.*, (Switzerland), 11 pages.
Exhibit 17 to the Statement of Defense dated Jan. 27, 2020 in *Evalve, Inc. et al.* v. *Edwards Lifesciences SA et al.*, (Switzerland), 12 pages.
Exhibit 18 to the Statement of Defense dated Jan. 27, 2020 in *Evalve, Inc. et al.* v. *Edwards Lifesciences SA et al.*, (Switzerland), 6 pages.
Exhibit 19 to the Statement of Defense dated Jan. 27, 2020 in *Evalve, Inc. et al.* v. *Edwards Lifesciences SA et al.*, (Switzerland), 2 pages.
Exhibit 20 to the Statement of Defense dated Jan. 27, 2020 in *Evalve, Inc. et al.* v. *Edwards Lifesciences SA et al.*, (Switzerland), 2 pages.
Exhibit 21 to the Statement of Defense dated Jan. 27, 2020 in *Evalve, Inc. et al.* v. *Edwards Lifesciences SA et al.*, (Switzerland), 13 pages.
Exhibit 22 to the Statement of Defense dated Jan. 27, 2020 in *Evalve, Inc. et al.* v. *Edwards Lifesciences SA et al.*, (Switzerland), 2 pages.
Abbott Technical Brief (Italian) dated Jan. 10, 2020 in *Abbott Cardiovascular Systems Inc. et al.* v. *Edwards Lifesciences LLC et al.*, (Italy), 51 pages.
Abbott Technical Brief Translation dated Jan. 10, 2020 in *Abbott Cardiovascular Systems Inc. et al.* v. *Edwards Lifesciences LLC et al.*, (Italy), 49 pages.
Edwards Technical Brief (Italian) dated Jan. 10, 2020 in *Abbott Cardiovascular Systems Inc. et al.* v. *Edwards Lifesciences LLC et al.*, (Italy), 24 pages.
Edwards Technical Brief Translation dated Jan. 10, 2020 in *Abbott Cardiovascular Systems Inc. et al.* v. *Edwards Lifesciences LLC et al.*, (Italy), 20 pages.
Extended Search Report dated Jan. 8, 2020 in EP Application No. 19198393.
Decision Denying Institution dated Jan. 16, 2020 in Inter Partes Review of U.S. Pat. No. 8,057,493, Case No. IPR2019-01301, 33 pages.
Interlocutory Decision dated Jan. 3, 2020 in Opposition of EP1624810, 37 pages.
Minutes of the oral proceedings dated Jan. 3, 2020 in Opposition of EP1624810, 23 pages.

\* cited by examiner

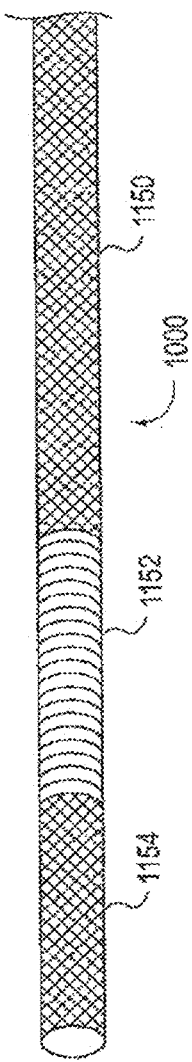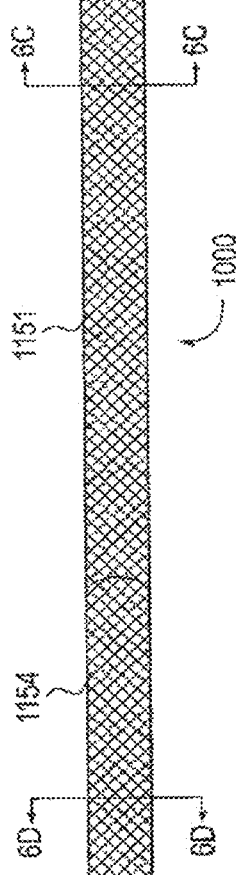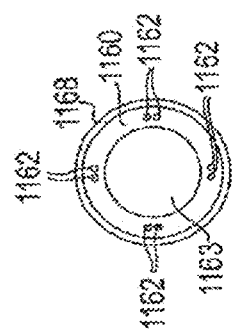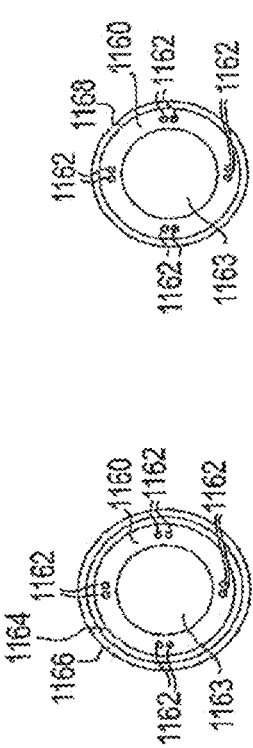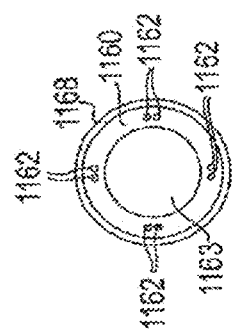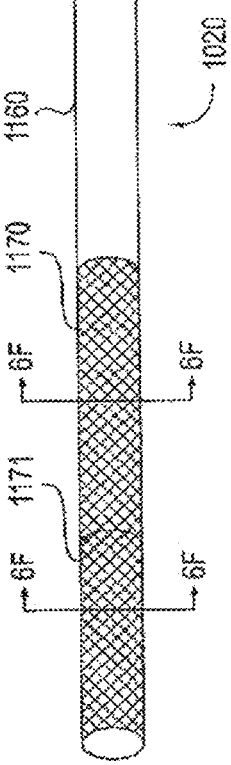

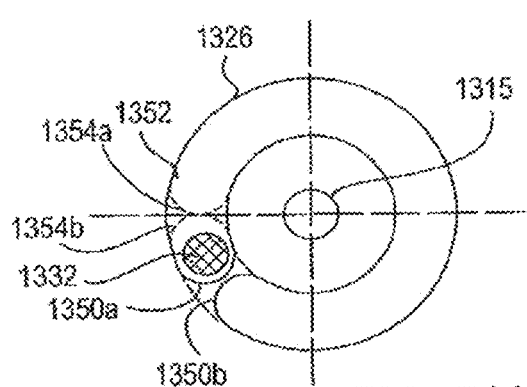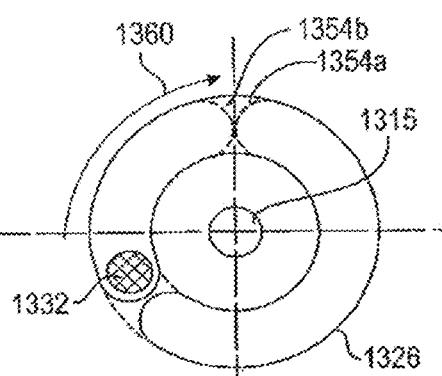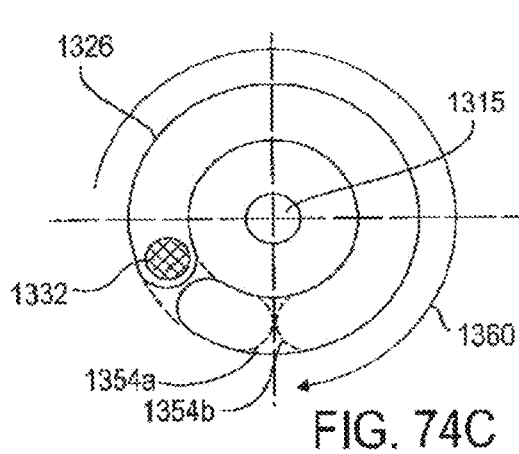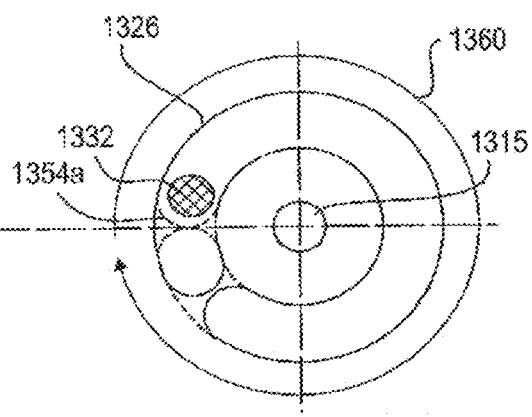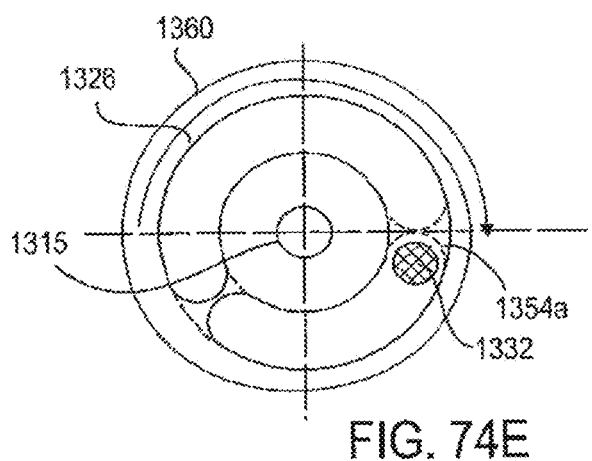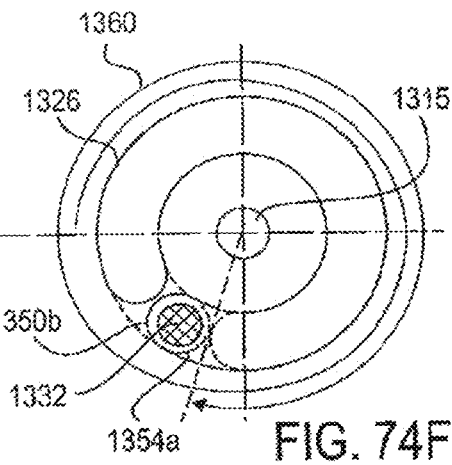

FIXATION DEVICES, SYSTEMS AND METHODS FOR ENGAGING TISSUE

CROSS-REFERENCES TO RELATED APPLICATIONS

This application is a continuation of U.S. patent application Ser. No. 15/483,523 filed Apr. 10, 2017, which is a continuation of U.S. patent application Ser. No. 15/334,992 filed Oct. 26, 2016, which is a continuation of U.S. patent application Ser. No. 14/259,826, now U.S. Pat. No. 9,510,829, filed Apr. 23, 2014, which is a divisional of U.S. patent application Ser. No. 13/899,901, now U.S. Pat. No. 8,740,920, filed May 22, 2013, which is a continuation of U.S. patent application Ser. No. 12/636,471, now U.S. Pat. No. 8,500,761, filed Dec. 11, 2009, which is a continuation of, and claims the benefit of priority from U.S. application Ser. No. 11/962,654, now U.S. Pat. No. 7,655,015, filed Dec. 21, 2007, which is a divisional of U.S. patent application Ser. No. 10/441,531, now U.S. Pat. No. 7,563,267, filed May 19, 2003, the full disclosures of which are hereby incorporated herein by reference.

BACKGROUND OF THE INVENTION

1. Field of the Invention

The present invention relates generally to medical methods, devices, and systems. In particular, the present invention relates to methods, devices, and systems for the endovascular, percutaneous or minimally invasive surgical treatment of bodily tissues, such as tissue approximation or valve repair. More particularly, the present invention relates to repair of valves of the heart and venous valves.

Surgical repair of bodily tissues often involves tissue approximation and fastening of such tissues in the approximated arrangement. When repairing valves, tissue approximation includes coapting the leaflets of the valves in a therapeutic arrangement which may then be maintained by fastening or fixing the leaflets. Such coaptation can be used to treat regurgitation which most commonly occurs in the mitral valve.

Mitral valve regurgitation is characterized by retrograde flow from the left ventricle of a heart through an incompetent mitral valve into the left atrium. During a normal cycle of heart contraction (systole), the mitral valve acts as a check valve to prevent flow of oxygenated blood back into the left atrium. In this way, the oxygenated blood is pumped into the aorta through the aortic valve. Regurgitation of the valve can significantly decrease the pumping efficiency of the heart, placing the patient at risk of severe, progressive heart failure.

Mitral valve regurgitation can result from a number of different mechanical defects in the mitral valve or the left ventricular wall. The valve leaflets, the valve chordae which connect the leaflets to the papillary muscles, the papillary muscles or the left ventricular wall may be damaged or otherwise dysfunctional. Commonly, the valve annulus may be damaged, dilated, or weakened, limiting the ability of the mitral valve to close adequately against the high pressures of the left ventricle.

The most common treatments for mitral valve regurgitation rely on valve replacement or repair including leaflet and annulus remodeling, the latter generally referred to as valve annuloplasty. A recent technique for mitral valve repair which relies on suturing adjacent segments of the opposed valve leaflets together is referred to as the "bow-tie" or "edge-to-edge" technique. While all these techniques can be very effective, they usually rely on open heart surgery where the patient's chest is opened, typically via a sternotomy, and the patient placed on cardiopulmonary bypass. The need to both open the chest and place the patient on bypass is traumatic and has associated high mortality and morbidity.

For these reasons, it would be desirable to provide alternative and additional methods, devices, and systems for performing the repair of mitral and other cardiac valves. Such methods, devices, and systems should preferably not require open chest access and be capable of being performed either endovascularly, i.e., using devices which are advanced to the heart from a point in the patient's vasculature remote from the heart or by a minimally invasive approach. Further, such devices and systems should provide features which allow repositioning and optional removal of a fixation device prior to fixation to ensure optimal placement. Still more preferably, the methods, devices, and systems would be useful for repair of tissues in the body other than heart valves. At least some of these objectives will be met by the inventions described hereinbelow.

DESCRIPTION OF THE BACKGROUND ART

Minimally invasive and percutaneous techniques for coapting and modifying mitral valve leaflets to treat mitral valve regurgitation are described in PCT Publication Nos. WO 98/35638; WO 99/00059; WO 99/01377; and WO 00/03759.

Maisano et al. (1998) *Eur. J. Cardiothorac. Surg.* 13:240-246; Fucci et al. (1995) *Eur. J. Cardiothorac. Surg.* 9:621-627; and Umana et al. (1998) *Ann. Thorac. Surg.* 66:1640-1646, describe open surgical procedures for performing "edge-to-edge" or "bow-tie" mitral valve repair where edges of the opposed valve leaflets are sutured together to lessen regurgitation. Dec and Fuster (1994) *N. Engl. J. Med.* 331:1564-1575 and Alvarez et al. (1996) *J. Thorac. Cardiovasc. Surg.* 112:238-247 are review articles discussing the nature of and treatments for dilated cardiomyopathy.

Mitral valve annuloplasty is described in the following publications. Bach and Bolling (1996) *Am. J. Cardiol.* 78:966-969; Kameda et al. (1996) *Ann. Thorac. Surg.* 61:1829-1832; Bach and Bolling (1995) *Am. Heart J.* 129:1165-1170; and Bolling et al. (1995) 109:676-683. Linear segmental annuloplasty for mitral valve repair is described in Ricchi et al. (1997) *Ann. Thorac. Surg.* 63:1805-1806. Tricuspid valve annuloplasty is described in McCarthy and Cosgrove (1997) *Ann. Thorac. Surg.* 64:267-268; Tager et al. (1998) *Am. J. Cardiol.* 81:1013-1016; and Abe et al. (1989) *Ann. Thorac. Surg.* 48:670-676.

Percutaneous transluminal cardiac repair procedures are described in Park et al. (1978) *Circulation* 58:600-608; Uchida et al. (1991) *Am. Heart J.* 121: 1221-1224; and Ali Khan et al. (1991) *Cathet. Cardiovasc. Diagn.* 23:257-262.

Endovascular cardiac valve replacement is described in U.S. Pat. Nos. 5,840,081; 5,411,552; 5,554,185; 5,332,402; 4,994,077; and 4,056,854. See also U.S. Pat. No. 3,671,979 which describes a catheter for temporary placement of an artificial heart valve.

Other percutaneous and endovascular cardiac repair procedures are described in U.S. Pat. Nos. 4,917,089; 4,484,579; and 3,874,338; and PCT Publication No. WO 91/01689.

Thoracoscopic and other minimally invasive heart valve repair and replacement procedures are described in U.S. Pat. Nos. 5,855,614; 5,829,447; 5,823,956; 5,797,960; 5,769,812; and 5,718,725.

BRIEF SUMMARY OF THE INVENTION

The invention provides devices, systems and methods for tissue approximation and repair at treatment sites. The devices, systems and methods of the invention will find use in a variety of therapeutic procedures, including endovascular, minimally-invasive, and open surgical procedures, and can be used in various anatomical regions, including the abdomen, thorax, cardiovascular system, heart, intestinal tract, stomach, urinary tract, bladder, lung, and other organs, vessels, and tissues. The invention is particularly useful in those procedures requiring minimally-invasive or endovascular access to remote tissue locations, where the instruments utilized must negotiate long, narrow, and tortuous pathways to the treatment site. In addition, many of the devices and systems of the invention are adapted to be reversible and removable from the patient at any point without interference with or trauma to internal tissues.

In preferred embodiments, the devices, systems and methods of the invention are adapted for fixation of tissue at a treatment site. Exemplary tissue fixation applications include cardiac valve repair, septal defect repair, vascular ligation and clamping, laceration repair and wound closure, but the invention may find use in a wide variety of tissue approximation and repair procedures. In a particularly preferred embodiment, the devices, systems and methods of the invention are adapted for repair of cardiac valves, and particularly the mitral valve, as a therapy for regurgitation. The invention enables two or more valve leaflets to be coapted using an "edge-to-edge" or "bow-tie" technique to reduce regurgitation, yet does not require open surgery through the chest and heart wall as in conventional approaches. Using the devices, systems and methods of the invention, the mitral valve can be accessed from a remote surgical or vascular access point and the two valve leaflets may be coapted using endovascular or minimally invasive approaches. While less preferred, in some circumstances the invention may also find application in open surgical approaches as well. According to the invention, the mitral valve may be approached either from the atrial side (antegrade approach) or the ventricular side (retrograde approach), and either through blood vessels or through the heart wall.

The devices, systems and methods of the invention are centered on variety of devices which may be used individually or in a variety of combinations to form interventional systems. In preferred embodiments, the interventional system includes a multi-catheter guiding system, a delivery catheter and an interventional device. Each of these components will be discussed herein.

In an exemplary embodiment, the invention provides a fixation device having a pair of distal elements (or fixation elements), each distal element having a free end and an engagement surface for engaging the tissue, wherein the distal elements are moveable between a first position for capturing the tissue and a second position for fixing the tissue. Preferably, the engagement surfaces are spaced apart in the first position and are closer together and generally face toward each other in the second position. The fixation device is preferably delivered to a target location in a patient's body by a delivery catheter having an elongated shaft, a proximal end and a distal end, the delivery catheter being configured to be positioned at the target location from a remote access point such as a vascular puncture or cut-down or a surgical penetration. In a preferred embodiment, the target location is a valve in the heart.

The fixation device is preferably delivered with the distal elements in a delivery position configured to minimize the profile of the device. When approaching the mitral valve from the atrial side, some embodiments of the fixation device allow the device to be delivered with the free ends of the distal elements pointing in a generally proximal direction forming an angle of less than about 90°, preferably less than about 20°, relative to the longitudinal axis of the delivery device shaft. In this position the engagement surfaces are facing generally toward each other, being disposed at an angle of less than about 180°, and preferably less than about 40°, relative to each other. For ventricular approaches, in the delivery position the free ends of the distal elements are pointing in a generally distal direction and form an angle of less than about 90°, preferably less than about 20° relative to the longitudinal axis of the delivery device shaft. In this position, the engagement surfaces are facing generally toward each other, usually being disposed at an angle of less than about 180°, and preferably less than about 90°, relative to each other. Alternatively, in some ventricular approaches, it may be preferred to have the free ends of the fixation elements pointing in a generally proximal direction and the engagement surfaces facing away from each other in the delivery position.

In order to provide for the reversibility and removability of the devices and systems of the invention, the distal elements preferably are movable to an inverted position that minimizes entanglement and interferences with surrounding tissues should the device be desired to be withdrawn. In mitral repair applications, this is particularly important due to the presence of chordae tendonae, valve leaflets and other tissues with which devices may become entangled. For approaches from the atrial side of the mitral valve, in the inverted position, the free ends will be pointing in a generally distal direction relative to the catheter shaft and the engagement surfaces will be facing generally away from each other, usually being disposed at an angle of more than about 180°, and preferably more than 270°, relative to each other. For ventricular approaches to the valve, in the inverted position the free ends will be pointing in a distal direction relative to the catheter shaft and the engagement surfaces will be facing generally toward each other, usually being disposed at an angle of less than about 180°, and preferably less than 90°, relative to each other.

In the open position, the engagement surfaces of the distal elements preferably form an angle of up to 180° relative to each other so as to maximize the area in which to capture the valve leaflets or other target tissue. The distal elements are preferably movable to a closed position in which the engagement surfaces engage each other or form an angle as small as 0° relative to each other. The distal elements are configured to be adjusted to and left permanently in any of various positions between the open and closed positions to allow for fixation of tissues of various thickness, geometry, and spacing.

In a preferred embodiment, the fixation device of the invention will further include at least one proximal element (or gripping element). Each proximal element and distal element will be movable relative to each other and configured to capture tissue between the proximal element and the engagement surface of the distal element. Preferably, the distal elements and proximal elements are independently movable but in some embodiments may be movable with the same mechanism. The proximal element may be preferably biased toward the engagement surface of the fixation element to provide a compressive force against tissue captured therebetween.

In another aspect, the invention provides a fixation device for engaging tissue comprising a coupling member configured for coupling a catheter and a pair of distal elements connected to the coupling member, each distal element having an engagement surface for engaging the tissue. The distal elements are moveable between an open position wherein the distal elements extend radially outwardly facing the engagement surfaces toward a first direction, and an inverted position wherein the distal elements have rotated away from the first direction facing the engagement surfaces radially outwardly.

In a further aspect, the distal elements of the invention are adapted to receive a suture passed through the target tissue. For example, implant pledgets may be detachably mounted to the distal elements so as to be positionable against a surface of tissue engaged by the distal elements. A suture may then be passed through the tissue and implant pledget, which are supported by the distal element. The implant pledgets are then detached from the distal elements, which may be withdrawn from the site, and the suture is tensioned and secured to the target tissue. The delivery catheter, in this embodiment, will further include a movable fixation tool or penetration element for penetrating the target tissue and the implant pledget. A suture is coupled to the penetration element and preferably an anchor is attached to the suture. The penetration element is movable relative to the catheter to penetrate the target tissue and the implant pledget, bringing with it the suture and anchor. The anchor is configured to deploy into an expanded configuration so as to securely engage the implant pledget opposite the target tissue, retaining the suture therein. For the mitral valve, an implant pledget and suture may be similarly deployed in both leaflets, and the sutures secured to one another to coapt the leaflets. Thus, in this embodiment, the distal elements are used to deliver implant pledgets and secure them to the target tissue, but are not themselves deployed at the site as in other embodiments. However, following deployment of the implant pledgets and associated sutures, the distal elements must be withdrawn from the body. For this purpose, the distal elements are movable to an inverted position like the embodiments described above to facilitate withdrawing the device without interference or injury to surrounding tissues.

In some applications such as the repair of the mitral valve, the fixation device is adapted to be detached from the delivery catheter and left permanently in the patient. In such applications, it is often desirable to promote tissue growth around the fixation device. For this purpose, some or all of the components of the fixation device are preferably covered with a covering or coating to promote tissue growth. In one embodiment, a biocompatible fabric cover is positioned over the distal elements and/or the proximal elements. The cover may optionally be impregnated or coated with various therapeutic agents, including tissue growth promoters, antibiotics, anti-clotting, blood thinning, and other agents. Alternatively or in addition, some or all of the fixation element and/or covering may be comprised of a bioerodable, biodegradable or bioabsorbable material so that it may degrade or be absorbed by the body after the repaired tissues have grown together.

The distal elements and proximal elements will be configured to provide high retention force so that the fixation device remains securely fastened to the target tissue throughout the cardiac cycle. At the same time, the distal and proximal elements will be configured to minimize trauma to the tissue engaged by them. This allows the fixation device to be removed from the tissue after initial application without creating clinically significant injury to the tissue. In order to enhance retention without creating significant trauma, the proximal elements and/or the distal elements may have friction-enhancing features on their surfaces that engage the target tissue. Such friction-enhancing features may include barbs, bumps, grooves, openings, channels, surface roughening, coverings, and coatings, among others. Optionally, magnets may be present in the proximal and/or distal elements. Preferably the friction-enhancing features and the magnets will be configured to increase the retention force of the distal and proximal elements on the tissue, while not leaving significant injury or scarring if the device is removed.

The distal and proximal elements may further have a shape and flexibility to maximize retention force and minimize trauma to the target tissue. In a preferred embodiment, the engagement surfaces of the distal elements have a concave shape configured to allow the proximal elements, along with the target tissue, to be nested or recessed within the distal elements. This increases the surface area of the tissue engaged by the distal elements and creates a geometry of tissue engagement that has a higher retention force than a planar engagement surface. To minimize trauma, the longitudinal edges as well as the free ends of the distal elements are preferably curved outwardly away from the engagement surface so that these edges present a rounded surface against the target tissue. The distal elements and/or the proximal elements may also be flexible so that they deflect to some degree in response to forces against the tissue engaged thereby, reducing the chances that the tissue will tear or bruise in response to such forces.

The fixation device will include an actuation mechanism for moving the distal elements between the open, closed, and inverted positions. A variety of actuation mechanisms may be used. In an exemplary embodiment, a coupling member connects the fixation device to the delivery catheter, and a stud is slidably coupled to the coupling member. In a "push to close/pull to open" embodiment, the distal elements are pivotably coupled to the stud and the actuation mechanism comprises a pair of link members connected between the distal elements and the coupling member, whereby sliding the stud relative to the coupling member pivots the distal elements inwardly or outwardly into the various positions. Alternatively, in a "push to open/pull to close" embodiment, the distal elements are pivotably coupled to the coupling member and the links connected between the distal elements and the stud.

The fixation device of the invention preferably includes a coupling member that is detachably connectable to the delivery catheter. The coupling member may have various constructions, but in an exemplary embodiment comprises an outer member having an axial channel, the outer member being coupled to one of either the distal elements or the actuation mechanism. An inner member extends slidably through the axial channel and is coupled to the other of either the distal elements or the actuation mechanism. The delivery catheter will be configured to detachably connect to both the inner member and the outer member. In one embodiment, the delivery catheter has a tubular shaft and an actuator rod slidably disposed in the tubular shaft. The junction of the outer member with the tubular shaft comprises a joining line, which may have a variety of shapes including sigmoid curves. The actuator rod extends from the delivery catheter through the axial channel in the outer member to maintain its connection with the tubular shaft. The actuator rod may be connected to the inner member by various connection structures, including threaded connections. By detachment of the actuator rod from the inner member and retraction of the actuator rod back into the tubular shaft, the outer member is released from the tubular shaft to allow deployment of the fixation device.

In a preferred embodiment, the fixation device further includes a locking mechanism that maintains the distal elements in a selected position relative to each other. Because the ideal degree of closure of the fixation device may not be known until it is actually applied to the target tissue, the locking mechanism is configured to retain the distal elements in position regardless of how open or closed they may be. While a variety of locking mechanisms may be used, in an exemplary embodiment the locking mechanism comprises a wedging element that is movable into frictional engagement with a movable component of the fixation device to prevent further movement of the distal elements. In embodiments utilizing the actuation mechanism described above, the component with which the wedging element engages may be the coupling member or the stud slidably coupled thereto. In one embodiment, the stud passes through an aperture in the coupling member that has a sloping sidewall, and the wedging element comprises a barbell disposed between the sidewall and the stud.

The fixation device preferably also includes an unlocking mechanism for releasing the locking mechanism, allowing the distal elements and proximal elements to move. In one embodiment, the unlocking mechanism comprises a harness coupled to the wedging element of the locking mechanism to reduce frictional engagement with the movable component of the fixation device. In an exemplary embodiment, the harness is slidably coupled to the coupling member and extends around the wedging element of the locking mechanism, whereby the harness can be retracted relative to the coupling member to disengage the wedging element from the stud.

In a further aspect, the invention provides an interventional system comprising a tubular guide having a proximal end, a distal end and a channel therebetween, the distal end of the tubular guide being deflectable about a first axis; a delivery catheter positionable through the channel, the delivery catheter having a flexible shaft with a proximal end, a distal end, a lumen therebetween, and an actuation element movably disposed in the lumen; and a fixation device having a coupling member releasably coupled to the distal end of the shaft, a first distal element movably coupled to the coupling member, and a first proximal element movable relative to the distal element, the first distal element being releasably coupled to the actuation element and movable therewith, the first distal element and the first proximal element being adapted to engage tissue therebetween.

The delivery device of the invention is adapted to allow the user to deliver the fixation device to the target site from a remote access point, whether through endovascular or surgical approaches, align the device with the target tissue, and to selectively close, open, invert, lock or unlock the distal element. In some embodiments, the delivery device will have a highly flexible, kink resistant, torsionally stiff shaft with minimal elongation and high compressive strength. The delivery device will also have the movable components and associated actuators to move the distal elements between the open, closed, and inverted positions, to move the proximal elements into engagement with the target tissue, to unlock the locking mechanism, and to detach the distal element from the delivery catheter. In a preferred embodiment, the delivery device comprises a delivery catheter having an elongated shaft which has an inner lumen. The distal end of the shaft is configured for detachable connection to the coupling member of the fixation device. An actuator rod is slidably disposed in the inner lumen and is adapted for detachable coupling to the stud or other component of the fixation device that moves the distal elements. A plurality of tubular guides, preferably in the form of metallic or polymeric coils, extend through the inner lumen of the shaft and are typically fixed to the shaft near its proximal and distal ends but are unrestrained therebetween, providing a highly flexible and kink-resistant construction. Lines for actuating the proximal elements and the unlocking mechanism of the fixation device extend through these tubular guides and are detachably coupled to the proximal element and unlocking mechanisms. These and other aspects of delivery catheters suitable for use in the present invention are described in copending application Ser. No. 10/441,687, filed on the same day as the present application, which has been incorporated herein by reference.

The delivery catheter may additionally include a tether that is detachably coupled to a portion of the fixation device for purposes of retrieval of the device following detachment from the delivery catheter. The tether may be a separate flexible filament extending from the delivery catheter to the fixation device, but alternatively may be a line coupled to either the unlocking mechanism or the proximal element and used also for actuating those components. In either case, the tether will be detachable from the fixation device so that it may be detached once the device has been deployed successfully.

The system of the invention may additionally include a guide that facilitates introduction and navigation of the delivery catheter and fixation device to the target location. The guide is preferably tubular with a channel extending between its proximal and distal ends in which the delivery catheter and fixation device may be slidably positioned. The distal end of the guide is steerable, usually being deflectable about at least one axis, and preferably about two axes. The guide will have a size, material, flexibility and other characteristics suitable for the application in which it is being used. For mitral valve repair, the guide is preferably configured to be introduced in a femoral vein and advanced through the inferior vena cava into the heart, across a penetration in the interatrial septum, and into alignment with the mitral valve in the left atrium. Alternatively, the guide may be configured for introduction in a femoral, axillary, or brachiocephalic artery and advancement through the aorta and aortic valve into the ventricle where it is steered into alignment with the mitral valve. In a further alternative, the guide may be configured for introduction through a puncture or incision in the chest wall and through an incision in the wall of the heart to approach the mitral valve.

In an exemplary embodiment, the guide comprises a multi-catheter guiding system which has two components, including an inner tubular member or inner guide catheter and an outer tubular member or outer guide catheter. The inner tubular member has a distal end deflectable about a first axis. The outer tubular member has a distal end deflectable about a second axis. Further, the inner tubular member may be rotatable relative to the outer tubular member about its longitudinal axis. Mobility in additional directions and about additional axes may optionally be provided. Additional aspects of guides usable in the system of the invention are described in pending application Ser. No. 10/441,508, which has been incorporated herein by reference.

The invention further provides methods of performing therapeutic interventions at a tissue site. In one embodiment, the method includes the steps of advancing an interventional tool having a proximal end, a distal end and a fixation device near the distal end to a location within a patient's body, wherein the fixation device includes a pair of distal elements each having a free end and an engagement surface; moving the distal elements to an open position wherein the free ends are spaced apart; positioning the distal elements such that the engagement surfaces engage tissue at the tissue site; and detaching the fixation device from the interventional tool. Preferably, the method further includes the step of inverting the distal elements to an inverted position wherein the free ends point generally in a distal direction. In some embodiments, the engagement surfaces will face generally away from each other in the inverted position, while in other embodiments, the engagement surfaces will face generally toward each other in the inverted position.

In an exemplary embodiment, the tissue site comprises first and second leaflets, and the step of moving the distal elements comprises coapting the leaflets. The leaflets may be part of a variety of tissue structures, but are preferably part of a cardiac valve such as the mitral valve. In antegrade approaches, the step of advancing will usually include inserting the fixation device through a valve annulus, e.g. from an atrium of the heart to a ventricle of the heart. In such approaches, the method may further include a step of withdrawing the fixation device through the valve annulus with the fixation device in the inverted position. Retrograde approaches are also provided, in which the step of advancing will include the step of passing the fixation device through a ventricle of the heart into an atrium of the heart. The step of advancing may further comprise transluminally positioning the fixation device through a blood vessel into the heart, and may include inserting the fixation device through an interatrial septum of the heart. Alternatively, the step of advancing may comprise inserting the device through a surgical penetration in a body wall.

The method may further include moving the distal elements to a closed position after the step of positioning, the free ends of the distal element being closer together in the closed position with the engagement surfaces facing generally toward each other. In addition, the method may include a step of deploying a proximal element on the fixation device toward each engagement surface to as to capture tissue therebetween. Before the step of inverting, the proximal elements are retracted away from the engagement surfaces. The method optionally includes a step of locking the distal elements in a desired position, and may further include a step of unlocking the distal elements so that they are movable again.

In a further aspect, a method according to the invention comprises advancing a catheter having a proximal end, a distal end and a fixation device near the distal end to a location within a body, wherein the fixation device includes a pair of distal elements each having an engagement surface; moving the distal elements to an open position wherein the distal elements extend radially outwardly facing the engagement surfaces toward a direction other than radially outwardly; and moving the distal elements to an inverted position wherein the engagement surfaces face radially outwardly.

In still another aspect, the invention provides a method for fixing tissues together comprising advancing a catheter having a proximal end, a distal end and a fixation device disposed near the distal end to a location near the tissues, wherein the fixation device includes a pair of distal elements each having a removable implant pledget; moving the distal elements so that each implant pledget engages one of the tissues; penetrating each tissue and engaged implant pledget and passing a tie therethrough; fastening the ties to fix the tissues together; and removing the fixation device leaving the implant pledget in place.

In an additional aspect of the invention, kits for performing an intervention at a tissue site in a patient's body include a fixation device and Instructions for Use setting forth the steps of using the fixation device according to the methods of the invention. The fixation device may be as described in any of the various examples set forth herein. The kits may further include a delivery tool or catheter for delivering the fixation device to the tissue site, as well as a tubular guide through which the delivery tool or catheter may be positioned.

Other aspects of the nature and advantages of the invention are set forth in the detailed description set forth below, taken in conjunction with the drawings.

BRIEF DESCRIPTION OF THE DRAWINGS

FIGS. 65A-65I illustrate embodiments of the present invention comprising sections constructed with the inclusion of braiding or coil.

FIGS. 74A-74F illustrate a ball restricting rotation of a disk.

DETAILED DESCRIPTION OF THE INVENTION

I. Cardiac Physiology

Figure 1:
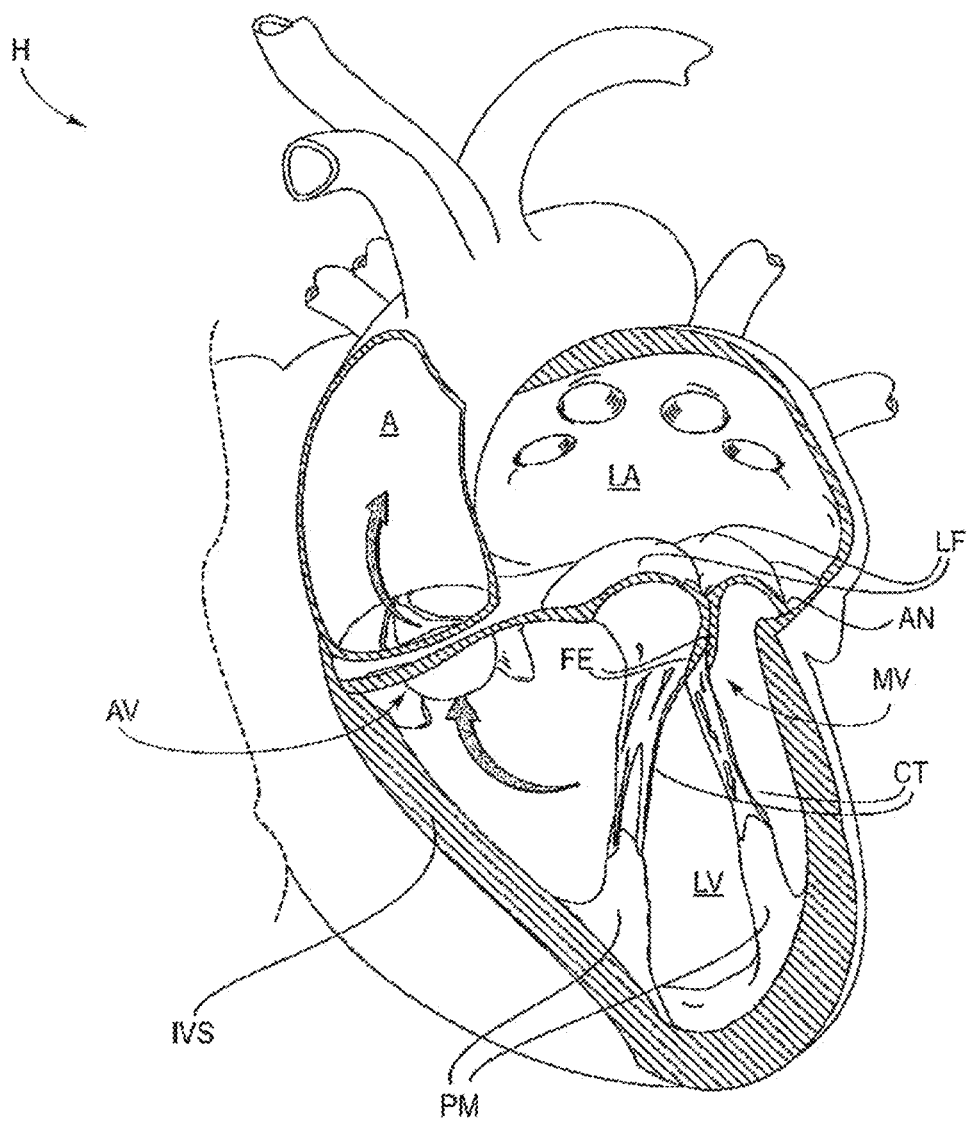
FIG. 1 illustrates the left ventricle and left atrium of the heart during systole.

The left ventricle LV of a normal heart H in systole is illustrated in FIG. 1. The left ventricle LV is contracting and blood flows outwardly through the tricuspid (aortic) valve AV in the direction of the arrows. Back flow of blood or "regurgitation" through the mitral valve MV is prevented since the mitral valve is configured as a "check valve" which prevents back flow when pressure in the left ventricle is higher than that in the left atrium LA. The mitral valve MV comprises a pair of leaflets having free edges FE which meet evenly to close, as illustrated in FIG. 1. The opposite ends of the leaflets LF are attached to the surrounding heart structure along an annular region referred to as the annulus AN. The free edges FE of the leaflets LF are secured to the lower portions of the left ventricle LV through chordae tendinae CT (referred to hereinafter as the chordae) which include plurality of branching tendons secured over the lower surfaces of each of the valve leaflets LF. The chordae CT in turn, are attached to the papillary muscles PM which extend upwardly from the lower portions of the left ventricle and intraventricular septum IVS.

Figure 2A:
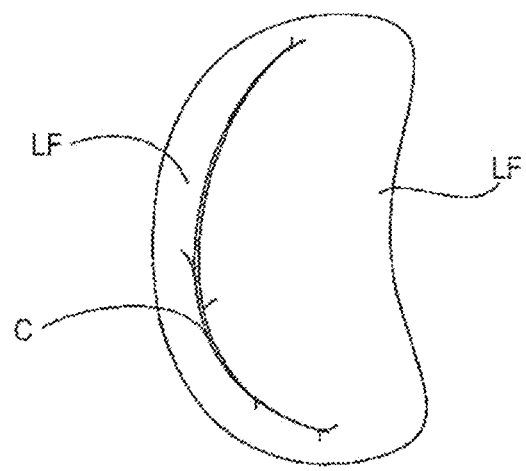
FIG. 2A illustrates free edges of leaflets in normal coaptation.
Figure 2B:
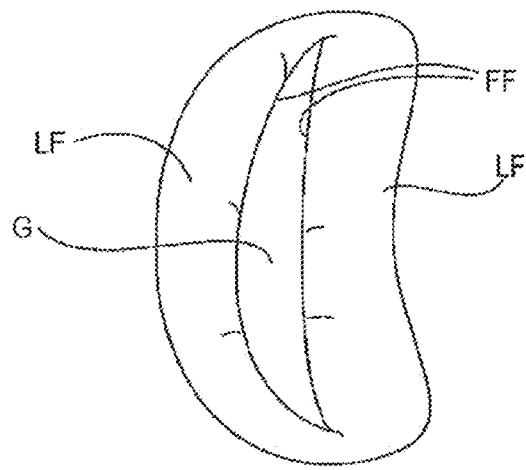
FIG. 2B illustrates the free edges in regurgitative coaptation.

A number of structural defects in the heart can cause mitral valve regurgitation. Regurgitation occurs when the valve leaflets do not close properly allowing leakage from the ventricle into the atrium. As shown in FIG. 2A, the free edges of the anterior and posterior leaflets normally meet along a line of coaptation C. An example of a defect causing regurgitation is shown in FIG. 2B. Here an enlargement of the heart causes the mitral annulus to become enlarged, making it impossible for the free edges FE to meet during systole. This results in a gap G which allows blood to leak through the valve during ventricular systole. Ruptured or elongated chordae can also cause a valve leaflet to prolapse since inadequate tension is transmitted to the leaflet via the chordae. While the other leaflet maintains a normal profile, the two valve leaflets do not properly meet and leakage from the left ventricle into the left atrium will occur. Such regurgitation can also occur in patients who have suffered ischemic heart disease where the left ventricle does not contract sufficiently to effect proper closure.

II. General Overview

The present invention provides methods and devices for grasping, approximating and fixating tissues such as valve leaflets to treat cardiac valve regurgitation, particularly mitral valve regurgitation. The present invention also provides features that allow repositioning and removal of the device if so desired, particularly in areas where removal may be hindered by anatomical features such as chordae CT. Such removal would allow the surgeon to reapproach the valve in a new manner if so desired.

Grasping will preferably be atraumatic providing a number of benefits. By atraumatic, it is meant that the devices and methods of the invention may be applied to the valve leaflets and then removed without causing any significant clinical impairment of leaflet structure or function. The leaflets and valve continue to function substantially the same as before the invention was applied. Thus, some minor penetration or denting of the leaflets may occur using the invention while still meeting the definition of "atraumatic". This enables the devices of the invention to be applied to a diseased valve and, if desired, removed or repositioned without having negatively affected valve function. In addition, it will be understood that in some cases it may be necessary or desirable to pierce or otherwise permanently affect the leaflets during either grasping, fixing or both. In some of these cases, grasping and fixation may be accomplished by a single device. Although a number of embodiments are provided to achieve these results, a general overview of the basic features will be presented herein. Such features are not intended to limit the scope of the invention and are presented with the aim of providing a basis for descriptions of individual embodiments presented later in the application.

Figure 3A:
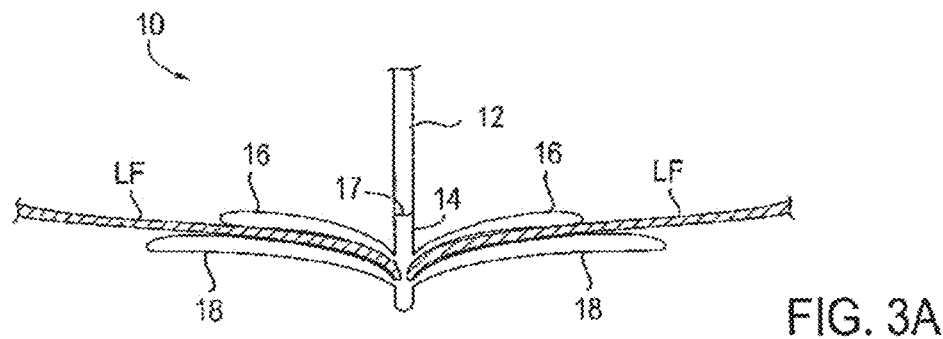
FIG. 3A-3C illustrate grasping of the leaflets with a fixation device, inversion of the distal elements of the fixation device and removal of the fixation device, respectively.

The devices and methods of the invention rely upon the use of an interventional tool that is positioned near a desired treatment site and used to grasp the target tissue. In endovascular applications, the interventional tool is typically an interventional catheter. In surgical applications, the interventional tool is typically an interventional instrument. In preferred embodiments, fixation of the grasped tissue is accomplished by maintaining grasping with a portion of the interventional tool which is left behind as an implant. While the invention may have a variety of applications for tissue approximation and fixation throughout the body, it is particularly well adapted for the repair of valves, especially cardiac valves such as the mitral valve. Referring to FIG. 3A, an interventional tool 10, having a delivery device, such as a shaft 12, and a fixation device 14, is illustrated having approached the mitral valve MV from the atrial side and grasped the leaflets LF. The mitral valve may be accessed either surgically or by using endovascular techniques, and either by a retrograde approach through the ventricle or by an antegrade approach through the atrium, as described above. For illustration purposes, an antegrade approach is described.

The fixation device 14 is releasably attached to the shaft 12 of the interventional tool 10 at its distal end. When describing the devices of the invention herein, "proximal" shall mean the direction toward the end of the device to be manipulated by the user outside the patient's body, and "distal" shall mean the direction toward the working end of the device that is positioned at the treatment site and away from the user. With respect to the mitral valve, proximal shall refer to the atrial or upstream side of the valve leaflets and distal shall refer to the ventricular or downstream side of the valve leaflets.

The fixation device 14 typically comprises proximal elements 16 (or gripping elements) and distal elements 18 (or fixation elements) which protrude radially outward and are positionable on opposite sides of the leaflets LF as shown so as to capture or retain the leaflets therebetween. The proximal elements 16 are preferably comprised of cobalt chromium, nitinol or stainless steel, and the distal elements 18 are preferably comprised of cobalt chromium or stainless steel, however any suitable materials may be used. The fixation device 14 is coupleable to the shaft 12 by a coupling mechanism 17. The coupling mechanism 17 allows the fixation device 14 to detach and be left behind as an implant to hold the leaflets together in the coapted position.

Figure 3B:
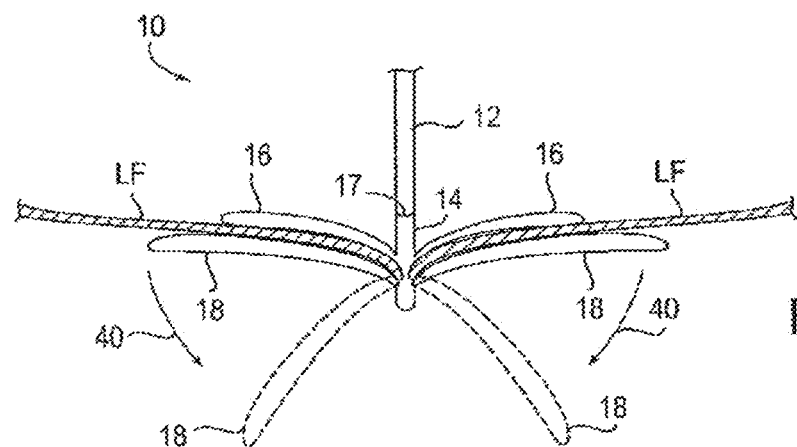
Figure 3C:
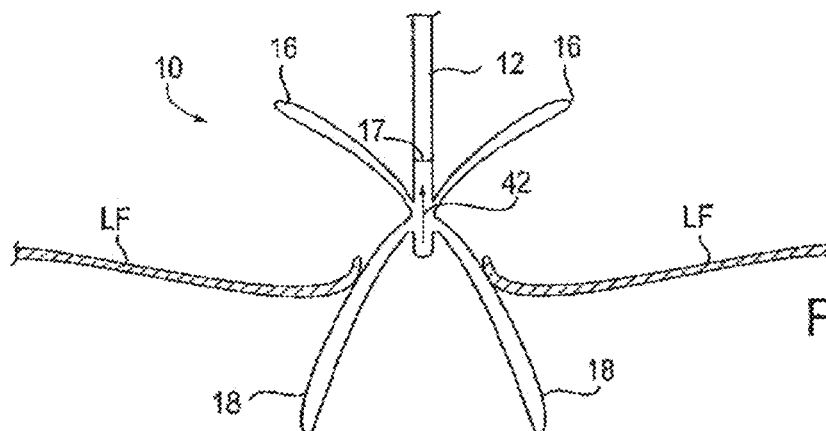

In some situations, it may be desired to reposition or remove the fixation device 14 after the proximal elements 16, distal elements 18, or both have been deployed to capture the leaflets LF. Such repositioning or removal may be desired for a variety of reasons, such as to reapproach the valve in an attempt to achieve better valve function, more optimal positioning of the device 14 on the leaflets, better purchase on the leaflets, to detangle the device 14 from surrounding tissue such as chordae, to exchange the device 14 with one having a different design, or to abort the fixation procedure, to name a few. To facilitate repositioning or removal of the fixation device 14 the distal elements 18 are releasable and optionally invertible to a configuration suitable for withdrawal of the device 14 from the valve without tangling or interfering with or damaging the chordae, leaflets or other tissue. FIG. 3B illustrates inversion wherein the distal elements 18 are moveable in the direction of arrows 40 to an inverted position. Likewise, the proximal elements 16 may be raised, if desired. In the inverted position, the device 14 may be repositioned to a desired orientation wherein the distal elements may then be reverted to a grasping position against the leaflets as in FIG. 3A. Alternatively, the fixation device 14 may be withdrawn (indicated by arrow 42) from the leaflets as shown in FIG. 3C. Such inversion reduces trauma to the leaflets and minimizes any entanglement of the device with surrounding tissues. Once the device 14 has been withdrawn through the valve leaflets, the proximal and distal elements may be moved to a closed position or configuration suitable for removal from the body or for reinsertion through the mitral valve.

Figure 4:
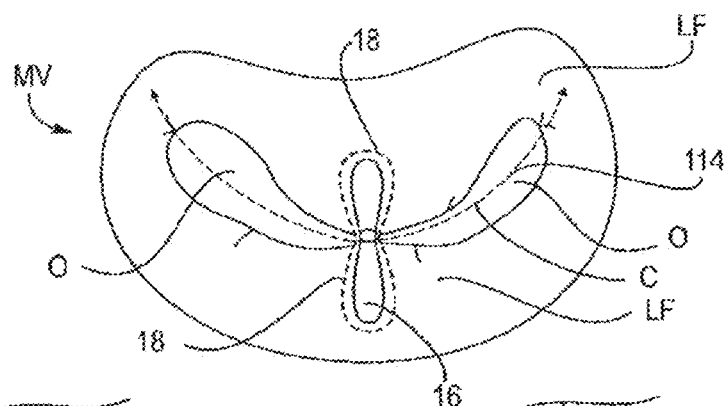
FIG. 4 illustrates the position of the fixation device in a desired orientation relative to the leaflets.

FIG. 4 illustrates the position of the fixation device 14 in a desired orientation in relation to the leaflets LF. This is a short-axis view of the mitral valve MV from the atrial side, therefore, the proximal elements 16 are shown in solid line and the distal elements 18 are shown in dashed line. The proximal and distal elements 16, 18 are positioned to be substantially perpendicular to the line of coaptation C. The device 14 may be moved roughly along the line of coaptation to the location of regurgitation. The leaflets LF are held in place so that during diastole, as shown in FIG. 4, the leaflets LF remain in position between the elements 16, 18 surrounded by openings O which result from the diastolic pressure gradient. Advantageously, leaflets LF are coapted such that their proximal or upstream surfaces are facing each other in a vertical orientation, parallel to the direction of blood flow through mitral valve MV. The upstream surfaces may be brought together so as to be in contact with one another or may be held slightly apart, but will preferably be maintained in the vertical orientation in which the upstream surfaces face each other at the point of coaptation. This simulates the double orifice geometry of a standard surgical bow-tie repair. Color Doppler echo will show if the regurgitation of the valve has been reduced. If the resulting mitral flow pattern is satisfactory, the leaflets may be fixed together in this orientation. If the resulting color Doppler image shows insufficient improvement in mitral regurgitation, the interventional tool 10 may be repositioned. This may be repeated until an optimal result is produced wherein the leaflets LF are held in place.

Figure 5A:
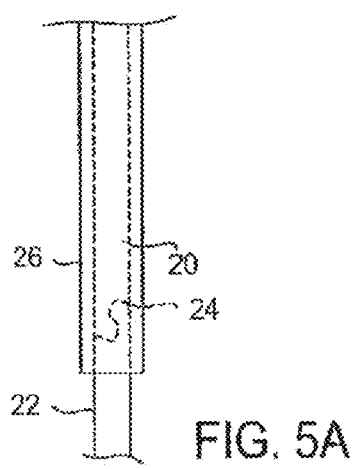
FIGS. 5A-5B, 6A-6B illustrate exemplary embodiments of coupling mechanisms of the instant application.
Figure 5B:
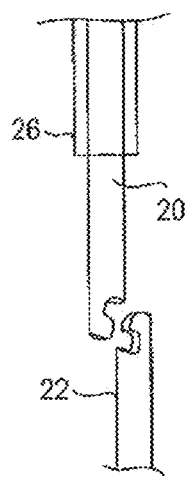

Once the leaflets are coapted in the desired arrangement, the fixation device 14 is then detached from the shaft 12 and left behind as an implant to hold the leaflets together in the coapted position. As mentioned previously, the fixation device 14 is coupled to the shaft 12 by a coupling mechanism 17. FIGS. 5A-5B, 6A-6B illustrate exemplary embodiments of such coupling mechanisms. FIG. 5A shows an upper shaft 20 and a detachable lower shaft 22 which are interlocked at a joining line or mating surface 24. The mating surface 24 may have any shape or curvature which will allow or facilitate interlocking and later detachment. A snuggly fitting outer sheath 26 is positioned over the shafts 20, 22 to cover the mating surface 24 as shown. FIG. 5B illustrates detachment of the lower shaft 22 from the upper shaft 20. This is achieved by retracting the outer sheath 26, so that the mating surface 24 is exposed, which allows the shafts 20, 22 to separate.

Figure 6A:
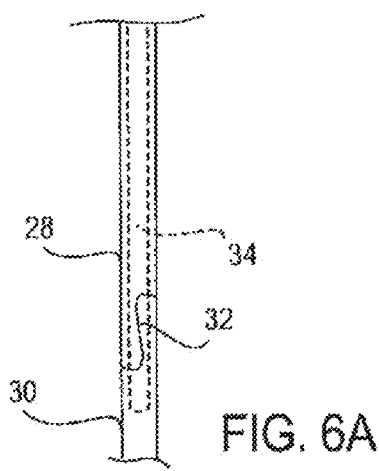
Figure 6B:
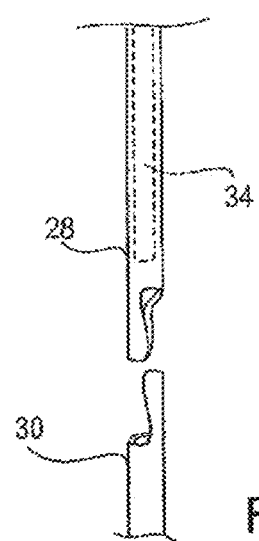

Similarly, FIG. 6A illustrates a tubular upper shaft 28 and a detachable tubular lower shaft 30 which are interlocked at a mating surface 32. Again, the mating surface 32 may have any shape or curvature which will allow or facilitate interlocking and later detachment. The tubular upper shaft 28 and tubular lower shaft 30 form an outer member having an axial channel. A snuggly fitting rod 34 or inner member is inserted through the tubular shafts 28, 30 to bridge the mating surface 32 as shown. FIG. 6B illustrates detachment of the lower shaft 30 from the upper shaft 28. This is achieved by retracting the rod 34 to a position above the mating surface 32 which in turn allows the shafts 28, 30 to separate. Other examples of coupling mechanisms are described and illustrated in commonly assigned U.S. Pat. No. 6,752,813, incorporated herein by reference for all purposes.

In a preferred embodiment, mating surface 24 (or mating surface 32) is a sigmoid curve defining a male element and female element on upper shaft 20 (or upper shaft 28) which interlock respectively with corresponding female and male elements on lower shaft 22 (or lower shaft 30). Typically, the lower shaft is the coupling mechanism 17 of the fixation device 14. Therefore, the shape of the mating surface selected will preferably provide at least some mating surfaces transverse to the axial axis of the a mechanism 19 to facilitate application of compressive and tensile forces through the coupling mechanism 17 to the fixation device 14, yet causing minimal interference when the fixation device 14 is to be released from the upper shaft.

III. Fixation Device

A. Introduction and Placement of Fixation Device

The fixation device 14 is delivered to the valve or the desired tissues with the use of a delivery device. The delivery device may be rigid or flexible depending on the application. For endovascular applications, the delivery device comprises a flexible delivery catheter which will be described in later sections. Typically, however, such a catheter comprises a shaft, having a proximal end and a distal end, and a fixation device releasably attached to its distal end. The shaft is usually elongate and flexible, suitable for intravascular introduction. Alternatively, the delivery device may comprise a shorter and less flexible interventional instrument which may be used for trans-thoracic surgical introduction through the wall of the heart, although some flexibility and a minimal profile will generally be desirable. A fixation device is releasably coupleable with the delivery device as illustrated in FIG. 3A. The fixation device may have a variety of forms, a few embodiments of which will be described herein.

Figure 7A:
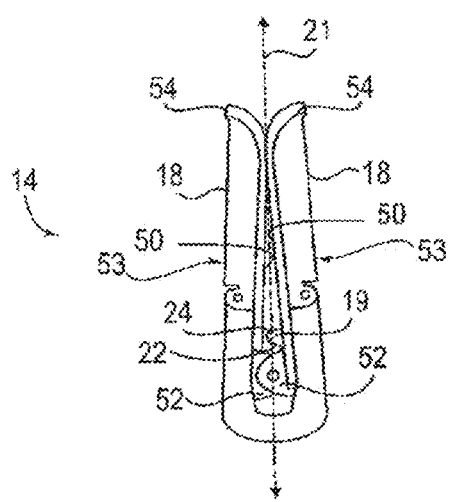
FIGS. 7A-7D illustrate an embodiment of a fixation device in various positions.

FIGS. 7A-7D illustrate an embodiment of a fixation device 14 in various positions or configurations. FIG. 7A illustrates the fixation device 14 in a closed configuration for delivery through the patient's vasculature and, in this example, through the mitral valve. The fixation device 14 includes a coupling member 19 which allows detachment of the fixation device 14 for implantation. In this example, the coupling member 19 is shown to include the lower shaft 22 and mating surface 24 of FIGS. 5A-5B, and therefore the coupling member 19 would function similarly as described above. The fixation device 14 also includes a pair of opposed distal elements 18, each distal element 18 having an engagement surface 50 facing inwardly toward the opposed distal element 18 in the closed configuration. Distal elements 18 preferably comprise elongate arms 53, each arm having a proximal end 52 rotatably connected to the coupling member 19 and a free end 54. Suitable connections for arms 53 to coupling member 19 include pins, living hinges, or other known rotational connection mechanisms. In the closed configuration of FIG. 7A, free ends 54 point in a first direction such that the arms 53 and engagement surfaces 50 are nearly parallel to each other and to an axis 21, and preferably are angled slightly inwardly toward each other. In a preferred embodiment, when tissue is not present between arms 53, the arms 53 may be closed until free ends 54 either touch each other or engage shaft 12 when fixation device 14 is attached thereto, thereby minimizing the profile of the fixation device 14 for passage through a delivery device.

Figure 7B:
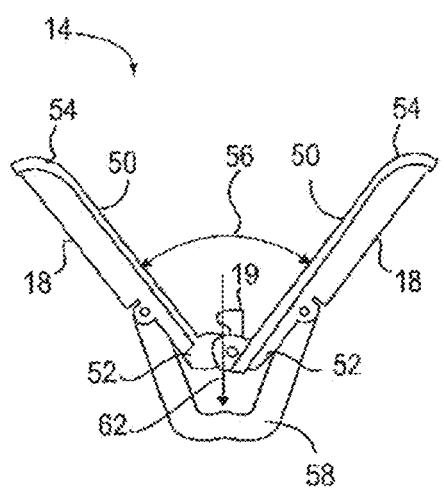
Figure 7C:
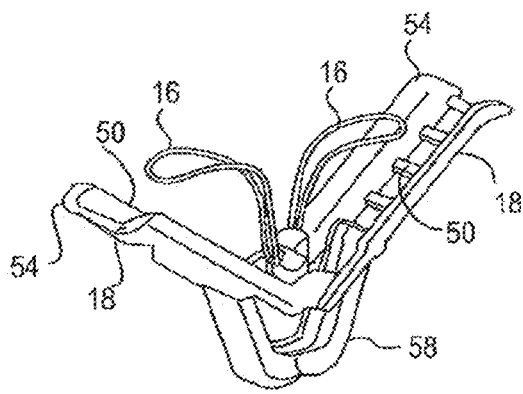

FIGS. 7B-7C illustrate the fixation device 14 in an open position wherein the engagement surfaces 50 are disposed at a separation angle 56 apart, wherein the separation angle 56 is typically up to approximately 180 degrees, preferably up to 90-180 degrees, and arms 53 are disposed generally symmetrically relative to axis 21. The arms 53 may be moveable to the open position by a variety of actuation mechanisms. For example, a plunger or actuator rod may be advanced through the coupling member 19, as indicated by arrow 62, so as to engage a spring or spring loaded actuation mechanism 58 which is attached to the distal elements 18. By exerting a force against the actuation mechanism 58, the distal elements 18 are rotated relative to coupling member 19. The distal elements 18 may be held in this open position by the actuator rod against the resistance provided by the spring of the actuation mechanism 58 which biases the distal elements 18 toward the closed position of FIG. 7A when the distal elements 18 are less than 180 degrees apart. The spring loading of the actuation mechanism 58 resists outward movement of the actuation mechanism 58 and urges the device 14 towards the closed position.

In this embodiment, proximal elements 16 comprise resilient loop-shaped wire forms biased outwardly and attached to the coupling member 19 so as to be biased to an open position shown in FIG. 7C but moveable rotationally inwardly when arms 53 are closed. The wire forms may be flexible enough to be rigidly attached to coupling member 19 and resiliently deflectable inwardly, or they may be attached by a rotational coupling such as a pin or living hinge. In use, leaflets LF are positioned between the proximal elements 16 and distal elements 18. Once, the leaflets LF are positioned between the proximal and distal elements 16, 18, the distal elements 18 may be closed, compressing the leaflets between engagement surfaces 50 and proximal elements 18. Depending upon the thickness of the leaflets, the arrangements of the leaflets, the position of the fixation device on the leaflets and other factors, the arms 53 may be maintained in the open position of FIG. 7B, moved to the fully closed position of FIG. 7A, or placed in any of various positions in between so as to coapt the leaflets LF and hold them in the desired position with the desired degree of force. In any case, the fixation device 14 will remain in place as an implant following detachment from the delivery catheter.

In some situations, as previously mentioned, it may be desirable to reopen the fixation device 14 following initial placement. To reopen the device 14, the actuator rod may be readvanced or reinserted through the coupling member 19 and readvanced to press against the actuation mechanism 58, as previously indicated by arrow 62 in FIG. 7B. Again, such advancement applies a force against the actuation mechanism 58 in the manner described above thus moving arms 53 outwardly to release force against leaflets and move engagement surfaces 50 away from proximal elements 16. The leaflets are then free to move relative to fixation device 14. The fixation device 14 may then be repositioned as desired and the actuator rod retracted to reclose the distal elements 18 to coapt the leaflets.

Figure 7D:
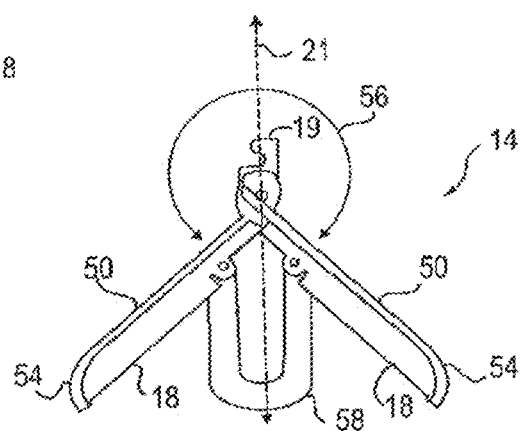

Under some circumstances, it may be further desirable to withdraw the fixation device 14 back through the valve or completely from the patient following initial insertion through the valve. Should this be attempted with the clip in the closed or open positions illustrated in FIGS. 7A-7C, there may be a risk that arms 53 could interfere or become entangled with the chordae, leaflets or other tissues. To avoid this, the fixation element 14 is preferably adapted for inversion of arms 53 so that free ends 54 point in a second direction, opposite to the first direction in which the free ends 54 pointed in the closed position, each arm 53 forming an obtuse angle relative to axis 21 as illustrated in FIG. 7D. The arms 53 may be rotated so that the engagement surfaces 50 are disposed at a separation angle 56 of up to 360 degrees, and preferably at least up to 270 degrees. This may be accomplished by exerting a force against actuation mechanism 58 with a push rod or plunger extending through coupling member 19 as described above. In this embodiment, once the distal elements 18 have rotated beyond 180 degrees apart, the spring loading of the actuation mechanism 58 biases the distal elements 18 toward the inverted position. The spring loading of the actuation mechanism 58 resists outward movement of the actuation mechanism 58 and urges the device 14 towards the inverted position.

With arms 53 in the inverted position, engagement surfaces 50 provide an atraumatic surface deflect tissues as the fixation device is withdrawn. This allows the device to be retracted back through the valve annulus without risk of injury to valvular and other tissues. In some cases, once the fixation device 14 has been pulled back through the valve, it will be desirable to return the device to the closed position for withdrawal of the device from the body (either through the vasculature or through a surgical opening).

The embodiment illustrated in FIGS. 7A-7D is assembled from separate components composed of biocompatible materials. The components may be formed from the same or different materials, including but not limited to stainless steel or other metals, Elgiloy®, nitinol, titanium, tantalum, metal alloys or polymers. Additionally, some or all of these components may be made of bioabsorbable materials that will be absorbed by surrounding tissues or will dissolve into the bloodstream following implantation. It has been found that in mitral valve repair applications the fixation devices of the invention are completely surrounded by tissue within a few months of implantation, after which the devices could dissolve or be absorbed without negative impact to the repair.

Figure 8A:
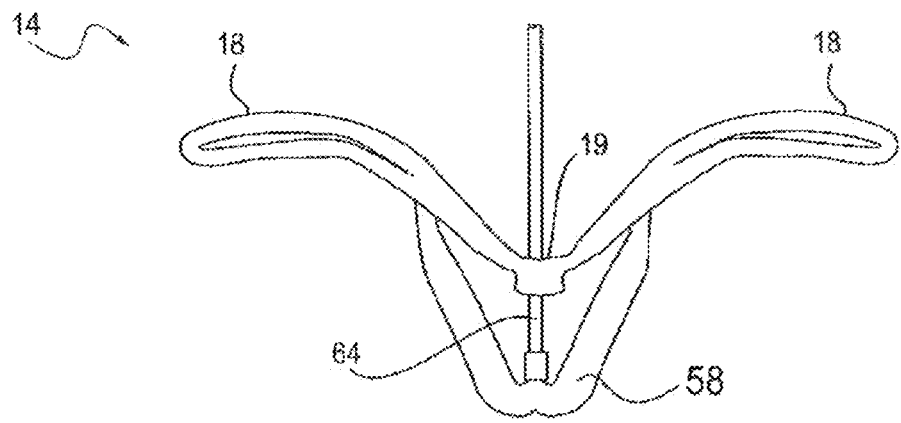
FIGS. 8A-8B illustrate an embodiment of the fixation device wherein some or all of the components are molded as one part.
Figure 8B:
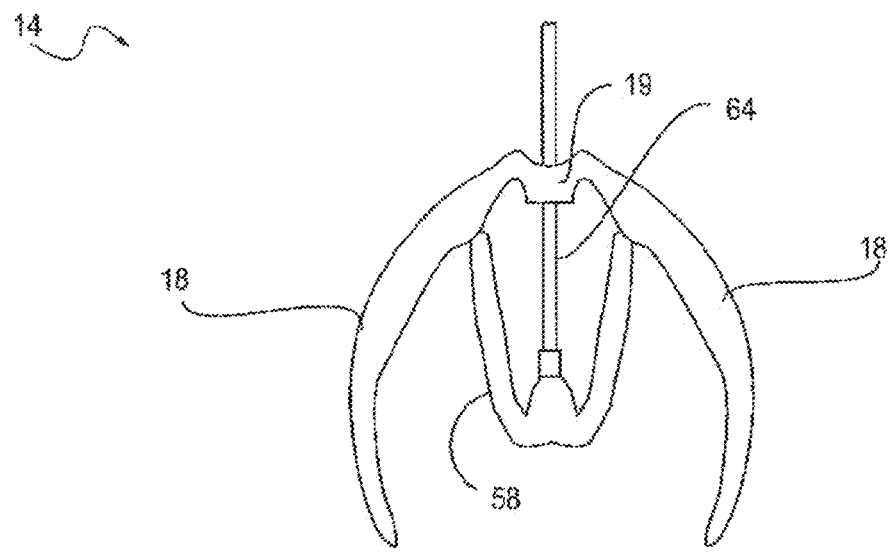

In a further embodiment, some or all of the components may be molded as one part, as illustrated in FIGS. 8A-8B. Here, the coupling member 19, distal elements 18 and actuation mechanism 58 of the fixation device 14 are all molded from a polymer material as one moveable piece. FIG. 8A shows the fixation device 14 in the open position. Advancement of an actuator rod 64 rotates the distal elements 18 relative to the coupling member 19 by a living hinge or by elastic deformation of the plastic at the point of connection between the elements 18 and the coupling member 19. Typically, this point of connection comprises a thinner segment of polymer to facilitate such bending. Likewise, the actuation mechanism 58 coupled to the distal elements 18 in the same manner. FIG. 8B shows the fixation device 14 in the inverted position.

Figure 9:
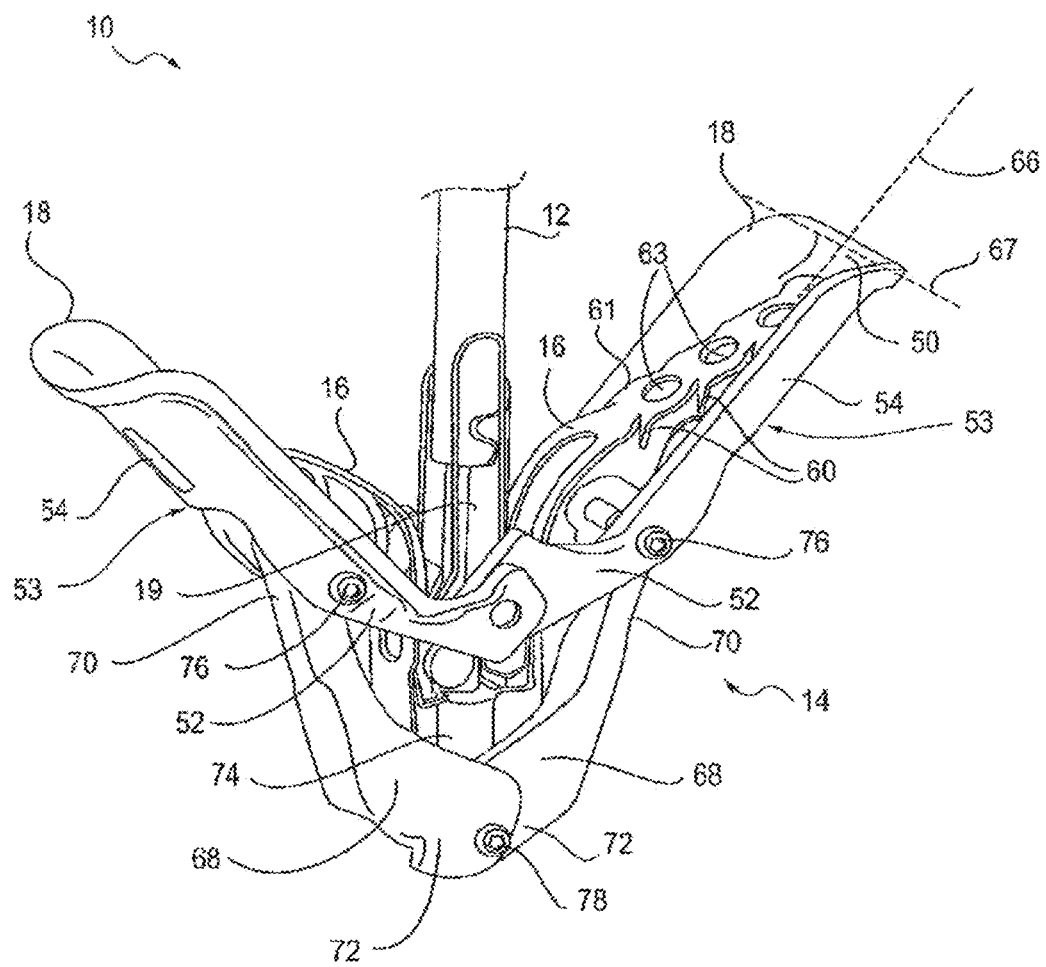
FIG. 9 illustrates another embodiment of the fixation device of the present invention.

FIG. 9 illustrates another embodiment of a fixation device 14. Here, the fixation device 14 is shown coupled to a shaft 12 to form an interventional tool 10. The fixation device 14 includes a coupling member 19 and a pair of opposed distal elements 18. The distal elements 18 comprise elongate arms 53, each arm having a proximal end 52 rotatably connected to the coupling member 19 and a free end 54. The free ends 54 have a rounded shape to minimize interference with and trauma to surrounding tissue structures. Preferably, each free end 54 defines a curvature about two axes, one being an axis 66 perpendicular to longitudinal axis of arms 53. Thus, the engagement surfaces 50 have a cupped or concave shape to surface area in contact with tissue and to assist in grasping and holding the valve leaflets. This further allows arms 53 to nest around the shaft 12 in the closed position to minimize the profile of the device. Preferably, arms 53 are at least partially cupped or curved inwardly about their longitudinal axes 66. Also, preferably, each free end 54 defines a curvature about an axis 67 perpendicular to axis 66 or the longitudinal axis of arms 53. This curvature is a reverse curvature along the most distal portion of the free end 54. Likewise, the longitudinal edges of the free ends 54 may flare outwardly. Both the reverse curvature and flaring minimize trauma to the tissue engaged therewith.

In a preferred embodiment suitable for mitral valve repair, the transverse width across engagement surfaces 50 (which determines the width of tissue engaged) is at least about 2 mm, usually 3-10 mm, and preferably about 4-6 mm. In some situations, a wider engagement is desired wherein the engagement surfaces 50 are larger, for example about 2 cm, or multiple fixation devices are used adjacent to each other. Arms 53 and engagement surfaces 50 are configured to engage a length of tissue of about 4-10 mm, and preferably about 6-8 mm along the longitudinal axis of arms 53. Arms 53 further include a plurality of openings to enhance grip and to promote tissue ingrowth following implantation.

The valve leaflets are grasped between the distal elements 18 and proximal elements 16. In some embodiments, the proximal elements 16 are flexible, resilient, and cantilevered from coupling member 19. The proximal elements are preferably resiliently biased toward the distal elements. Each proximal element 16 is shaped and positioned to be at least partially recessed within the concavity of the distal element 18 when no tissue is present. When the fixation device 14 is in the open position, the proximal elements 16 are shaped such that each proximal element 16 is separated from the engagement surface 50 near the proximal end 52 of arm 53 and slopes toward the engagement surface 50 near the free end 54 with the free end of the proximal element contacting engagement surface 50, as illustrated in FIG. 9. This shape of the proximal elements 16 accommodates valve leaflets or other tissues of varying thicknesses.

Proximal elements 16 include a plurality of openings 63 and scalloped side edges 61 to increase grip on tissue. The proximal elements 16 optionally include frictional accessories, frictional features or grip-enhancing elements to assist in grasping and/or holding the leaflets. In preferred embodiments, the frictional accessories comprise barbs 60 having tapering pointed tips extending toward engagement surfaces 50. It may be appreciated that any suitable frictional accessories may be used, such as prongs, windings, bands, barbs, grooves, channels, bumps, surface roughening, sintering, high-friction pads, coverings, coatings or a combination of these. Optionally, magnets may be present in the proximal and/or distal elements. It may be appreciated that the mating surfaces will be made from or will include material of opposite magnetic charge to cause attraction by magnetic force. For example, the proximal elements and distal elements may each include magnetic material of opposite charge so that tissue is held under constant compression between the proximal and distal elements to facilitate faster healing and ingrowth of tissue. Also, the magnetic force may be used to draw the proximal elements 16 toward the distal elements 18, in addition to or alternatively to biasing of the proximal elements toward the distal elements. This may assist in deployment of the proximal elements 16. In another example, the distal elements 18 each include magnetic material of opposite charge so that tissue positioned between the distal elements 18 is held therebetween by magnetic force.

The proximal elements 16 may be covered with a fabric or other flexible material as described below to enhance grip and tissue ingrowth following implantation. Preferably, when fabrics or coverings are used in combination with barbs or other frictional features, such features will protrude through such fabric or other covering so as to contact any tissue engaged by proximal elements 16.

In an exemplary embodiment, proximal elements 16 are formed from metallic sheet of a spring-like material using a stamping operation which creates openings 63, scalloped edges 61 and barbs 60. Alternatively, proximal elements 16 could be comprised of a spring-like material or molded from a biocompatible polymer. It should be noted that while some types of frictional accessories that can be used in the present invention may permanently alter or cause some trauma to the tissue engaged thereby, in a preferred embodiment, the frictional accessories will be atraumatic and will not injure or otherwise affect the tissue in a clinically significant way. For example, in the case of barbs 60, it has been demonstrated that following engagement of mitral valve leaflets by fixation device 14, should the device later be removed during the procedure barbs 60 leave no significant permanent scarring or other impairment of the leaflet tissue and are thus considered atraumatic.

The fixation device 14 also includes an actuation mechanism 58. In this embodiment, the actuation mechanism 58 comprises two link members or legs 68, each leg 68 having a first end 70 which is rotatably joined with one of the distal elements 18 at a riveted joint 76 and a second end 72 which is rotatably joined with a stud 74. The legs 68 are preferably comprised of a rigid or semi-rigid metal or polymer such as Elgiloy®, cobalt chromium or stainless steel, however any suitable material may be used. While in the embodiment illustrated both legs 68 are pinned to stud 74 by a single rivet 78, it may be appreciated, however, that each leg 68 may be individually attached to the stud 74 by a separate rivet or pin. The stud 74 is joinable with an actuator rod 64 (not shown) which extends through the shaft 12 and is axially extendable and retractable to move the stud 74 and therefore the legs 68 which rotate the distal elements 18 between closed, open and inverted positions. Likewise, immobilization of the stud 74 holds the legs 68 in place and therefore holds the distal elements 18 in a desired position. The stud 74 may also be locked in place by a locking feature which will be further described in later sections.

In any of the embodiments of fixation device 14 disclosed herein, it may be desirable to provide some mobility or flexibility in distal elements 18 and/or proximal elements 16 in the closed position to enable these elements to move or flex with the opening or closing of the valve leaflets. This provides shock absorption and thereby reduces force on the leaflets and minimizes the possibility for tearing or other trauma to the leaflets. Such mobility or flexibility may be provided by using a flexible, resilient metal or polymer of appropriate thickness to construct the distal elements 18. Also, the locking mechanism of the fixation device (described below) may be constructed of flexible materials to allow some slight movement of the proximal and distal elements even when locked. Further, the distal elements 18 can be connected to the coupling mechanism 19 or to actuation mechanism 58 by a mechanism that biases the distal element into the closed position (inwardly) but permits the arms to open slightly in response to forces exerted by the leaflets. For example, rather than being pinned at a single point, these components may be pinned through a slot that allowed a small amount of translation of the pin in response to forces against the arms. A spring is used to bias the pinned component toward one end of the slot.

Figure 10A:
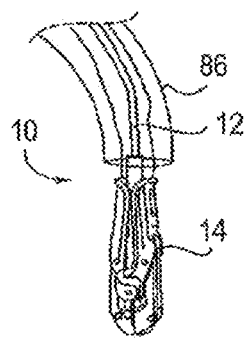
FIGS. 10A-10B, 11A-11B, 12A-12B, 13A-13B, 14-16 illustrate embodiments of a fixation device in various possible positions during introduction and placement of the device within the body to perform a therapeutic procedure.
Figure 10B:
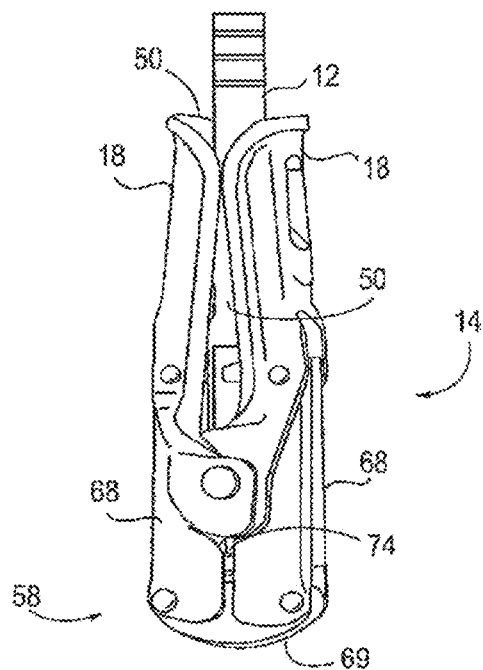

FIGS. 10A-10B, 11A-11B, 12A-12B, 13A-13B, and FIGS. 14-16 illustrate embodiments of the fixation device 14 of FIG. 9 in various possible positions during introduction and placement of the device 14 within the body to perform a therapeutic procedure. FIG. 10A illustrates an embodiment of an interventional tool 10 delivered through a catheter 86. It may be appreciated that the interventional tool 10 may take the form of a catheter, and likewise, the catheter 86 may take the form of a guide catheter or sheath. However, in this example the terms interventional tool 10 and catheter 86 will be used. The interventional tool 10 comprises a fixation device 14 coupled to a shaft 12 and the fixation device 14 is shown in the closed position. FIG. 10B illustrates a similar embodiment of the fixation device of FIG. 10A in a larger view. In the closed position, the opposed pair of distal elements 18 are positioned so that the engagement surfaces 50 face each other. Each distal element 18 comprises an elongate arm 53 having a cupped or concave shape so that together the arms 53 surround the shaft 12 and optionally contact each other on opposite sides of the shaft. This provides a low profile for the fixation device 14 which is readily passable through the catheter 86 and through any anatomical structures, such as the mitral valve. In addition, FIG. 10B further includes an actuation mechanism 58. In this embodiment, the actuation mechanism 58 comprises two legs 68 which are each movably coupled to a base 69. The base 69 is joined with an actuator rod 64 which extends through the shaft 12 and is used to manipulate the fixation device 14. In some embodiments, the actuator rod 64 attaches directly to the actuation mechanism 58, particularly the base 69. However, the actuator rod 64 may alternatively attach to a stud 74 which in turn is attached to the base 69. In some embodiments, the stud 74 is threaded so that the actuator rod 64 attaches to the stud 74 by a screw-type action. However, the rod 64 and stud 74 may be joined by any mechanism which is releasable to allow the fixation device 14 to be detached from shaft 12.

Figure 11A:
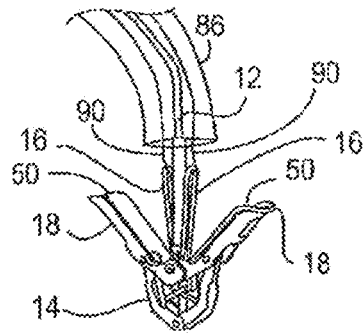
Figure 11B:
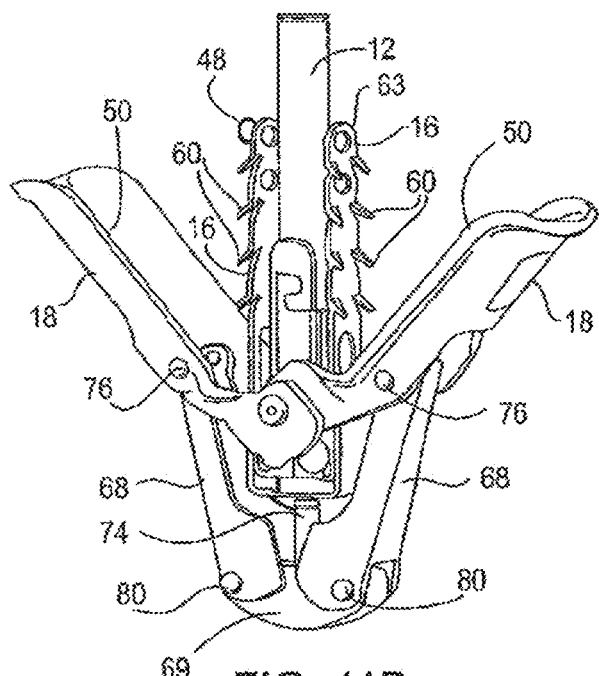

FIGS. 11A-11B illustrate the fixation device 14 in the open position. In the open position, the distal elements 18 are rotated so that the engagement surfaces 50 face a first direction. Distal advancement of the stud 74 relative to coupling member 19 by action of the actuator rod 64 applies force to the distal elements 18 which begin to rotate around joints 76 due to freedom of movement in this direction. Such rotation and movement of the distal elements 18 radially outward causes rotation of the legs 68 about joints 80 so that the legs 68 are directly slightly outwards. The stud 74 may be advanced to any desired distance correlating to a desired separation of the distal elements 18. In the open position, engagement surfaces 50 are disposed at an acute angle relative to shaft 12, and are preferably at an angle of between 90 and 180 degrees relative to each other. In one embodiment, in the open position the free ends 54 of arms 53 have a span therebetween of about 10-20 mm, usually about 12-18 mm, and preferably about 14-16 mm.

Proximal elements 16 are typically biased outwardly toward arms 53. The proximal elements 16 may be moved inwardly toward the shaft 12 and held against the shaft 12 with the aid of proximal element lines 90 which can be in the form of sutures, wires, nitinol wire, rods, cables, polymeric lines, or other suitable structures. The proximal element lines 90 may be connected with the proximal elements 16 by threading the lines 90 in a variety of ways. When the proximal elements 16 have a loop shape, as shown in FIG. 11A, the line 90 may pass through the loop and double back. When the proximal elements 16 have an elongate solid shape, as shown in FIG. 11B, the line 90 may pass through one or more of the openings 63 in the element 16. Further, a line loop 48 may be present on a proximal element 16, also illustrated in FIG. 11B, through which a proximal element line 90 may pass and double back. Such a line loop 48 may be useful to reduce friction on proximal element line 90 or when the proximal elements 16 are solid or devoid of other loops or openings through which the proximal element lines 90 may attach. A proximal element line 90 may attach to the proximal elements 16 by detachable means which would allow a single line 90 to be attached to a proximal element 16 without doubling back and would allow the single line 90 to be detached directly from the proximal element 16 when desired. Examples of such detachable means include hooks, snares, clips or breakable couplings, to name a few. By applying sufficient tension to the proximal element line 90, the detachable means may be detached from the proximal element 16 such as by breakage of the coupling. Other mechanisms for detachment may also be used. Similarly, a lock line 92 may be attached and detached from a locking mechanism by similar detachable means.

In the open position, the fixation device 14 can engage the tissue which is to be approximated or treated. The embodiment illustrated in FIGS. 9-11 is adapted for repair of the mitral valve using an antegrade approach from the left atrium. The interventional tool 10 is advanced through the mitral valve from the left atrium to the left ventricle. The distal elements 18 are oriented to be perpendicular to the line of coaptation and then positioned so that the engagement surfaces 50 contact the ventricular surface of the valve leaflets, thereby grasping the leaflets. The proximal elements 16 remain on the atrial side of the valve leaflets so that the leaflets lie between the proximal and distal elements. In this embodiment, the proximal elements 16 have frictional accessories, such as barbs 60 which are directed toward the distal elements 18. However, neither the proximal elements 16 nor the barbs 60 contact the leaflets at this time.

The interventional tool 10 may be repeatedly manipulated to reposition the fixation device 14 so that the leaflets are properly contacted or grasped at a desired location. Repositioning is achieved with the fixation device in the open position. In some instances, regurgitation may also be checked while the device 14 is in the open position. If regurgitation is not satisfactorily reduced, the device may be repositioned and regurgitation checked again until the desired results are achieved.

Figure 12A:
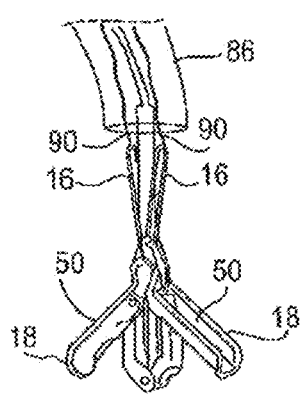
Figure 12B:
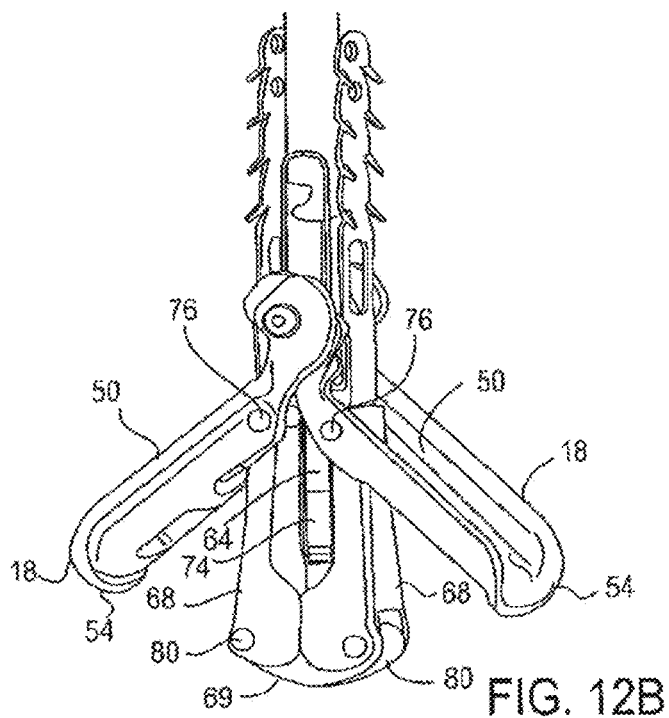

It may also be desired to invert the fixation device 14 to aid in repositioning or removal of the fixation device 14. FIGS. 12A-12B illustrate the fixation device 14 in the inverted position. By further advancement of stud 74 relative to coupling member 19, the distal elements 18 are further rotated so that the engagement surfaces 50 face outwardly and free ends 54 point distally, with each arm 53 forming an obtuse angle relative to shaft 12. The angle between arms 53 is preferably in the range of about 270 to 360 degrees. Further advancement of the stud 74 further rotates the distal elements 18 around joints 76. This rotation and movement of the distal elements 18 radially outward causes rotation of the legs 68 about joints 80 so that the legs 68 are returned toward their initial position, generally parallel to each other. The stud 74 may be advanced to any desired distance correlating to a desired inversion of the distal elements 18. Preferably, in the fully inverted position, the span between free ends 54 is no more than about 20 mm, usually less than about 16 mm, and preferably about 12-14 mm. In this illustration, the proximal elements 16 remain positioned against the shaft 12 by exerting tension on the proximal element lines 90. Thus, a relatively large space may be created between the elements 16, 18 for repositioning. In addition, the inverted position allows withdrawal of the fixation device 14 through the valve while minimizing trauma to the leaflets. Engagement surfaces 50 provide an atraumatic surface for deflecting tissue as the fixation device is retracted proximally. It should be further noted that barbs 60 are angled slightly in the distal direction (away from the free ends of the proximal elements 16), reducing the risk that the barbs will catch on or lacerate tissue as the fixation device is withdrawn.

Figure 13A:
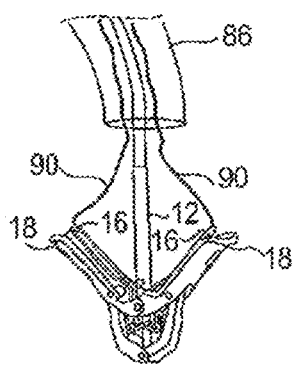
Figure 13B:
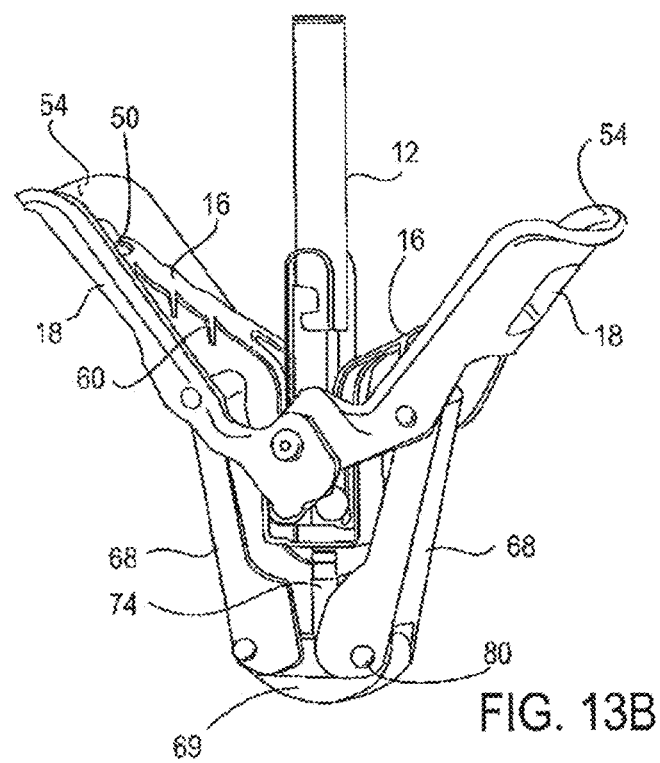

Once the fixation device 14 has been positioned in a desired location against the valve leaflets, the leaflets may then be captured between the proximal elements 16 and the distal elements 18. FIGS. 13A-13B illustrate the fixation device 14 in such a position. Here, the proximal elements 16 are lowered toward the engagement surfaces 50 so that the leaflets are held therebetween. In FIG. 13B, the proximal elements 16 are shown to include barbs 60 which may be used to provide atraumatic gripping of the leaflets. Alternatively, larger, more sharply pointed barbs or other penetration structures may be used to pierce the leaflets to more actively assist in holding them in place. This position is similar to the open position of FIGS. 11A-11B, however the proximal elements 16 are now lowered toward arms 53 by releasing tension on proximal element lines 90 to compress the leaflet tissue therebetween. At any time, the proximal elements 16 may be raised and the distal elements 18 adjusted or inverted to reposition the fixation device 14, if regurgitation is not sufficiently reduced.

Figure 14:
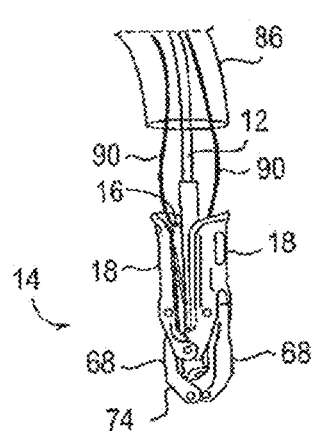

After the leaflets have been captured between the proximal and distal elements 16, 18 in a desired arrangement, the distal elements 18 may be locked to hold the leaflets in this position or the fixation device 14 may be returned to or toward a closed position. Such locking will be described in a later section. FIG. 14 illustrates the fixation device 14 in the closed position wherein the leaflets (not shown) are captured and coapted. This is achieved by retraction of the stud 74 proximally relative to coupling member 19 so that the legs 68 of the actuation mechanism 58 apply an upwards force to the distal elements 18 which in turn rotate the distal elements 18 so that the engagement surfaces 50 again face one another. The released proximal elements 16 which are biased outwardly toward distal elements 18 are concurrently urged inwardly by the distal elements 18. The fixation device 14 may then be locked to hold the leaflets in this closed position as described below.

Figure 15:
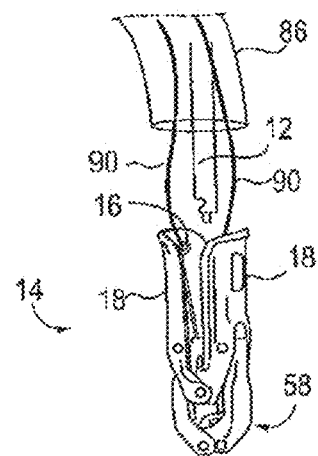

As shown in FIG. 15, the fixation device 14 may then be released from the shaft 12. As mentioned, the fixation device 14 is releasably coupleable to the shaft 12 by coupling member 19. FIG. 15 illustrates the coupling structure, a portion of the shaft 12 to which the coupling member 19 of the fixation device 14 attaches. As shown, the proximal element lines 90 may remain attached to the proximal elements 16 following detachment from shaft 12 to function as a tether to keep the fixation device 14 connected with the catheter 86. Optionally, a separate tether coupled between shaft 12 and fixation device 14 may be used expressly for this purpose while the proximal element lines 90 are removed. In any case, the repair of the leaflets or tissue may be observed by non-invasive visualization techniques, such as echocardiography, to ensure the desired outcome. If the repair is not desired, the fixation device 14 may be retrieved with the use of the tether or proximal element lines 90 so as to reconnect coupling member 19 with shaft 12.

In an exemplary embodiments, proximal element lines 90 are elongated flexible threads, wire, cable, sutures or lines extending through shaft 12, looped through proximal elements 16, and extending back through shaft 12 to its proximal end. When detachment is desired, one end of each line may be released at the proximal end of the shaft 12 and the other end pulled to draw the free end of the line distally through shaft 12 and through proximal element 16 thereby releasing the fixation device.

Figure 16:
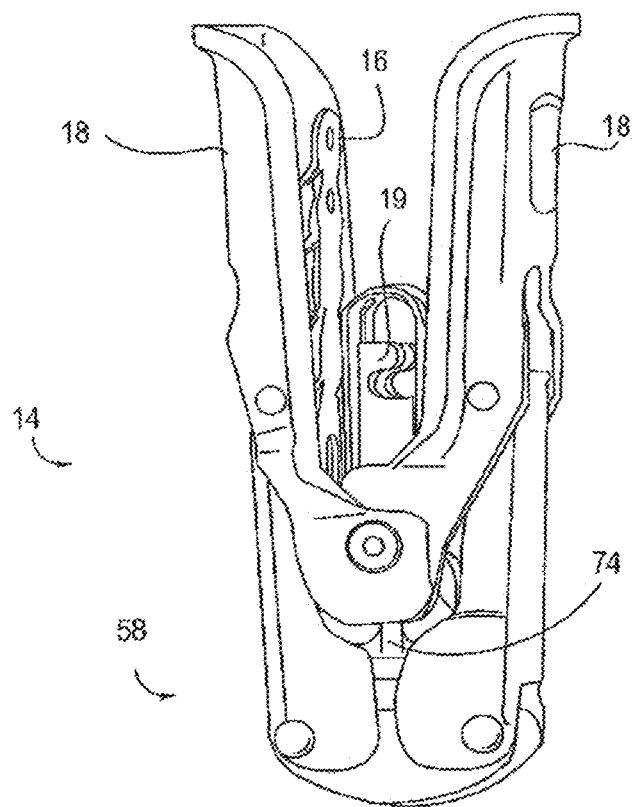

FIG. 16 illustrates a released fixation device 14 in a closed position. As shown, the coupling member 19 remains separated from the shaft 12 of the interventional tool 10 and the proximal elements 16 are deployed so that tissue (not shown) may reside between the proximal elements 16 and distal elements 18.

While the above described embodiments of the invention utilize a push-to-open, pull-to-close mechanism for opening and closing distal elements 18, it should be understood that a pull-to-open, push-to-close mechanism is equally possible. For example, distal elements 18 may be coupled at their proximal ends to stud 74 rather than to coupling member 19, and legs 68 may be coupled at their proximal ends to coupling member 19 rather than to stud 74. In this example, when stud 74 is pushed distally relative to coupling member 19, distal elements 18 would close, while pulling on stud 74 proximally toward coupling member 19 would open distal elements 18.

B. Covering on Fixation Device

The fixation device 14 may optionally include a covering. The covering may assist in grasping the tissue and may later provide a surface for tissue ingrowth. Ingrowth of the surrounding tissues, such as the valve leaflets, provides stability to the device 14 as it is further anchored in place and may cover the device with native tissue thus reducing the possibility of immunologic reactions. The covering may be comprised of any biocompatible material, such as polyethylene terepthalate, polyester, cotton, polyurethane, expanded polytetrafluoroethylene (ePTFE), silicon, or various polymers or fibers and have any suitable form, such as a fabric, mesh, textured weave, felt, looped or porous structure. Generally, the covering has a low profile so as not to interfere with delivery through an introducer sheath or with grasping and coapting of leaflets or tissue.

Figure 17A:
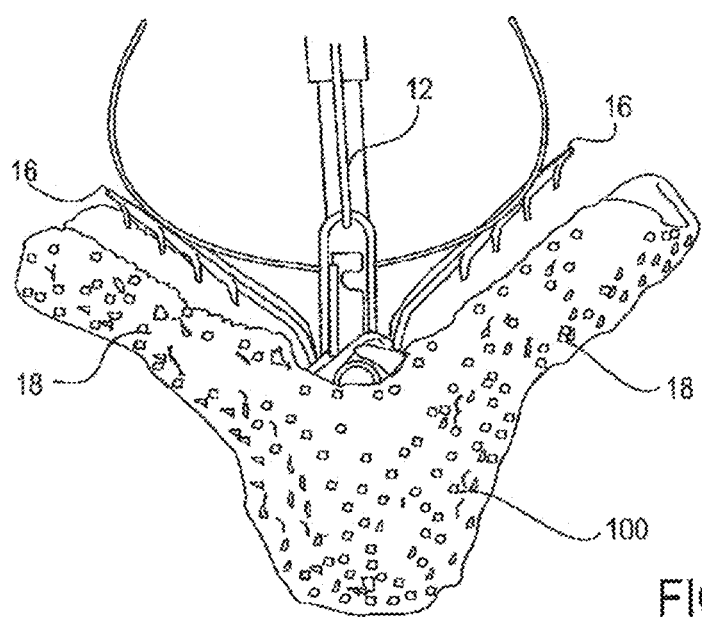
FIGS. 17A-17C illustrate a covering on the fixation device wherein the device is in various positions.
Figure 17B:
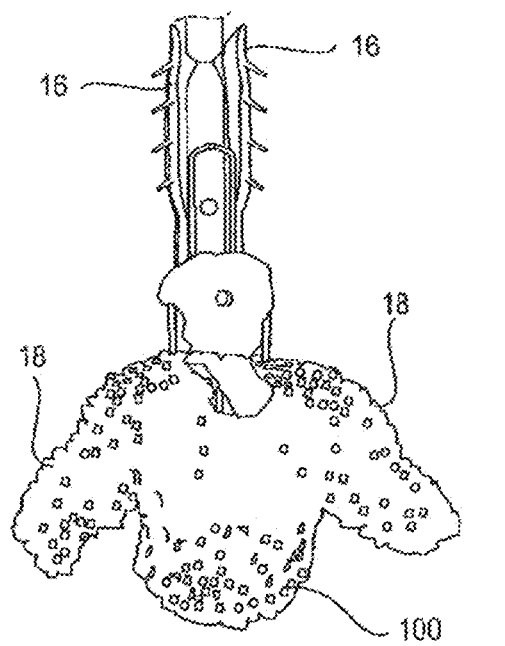
Figure 17C:
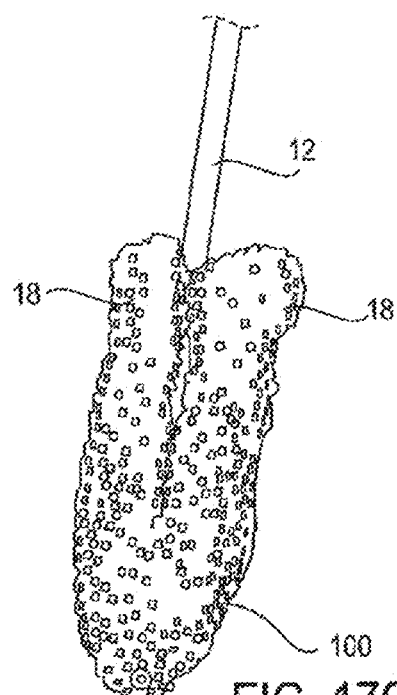

FIGS. 17A-17C illustrate a covering 100 on the fixation device 14 wherein the device 14 is in various positions. FIG. 17A shows the covering 100 encapsulating the distal elements 18 and the actuation mechanism 58 while the device 14 is in the open position. Thus, the engagement surfaces 50 are covered by the covering 100 which helps to minimize trauma on tissues and provides additional friction to assist in grasping and retaining tissues. FIG. 17B shows the device 14 of FIG. 17A in the inverted position. The covering 100 is loosely fitted and/or is flexible or elastic such that the device 14 can freely move to various positions and the covering 100 conforms to the contours of the device 14 and remains securely attached in all positions. FIG. 17C shows the device 14 in the closed position. Thus, when the fixation device 14 is left behind as an implant in the closed position, the exposed surfaces of the device 14 are substantially covered by the covering 100. It may be appreciated that the covering 100 may cover specific parts of the fixation device 14 while leaving other parts exposed. For example, the covering 100 may comprise sleeves that fit over the distal elements 18 and not the actuation mechanism 58, caps that fit over the distal ends 54 of the distal elements 18 or pads that cover the engagement surfaces 50, to name a few. It may be appreciated that, the covering 100 may allow any frictional accessories, such as barbs, to be exposed. Also, the covering 100 may cover the proximal elements 16 and/or any other surfaces of the fixation device 14. In any case, the covering 100 should be durable to withstand multiple introduction cycles and, when implanted within a heart, a lifetime of cardiac cycles.

The covering 100 may alternatively be comprised of a polymer or other suitable materials dipped, sprayed, coated or otherwise adhered to the surfaces of the fixation device 14. Optionally, the polymer coating may include pores or contours to assist in grasping the tissue and/or to promote tissue ingrowth.

Any of the coverings 100 may optionally include drugs, antibiotics, anti-thrombosis agents, or anti-platelet agents such as heparin, COUMADIN® (Warfarin Sodium), to name a few. These agents may, for example, be impregnated in or coated on the coverings 100. These agents may then be delivered to the grasped tissues surrounding tissues and/or bloodstream for therapeutic effects.

C. Fixation Device Locking Mechanisms

Figure 18:
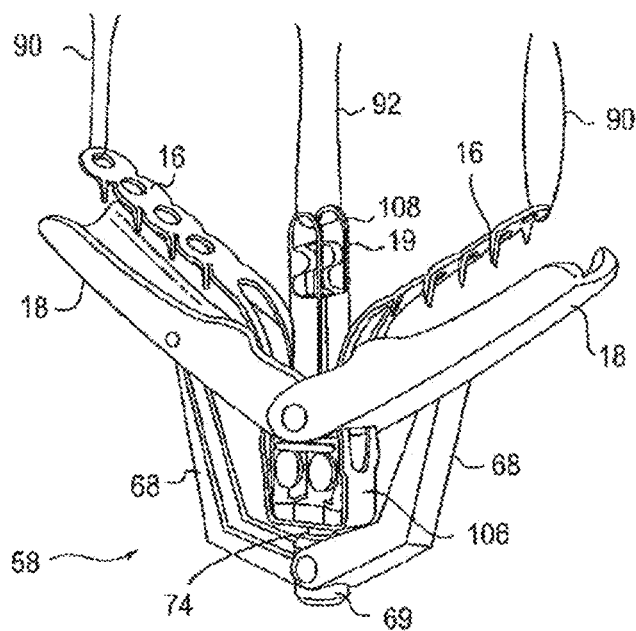
FIG. 18 illustrates an embodiment of the fixation device including proximal elements and a locking mechanism.

As mentioned previously, the fixation device 14 optionally includes a locking mechanism for locking the device 14 in a particular position, such as an open, closed or inverted position or any position therebetween. It may be appreciated that the locking mechanism includes an unlocking mechanism which allows the device to be both locked and unlocked. FIGS. 18-21 illustrate an embodiment of a locking mechanism 106. Referring to FIG. 18, in this embodiment, the locking mechanism 106 is disposed between the coupling member 19 and the base 69 of the actuation mechanism 58. The base 69 is fixedly attached to the stud 74 which extends through the locking mechanism 106. The stud 74 is releasably attached to the actuator rod 64 which passes through the coupling member 19 and the shaft 12 of the interventional tool 10. The base 69 is also connected to the legs 68 of the actuation mechanism 58 which are in turn connected to the distal elements 18.

FIG. 18 also illustrates the proximal elements 16, which in this embodiment straddle the locking mechanism and join beneath the locking mechanism 106. The proximal elements 16 are shown supported by proximal element lines 90. The proximal elements 16 are raised and lowered by manipulation of the proximal element lines 90. In addition, lock lines 92 are shown connected with a release harness 108 of the locking mechanism 106. The lock lines 92 are used to lock and unlock the locking mechanism 106 as will be described below. The proximal element lines 90 and lock lines 92 may be comprised of any suitable material, typically wire, nitinol wire, cable, suture or thread, to name a few. In addition, the proximal element lines 90 and/or lock lines 92 may include a coating, such as parylene. Parylene is a vapor deposited pinhole free protective film which is conformal and biocompatible. It is inert and protects against moisture, chemicals, and electrical charge.

Figure 19:
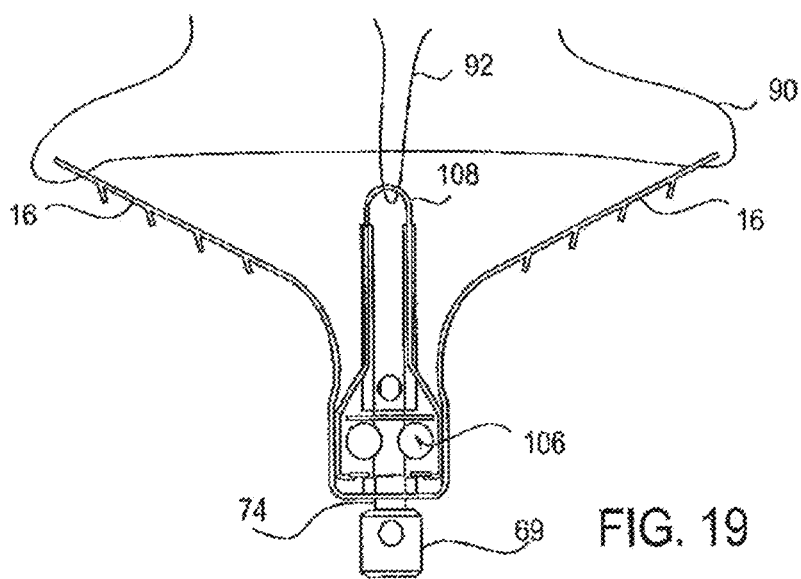
FIG. 19 provides a cross-sectional view of the locking mechanism of FIG. 18.

FIG. 19 provides a front view of the locking mechanism 106 of FIG. 18. However, here the proximal elements 16 are supported by a single proximal element line 90 which is through both of the proximal elements 16. In this arrangement both of the elements are raised and lowered simultaneously by action of a single proximal element line 90. Whether the proximal elements 16 are manipulated individually by separate proximal element lines 90 or jointly by a single proximal element line 90, the proximal element lines 90 may extend directly through openings in the proximal elements and/or through a layer or portion of a covering 100 on the proximal elements, or through a suture loop above or below a covering 100.

Figure 20:
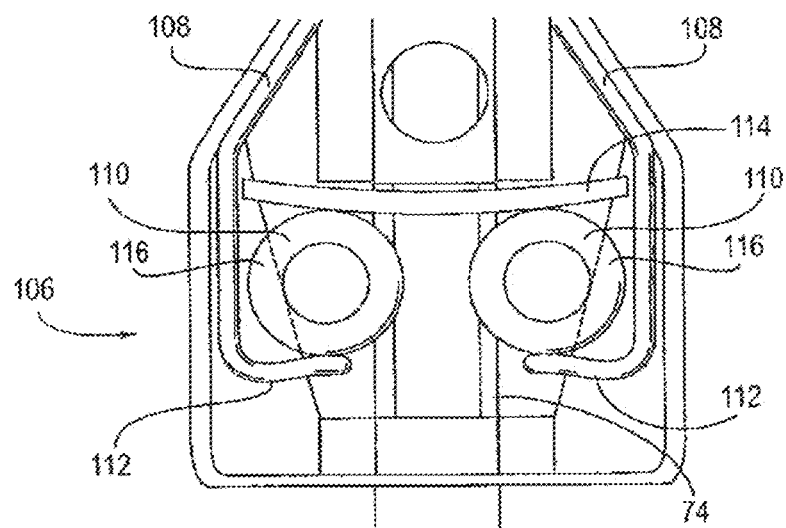
FIGS. 20-21 provide a cross-sectional view of the locking mechanism in the unlocked and locked positions respectively.
Figure 21:
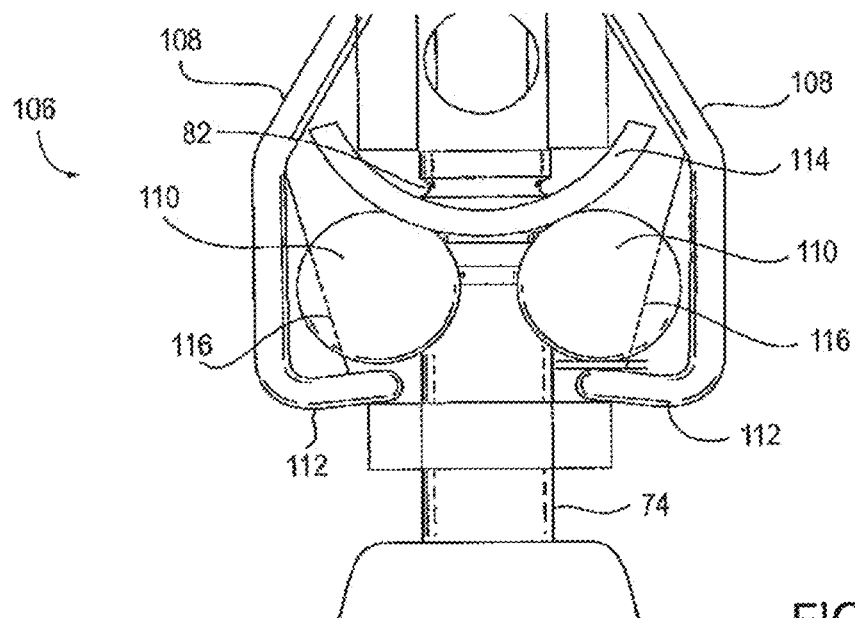

FIGS. 20-21 illustrate the locking mechanism 106 showing the locking mechanism 106 in the unlocked and locked positions respectively. Referring to FIG. 20, the locking mechanism 106 includes one or more wedging elements, such as rolling elements. In this embodiment, the rolling elements comprise a pair of barbells 110 disposed on opposite sides of the stud 74, each barbell having a pair of generally cylindrical caps and a shaft therebetween. The barbells 110 and the stud 74 are preferably comprised of cobalt chromium or stainless steel, however any suitable material may be used. The barbells 110 are manipulated by hooked ends 112 of the release harness 108. When an upwards force is applied to the harness 108 by the lock line 92 (illustrated in FIG. 18), the hooked ends 112 raise the barbells 110 against a spring 114, as shown in FIG. 20. This draws the barbells 110 up along a sidewall or sloping surface 116 which unwedges the barbells 110 from against the stud 74. In this position, the stud 74 is free to move. Thus, when the lock line 92 raises or lifts the harness 108, the locking mechanism 106 is in an unlocked position wherein the stud 74 is free to move the actuation mechanism 58 and therefore the distal elements 18 to any desired position. Release of the harness 108 by the lock line 92 transitions the locking mechanism 106 to a locked position, illustrated in FIG. 21. By releasing the upwards force on the barbells 110 by the hooked ends 112, the spring 114 forces the barbells 110 downwards and wedges the barbells 110 between the sloping surface 116 and the stud 74. This restricts motion of the stud 74, which in turn locks the actuation mechanism 58 and therefore distal elements 18 in place. In addition, the stud 74 may include one or more grooves 82 or indentations which receive the barbells 110. This may provide more rapid and positive locking by causing the barbells 110 to settle in a definite position, increase the stability of the locking feature by further preventing movement of the barbells 110, as well as tangible indication to the user that the barbell has reached a locking position. In addition, the grooves 82 may be used to indicate the relative position of the distal elements 18, particularly the distance between the distal elements 18. For example, each groove 82 may be positioned to correspond with a 0.5 or 1.0 mm decrease in distance between the distal elements 18. As the stud 74 is moved, the barbells 110 will contact the grooves 82; by counting the number of grooves 82 that are felt as the stud 74 is moved, the user can determine the distance between the distal elements 18 and can provide the desired degree of coaptation based upon leaflet thickness, geometry, spacing, blood flow dynamics and other factors. Thus, the grooves 82 may provide tactile feedback to the user.

The locking mechanism 106 allows the fixation device 14 to remain in an unlocked position when attached to the interventional tool 10 during grasping and repositioning and then maintain a locked position when left behind as an implant. It may be appreciated, however, that the locking mechanism 106 may be repeatedly locked and unlocked throughout the placement of the fixation device 14 if desired. Once the final placement is determined, the lock line 92 and proximal element lines 90 are removed and the fixation device is left behind.

Figure 23:
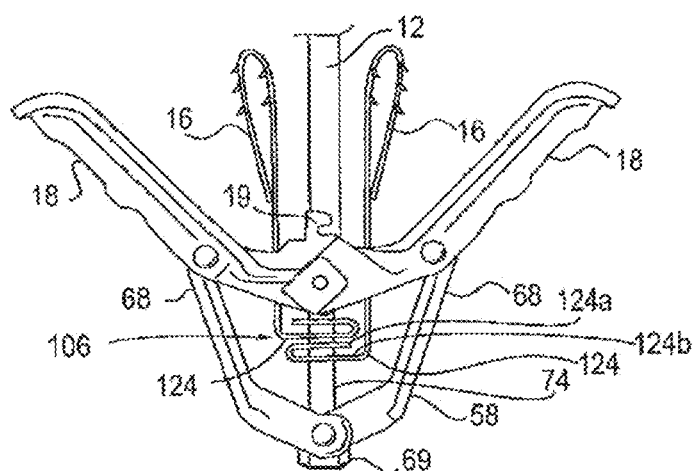
FIGS. 23, 24A-24B illustrate another embodiment of a locking mechanism.
Figure 24A:
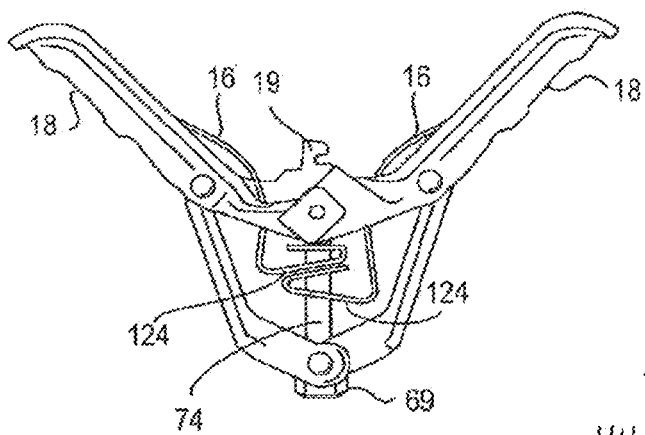
Figure 24B:
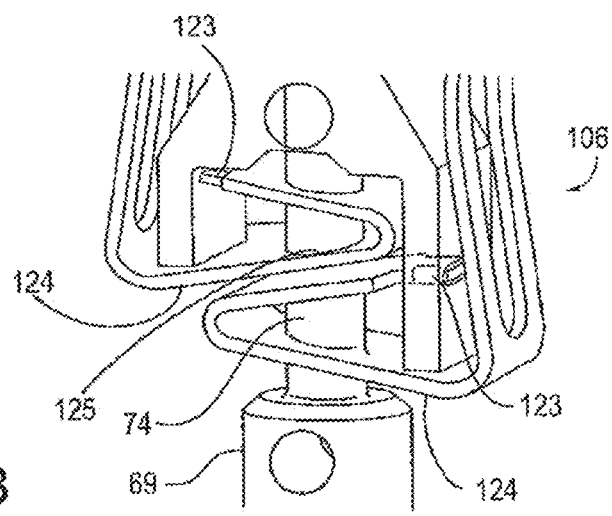

FIGS. 23, 24A-24B illustrate another embodiment of a locking mechanism 106. Referring to FIG. 23, in this embodiment, the locking mechanism 106 is again disposed between the coupling member 19 and the base 69 of the actuation mechanism 58. The base 69 is connected to the stud 74 which extends through the locking mechanism 106, and connects to an actuator rod which extends through the coupling member 19 and the shaft 12 of the interventional tool 10. The base 69 is also connected to the legs 68 of the actuation mechanism 58 which are in turn connected to the distal elements 18. FIG. 23 also illustrates the proximal elements 16 which manipulate the locking mechanism 106 in this embodiment. The locking mechanism 106 comprises folded leaf structures 124 having overlapping portions 124a, 124b, each folded structure 124 being attached to a proximal element 16. In FIG. 23 and FIG. 24A, the folded structures 124 are shown without the remainder of the locking mechanism 106 for clarity. Proximal elements 16 are flexible and resilient and are biased outwardly. The folded leaf structures 124 include holes 125 (FIG. 24B) in each overlapping portion 124a, 124b so that the stud 74 passes through the holes 125 of the portions 124a, 124b as shown. The locking mechanism includes slots into which ends 123 of the folded leaf structures 124 are fixed. When the proximal elements 16 are in an undeployed position, as in FIG. 23, the folded leaf structures 124 lie substantially perpendicular to the stud 74 so that the holes 125 in each overlapping portion are vertically aligned. This allows the stud 74 to pass freely through the holes and the locking mechanism 106 is considered to be in an unlocked position.

Deployment of the proximal elements 16, as shown in FIG. 24A, tilts the folded leaf structures 124 so as to be disposed in a non-perpendicular orientation relative to the stud 74 and the holes 125 are no longer vertically aligned with one another. In this arrangement, the stud 74 is not free to move due to friction against the holes of the folded leaf structure 124. FIG. 24B provides a larger perspective view of the folded structures 124 in this position. Thus, the locking mechanism 106 is considered to be in a locked position. This arrangement allows the fixation device 14 to maintain an unlocked position during grasping and repositioning and then maintain a locked position when the proximal elements 16 are deployed and the fixation device 14 is left behind as an implant. It may be appreciated, however, that the locking mechanism 106 may be repeatedly locked and unlocked throughout the placement of the fixation device 14 if desired.

Figure 25:
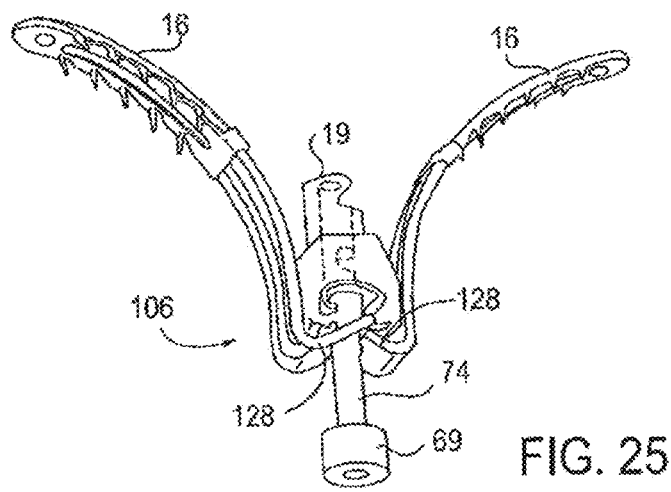
FIGS. 25, 26A-26B illustrate yet another embodiment of a locking mechanism.
Figure 26A:
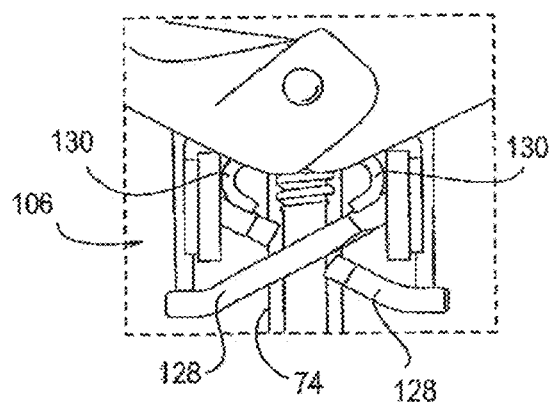
Figure 26B:
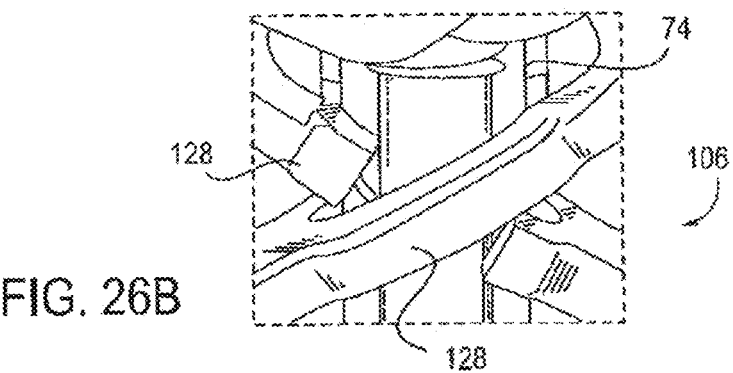

FIGS. 25, 26A-26B illustrate another embodiment of a locking mechanism 106. Referring to FIG. 25, in this embodiment, the locking mechanism 106 is again disposed between the coupling member 19 and the base 69 of the actuation mechanism 58. And, the base 69 is connected to the stud 74 which extends through the locking mechanism 106 and connects to an actuator rod which extends through the coupling member 19 and the shaft of the interventional tool 10. FIG. 25 illustrates the proximal elements 16 which manipulate the locking mechanism 106 in this embodiment. The locking mechanism 106 comprises C-shaped structures 128, each C-shaped structure 128 attached to a proximal element 16. The C-shaped structures 128 hook around the stud 74 so that the stud 74 passes through the "C" of each structure 128 as shown in FIGS. 26A-26B. As shown, the structures 128 cross each other and the "C" of each structure 128 faces each other. A spring 130 biases the C-shaped structures into engagement with one another. When the proximal elements are in an undeployed position, as in FIG. 26A, the C-shaped structures 128 are urged into an orientation more orthogonal to the axial direction defined by stud 74, thus bringing the "C" of each structure 128 into closer axial alignment. This allows the stud 74 to pass freely through the "C" of each structure 128. Deployment of the proximal elements 16 outwardly urges the C-shaped structures into a more angular, non-orthogonal orientation relative to stud 74 causing the sidewalls of the "C" of each structure 128 to engage stud 74 more forcefully. In this arrangement, the stud 74 is not free to move due to friction against the "C" shaped structures 128.

D. Additional Embodiments of Fixation Devices

Figure 22A:
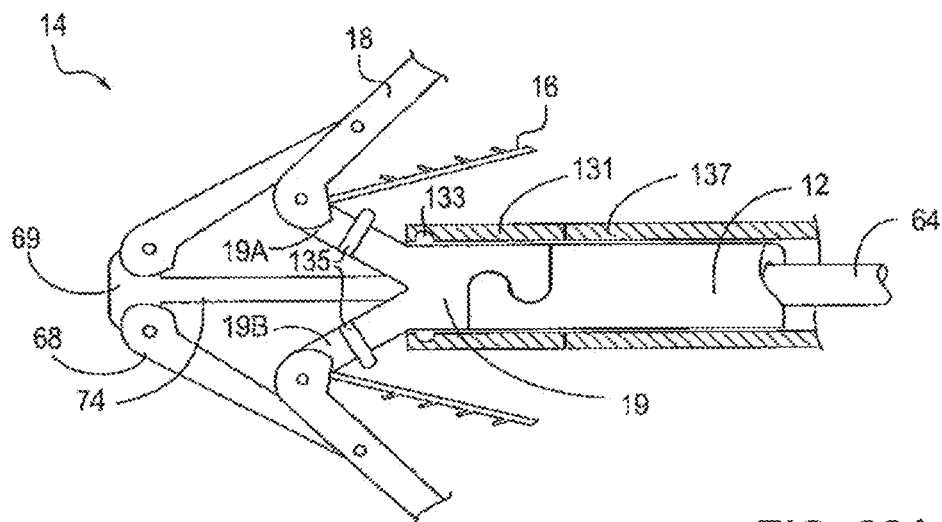
FIGS. 22A-22B illustrate a variation of the fixation device to facilitate capture of more widely-separated leaflets or other tissue flaps.
Figure 22B:
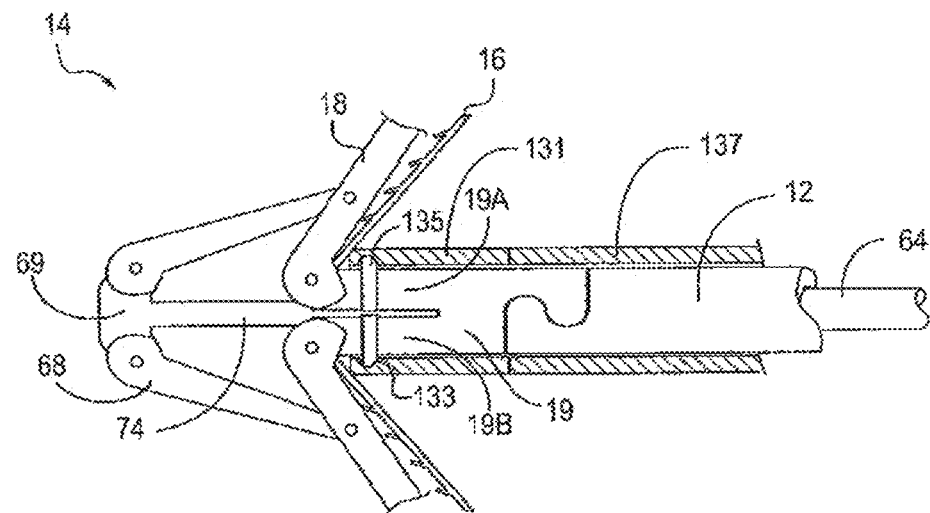

FIGS. 22A-22B illustrate a variation of the fixation device 14 described above in which the distal and proximal elements 16, 18 on each side of the fixation device are movable laterally toward and away from each other to facilitate capture of more widely-separated leaflets or other tissue flaps. The coupling member 19 is bifurcated into two resilient and flexible branches 19A, 19B which are biased outwardly into the position shown in FIG. 22A, but which are movable to the position shown in FIG. 22B. As an alternative, branches 19A, 19B may be more rigid members connected to coupling member 19 by pins or hinges so as to be pivotable toward and away from each other. Each of proximal elements 16 and distal elements 18 are coupled at their proximal ends to one branch 19A or 19B of the coupling member 19. Legs 68 are coupled at their proximal ends to base 69, and therefore stud 74, and at their distal ends to distal elements 18, as described above. Translation of stud 74 distally or proximally relative to coupling member 19 opens or closes distal elements 18 as in formerly described embodiments. A collar 131 is slidably disposed over coupling member 19 and has an annular groove 133 on its inner wall configured to slide over and frictionally engage detents 135 on branches 19A, 19B. A sheath 137 is positioned coaxially over shaft 12 and is slidable relative thereto to facilitate pushing collar 131 distally over coupling member 19.

In use, the embodiment of FIGS. 22A-22B is introduced with distal and proximal elements 16, 18 in the closed position. Collar 131 is pushed distally against, but not over, detents 135 so that branches 19A, 19B are disposed together and fixation device 14 has a minimal profile. When the user is ready to capture the target tissue (e.g. valve leaflets), sheath 137 is retracted so that collar 131 slides proximally over coupling member 19. This allows branches 19A, 19B to separate into the position of FIG. 22A. Actuator 64 is pushed distally so as to open distal elements 18. Tension is maintained on proximal element lines 90 (not shown in FIGS. 22A-22B) so that proximal elements 16 remain separated from distal elements 18. When tissue is positioned between the proximal and distal elements, tension is released on proximal element lines 90 allowing the tissue to be captured between the proximal and distal elements. Sheath 137 may then be advanced distally so that collar 131 urges branches 19A, 19B back together. Sheath 137 is advanced until groove 133 in collar 131 slides over detents 135 and is frictionally maintained thereon as shown in FIG. 22B. Sheath 137 may then be retracted from collar 131. Distal elements 18 may be closed, opened or inverted by advancing or retracting stud 74 via actuator 64, as in the embodiments described above. It should be understood that the embodiment of FIGS. 22A-22B preferably includes a locking mechanism as described above, which has been omitted from the figures for clarity.

In a further alternative of the embodiment of FIGS. 22A-22B, fixation device 14 may be configured to allow for independent actuation of each of the lateral branches 19A, 19B and/or distal elements 18. In an exemplary embodiment, shaft 12 and coupling member 19 may be longitudinally split into two identical halves such that a first branch 19A may be drawn into collar 131 independently of a second branch 19B. Similarly, actuator shaft 64 may be longitudinally split so that each half can slide independently of the other half, thus allowing one of distal elements 18 to be closed independently of the other distal element 18. This configuration permits the user to capture one of the valve leaflets between one of the distal and proximal elements 16, 18, then draw the corresponding branch 19A into the collar 131. The fixation device 14 may then be repositioned to capture a second of the valve leaflets between the other proximal and distal elements 16, 18, after which the second branch 19B may be drawn into collar 131 to complete the coaptation. Of course, the closure of distal elements 18 may occur either before or after branches 19A, 19B are drawn into collar 131.

Figure 27:
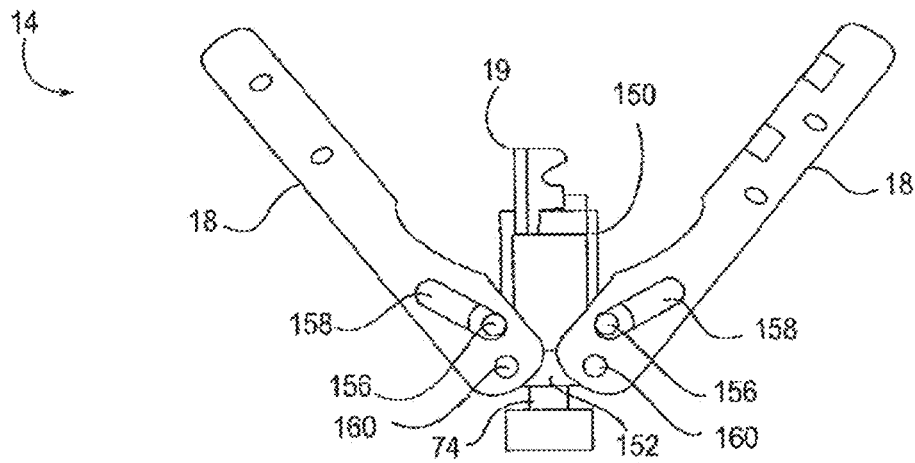
FIGS. 27-28 illustrate an additional embodiment of the fixation device wherein separation of couplers rotate the distal elements around pins.
Figure 28:
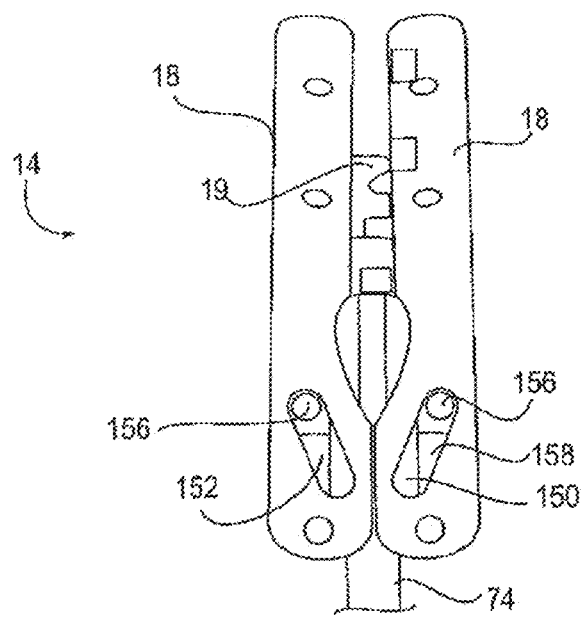

FIGS. 27-28 illustrate an additional embodiment of the fixation device 14. As shown in FIG. 27, the fixation device 14 includes a coupling member 19 which couples the device 14 to the shaft 12 of the interventional tool 10. Here, the device 14 also includes a top coupler 150 attached to coupling member 19 and a bottom coupler 152 attached to the stud 74 so that the two couplers are axially moveable relative to one another. The distal elements 18 are rotatably attached to the top coupler 150 by upper pins 156 and rotatably attached to the bottom coupler 152 by lower pins 160. When the bottom coupler 152 is advanced, the pins 156, 160 are drawn apart. The upper pins 156 are disposed within slots 158 as shown. When the bottom coupler 152 is advanced distally relative to top coupler 150, pins 156, 160 are drawn apart. Angling of the slots 158 causes the distal elements 18 to rotate toward the coupling member 19 as the pins 156, 160 are drawn apart. Relative movement of the couplers 150, 152 may be achieved by any suitable mechanism including sliding or threading.

FIG. 28 illustrates the fixation device 14 in the closed position. Here, the device 14 has a low profile (width in the range of approximately 0.140-0.160 inches orthogonal to the axial direction defined by shaft 12/stud 74) so that the device 14 may be easily passed through a catheter and through any tissue structures. To open the device 14 the bottom coupler 152 is then retracted or the couplers 150, 152 brought toward one another to rotate the distal elements 18 outward. The components of the fixation device 14 may be formed from stainless steel or other suitable metal, such as by machining, or formed from a polymer, such as by injection molding. In addition, portions of the fixation device 14, particularly the distal elements 18, may be covered with a covering such as described above, to promote tissue ingrowth, reduce trauma, enhance friction and/or release pharmacological agents. Alternatively, the device 14 may have a smooth surface which prevents cellular adhesion thereby reducing the accumulation of cells having potential to form an emboli.

Figure 29:
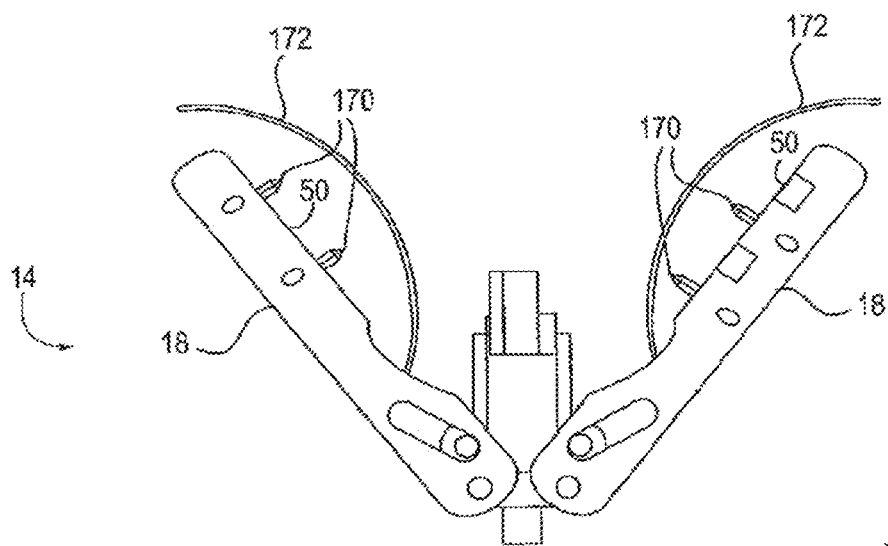
FIGS. 29-30 illustrate the fixation device of FIGS. 27-28 with additional features such as barbs and bumpers.
Figure 30:
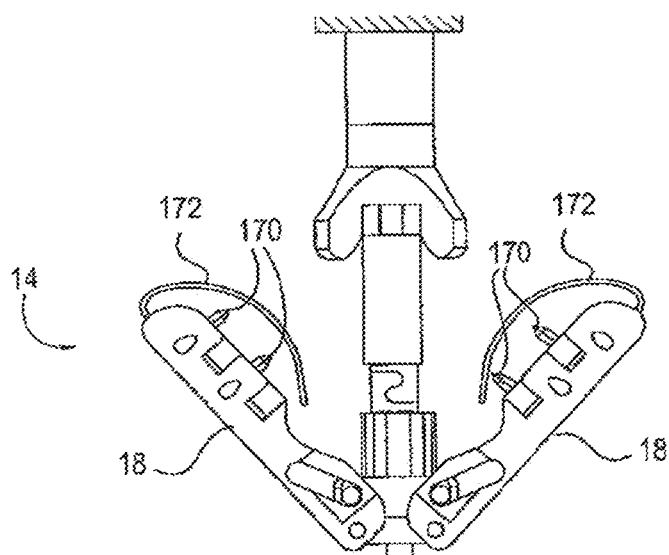

Optionally, the fixation device 14 may include tissue retention features such as barbs 170 and/or bumpers 172, illustrated in FIGS. 29-30. The barbs 170 may extend from the engagement surfaces 50 of the distal elements 18, as shown, and may be present in any number and any arrangement. Thus, the barbs 170 will engage the leaflets or tissue during grasping to assist in holding the tissue either by frictional engagement, minor surface penetration or by complete piercing of the tissue, depending on the length and shape of the barbs 170 selected. Alternatively or in addition, bumpers 172 may extend from the distal elements 18. As shown in FIG. 29, each bumpers 172 may extend from the proximal end 52 of the distal element 18 and curve toward the free end 54 of the distal element 18. Or, as shown in FIG. 30, each bumper 172 may extend from the free end 54 and curve toward the proximal end 52. Bumpers 172 are preferably constructed of a resilient metal or polymer and may have any of various geometries, including a solid thin sheet or a loop-shaped wire form. The bumpers 172 may help to actively engage and disengage tissue from the barbs 170 during opening and closing of the fixation device 14. Further, to assist in grasping a tissue, the engagement surfaces 50 may have any texture or form to increase friction against the grasped tissue. For example, the surfaces 50 may include serrations, scales, felt, barbs, polymeric frictional elements, knurling or grooves, to name a few.

Figure 31:
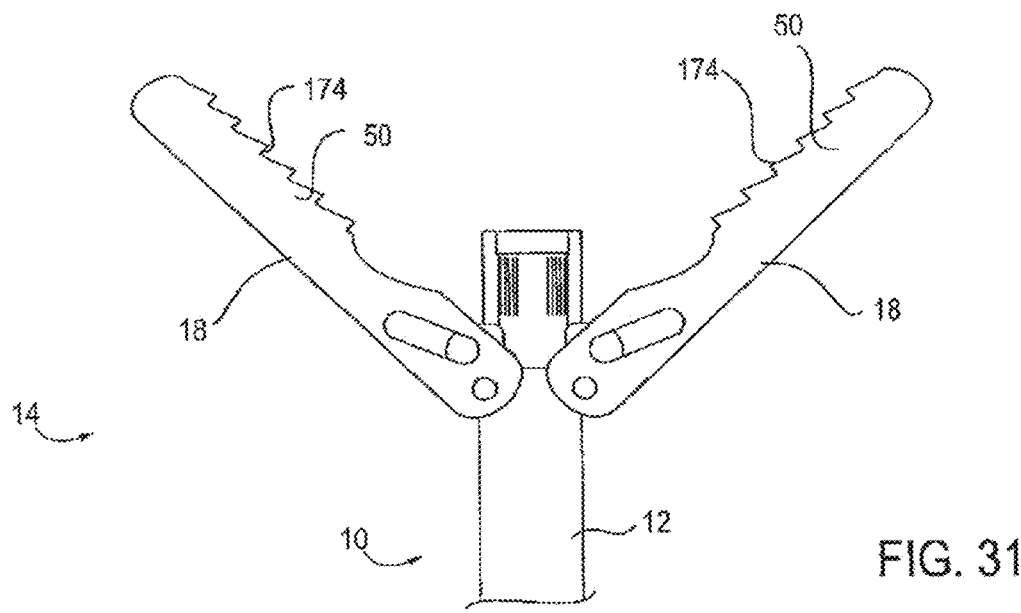
FIG. 31 illustrates an embodiment of the fixation device having engagement surfaces with a serrated edge and wherein the fixation device is mounted for a ventricular approach to a mitral valve.

FIG. 31 illustrates the engagement surface 50 having a serrated edge 174 to improve grip on tissue engaged. FIG. 31 also illustrates an embodiment of the fixation device 14 mounted on an interventional tool 10 or delivery catheter for ventricular approach to the mitral valve. Here the device 14 is mounted on the shaft 12 with the engagement surfaces 50 facing distally relative to shaft 12 (and facing upstream relative to the mitral valve). Thus, when the mitral valve is approached from the ventricular side, the engagement surfaces 50 can be pressed against the downstream surfaces of the valve without passing through the valve. It may be appreciated that any of the embodiments of the fixation device 14 described herein may be mounted on shaft 12 in this orientation for approach to any valve or tissue, including embodiments that include both proximal and distal elements.

It may be appreciated that when the fixation device 14 is mounted on the shaft 12 in orientation illustrated in FIG. 31, the position of the distal elements and the proximal elements are reversed. In such instances it is useful to keep in mind that the distal elements contact the distal surface or downstream surface of the leaflets and the proximal elements contact the proximal surface or upstream surface of the leaflets. Thus, regardless of the approach to the valve and the relative position of the proximal and distal elements on the fixation device, the proximal and distal elements remain consistent in relation to the valve.

Figure 32:
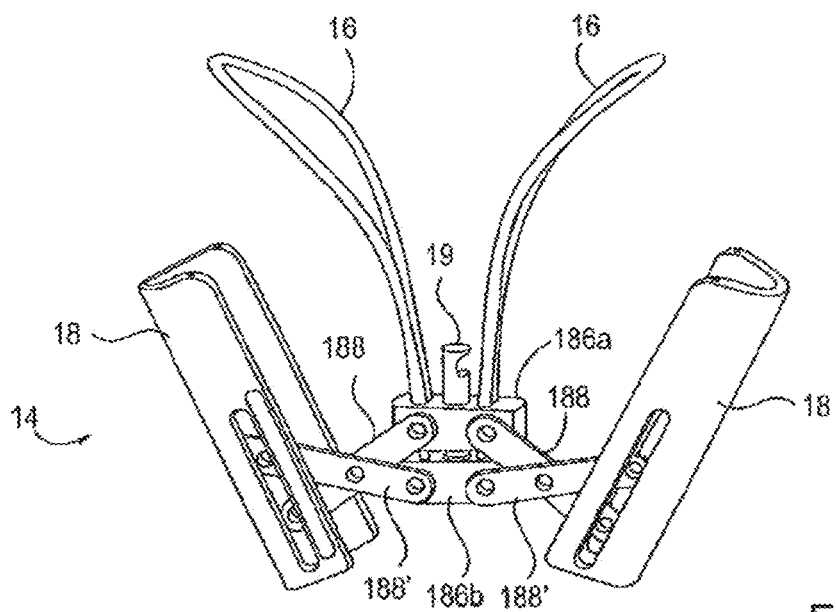
FIGS. 32-34 illustrate an additional embodiment of the fixation device which allows tissue to be grasped between the distal elements and the proximal elements while in an arrangement wherein the distal elements are parallel to each other.
Figure 33:
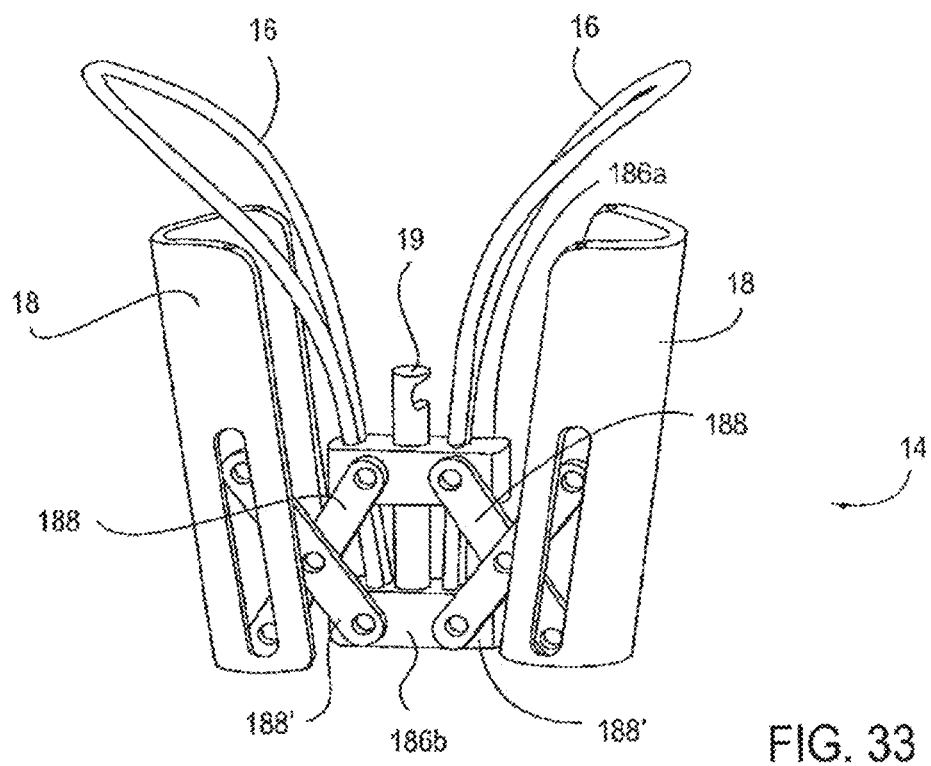
Figure 34:
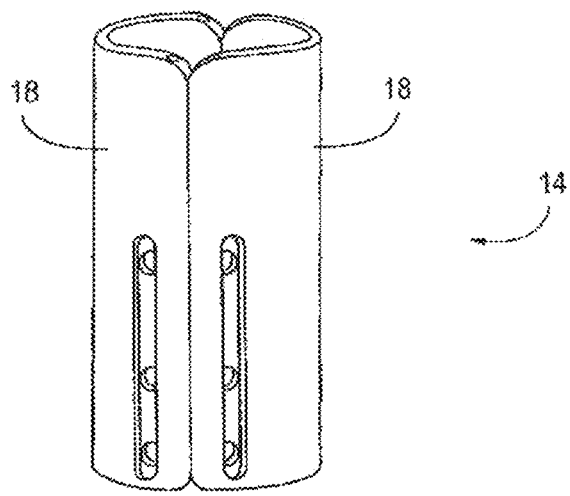

FIGS. 32-34 illustrate an additional embodiment of the fixation device 14. As shown in FIG. 32, the fixation device 14 includes a coupling member 19, proximal elements 16 and distal elements 18 which are each connected to a set of base components 186. The distal elements 18 are connected to the base components 186 (top base component 186a and a bottom base component 186b) by extension arms 188. In this embodiment, each distal element 18 is connected by two extension arms 188 in a crossed arrangement so that one extension arm 188 connects the distal element 18 to the top base component 186a and the other extension arm 188' connects the distal element 18 to the bottom base component 186b. The top base component 186a can be separated from the bottom base component 186b by any suitable method which may be torque driven, spring driven or push/pull. Increasing the separation distance between the base components 186 draws the distal elements 18 inwards toward the base components 186, as shown in FIG. 33. This allows the tissue to be grasped between the distal elements 18 and proximal elements 16 while in an arrangement wherein the distal elements 18 are parallel to each other. This may prevent inconsistent compression of the tissue and may better accommodate tissues or leaflets of varying thicknesses. As shown in FIG. 34, the distal elements 18 may be drawn together and the proximal elements 16 may be retracted to form a low profile fixation device 14.

Figure 35:
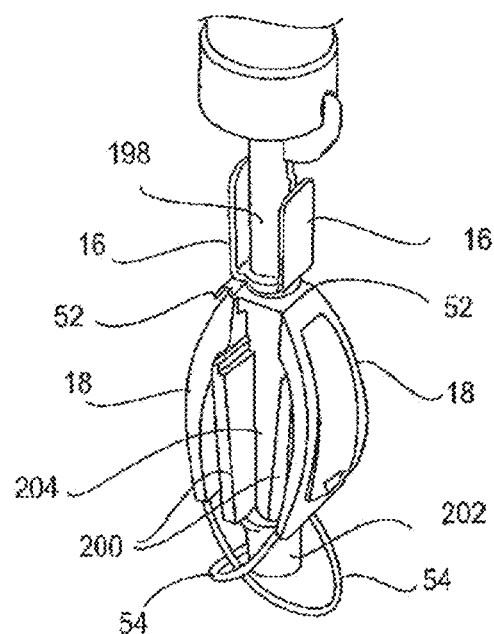
FIGS. 35-39, 40A-40D, 41-42, 43A-43C illustrate another embodiment of the fixation device wherein the fixation device includes distal elements having implant pledgets.
Figure 36:
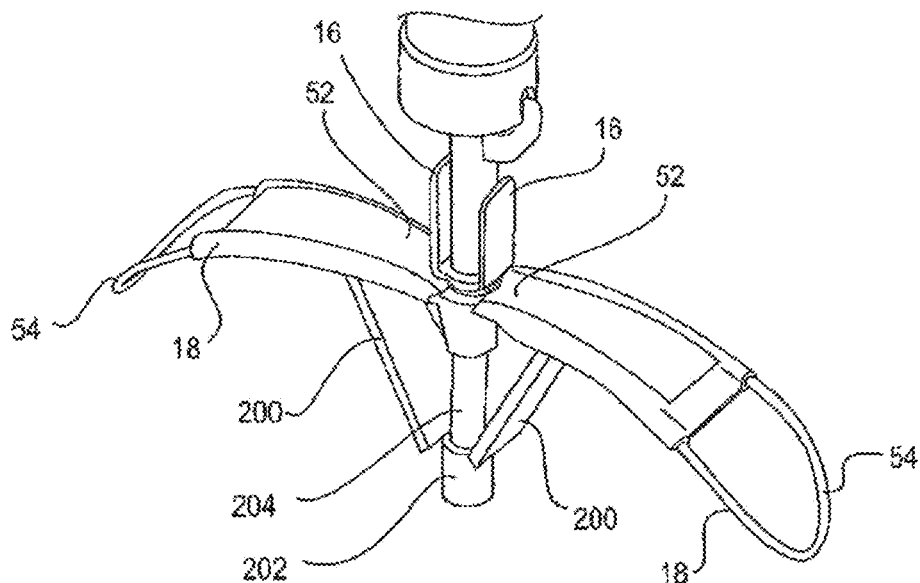
Figure 37:
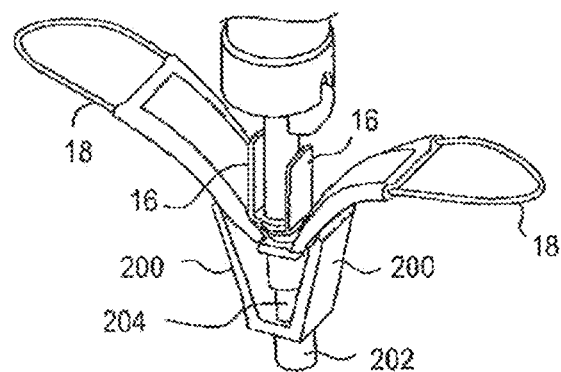

FIGS. 35-39, 40A-40D, 41-42, 43A-43C illustrate another embodiment of the fixation device 14. In this embodiment, the device 14 is deliverable in the inverted position and moveable to the open position for grasping of the tissue. FIG. 35 illustrates the fixation device 14 in the inverted position. The fixation device 14 includes a shaft 198, proximal elements 16 and distal elements 18. Each distal element 18 has a proximal end 52 rotatably connected to the shaft 198 and a free end 54. The fixation device 14 also includes an actuator rod 204, a base 202 and a pair of deployment arms 200 attached to the base 202 as shown. In the inverted position, the extender 204 is extended and deployment arms 200 are disposed between the actuator rod 204 and the distal elements 18. As shown in FIG. 36, the actuator rod 204 may be retracted so that the deployment arms 200 press against the distal elements 18, rotating the distal elements 18 from the inverted position to the open position. The angle of the distal elements 18 may be adjusted by retracting or extending the actuator rod 204 various distances. As shown in FIG. 37, further retraction of the actuator rod 204 raises the distal elements 18 further.

Figure 38:
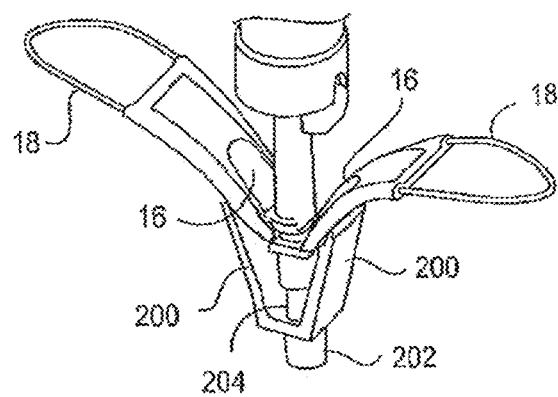

In the open position, tissue or leaflets may be grasped between the distal elements 18 and proximal elements 16. FIG. 38 illustrates the proximal elements 16 in their released position wherein the tissue or leaflet would be present therebetween. Hereinafter, the tissue will be referred to as leaflets. In this embodiment, each distal element 18 includes an implant pledget 210, typically press-fit or nested within each distal element 18. The implant pledgets 210 will be attached to the leaflets by ties, such as sutures or wires, and will be used to hold the leaflets in desired coaptation. The implant pledgets 210 will then be separated from the fixation device 14 and will remain as an implant.

Figure 39:
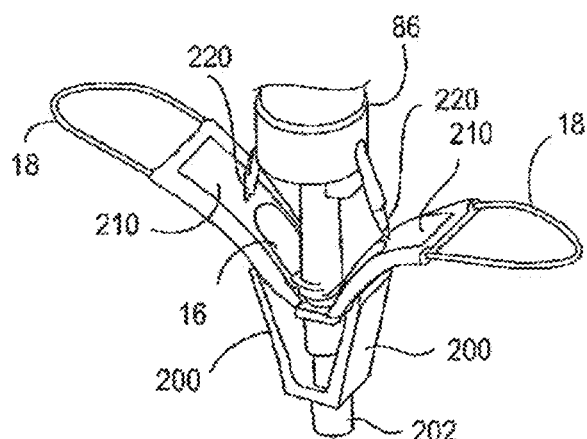
Figure 40A:
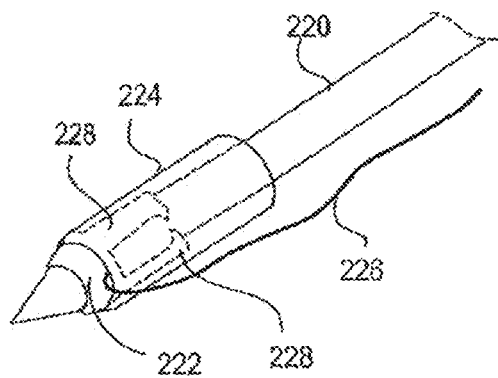

To attach the implant pledgets 210 to the leaflets, the leaflets and implant pledgets 210 are punctured by fixation tools 220, as shown in FIG. 39. The fixation tools 220 extend from the catheter 86, pass through the leaflets and puncture the implant pledgets 210. Thus, the pledgets 210 are comprised of a puncturable material, such as structural mesh. The fixation tools 220 are used to deliver an anchor 222 as illustrated in larger view in FIGS. 40A-40D. FIG. 40A shows the fixation tool 220 including a sleeve 224 surrounding the fixation tool 220 and an anchor 222 loaded therebetween. In this embodiment, the anchor includes one or more flaps 228 which are held within the sleeve 224. It may be appreciated that the anchor 222 may have any suitable form. Additional exemplary embodiments of anchors are provided in commonly assigned U.S. Pat. No. 6,752,813 incorporated herein for all purposes. A suture 226 is attached to the anchor 222 and extends through the sleeve 224 or on the outside of the sleeve 224, as shown, to the catheter 86. The fixation tools 220 are advanced so that the anchor 222 passes through the leaflet (not shown) and the pledget 210, as shown in FIG. 41.

Figure 40B:
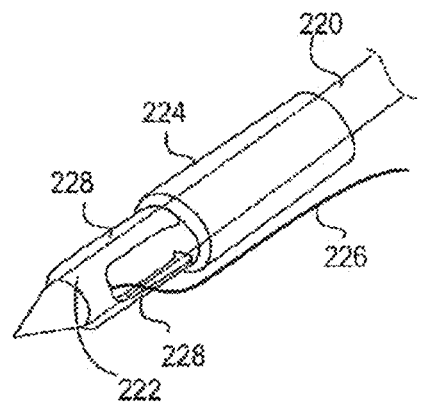
Figure 40C:
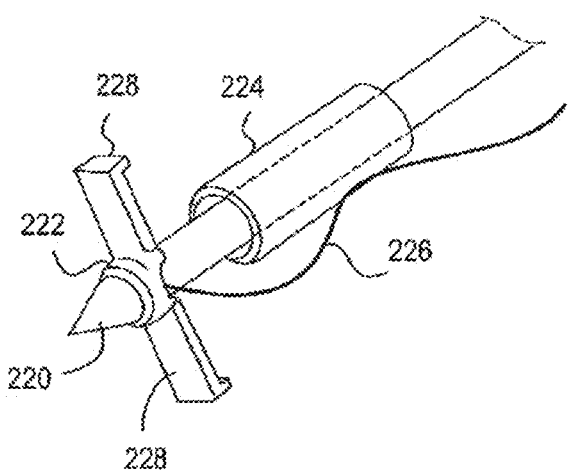
Figure 40D:
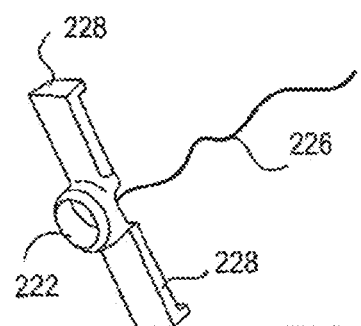
Figure 41:
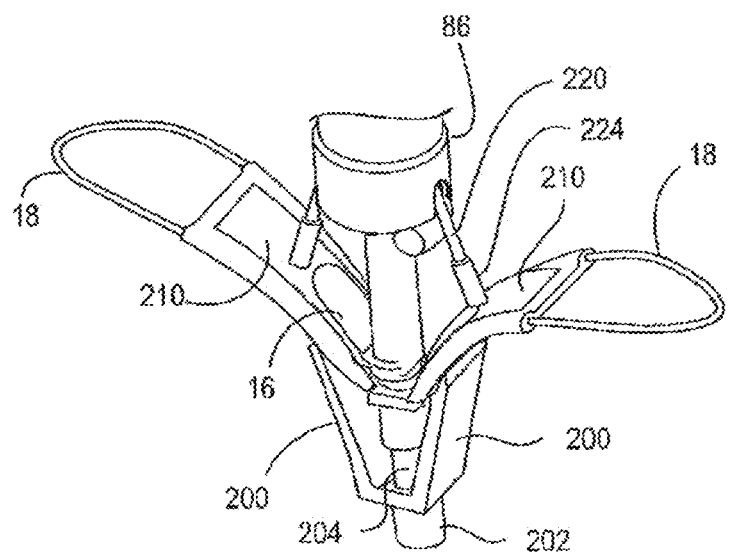
Figure 42:
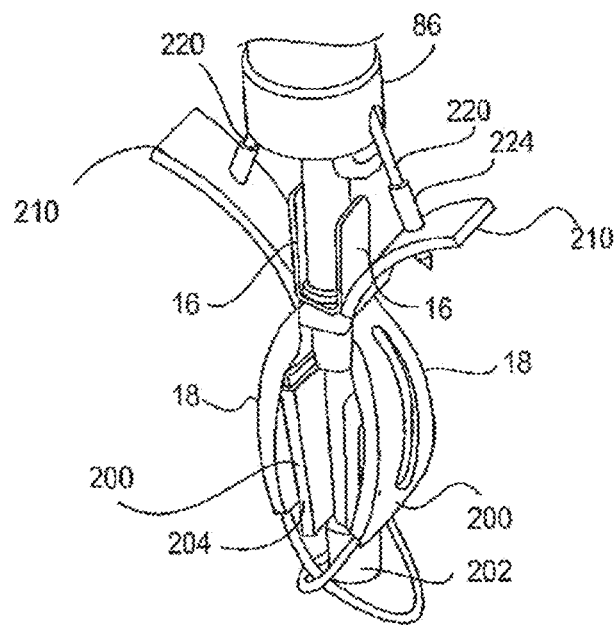

Referring now to FIG. 40B, the sleeve 224 is then retracted to expose the flaps 228 which releases the anchor 222 from the confines of the sleeve 224. The flaps 228 extend radially outwardly, illustrated in FIG. 40C, by spring loading, shape memory or other self-expanding mechanism. Thus, the flaps 228 are positioned against the distal side of the pledget 210, the suture 226 passing through the pledget 210 and the leaflet, as shown in FIG. 41. At this point, the pledgets 210 can be removed from the distal elements 18. By extending the actuator rod 204 distally, the base 202 draws the deployment arms 200 distally which returns the distal elements 18 to the inverted position, as shown in FIG. 42. Since the pledgets 210 have been pierced by the fixation tools 220 and the anchors 222 have been deployed, the pledgets 210 and the leaflets disengage from distal elements 18 and remain in position. The proximal elements 16 may also be returned to their initial position as shown, using any of various mechanisms as have been described above in connection with other embodiments. Referring now to FIG. 40D, the fixation tool 220 is then removed while the anchor 222 remains in place with suture 226 attached.

Figure 43A:
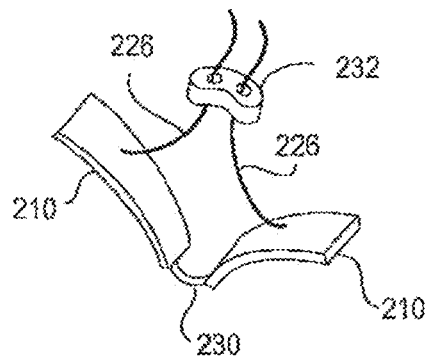
Figure 43B:
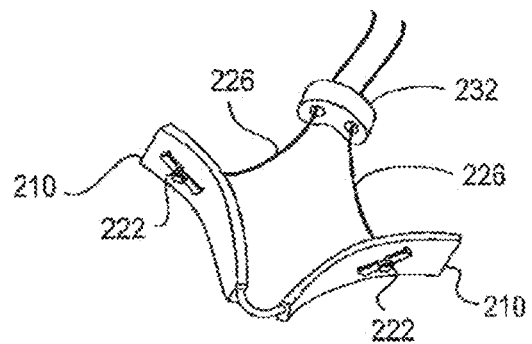
Figure 43C:
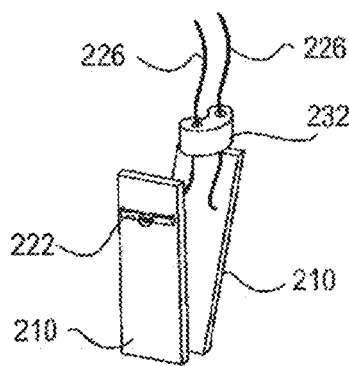

The implant pledgets 210 are then separated from the fixation device 14 and left behind to maintain coaptation of the leaflets in the desired position. FIGS. 43A-43C illustrate the implant pledgets 210 from various perspective views. FIG. 43A provides a perspective top view showing that the pledgets 210 are connected by a link 230 that allows the pledgets 210 to be released from one side of the fixation device 14. In addition, the sutures 226 are fixed together, either by knot tying or placement of a suture fastener 232 as shown. It may be appreciated that the suture fastener 232 may have any suitable form. Additional exemplary embodiments of suture fasteners 232 are provided in commonly-assigned U.S. Pat. No. 7,048,754, which is incorporated herein by reference for all purposes. FIG. 43B provides a perspective bottom view showing the anchor 222 positioned against the bottom side of the pledget 210. Likewise, FIG. 43C provides a perspective side view also showing the anchor 222 positioned against the bottom side of the pledget 210.

Figure 44A:
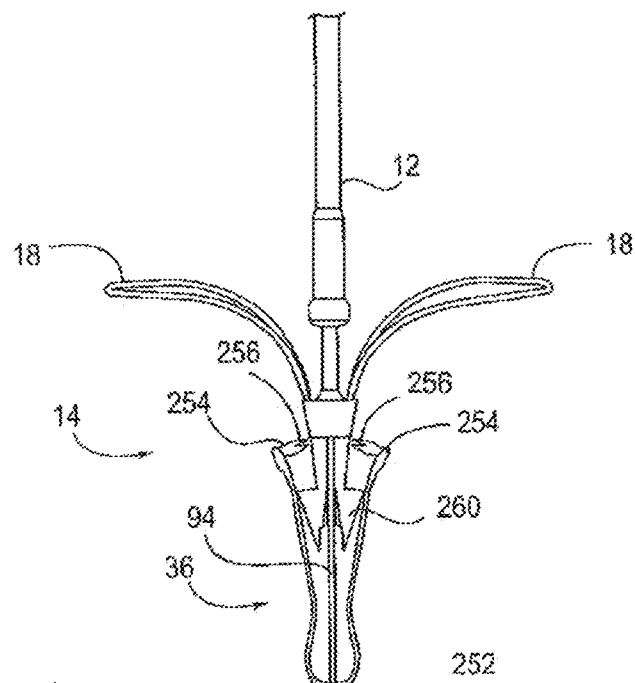
FIGS. 44A-44B, 45-46 illustrate another embodiment of the fixation device wherein the distal elements are comprised of a semi-rigid material having a folded shape.
Figure 44B:
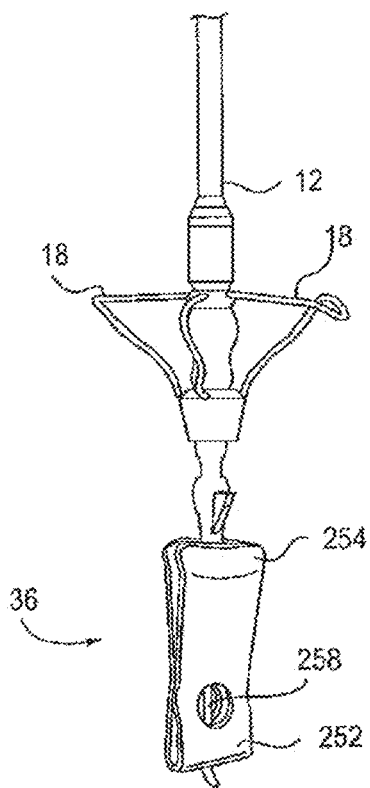
Figure 45:
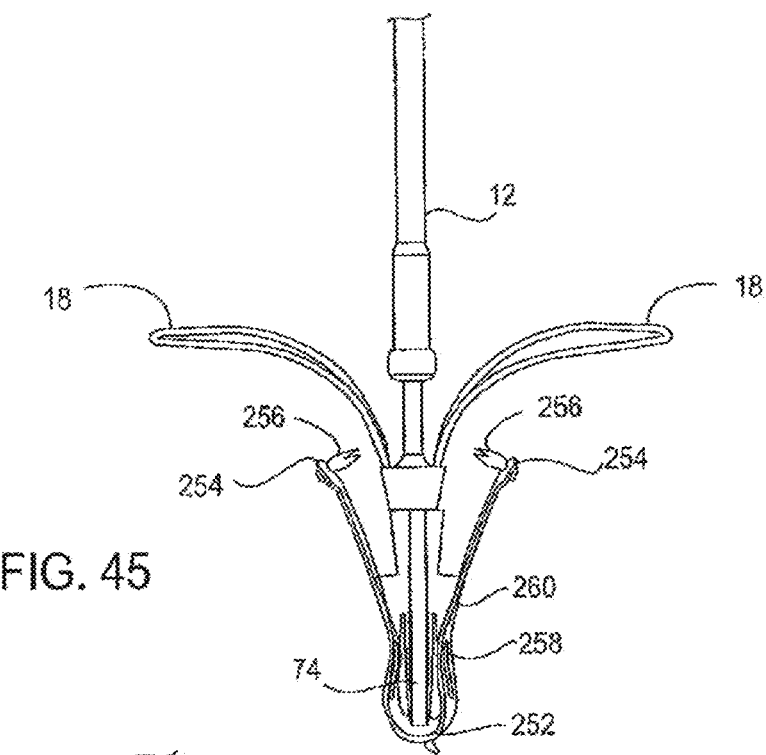
Figure 46:
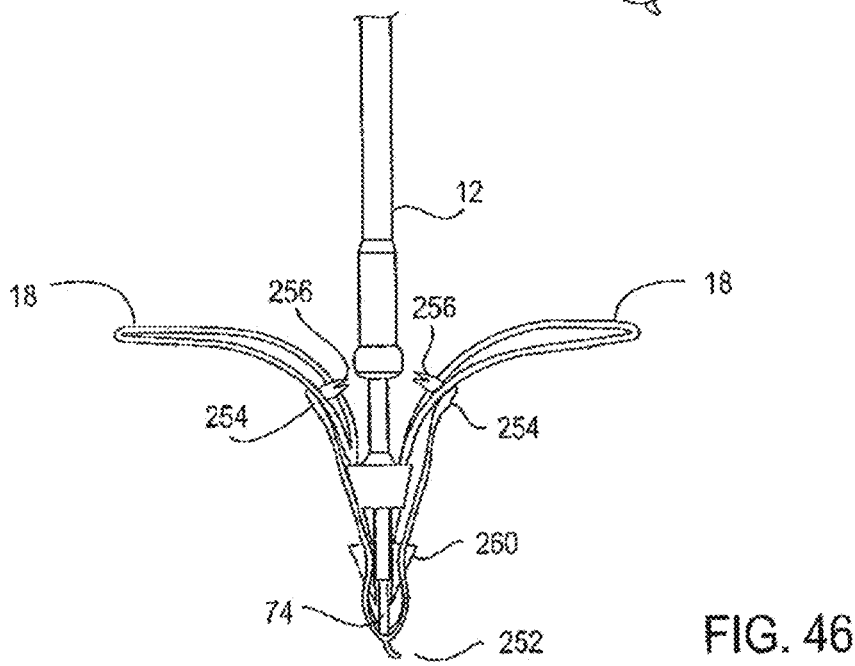

FIGS. 44A-44B, 45-46 illustrate another embodiment of the fixation device 14. As shown in FIG. 44A, the fixation device 14 is mounted on the shaft 12 and is comprised of distal elements 18 and a retention clip 36 comprised of a semi-rigid material having a folded shape. The material may be any suitable material providing rigidity with recoiling properties such as various metals or plastics. The folded shape is such that a fold 252 is directed distally and free ends 254 are directed proximally toward the distal elements 18. Penetration elements 256 are disposed near the free ends 254 and directed toward the shaft 12. In addition, an opening 258 is located near the fold 252, as illustrated in FIG. 44B which provides a perspectives view of the device 14. Referring back to FIG. 44A, the fold 252 is attached to an actuator rod 74 which passes through the shaft 12 and an arrow-shaped structure 260 is disposed on the shaft 12 between the free ends 254, proximal to the opening 258, as shown. In this arrangement, the fixation device 14 is advanced through the valve so that the distal elements 18 are disposed below the leaflets. The device may then be retracted proximally to capture the leaflets within the distal elements 18. As shown in FIG. 45, retraction of the actuator rod 74 draws the retention clip 36 toward the distal elements 18 so that the sloping sides of the arrow-shaped structure 260 force the free ends 254 outward, away from the shaft 12. Further retraction of actuator rod 74 results in the sloping sides of arrow shaped structure 260 falling into the opening 258 in retention clip 36, causing retention clip 36 to recoil back to the closed position as shown in FIG. 46, with the free ends 254 extending through the distal elements 18. This allows the penetration elements 256 to penetrate the leaflets (not shown) to secure engagement therewith. The actuator rod 74 is then detached from the retention clip 36 and shaft 12 is detached from distal elements 18 which are left in place to hold the leaflets in a coapted arrangement.

It may be appreciated that the foregoing embodiment may also include proximal elements 16 configured to be positioned on the upstream side of the valve leaflets to assist in the capture and fixation. Such proximal elements may be mounted to shaft 12 so as to be removed following fixation of the leaflets, or the proximal elements may be connected to distal elements 18 and/or retention clip 36 to be implanted therewith.

In further embodiments, the proximal elements may be manipulated to enhance gripping. For example, the proximal elements may be lowered to grasp leaflets or tissue between the proximal and distal elements, and then the proximal elements may be moved to drag the leaflets or tissue into the fixation device. In another example, the proximal elements may be independently lowered to grasp the leaflets or tissue. This may be useful for sequential grasping. In sequential grasping, one proximal element is lowered to capture a leaflet or tissue portion between the proximal and distal elements. The fixation device is then moved, adjusted or maneuvered to a position for grasping another leaflet or tissue portion between another set of proximal and distal elements. In this position, the second proximal element is then lowered to grasp this other leaflet or tissue portion.

IV. Delivery Device

A. Overview of Delivery Device

Figure 47:
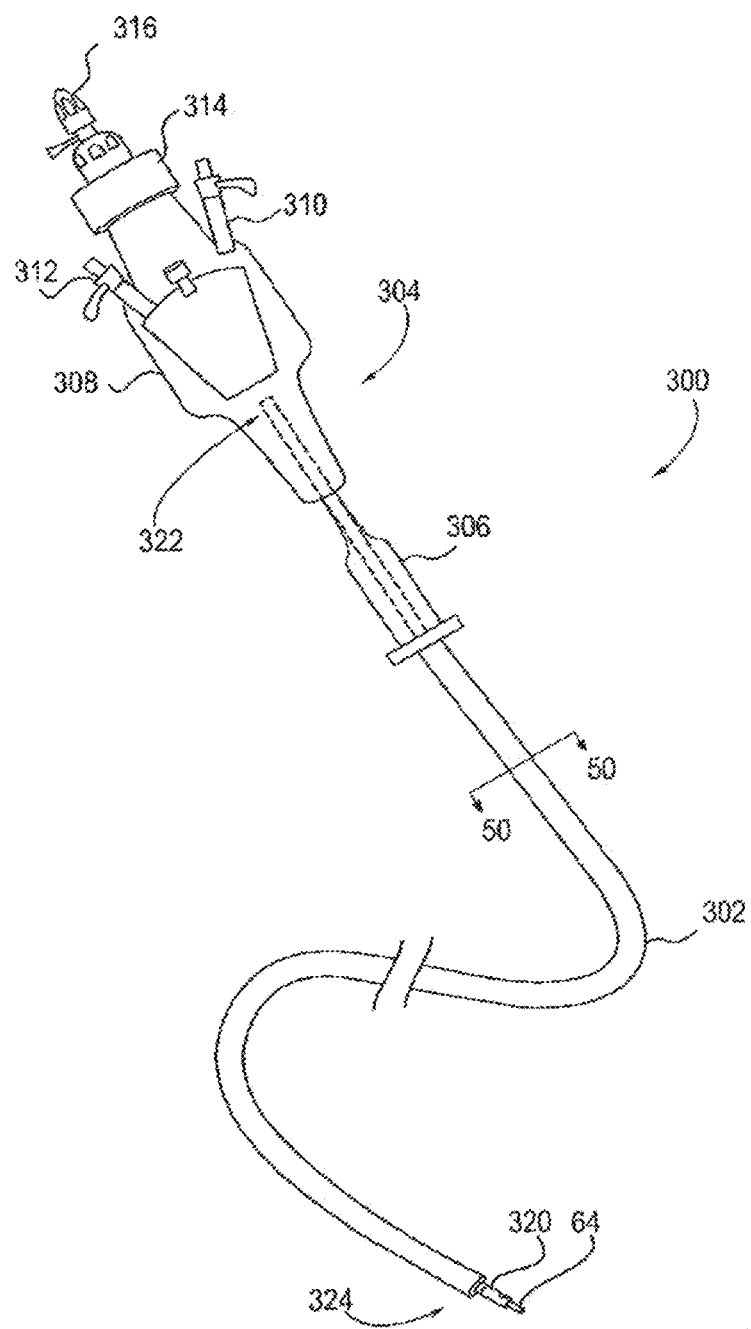
FIG. 47 is a perspective view of an embodiment of a delivery catheter for a fixation device.

FIG. 47 provides a perspective view of an embodiment of a delivery device or delivery catheter 300 which may be used to introduce and position a fixation device as described above. The delivery catheter 300 includes a shaft 302, having a proximal end 322 and a distal end 324, and a handle 304 attached to the proximal end 322. A fixation device (not shown) is removably coupleable to the distal end 324 for delivery to a site within the body, typically for endovascular delivery to the mitral valve. Thus, extending from the distal end 324 is a coupling structure 320 for coupling with a fixation device. Also extending from the distal end 324 is an actuator rod 64. The actuator rod 64 is connectable with the fixation device and acts to manipulate the fixation device, typically opening and closing the distal elements. Such coupling to a fixation device is illustrated in FIG. 48.

Figure 48:
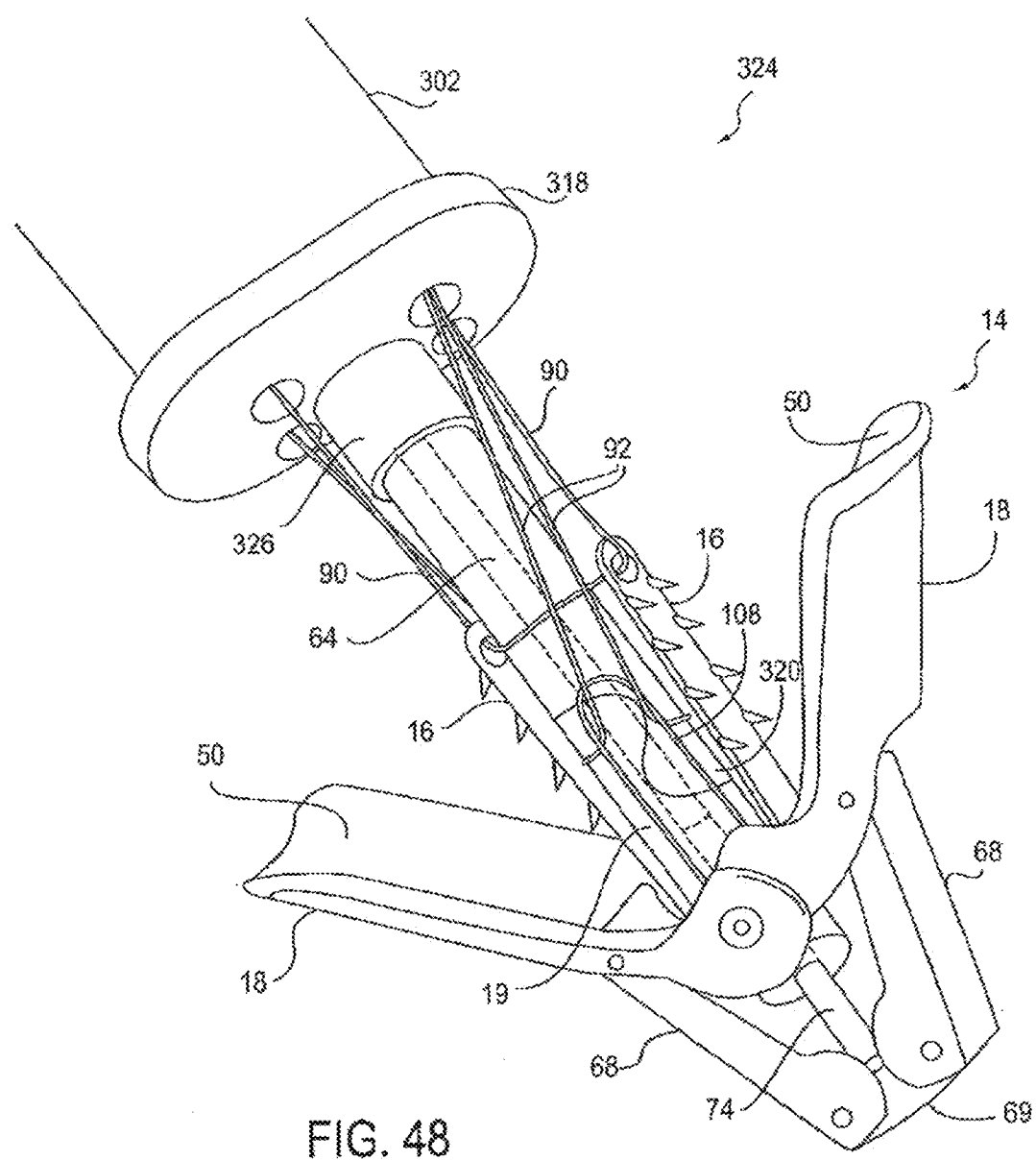
FIG. 48 illustrates an embodiment of a fixation device coupled to the distal end of a delivery catheter.

FIG. 48 illustrates an embodiment of a fixation device 14 coupled to the distal end 324 of the delivery catheter 300. The shaft 302 is shown having a nose 318 near its distal end 324. In this embodiment, the nose 318 has a flanged shape. Such a flanged shape prevents the nose 318 from being retracted into a guiding catheter or introducer as will be discussed in later sections. However, it may be appreciated that the nose 318 may have any shape including bullet, rounded, blunt or pointed, to name a few. Extending from the nose 318 is a compression coil 326 through which the coupling structure 320 and actuator rod 64 pass. The actuator rod 64 is coupleable, as shown, with the stud 74 of the fixation device 14. Such coupling is illustrated in FIG. 49.

Figure 49:
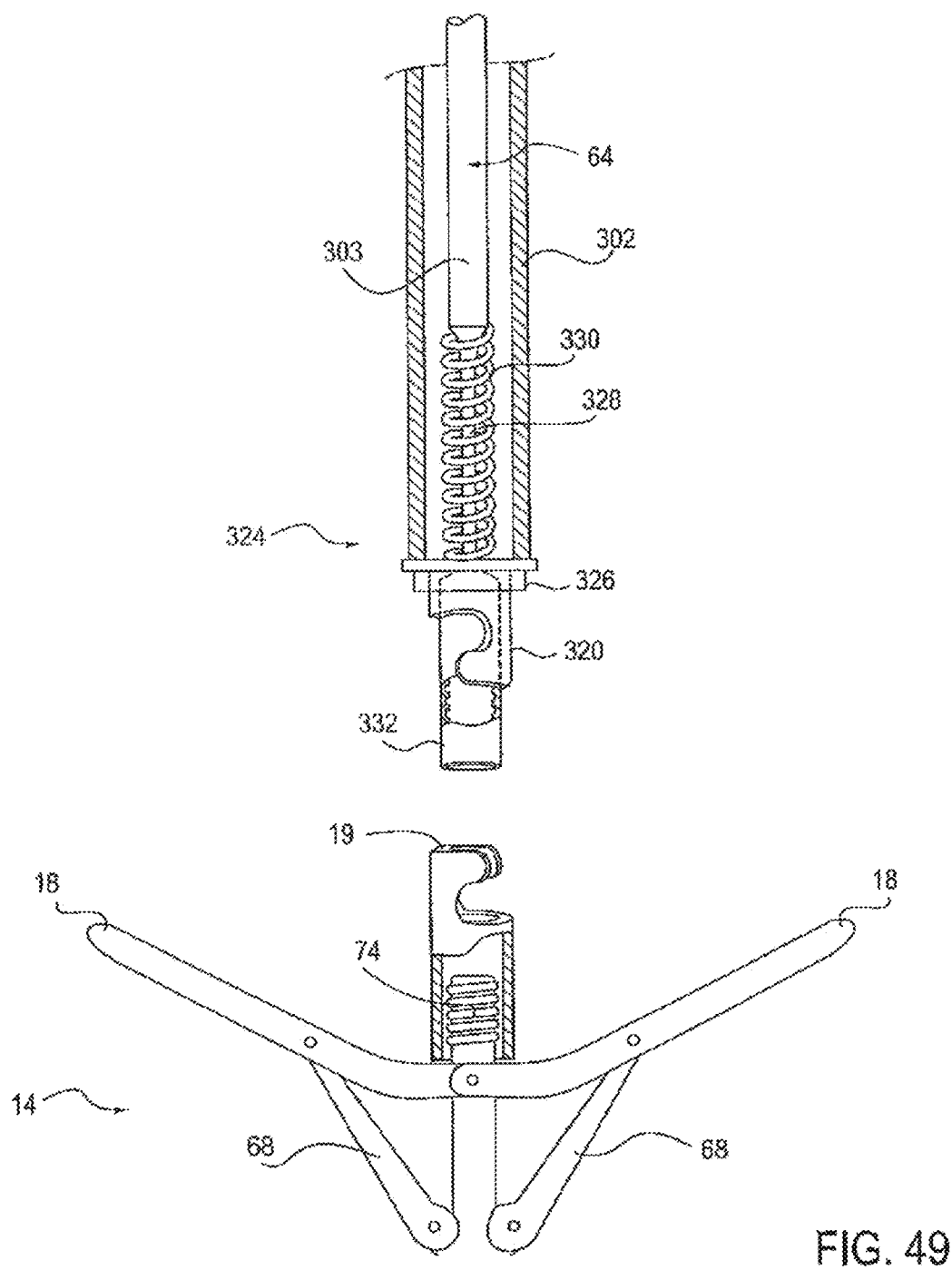
FIG. 49 illustrates a portion of the shaft of a delivery catheter and a fixation device which is coupleable with the catheter.

FIG. 49 illustrates a portion of the shaft 302 of the delivery catheter 300 and a fixation device 14 which is coupleable with the catheter 300. Passing through the shaft 302 is the actuator rod 64. In this embodiment, the actuator rod 64 comprises a proximal extremity 303 and a distal extremity 328, the distal extremity 328 of which is surrounded by a coil 330. The proximal extremity 303 is typically comprised of stainless steel, nitinol, or Elgiloy®, to name a few, and may have a diameter in the range of 0.010 in. to 0.040 in., preferably 0.020 in. to 0.030 in., more preferably 0.025 in., and a length in the range of 48 to 72 in. The distal extremity 328 may be tapered, is typically comprised of stainless steel, nitinol, or Elgiloy®, to name a few, and may have a diameter in the range of 0.011 to 0.025 in and a length in the range of 4 to 12 in. Such narrowing increases flexibility of the distal end 324 of the actuator rod 64. The actuator rod 64 further comprises a joiner 332 which is attached to the distal extremity 328. The joiner 332 is removably attachable with stud 74 of the fixation device 14. In this embodiment, the joiner 332 has internal threads which mate with external threads on the stud 74 of the fixation device 14. As described previously, the stud 74 is connected with the distal elements 18 so that advancement and retraction of the stud 74, by means of the actuator rod 64, manipulates the distal elements. Likewise, the coupling member 19 of the fixation device 14 mates with the coupling structure 320 of the catheter 300. Thus, the coupling member 19 and coupling structure 320 function as previously described in relation to FIGS. 6A-6B.

Referring back to FIG. 48, the fixation device 14 may also include a locking mechanism which includes a release harness 108, as previously described in relation to FIGS. 18-21. Lock lines 92 are connected with the release harness 108 to lock and unlock the locking mechanism 106 as previously described. The lock lines 92 extend through the shaft 302 of the delivery catheter 300 and may connect with the release harness 108 in various arrangements as will be illustrated in later sections. Similarly, proximal element lines 90 extend through the shaft 302 of the delivery catheter 300 and connect with the proximal elements 16. The proximal elements 16 are raised and lowered by manipulation of the proximal element lines 90 as previously described. The proximal element lines 90 may connect with the proximal elements 16 in various arrangements as will be illustrated in later sections.

Referring back to FIG. 47, the handle 304 attached to the proximal end 322 of the shaft 302 is used to manipulate the coupled fixation device 14 and to optionally decouple the fixation device 14 for permanent implantation. As described, the fixation device 14 is primarily manipulated by the actuator rod 64, proximal element lines 90 and lock lines 92. The actuator rod 64 manipulates the distal elements 18, the proximal element lines 90 manipulate the proximal elements 16 and the lock lines 92 manipulate the locking mechanism. In this embodiment, the actuator rod 64 may be translated (extended or retracted) to manipulate the distal elements 18. This is achieved with the use of the actuator rod control 314 which will be described in later sections. The actuator rod 64 may also be rotated to engage or disengage the threaded joiner with the threaded stud 74. This is achieved with the use of the actuator rod handle 316 which will also be described in later sections. Further, the proximal element lines 90 may be extended, retracted, loaded with various amounts of tension or removed with the use of the proximal element line handle 312. And, the lock lines 92 may be may be extended, retracted, loaded with various amounts of tension or removed with the use of the lock line handle 310. Both of these handles 310, 312 will be described in more detail in later sections. The actuator rod handle 316, actuator rod control 314, proximal element line handle 312 and lock line handle 310 are all joined with a main body 308 within which the actuator rod 64, proximal element lines 90 and lock lines 92 are guided into the shaft 302. The handle 304 further includes a support base 306 connected with the main body 308. The main body 308 is slideable along the support base 306 to provide translation of the shaft 302. Further, the main body 308 is rotatable around the support base 306 to rotate the shaft.

B. Delivery Catheter Shaft

Figure 50:
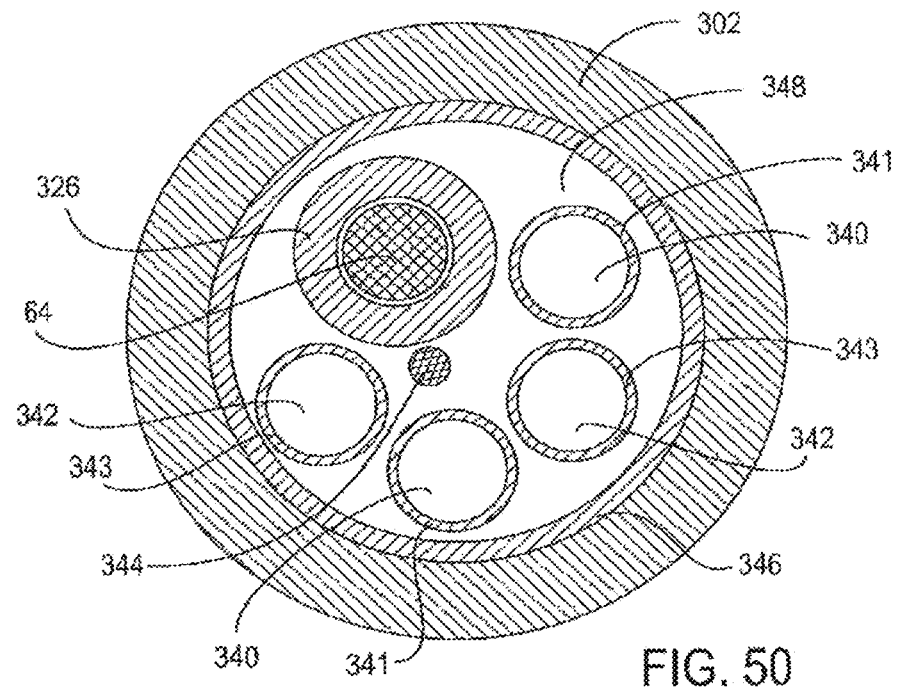
FIGS. 50-52 are cross-sectional views of embodiments of the shaft of the delivery catheter.

FIG. 50 illustrates a cross-sectional view of the delivery catheter shaft 302 of FIG. 47. In this embodiment, the shaft 302 has a tubular shape with inner lumen 348 and is comprised of a material which provides hoop strength while maintaining flexibility and kink resistance, such as a braided laminated material. Such material may include stainless steel braided or coiled wire embedded in a polymer such as polyurethane, polyester, Pebax, Grilamid TR55, and AESNO to name a few. To provide further support and hoop strength, a support coil 346 is disposed within the lumen 348 of shaft 302 as illustrated in FIG. 50.

Passing through the support coil 346 are a variety of elongated bodies, including tubular guides and cylindrical rods. For example, one type of tubular guide is a compression coil 326 extending through lumen 348 from the proximal end 322 to the distal end 324 of the shaft 302, and the actuator rod 64 extends through the compression coil 326. Therefore, the compression coil typically has a length in the range of 48 to 60 in. and an inner diameter in the range of 0.020 to 0.035 in. to allow passage of the actuator rod 64 therethrough. The actuator rod 64 is manipulable to rotate and translate within and relative to the compression coil 326. The compression coil 326 allows lateral flexibility of the actuator rod 64 and therefore the shaft 302 while resisting buckling and providing column strength under compression. The compression coil may be comprised of 304V stainless steel to provide these properties.

To provide additional tensile strength for the shaft 302 and to minimize elongation, a tension cable 344 may also pass through the support coil 346. The tension cable 344 extends through lumen 348 from the proximal end 322 to the distal end 324 of the shaft 302. Therefore, the tension cable 344 typically has a diameter in the range of 0.005 in. to 0.010 in. and a length in the range of 48 to 60 in. In preferred embodiments, the tension cable 344 is comprised of 304V stainless steel.

In addition, at least one lock line shaft 341 having a tubular shape may be present having a lock line lumen 340 through which lock lines 92 pass between the lock line handle 310 and the locking mechanism 106. The lock line shaft 341 extends through lumen 348 from the proximal end 322 to the distal end 324 of the shaft 302. Therefore, the lock line shaft 341 typically has a length in the range of 48 to 60 in., an inner diameter in the range of 0.016 to 0.030 in., and an outer diameter in the range of 0.018 to 0.034 in. In preferred embodiments, the lock line shaft 341 is comprised of a 304V stainless steel coil however other structures or materials may be used which provide kink resistance and compression strength.

Similarly, at least one proximal element line shaft 343 having a tubular shape may be present having a proximal element line lumen 342. Proximal element lines 90 pass through this lumen 342 between the proximal element line handle 312 and the proximal elements 16. Thus, the proximal element line shaft 343 extends through lumen 348 from the proximal end 322 to the distal end 324 of the shaft 302. Therefore, the proximal element line shaft 343 typically has a length in the range of 48 to 60 in., an inner diameter in the range of 0.016 to 0.030 in., and an outer diameter in the range of 0.018 to 0.034 in. In preferred embodiments, the proximal element line shaft 343 is comprised of a 304V stainless steel coil however other structures or materials may be used which provide kink resistance and compression strength.

In this embodiment, the elongated bodies (compression coil 326 enclosed actuator rod 64, tension cable 344, lock line shaft 342, proximal element line shaft 343) each "float" freely in inner lumen 348 within the support coil 346 and are fixed only at the proximal end 322 and distal end 324 of shaft 302. The lumen 348 is typically filled and flushed with heparinized saline during use. Alternatively or in addition, the lumen 348 may be filled with one or more fillers, such as flexible rods, beads, extruded sections, gels or other fluids. Preferably the fillers allow for some lateral movement or deflection of the elongated bodies within lumen 348 but in some cases may restrict such movement. Typically, the elongated bodies are fixed at the proximal and distal ends of the shaft and are free to move laterally and rotationally therebetween. Such freedom of movement of the elongated bodies provides the shaft 302 with an increased flexibility as the elongated bodies self-adjust and reposition during bending and/or torquing of the shaft 302. It may be appreciated that the elongated bodies may not be fixed at the proximal and distal ends. The elongated bodies are simply unconstrained relative to the shaft 302 in at least one location so as to be laterally moveable within the lumen 348. Preferably the elongated bodies are unrestrained in at least a distal portion of the catheter, e.g. 5-15 cm from the distal end 324, so as to provide maximum flexibility in the distal portion.

Figure 51:
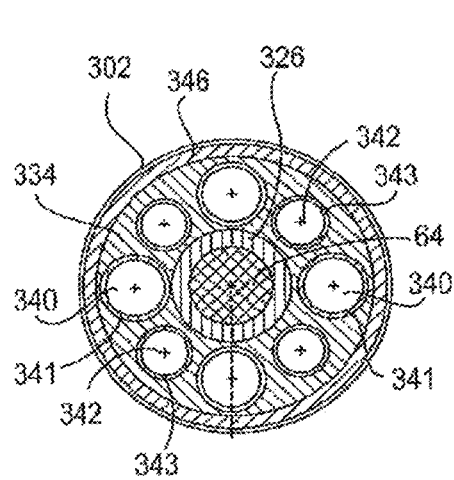

It may be appreciated, however, that alternate shaft 302 designs may also be used. For example, referring to FIG. 51, in this embodiment the shaft 302 again has a tubular shape with an inner lumen 348 and a support coil 346 disposed within the lumen 348 of shaft 302. Filling the inner lumen 348 within the support coil 346 is an extrusion 334 having lumens through which pass a variety of elongated bodies, including the compression coil 326 enclosed actuator rod 64, tension cable 344, lock line shafts 342, and proximal element line shafts 343, as shown. The support coil 346 and elongated bodies may have the same geometries and be comprised of the same materials as described above in relation to FIG. 50.

Figure 52:
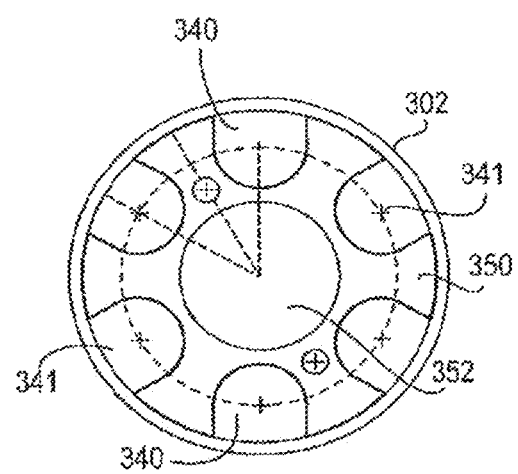

Alternatively, as shown in FIG. 52, the shaft 302 may include an internal partition 350 to create multiple lumens within the shaft 302. For example, the partition 350 may have a central lumen 352 for passage of the actuator rod 64, optionally surrounded by the compression coil 326. In addition, the partition 350 may also create at least one lock line lumen 340 for passage of a lock line 92 and at least one proximal element line lumen 341 for passage of a proximal element line 90. Optionally, each of the lumens defined by partition 350 may be lined with a kink-resistant element, such as a coil as in previous embodiments.

Figure 52A:
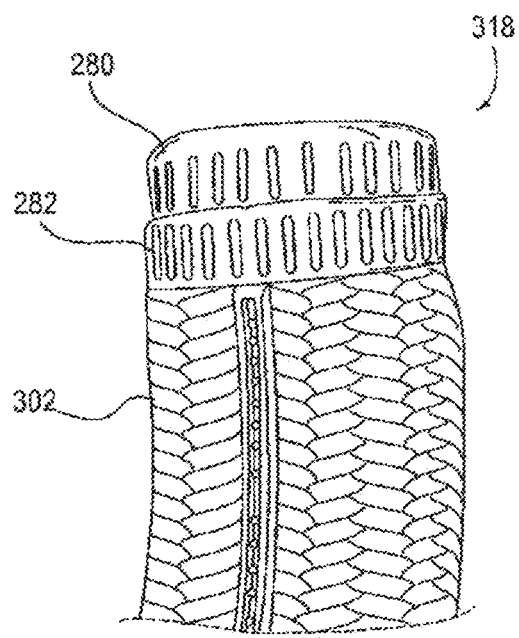
FIGS. 52A-52B illustrate embodiments of the nose of the shaft of the delivery catheter.
Figure 52B:
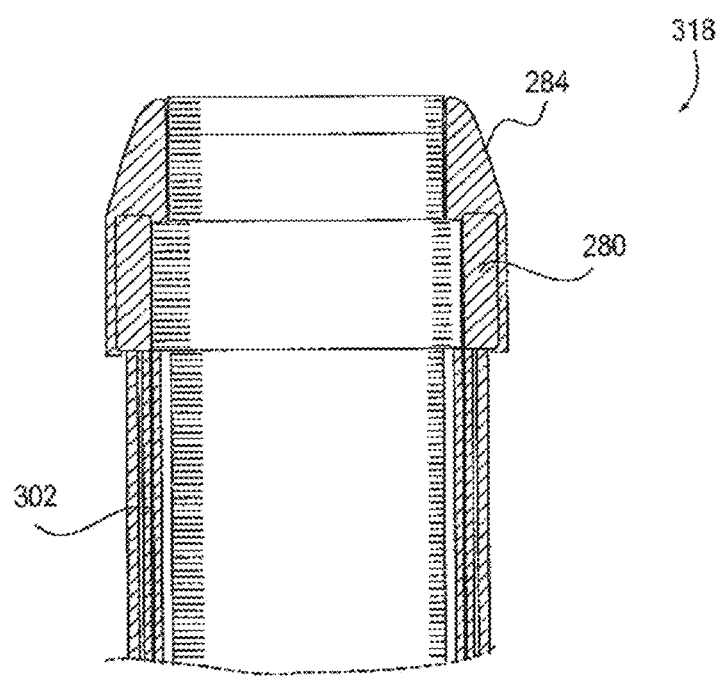

FIGS. 52A-52C illustrate embodiments of the nose 318 of the shaft 302. In FIG. 52A, the nose 318 comprises a tip ring 280 and a lock ring 282. In preferred embodiments, Epoxy and PEBAX are deposited between the tip ring 280 and the lock ring 282 to bond them together. The lock ring 282 has a geometry to mate with the tip ring 280 to maintain relative alignment between the two. FIG. 52B illustrates another embodiment of the nose 318 of the shaft 302. Here, the tip ring 280 is covered by a soft tip 284 to provide a more atraumatic tip and a smoother transition to the shaft.

C. Lock Line Arrangements

Figure 53A:
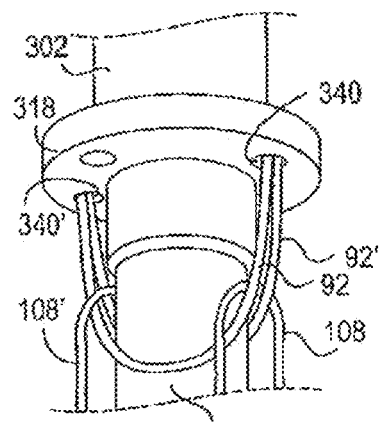
FIG. 53A-53C illustrate various arrangements of lock lines engaging release harnesses of a locking mechanism.
Figure 53B:
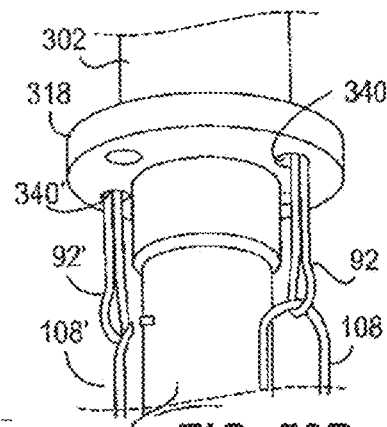
Figure 53C:
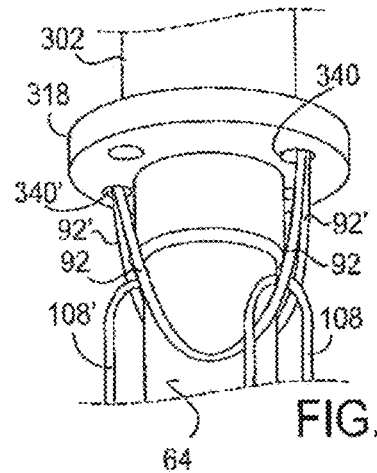

As mentioned previously, when lock lines 92 are present, the lines 92 pass through at least one lock line lumen 340 between the lock line handle 310 and the locking mechanism 106. The lock lines 92 engage the release harnesses 108 of the locking mechanism 106 to lock and unlock the locking mechanism 106 as previously described. The lock lines 92 may engage the release harnesses 108 in various arrangements, examples of which are illustrated in FIGS. 53A-53C. In each embodiment, two lock line lumens 340 are present within the shaft 302 of the delivery catheter 300 terminating at the nose 318. The lumens 340 are disposed on alternate sides of the actuator rod 64 so that each lumen 340 is directed toward a release harness 108.

FIG. 53A illustrates an embodiment wherein two lock lines 92, 92' pass through a single lock line lumen 340 and are threaded through a release harness 108 on one side of the actuator rod 64 (the actuator rod 64 is shown without surrounding housing such as coupling structure, for clarity). The lock lines 92, 92' are then separated so that each lock line passes on an opposite side of the actuator rod 64. The lock lines 92, 92' then pass through the release harness 108' on the opposite side of the actuator rod 64 and continue together passing through a another single lock line lumen 340'. This lock line arrangement is the same arrangement illustrated in FIG. 48.

FIG. 53B illustrates an embodiment wherein one lock line 92 passes through a single lock line lumen 340, is threaded through a release harness 108 on one side of the actuator rod 64, and is returned to the lock line lumen 340. Similarly, another lock line 92' passes through another single lock line lumen 340', is threaded through a different release harness 108' located on the opposite side of the actuator rod 64, and is returned to the another single lock line lumen 340'.

FIG. 53C illustrates an embodiment wherein both lock lines 92, 92' pass through a single lock line lumen 340. One lock line 92 is threaded through a release harness 108 on one side of the actuator rod 64 and is then passed through another lock line lumen 340' on the opposite side of the actuator rod 64. The other lock line 92' is threaded through another release harness 108' on the other side of the actuator rod 64' and is then passed through the another lock line lumen 340' with the previous lock line 92.

It may be appreciated that a variety of lock line arrangements may be used and are not limited to the arrangements illustrated and described above. The various arrangements allow the harnesses 108 to be manipulated independently or jointly, allow various amounts of tension to be applied and vary the force required for removal of the lock lines when the fixation device is to be left behind. For example, a single lock line passing through one or two lumens may be connected to both release harnesses for simultaneous application of tension.

D. Proximal Element Line Arrangements

Figure 54A:
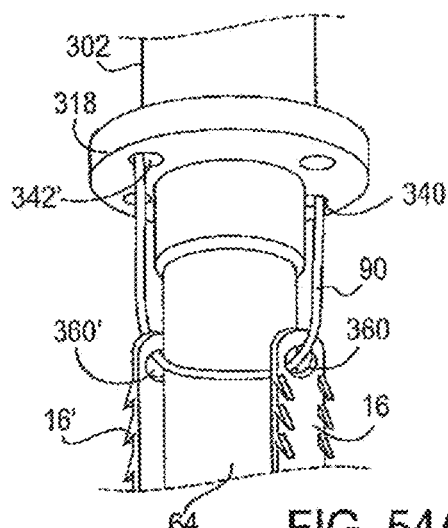
FIGS. 54A-54B illustrate various arrangements of proximal element lines engaging proximal elements of a fixation device.
Figure 54B:
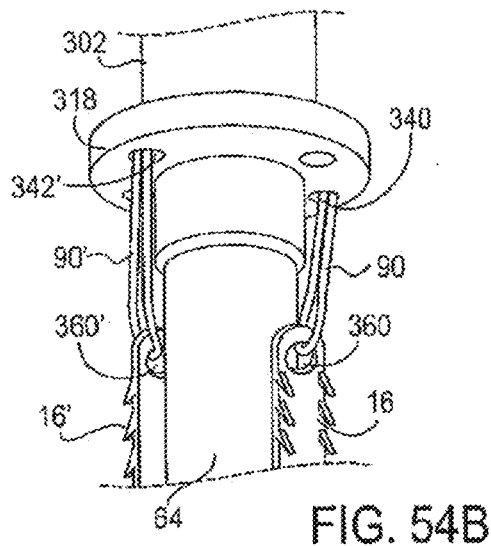

As mentioned previously, when proximal element lines 90 are present, the lines 90 pass through at least one proximal element line lumen 342 between the proximal element line handle 312 and at least one proximal element 16. The proximal element lines 90 engage the proximal elements 16 to raise or lower the element 16 as previously described. The proximal element lines 90 may engage the proximal elements 16 in various arrangements, examples of which are illustrated in FIGS. 54A-54B. In each embodiment, two proximal element line lumens 342 are present within the shaft 302 of the delivery catheter 300 terminating at the nose 318. The lumens 342 are disposed on alternate sides of the actuator rod 64 (the actuator rod 64 is shown without surrounding housing such as coupling structure, for clarity) so that each lumen 342 is directed toward a proximal element 16.

FIG. 54A illustrates an embodiment wherein one proximal element line 90 passes through a single proximal element line lumen 342. The proximal element line 90 is threaded through an eyelet 360 of a proximal element 16 on one side of the actuator rod 64, passes over the actuator rod 64 and is threaded through an eyelet 360' of another proximal element 16' on the other side of the actuator rod 64. The proximal element line 90 then passes through another single proximal element line lumen 342'. This proximal element line arrangement is the same arrangement illustrated in FIG. 48.

FIG. 54B illustrates an embodiment wherein one proximal element line 90 passes through a single proximal element line lumen 342, is threaded through an eyelet 360 of a proximal element 16 on one side of the actuator rod 64, and is returned to the proximal element line lumen 342. Similarly, another proximal element line 90' passes through another single proximal element line lumen 342' on the opposite side of the actuator rod 64, and is returned to the another single proximal element line lumen 342'.

It may be appreciated that a variety of proximal element line arrangements may be used and are not limited to the arrangements illustrated and described above. The various arrangements allow the proximal elements to be manipulated independently or jointly, allow various amounts of tension to be applied and vary the force required for removal of the proximal element lines when the fixation device is to be left behind. For example, a single proximal element line passing through one or two lumens in shaft 302 may be used for simultaneous actuation of both proximal elements.

E. Main Body of Handle

Figure 55:
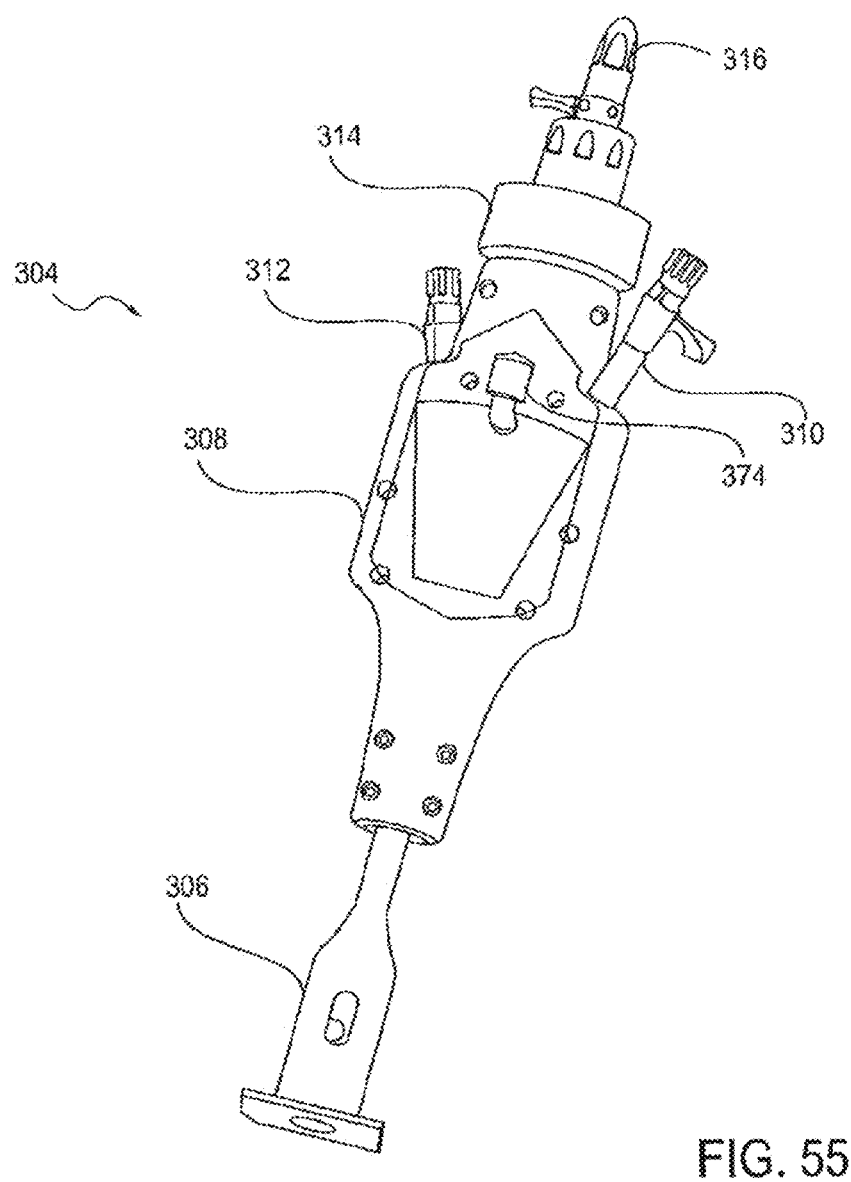
FIG. 55 illustrates an embodiment of the handle of the delivery catheter.

FIG. 55 illustrates an embodiment of the handle 304 of the delivery catheter 300. As mentioned previously, the actuator rod handle 316, actuator rod control 314, proximal element line handle 312 and lock line handle 310 are all joined with the main body 318. The handle 304 further includes a support base 306 connected with the main body 308. The main body 308 is slideable along the support base 306 to provide translation of the shaft 302 and the main body 308 is rotatable around the support base 306 to rotate the shaft.

Figure 56:
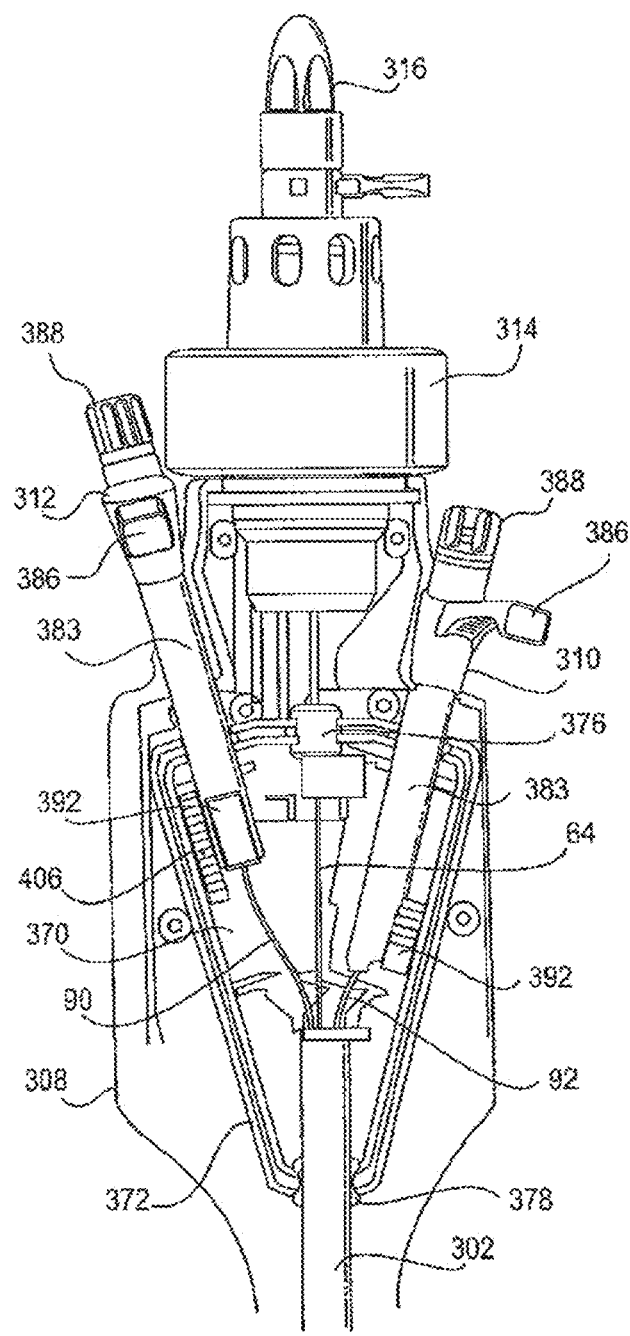
FIG. 56 is a cross-sectional view of the main body of the handle.

FIG. 56 provides a partial cross-sectional view of the main body 308 of the handle 304 depicted in FIG. 55. As shown, the main body 308 includes a sealed chamber 370 within which the actuator rod 64, proximal element lines 90 and lock lines 92 are guided into the shaft 302. The sealed chamber 370 is in fluid communication with the inner lumen 348 of shaft 302 and is typically filled with saline and flushed with heparin or heparinized saline. The sealed chamber 370 has a seal 372 along its perimeter to prevent leakage and the introduction of air to the chamber 370. Any air in the chamber 370 may be bled from the chamber 370 by one or more luers 374 which pass through the main body 308 into the chamber 370 as illustrated in FIG. 55. In this embodiment, the handle 304 includes two such luers 374, one on each side of the main body 308 (second luer symmetrically positioned on backside of main body 308 in FIG. 55, hidden from view). Referring now to FIG. 56, the sealed chamber 370 also has various additional seals, such as an actuator rod seal 376 which surrounds the actuator rod 64 where the actuator rod 64 enters the sealed chamber 370, and a shaft seal 378 which surrounds the shaft 302 where the shaft 302 enters the sealed chamber 370.

F. Lock Line Handle and Proximal Element Line Handle

As mentioned previously, the lock lines 92 may be may be extended, retracted, loaded with various amounts of tension or removed using the lock line handle 310. Likewise, the proximal element lines 90 may be extended, retracted, loaded with various amounts of tension or removed using the proximal element line handle 312. Both of these handles 310, 312 may be similarly designed to manipulate the appropriate lines 90, 92 passing therethrough.

Figure 57:
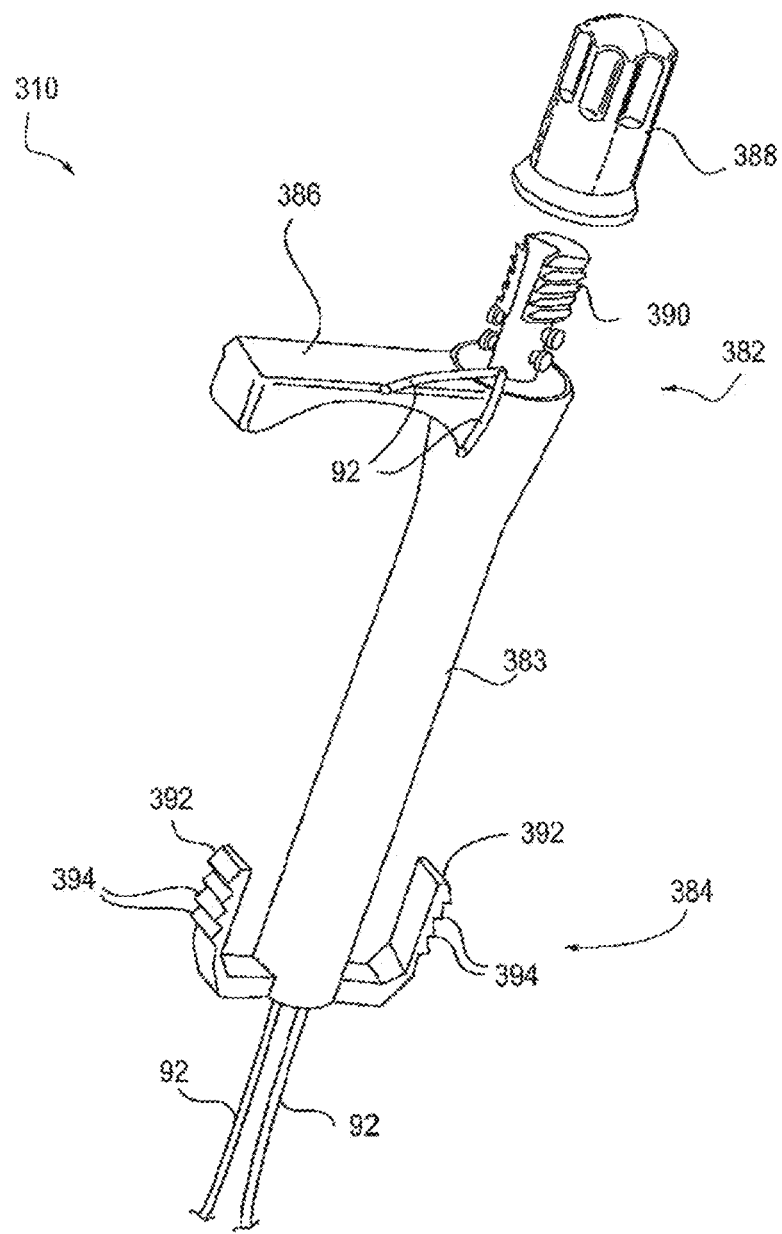
FIG. 57 illustrates an embodiment of a lock line handle.

FIG. 57 illustrates an embodiment of a lock line handle 310 having lock lines 92 passing therethrough. The lock line handle 310 has a distal end 384, a proximal end 382 and an elongate shaft 383 therebetween. The distal end 382 is positionable within the sealed chamber 370 so that the proximal end 382 extends out of the chamber 370, beyond the main body 308. The free ends of the lock lines 92 are disposed near the proximal end 382, passing through the wall of the handle 310 near a threaded nub 390. The handle 310 further includes a cap 388 which is positionable on the nub 309. Internal threading with the cap 388 mates with the threading on the threaded nub 390 so that the cap 388 holds the free ends of the lock lines 92 between the cap 388 and the nub 390 and/or other portions of the handle 310 by friction. The lock lines 92 pass through a central lumen (not shown) of the elongate shaft 383, extend through the sealed chamber 370 (as shown in FIG. 56) and extend through the shaft 302 to the locking mechanism 106.

Disposed near the distal end 384 of the handle 310 is at least one wing 392. In the embodiment of FIG. 57, two wings 392 are present, each wing 392 disposed on opposite sides of the elongate shaft 383. The wings 392 extend radially outwardly and curve proximally so that a portion is parallel to the elongate shaft 383, as shown. It may be appreciated that the wings 392 may alternatively have the shape of solid or continuous protrusions which extend radially and have a portion which is parallel to the elongate shaft 383. The wings 392 are used to hold the lock line handle 310 in a desired position which in turn holds the lock under a desired load of tension, as will be described further below. The handle 310 also includes a finger grip 386 near the proximal end 382 which extends radially outwardly in alignment with the radial extension of the at least one wing 392. Thus, the user may determine the orientation of the wings 392 within the sealed chamber 370 from the orientation of the finger grip 386 outside of the main body 308. The finger grip 386 may also serve an ergonomic purpose to assist in manipulating the handle 310.

Figure 57A:
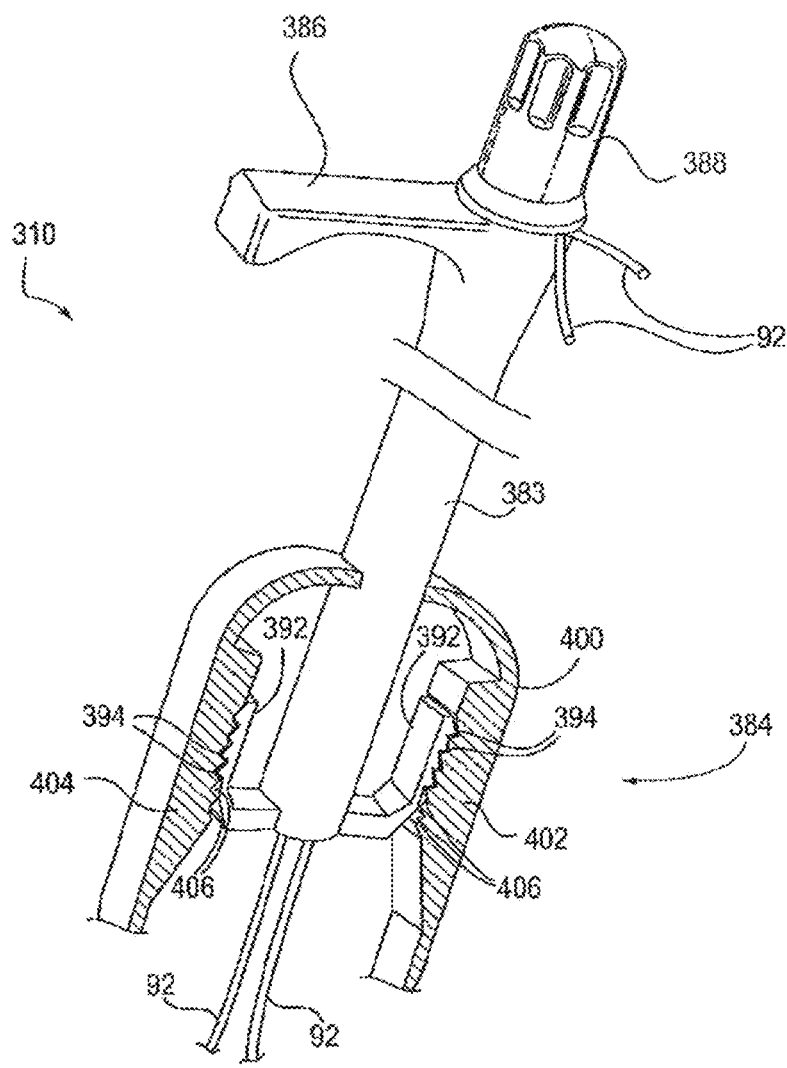
FIG. 57A illustrates the lock line handle of FIG. 57 positioned within a semi-tube which is disposed within the sealed chamber.
Figure 58A:
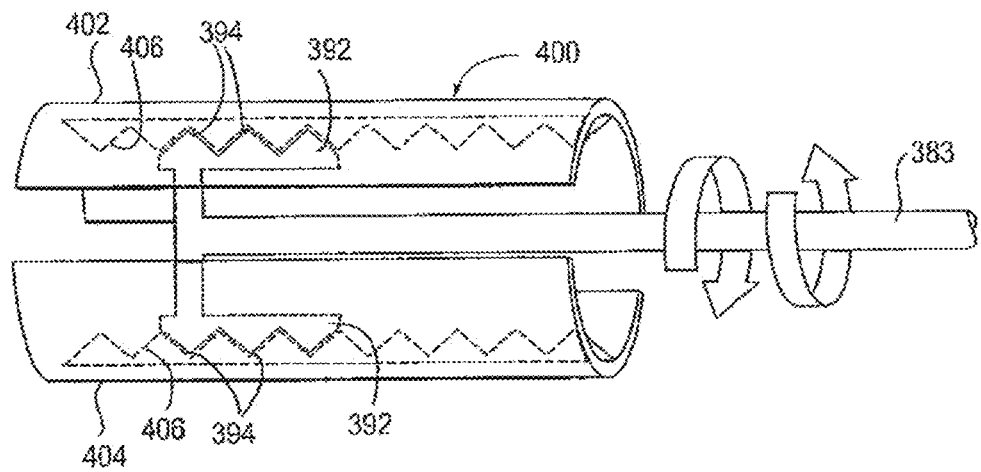
FIGS. 58A-58B illustrate a mechanism for applying tension to lock lines.
Figure 58B:
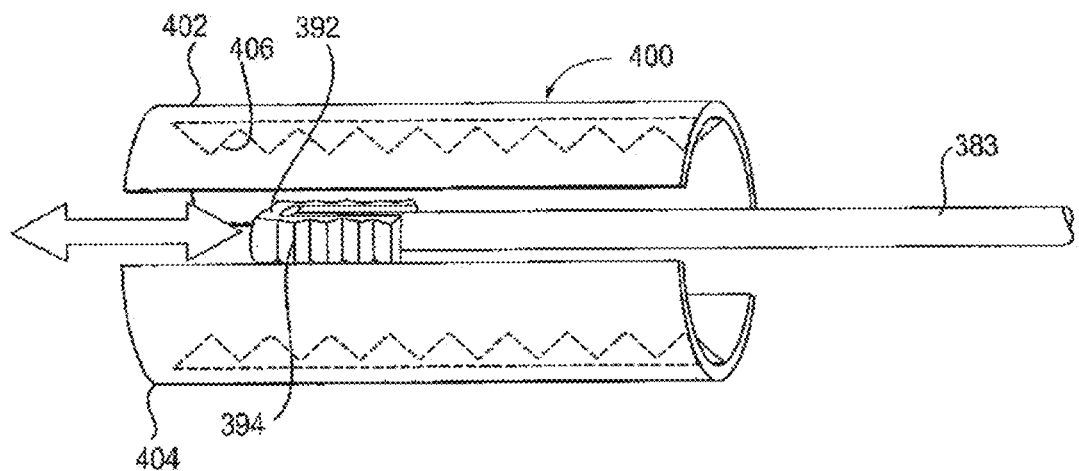

The portion of the wings 392 parallel to the elongate shaft 383 have grooves or serrations 394. The serrations 394 are used to apply tension to the lock lines 92. As shown in FIG. 57A, the lock line handle 310 is positioned within a semi-tube 400 which is disposed within the sealed chamber 370. The semi-tube 400 comprises a top half 402 and a bottom half 404, each half 402, 404 having grooves or serrations 406 which mate with the serrations 394 of the wings 392. Thus, when the wings 392 are rotated to mate the serrations 394, 406, as shown in FIG. 58A, the elongate shaft 383 is held in place. Likewise, the wings 392 may be rotated, as shown in FIG. 58B, so that the wings 392 are disposed between the halves 402, 404 and the serrations 394, 406 are disengaged. In this position, the shaft 383 may be translated to apply or release tension in the lock lines 92. Thus, tension in the lines 92 may be adjusted by rotating the shaft 383 to disengage the serrations 394, 406, translating the shaft 383 and then rotating the shaft 383 back to reengage the serrations 394, 406. Alternatively, the finger grip 386 may be pulled to apply tension to the lock lines 92. Pulling the finger grip 386 translates the lock line handle 310 within the semi-tube 400. Such translation is achievable due to angling of the serrations 394, 406 and flexibility of wings 382. However, the angling of the serrations 394, 406 prevents translation in the opposite direction, i.e. by pushing the finger grip 386. Therefore, to release tension from the lock lines 92, the shaft 383 is rotated to disengage the serrations 394, 406, allowing translation of the shaft 383, and then the shaft 383 is rotated back to reengage the serrations 394, 406.

To remove the lock lines 92, the cap 388 is removed from the threaded nub 390 exposing the free ends of the lock lines 92. If one lock line 92 is present having two free ends, continuous pulling on one of the free ends draws the entire length of lock line 92 out of the catheter 300. If more than one lock line 92 is present, each lock line 92 will have two free ends. Continuous pulling on one of the free ends of each lock line 92 draws the entire length of each lock line 92 out of the catheter 300.

It may be appreciated that the proximal element line handle 312 has corresponding features to the lock line handle 310 and operates in the same manner as illustrated in FIGS. 57A, 58A-58B. It may also be appreciated that other mechanisms may be used for manipulating the lock lines 92 and proximal element lines 90, such as including buttons, springs, levers and knobs.

G. Actuator Rod Control and Handle

Figure 59:
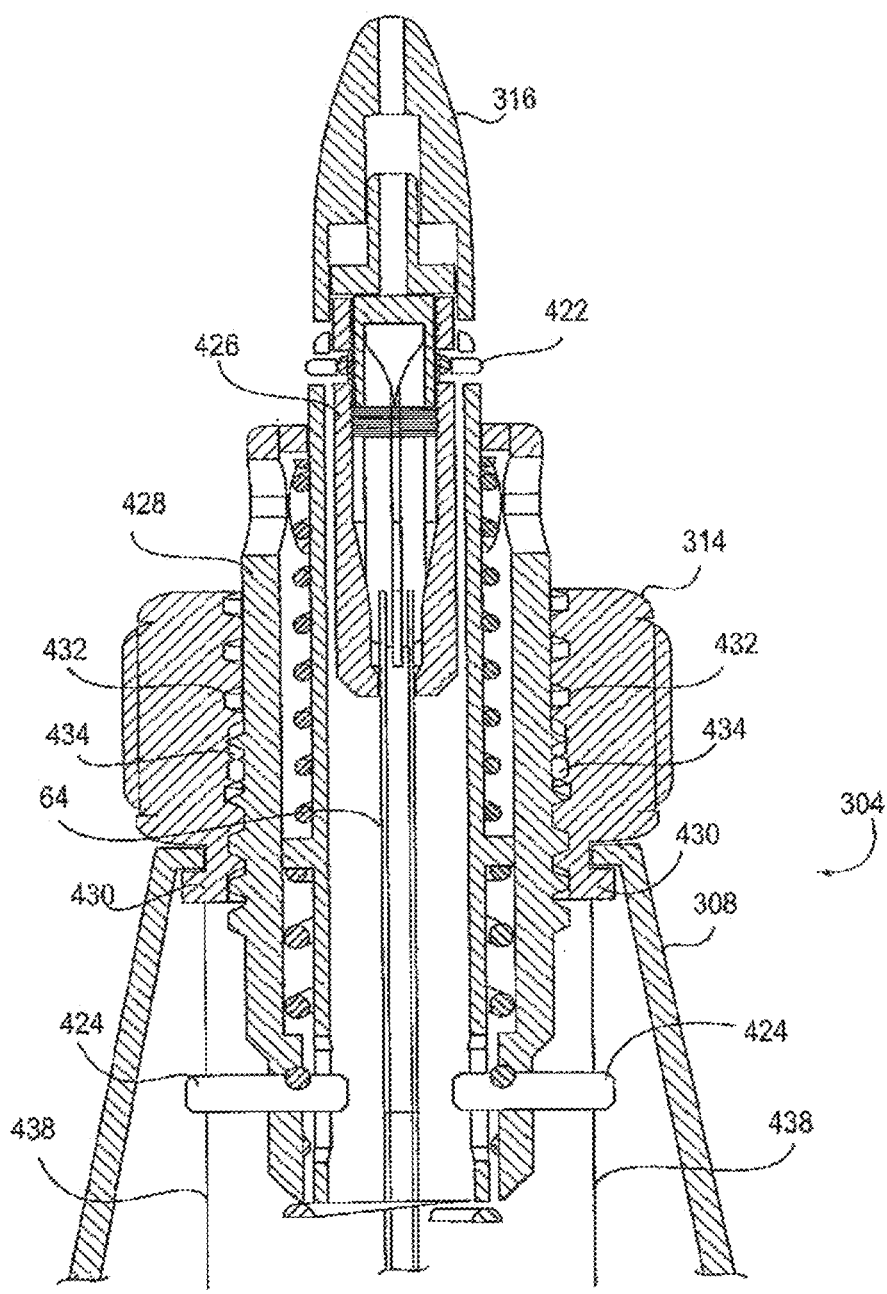
FIGS. 59, 59A-59B illustrate features of the actuator rod control and handle.

The actuator rod 64 may be manipulated using the actuator rod control 314 and the actuator rod handle 316. FIG. 59 provides a cross-sectional view of a portion of the handle 304 which includes the actuator rod control 314 and the actuator rod handle 316. The actuator rod handle 316 is located at the proximal end of the handle 314. The actuator rod handle 316 is fixedly attached to the proximal end of the actuator rod 64. The actuator rod 64 is inserted through a collet 426 which is disposed within a holder 428 as shown. The holder 428 has external threads 434 which mate with internal threads 432 of the actuator rod control 314. Thus, rotation of the actuator rod control 314 causes the holder 428 to translate along the actuator rod control 314 by action of the threading, as will be described in more detail below. The actuator rod control 314 is rotatably coupled with the main body 308 of the handle 304 and is held in place by a lip 430.

Figure 59A:
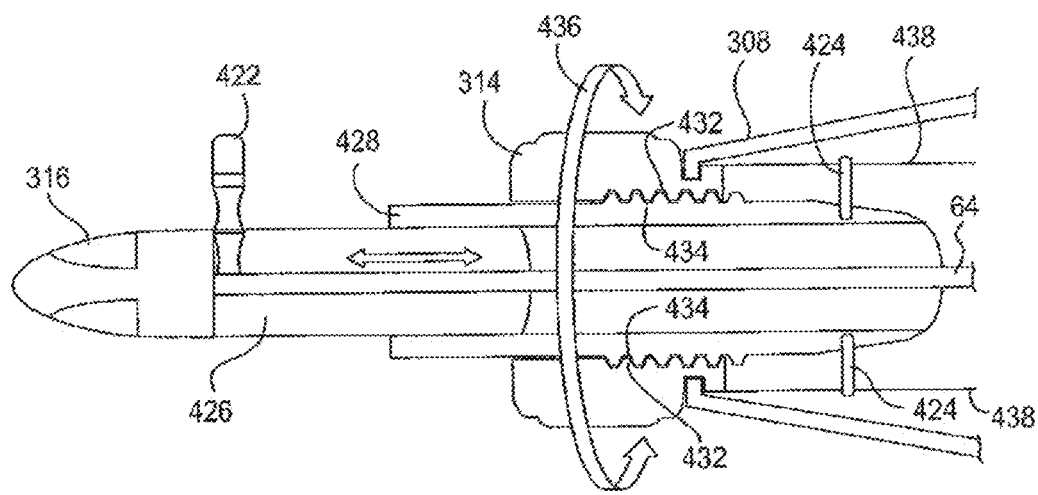

Referring to FIG. 59A, the actuator rod control 314 may be manually rotated in a clockwise or counter clockwise direction, as indicated by arrow 436. Rotation of the actuator rod control 314 translates (extends or retracts) the actuator rod 64 to manipulate the distal elements 18 of the fixation device 14. Specifically, rotation of the actuator rod control 314 causes the external threads 434 of the adjacent holder 428 to translate along the mated internal threads 432 of the actuator rod control 314. Rotation of the holder 428 itself is prevented by holding pins 424 which protrude from the holder 428 and nest into grooves 438 in the main body 308 of the handle 304. As the holder 428 translates, each holding pin 424 translates along its corresponding groove 438. Since the collet 426 is attached to the holder 428, the collet 426 translates along with the holder 428. To simultaneously translate the actuator rod 64, the actuator rod 64 is removably attached to the collet 426 by a pin 422. The pin 422 may have any suitable form, including a clip-shape which partially wraps around the collet 426 as illustrated in FIG. 59. Thus, rotation of the actuator rod control 314 provides fine control of translation of the actuator rod 64 and therefore fine control of positioning the distal elements 18.

Figure 59B:
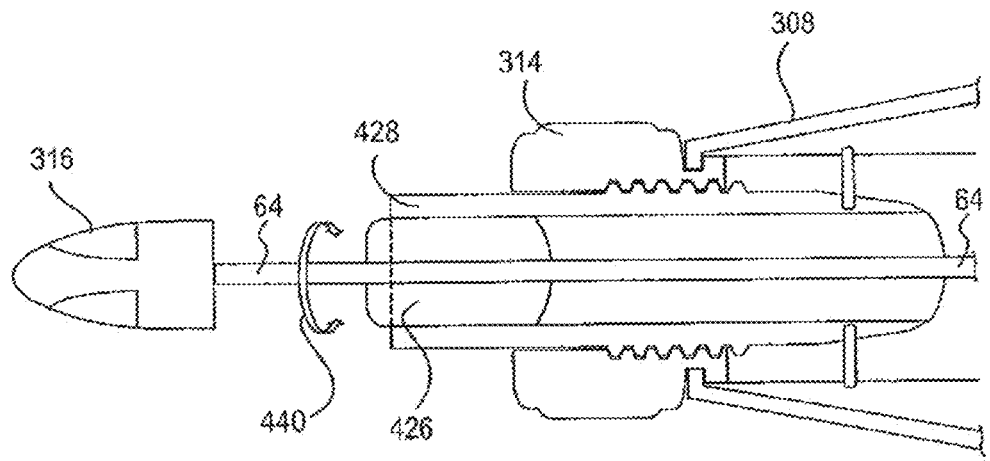

Referring to FIG. 59B, removal of the pin 422, as shown, allows disengagement of the actuator rod handle 316 and fixedly attached actuator rod 64 from the collet 426. Once disengaged, the actuator rod 64 may be rotated, as indicated by arrow 440, by manually rotating the actuator rod handle 316. As described previously, rotation of the actuator rod 64 engages or disengages the threaded joiner 332 of the delivery catheter 300 from the threaded stud 74 of the fixation device 14. This is used to attach or detach the fixation device 14 from the delivery catheter 300. In addition, when the actuator rod 64 is in the disengaged state, the actuator rod 64 may optionally be retracted and optionally removed from the catheter 300 by pulling the actuator rod handle 316 and withdrawing the actuator rod 64 from the handle 304.

Depending on the application, the location of the target site, and the approach selected, the devices of the invention may be modified in ways well known to those of skill in the art or used in conjunction with other devices that are known in the art. For example, the delivery catheter may be modified in length, stiffness, shape and steerability for a desired application. Likewise, the orientation of the fixation device relative to the delivery catheter may be reversed or otherwise changed. The actuation mechanisms may be changed to be driven in alternate directions (push to open, pull to close, or pull to open, push to close). Materials and designs may be changed to be, for example, more flexible or more rigid. And, the fixation device components may be altered to those of different size or shape. Further, the delivery catheter of the present invention may be used to deliver other types of devices, particularly endovascular and minimally invasive surgical devices used in angioplasty, atherectomy, stent-delivery, embolic filtration and removal, septal defect repair, tissue approximation and repair, vascular clamping and ligation, suturing, aneurysm repair, vascular occlusion, and electrophysiological mapping and ablation, to name a few. Thus, the delivery catheter of the present invention may be used for applications in which a highly flexible, kink-resistant device is desirable with high compressive, tensile and torsional strength.

V. Multi-Catheter Guiding System

A. Overview of Guiding System

Figure 60:
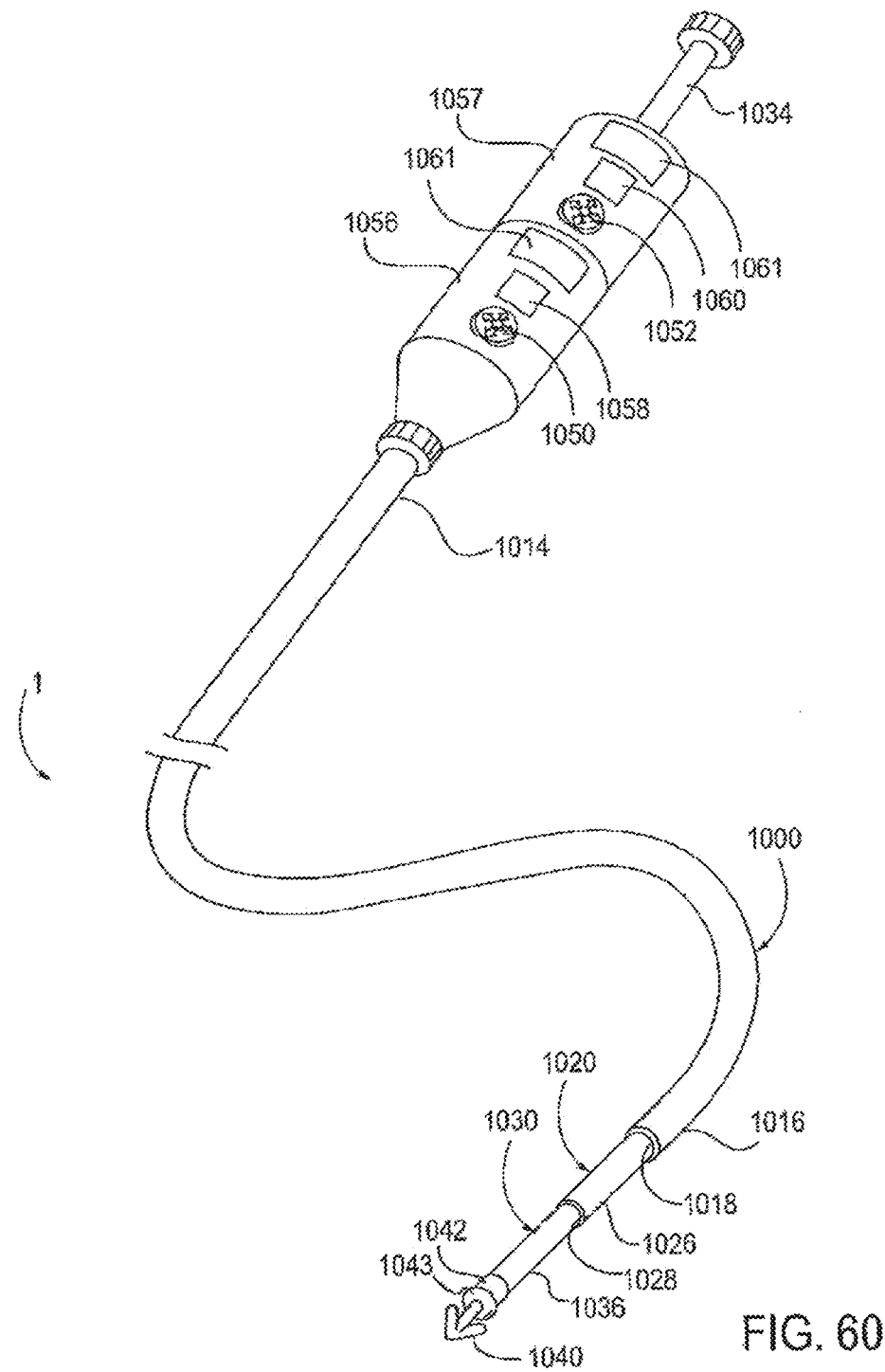
FIG. 60 is a perspective view of an embodiment of a multi-catheter guiding system of the present invention, and an interventional catheter positioned therethrough.

Referring to FIG. 60, an embodiment of a multi-catheter guiding system 1 of the present invention is illustrated. The system 1 comprises an outer guide catheter 1000, having a proximal end 1014, a distal end 1016, and a central lumen 1018 therethrough, and an inner guide catheter 1020, having a proximal end 1024, distal end 1026 and central lumen 1028 therethrough, wherein the inner guide catheter 1020 is positioned coaxially within the central lumen 1018 of the outer guide catheter 1000, as shown. The distal ends 1016, 1026 of catheters 1000, 1020, respectively, are sized to be passable to a body cavity, typically through a body lumen such as a vascular lumen. Thus, the distal end 1016 preferably has an outer diameter in the range of approximately 0.040 in. to 0.500 in., more preferably in the range of 0.130 in. to 0.320 in. The central lumen 1018 is sized for the passage of the inner guide catheter 1020; the distal end 1026 preferably has an outer diameter in the range of approximately 0.035 in. to 0.280 in., more preferably 0.120 in to 0.200 in. The central lumen 1028 is sized for the passage of a variety of devices therethrough. Therefore, the central lumen 1028 preferably has an inner diameter in the range of approximately 0.026 in. to 0.450 in., more preferably in the range of 0.100 in. to 0.180 in.

FIG. 60 illustrates an interventional catheter 1030 positioned within the inner guide catheter 1020 which may optionally be included in system 1, however other interventional devices may be used. The interventional catheter 1030 has a proximal end 1034 and a distal end 1036, wherein an interventional tool 1040 is positioned at the distal end 1036. In this embodiment, the interventional tool 1040 comprises a detachable fixation device or clip. Optionally, the interventional catheter 1030 may also include a nosepiece 1042 having a stop 1043, as shown. The stop 1043 prevents the interventional tool 1040 from entering the central lumen 1028 of the inner guide catheter 1020. Thus, the interventional catheter 1030 may be advanced and retracted until the stop 1043 contacts the distal end 1026 of the inner guiding catheter 1020 preventing further retraction. This may provide certain advantages during some procedures. It may be appreciated that in embodiments which include such a stop 1043, the interventional catheter 1030 would be pre-loaded within the inner guide catheter 1020 for advancement through the outer guiding catheter 1000 or both the interventional catheter 1030 and the inner guiding catheter 1020 would be pre-loaded into the outer guiding catheter 1000 for advancement to the target tissue. This is because the stop 1043 prevents advancement of the interventional catheter 1030 through the inner guiding catheter 1020.

The outer guide catheter 1000 and/or the inner guide catheter 1020 are precurved and/or have steering mechanisms, embodiments of which will be described later in detail, to position the distal ends 1016, 1026 in desired directions. Precurvature or steering of the outer guide catheter 1000 directs the distal end 1016 in a first direction to create a primary curve while precurvature and/or steering of the inner guide catheter 1020 directs distal end 1026 in a second direction, differing from the first, to create a secondary curve. Together, the primary and secondary curves form a compound curve. Advancement of the interventional catheter 1030 through the coaxial guide catheters 1000, 1020 guides the interventional catheter 1030 through the compound curve toward a desired direction, usually in a direction which will allow the interventional catheter 1030 to reach its target.

Steering of the outer guide catheter 1000 and inner guide catheter 1020 may be achieved by actuation of one or more steering mechanisms. Actuation of the steering mechanisms is achieved with the use of actuators which are typically located on handles connected with each of the catheters 1000, 1020. As illustrated in FIG. 60, handle 1056 is connected to the proximal end 1014 of the outer guide catheter 1000 and remains outside of the patient's body during use. Handle 1056 includes steering actuator 1050 which may be used to bend, arc or reshape the outer guide catheter 1000, such as to form a primary curve. Handle 1057 is connected to the proximal end (not shown) of the inner guide catheter 1020 and may optionally join with handle 1056 to form one larger handle, as shown. Handle 1057 includes steering actuator 1052 which may be used to bend, arc or reshape the inner guide catheter 1020, such as to form a secondary curve and move the distal end 1026 of the inner guide catheter 1020 through an angle theta, as will be described in a later section.

In addition, locking actuators 1058, 1060 may be used to actuate locking mechanisms to lock the catheters 1000, 1020 in a particular position. Actuators 1050, 1052, 1058, 1060 are illustrated as buttons, however it may be appreciated that these and any additional actuators located on the handles 1056, 1057 may have any suitable form including knobs, thumbwheels, levers, switches, toggles, sensors or other devices. Other embodiments of the handles will be described in detail in a later section.

In addition, the handle 1056 may include a numerical or graphical display 1061 of information such as data indicating the position the catheters 1000, 1020, or force on actuators. It may also be appreciated that actuators 1050, 1052, 1058, 1060 and any other buttons or screens may be disposed on a single handle which connects with both the catheters 1000, 1020.

B. Example Positions

Figure 61A:
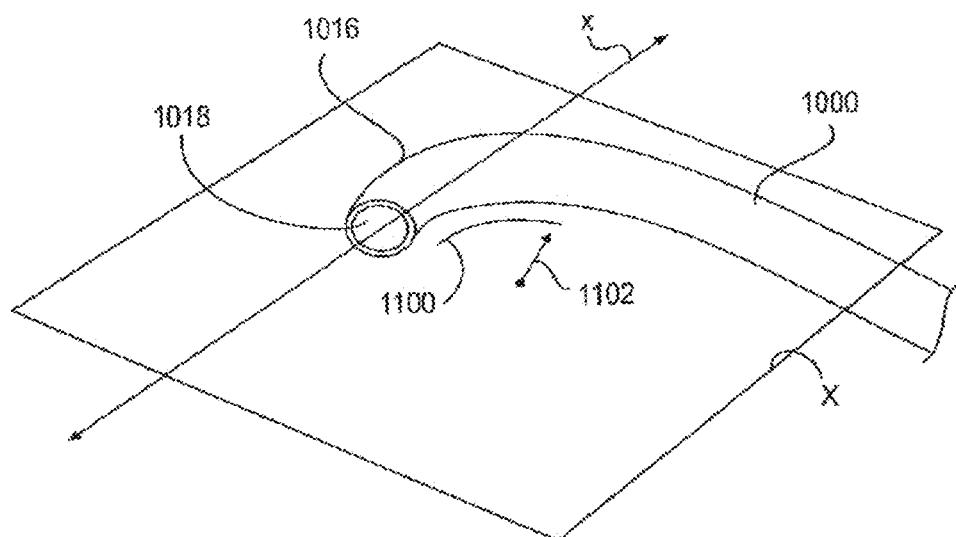
FIG. 61A illustrates a primary curvature in an outer guide catheter.

FIGS. 61A-61D illustrate examples of positions that the catheters 1000, 1020 may hold. Referring to FIG. 61A, the outer guide catheter 1000 may be precurved and/or steered into a position which includes a primary curve 1100. The primary curve 1100 typically has a radius of curvature 1102 in the range of approximately 0.125 in. to 1.000 in., preferably in the range of approximately 0.250 in. to 0.500 in. or forms a curve in the range of approximately 0° to 120°. As shown, when the position includes only a primary curve 1100, the distal end 16 lies in a single plane X. An axis x, transversing through the center of the central lumen 18 at the distal end 16, lies within plane X.

Figure 61B:
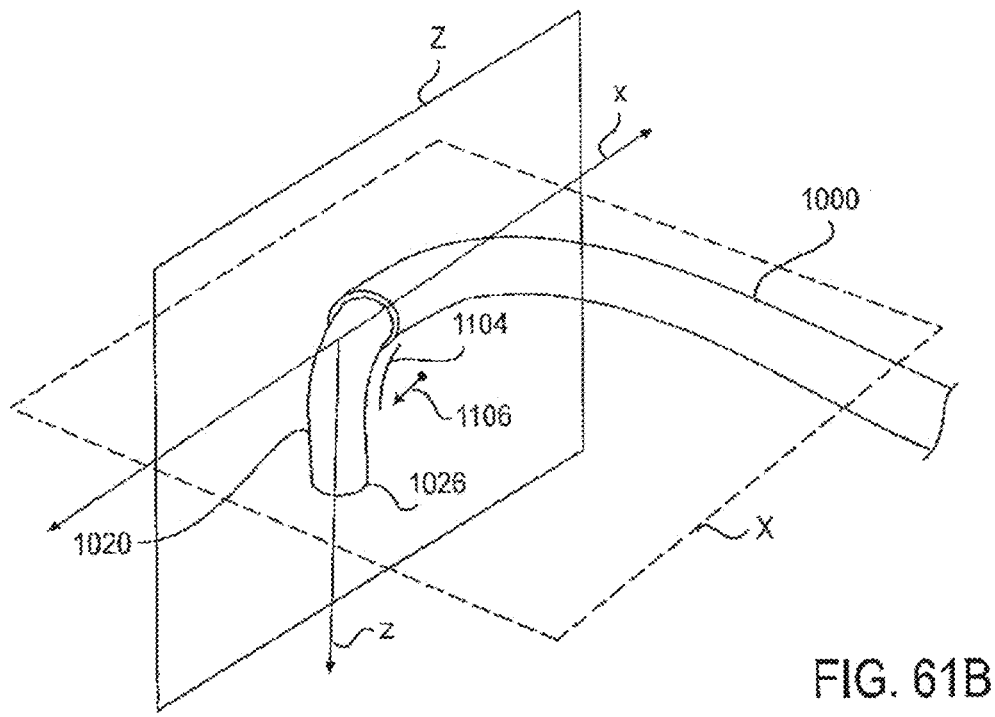
FIG. 61B illustrates a secondary curvature in an inner guide catheter.

Referring to FIG. 61B, the inner guide catheter 1020 extends through the central lumen 1018 of the outer guide catheter 1000. The inner guide catheter 1020 may be precurved and/or steered into a position which includes a secondary curve 1104. The secondary curve 1104 typically has a radius of curvature 10600 in the range of approximately 0.050 in. to 0.750 in., preferably in the range of approximately 0.125 in. to 0.250 in. or forms a curve in the range of approximately 0° to 180°. The secondary curve 1104 can lie in the same plane as the primary curve 1100, plane X, or it can lie in a different plane, such as plane Z as shown. In this example, plane Z is substantially orthogonal to plane X. Axis z, transversing through the center of the central lumen 1028 of the inner guide catheter 1020 at the distal end 1026, lies within plane Z. In this example, axis x and axis z are at substantially 90 degree angles to each other; however, it may be appreciated that axis x and axis z may be at any angle in relation to each other. Also, although in this example the primary curve 1100 and the secondary curve 1104 lie in different planes, particularly in substantially orthogonal planes, the curves 1100, 1104 may alternatively lie in the same plane.

Figure 61C:
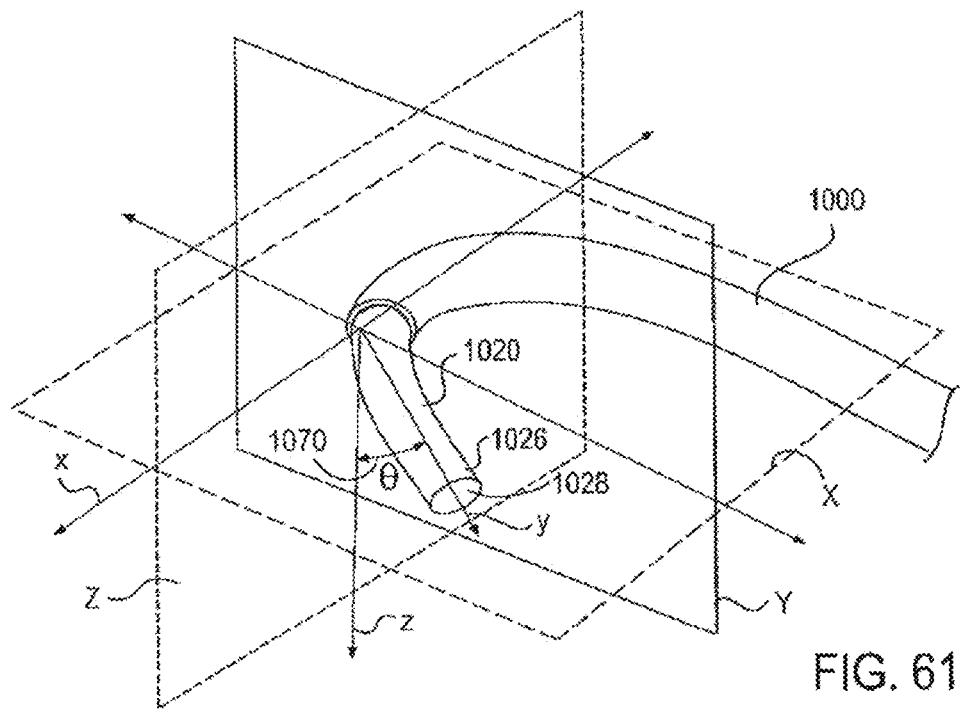
FIGS. 61C-61D illustrate example movement of an inner guide catheter through angle thetas.

Referring now to FIG. 61C, the inner guide catheter 1020 may be further manipulated to allow the distal end 1026 to move through an angle theta 1070. The angle theta 1070 is in the range of approximately −180° to +180°, typically in the range of −90° to +90°, possibly in the range of −60° to +60°, −45° to +45°, −30° to +30° or less. As shown, the angle theta 1070 lies within a plane Y. In particular, axis y, which runs through the center of the central lumen 1028 at the distal end 1026, forms the angle theta 1070 with axis z. In this example, plane Y is orthogonal to both plane X and plane Z. Axes x, y, z all intercept at a point within the central lumen 1028 which also coincides with the intersection of planes X, Y, Z.

Figure 61D:
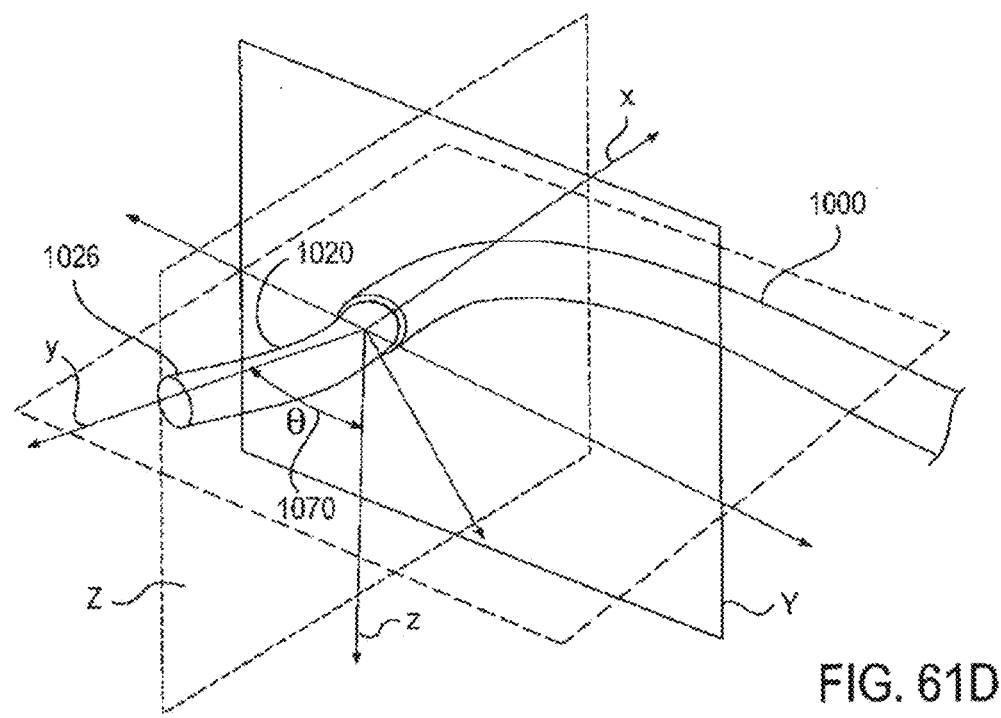

Similarly, FIG. 61D illustrates movement of the distal end 1026 through an angle theta 1070 on the opposite side of axis z. Again, the angle theta 1070 is measured from the axis z to the axis y, which runs through the center of the central lumen 1016 at the distal end 1026. As shown, the angle theta 1070 lies in plane Y. Thus, the primary curve 1100, secondary curve 1104, and angle theta 1070 can all lie in different planes, and optionally in orthogonal planes. However, it may be appreciated that the planes within which the primary curve 1100, secondary curve 1104 and angle theta 1070 lie may be mutually dependent and therefore would allow the possibility that some of these lie within the same plane.

Figure 62A:
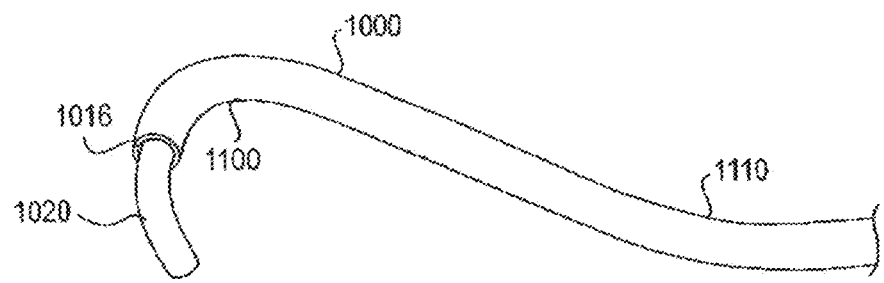
FIG. 62A is a perspective side view of a multi-catheter guiding system having an additional curve in the outer guide catheter.
Figure 62B:
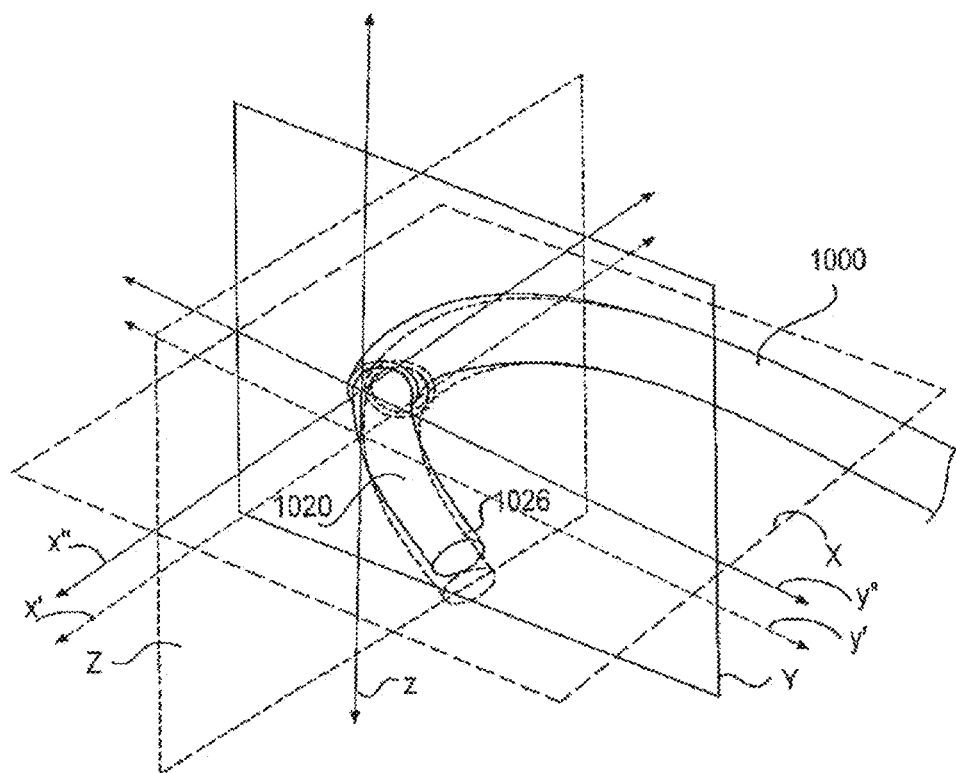
FIG. 62B illustrates lifting of the outer guide catheter due to the additional curve of FIG. 62A.

In addition, the outer guide catheter 1000 may be preformed and/or steerable to provide additional curves or shapes. For example, as illustrated in FIG. 62A, an additional curve 1110 may be formed by the outer guide catheter 1000 proximal to the primary curve 1100. In this example, the curve 1110 provides lift or raises the distal end 1016 of the outer guide catheter 1000, which in turn raises the distal end 1026 of the inner guide catheter 1020. Such lifting is illustrated in FIG. 62B. Here, the system 1 is shown prior to lifting in dashed line wherein the axis y' passes through the intersection of axis z and axis x'. After application of curve 1110, the distal portion of the system 1 is lifted in the direction of axis z so that axis x' is raised to axis x" and axis y' is raised to axis y". This raises distal end 1026 to a desired height.

Figure 63A:
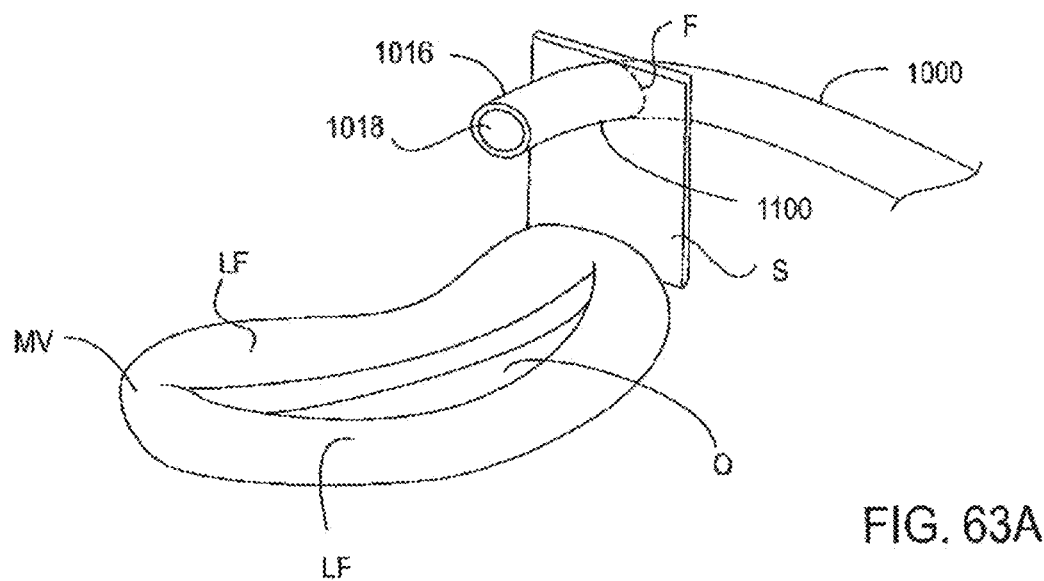
FIGS. 63A-63D illustrate a method of using the multi-catheter guiding system for accessing the mitral valve.

The articulated position of the multi-catheter guiding system 1 illustrated in FIGS. 61A-61D and FIGS. 62A-62B is particularly useful for accessing the mitral valve. FIGS. 63A-63D illustrate a method of using the system 1 for accessing the mitral valve MV. To gain access to the mitral valve, the outer guide catheter 1000 may be tracked over a dilator and guidewire from a puncture in the femoral vein, through the inferior vena cava and into the right atrium. As shown in FIG. 63A, the outer guide catheter 1000 may be punctured through a fossa F in the interatrial septum S. The outer guide catheter 1000 is then advanced through the fossa F and curved by the primary curve 1100 so that the distal end 1016 is directed over the mitral valve MV. Again, it may be appreciated that this approach serves merely as an example and other approaches may be used, such as through the jugular vein, femoral artery, port access or direct access, to name a few. Positioning of the distal end 1016 over the mitral valve MV may be accomplished by precurvature of the outer guide catheter 1000, wherein the catheter 1000 assumes this position when the dilator and guidewire are retracted, and/or by steering of the outer guide catheter 1000 to the desired position. In this example, formation of the primary curve 1100 moves the distal end 1016 within a primary plane, corresponding to previous plane X, substantially parallel to the valve surface. This moves the distal end 1016 laterally along the short axis of the mitral valve MV, and allows the distal end 1016 to be centered over the opening O between the leaflets LF.

Figure 63B:
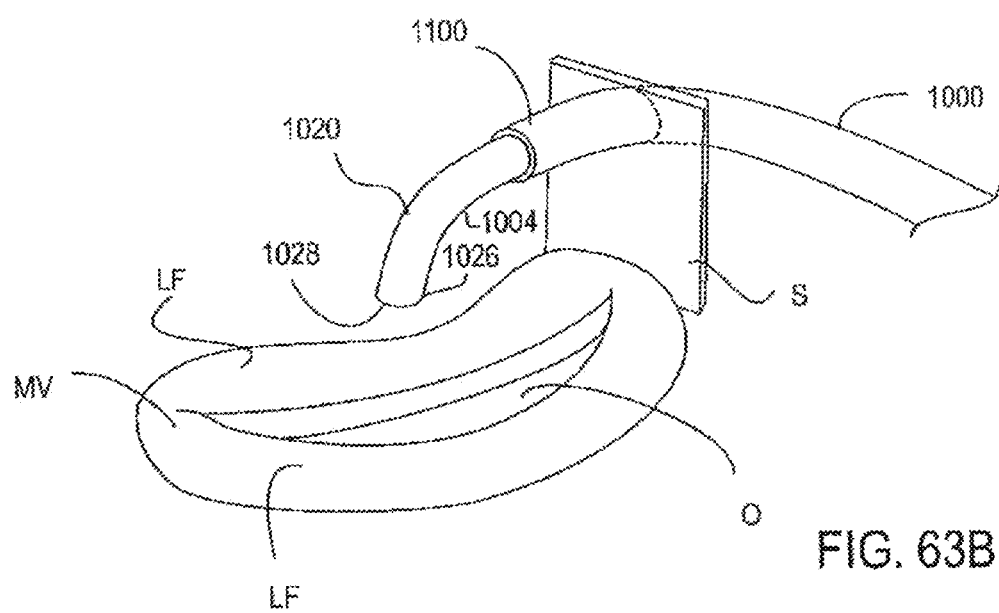

Referring to FIG. 63B, the inner guide catheter 1020 is advanced through the central lumen 1018 of the outer guide catheter 1000 and the distal end 1026 is positioned so that the central lumen 1028 is directed toward the target tissue, the mitral valve MV. In particular, the central lumen 1028 is to be directed toward a specific area of the mitral valve MV, such as toward the opening O between the valve leaflets LF, so that a particular interventional procedure may be performed. In FIG. 63B, the inner guide catheter 1020 is shown in a position which includes a secondary curve 1104 in a secondary plane, corresponding to previous plane Z. Formation of the secondary curve 1104 moves the distal end 1026 vertically and angularly between the commissures C, directing the central lumen 1028 toward the mitral valve MV. In this position an interventional device or catheter 1030 which is passed through the central lumen 1028 would be directed toward and/or through the opening O. Although the primary curve 1100 and the secondary curve 1104 may be varied to accommodate different anatomical variations of the valve MV and different surgical procedures, further adjustment may be desired beyond these two curvatures for proper positioning of the system 1.

Figure 63C:
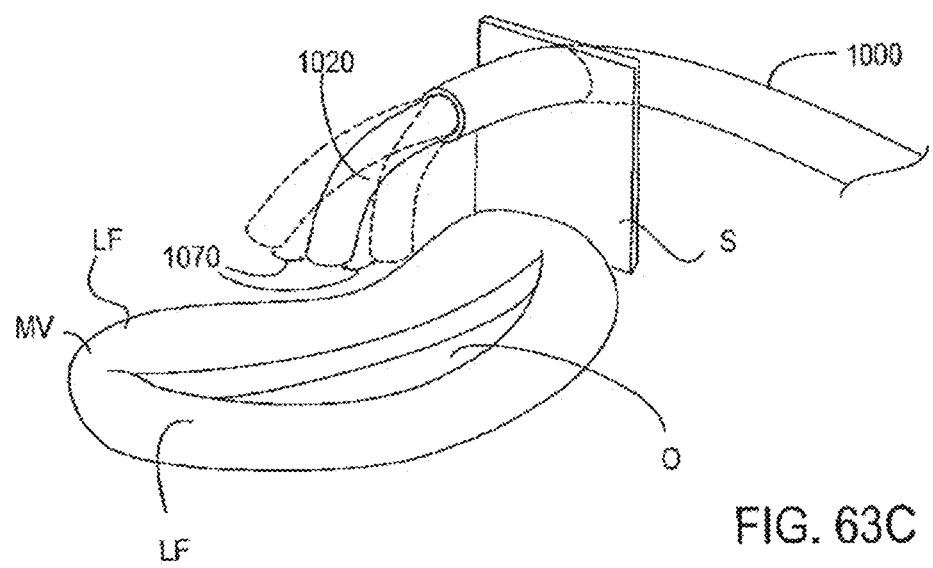

Referring to FIG. 63C, the distal end 1026 of the inner guide catheter 1020 may be positioned through an angle theta 1070. This moves the distal end 1026 vertically and angularly through a theta plane, corresponding to previous plane Y. Movement of the distal end 1026 through the angle plane theta 1070 in either direction is shown in dashed line in FIG. 63B. Such movement can be achieved by precurvature and/or by steering of the catheter 1020. Consequently, the central lumen 1028 can be directed toward the mitral valve MV within a plane which differs from the secondary plane. After such movements, the inner guide catheter 1020 will be in a position so that the opening of the central lumen 1028 at the end 1016 faces the desired direction. In this case, the desired direction is toward the center of and orthogonal to the mitral valve.

In some instances, it is desired to raise or lower the distal end 1026 so that it is at a desired height in relation to the mitral valve MV. This may be accomplished by precurvature and/or by steering of the outer guide catheter 1000 to form additional curve 1110. Generally this is used to lift the distal end 1026 above the mitral MV wherein such lifting was illustrated in FIG. 62B.

Figure 63D:
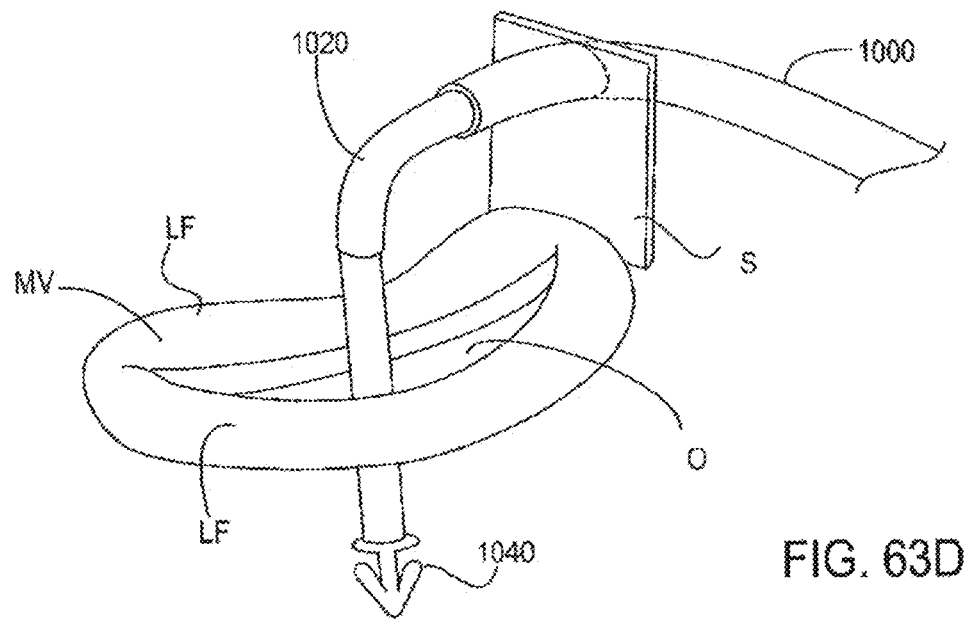

When the curvatures in the catheters 1000, 1020 are formed by steering mechanisms, the steering mechanisms may be locked in place by a locking feature. Locking can provide additional stiffness and stability in the guiding system 1 for the passage of interventional devices or catheters 1030 therethrough, as illustrated in FIG. 60. The interventional catheter 1030 can be passed through the central lumen 1028 toward the target tissue, in this case the mitral valve MV. Positioning of the distal end 1026 over the opening O, as described above, allows the catheter 1030 to pass through the opening O between the leaflets LF if desired, as shown in FIG. 63D. At this point, any desired procedure may be applied to the mitral valve for correction of regurgitation or any other disorder.

C. Steering Mechanisms

As described previously, the curvatures may be formed in the catheters 1000, 1020 by precurving, steering or any suitable means. Precurving involves setting a specific curvature in the catheter prior to usage, such as by heat setting a polymer or by utilizing a shape-memory alloy. Since the catheters are generally flexible, loading of the catheter on a guidewire, dilator obturator or other introductory device straightens the catheter throughout the curved region. Once the catheter is positioned in the anatomy, the introductory device is removed and the catheter is allowed to relax back into the precurved setting.

Figure 64A:
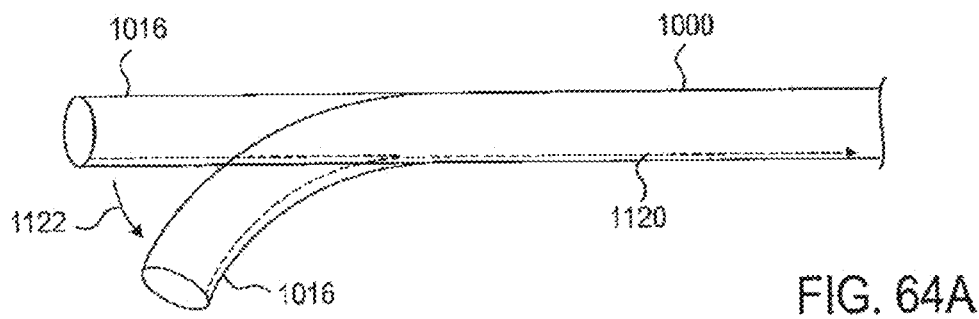
FIGS. 64A-64D illustrate curvature of a guide catheter of the present invention by the actuation of one or more pullwires.
Figure 64B:
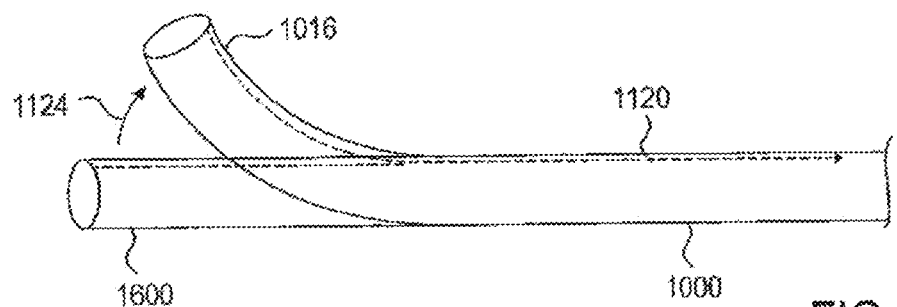
Figure 64C:
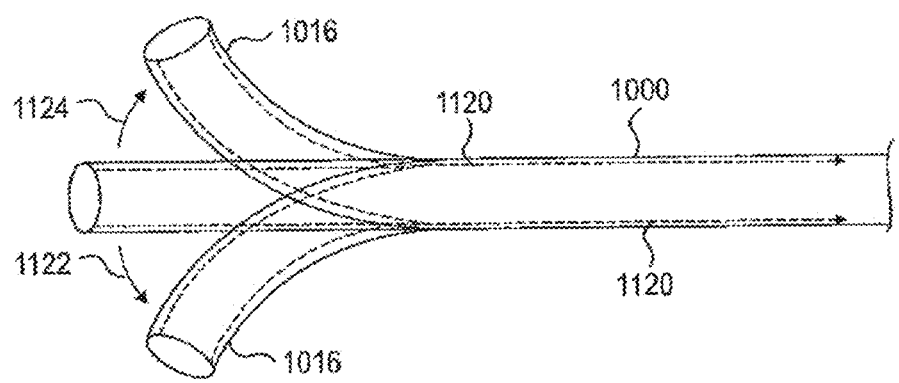
Figure 64D:
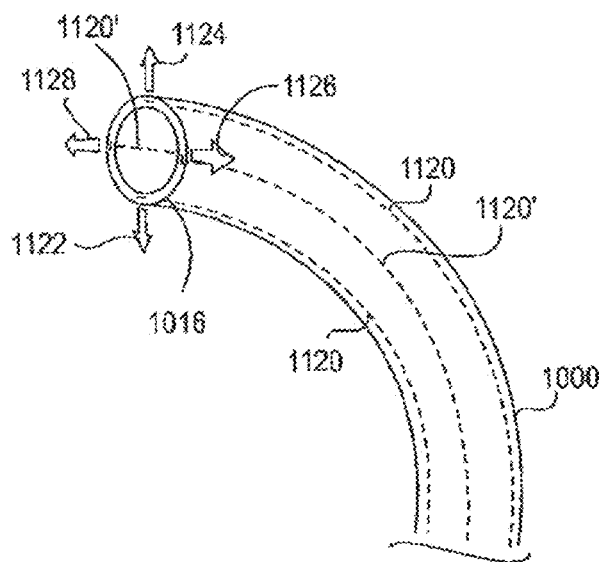

To provide a higher degree of control and variety of possible curvatures, steering mechanisms may be used to create the curvatures and position the catheters. In some embodiments, the steering mechanisms comprise cables or pullwires within the wall of the catheter. As shown in FIG. 64A, the outer guide catheter 1000 may include a pullwire 1120 slidably disposed in lumens within the wall of the catheter 1000 extending to the distal end 1016. By applying tension to the pullwire 1120 in the proximal direction, the distal end 1016 curves in the direction of the pullwire 1120 as illustrated by arrow 1122. Likewise, as shown in FIG. 64A, placement of the pullwire 1120 along the opposite side of the catheter 1000 will allow the distal end 1016 to curve in the opposite direction, as illustrated by arrow 1124, when tension is applied to the pullwire 1120. Thus, referring to FIG. 64C, diametrically opposing placement of pullwires 1120 within the walls of the catheter 1000 allows the distal end 1016 to be steered in opposite directions. This provides a means of correcting or adjusting a curvature. For example, if tension is applied to one pullwire to create a curvature, the curvature may be lessened by applying tension to the diametrically opposite pullwire. Referring now to FIG. 64D, an additional set of opposing pullwires 1120' may extend within the wall of the catheter 1000 as shown. This combination of pullwires 1120, 1120' allows curvature of the distal end in at least four directions illustrated by arrows 1122, 1124, 1126, 1128. In this example, pullwires 1120 create the primary curve 1100 of the outer guide catheter 1000 and the pullwires 1120' create the lift. It may be appreciated that FIGS. 64A-64D also pertain to the inner guide catheter 1020. For example, in FIG. 64D, pullwires 1120 may create the secondary curve 1104 of the inner guide catheter 1020 and the pullwires 1120' create the angle theta 1070.

Figure 64E:
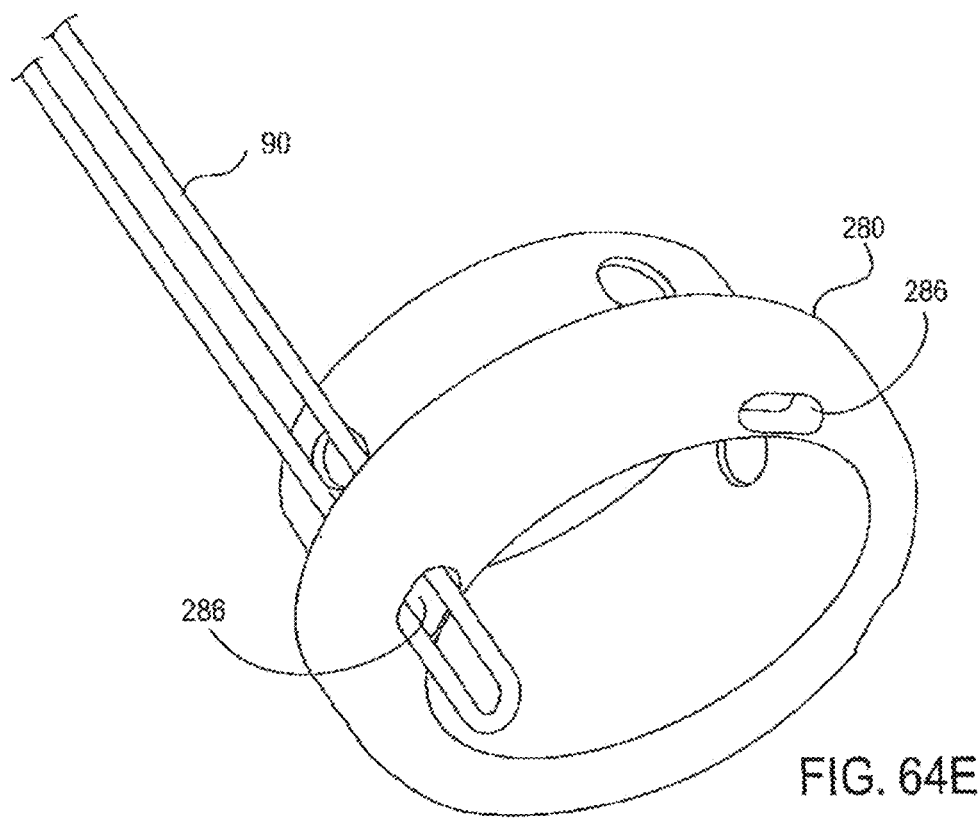
FIG. 64E illustrates attachment of a pullwire to a tip ring.

Such pullwires 1120 and/or pullwires 1120' and associated lumens may be placed in any arrangement, singly or in pairs, symmetrically or nonsymmetrically and any number of pullwires may be present. This may allow curvature in any direction and about various axes. The pullwires 1120, 1120' may be fixed at any location along the length of the catheter by any suitable method, such as gluing, tying, soldering, or potting, to name a few. When tension is applied to the pullwire, the curvature forms from the point of attachment of the pullwire toward the proximal direction. Therefore, curvatures may be formed throughout the length of the catheter depending upon the locations of the points of attachment of the pullwires. Typically, however, the pullwires will be attached near the distal end of the catheter, optionally to an embedded tip ring 280, illustrated in FIG. 64E. As shown, the pullwire 1120 passes through an orifice 286 in the tip ring 280, forms a loop shape and then passes back through the orifice 286 and travels back up through the catheter wall (not shown). In addition, the lumens which house the pullwires may be straight, as shown in FIGS. 64A-64D, or may be curved.

D. Catheter Construction

The outer guide catheter 1000 and inner guide catheter 1020 may have the same or different construction which may include any suitable material or combination of materials to create the above described curvatures. For clarity, the examples provided will be in reference to the outer guide catheter 1000, however it may be appreciated that such examples may also apply to the inner guide catheter 1020.

In embodiments in which the catheter is precurved rather than steerable or in addition to being steerable, the catheter 1000 may be comprised of a polymer or copolymer which is able to be set in a desired curvature, such as by heat setting. Likewise, the catheter 1000 may be comprised of a shape-memory alloy.

In embodiments in which the catheter is steerable, the catheter 1000 may be comprised of one or more of a variety of materials, either along the length of the catheter 1000 or in various segments. Example materials include polyurethane, Pebax, nylon, polyester, polyethylene, polyimide, polyethylenetelephthalate (PET), polyetheretherketone (PEEK). In addition, the walls of the catheter 1000 may be reinforced with a variety of structures, such as metal braids or coils. Such reinforcements may be along the length of the catheter 1000 or in various segments.

For example, referring to FIG. 65A, the catheter 1000 may have a proximal braided segment 1150, a coiled segment 1152 and distal braided segment 1154. The proximal braided segment 1150 provides increased column strength and torque transmission. The coiled segment 1152 provides increased steerability. The distal braided segment 1154 provides a blend of steerability and torque/column strength. In another example, referring to FIG. 65B, the outer guiding catheter 1000 has a proximal double-layer braided segment 1151 and a distal braided segment 1154. Thus, the proximal double-layer segment 1151 comprises a multi-lumen tube 1160 (having steering lumens 1162 for pullwires, distal ends of the steering lumens 1162 optionally embedded with stainless steel coils for reinforcement, and a central lumen 1163), an inner braided layer 1164, and an outer braided layer 1166, as illustrated in the cross-sectional view of FIG. 65C. Similarly, FIG. 65D provides a cross-sectional view of the distal braided segment 1154 comprising the multi-lumen tube 1160 and a single braided layer 1168. In a further example, referring to FIG. 65E, the inner guiding catheter 1020 comprises a multi-lumen tube 1160 without reinforcement at its proximal end, a single braided layer middle segment 1170 and a single braided layer distal segment 1171. Each of the single braided layer segments 1170, 1171 have a multi-lumen tube 1160 and a single layer of braiding 1168, as illustrated in cross-sectional view FIG. 65F. However, the segments 1170, 1171 are comprised of polymers of differing durometers, typically decreasing toward the distal end.

Figure 65G:
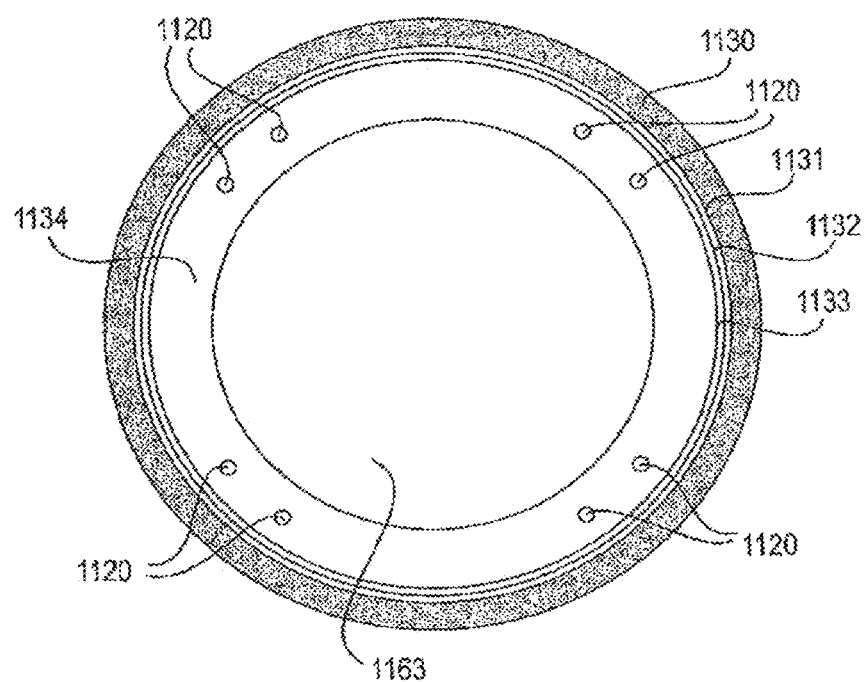

FIG. 65G illustrates an other example of a cross-section of a distal section of an outer guiding catheter 1000. Here, layer 1130 comprises 55D Pebax and has a thickness of approximately 0.0125 in. Layer 1131 comprises a 30 ppi braid and has a thickness of approximately 0.002 in. by 0.0065 in. Layer 1132 comprises 55D Pebax and has a thickness of approximately 0.006 in. Layer 1133 comprises 30 ppi braid and has a thickness of approximately 0.002 in by 0.0065 in. And finally, layer 1134 comprises Nylon 11 and includes steering lumens for approximately 0.0105 in. diameter pullwires 1120. Central lumen 1163 is of sufficient size for passage of devices.

Figure 65H:
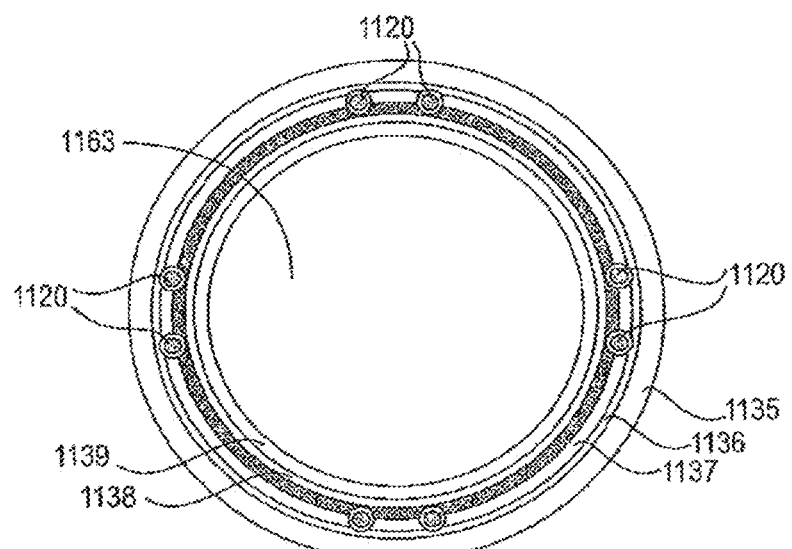
Figure 65I:
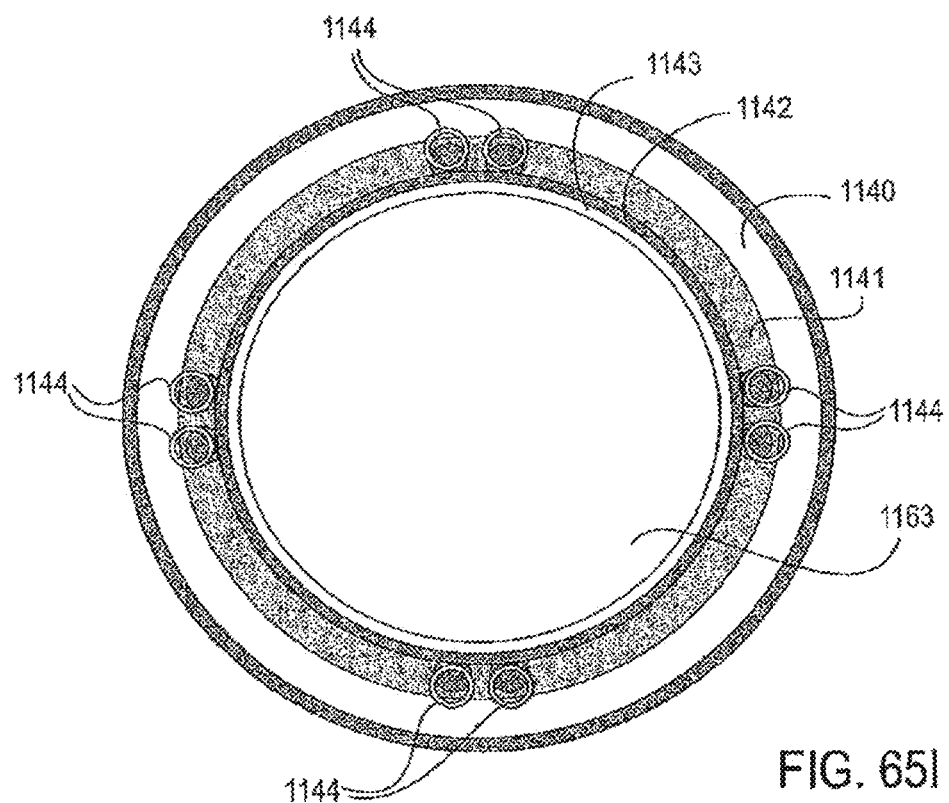

FIGS. 65H-65I illustrate additional examples of cross-sections of an inner guiding catheter 1020, FIG. 65I illustrating a cross-section of a portion of the distal end and FIG. 65I illustrating a cross-section of a more distal portion of the distal end. Referring to FIG. 65H, layer 1135 comprises 40D polymer and has a thickness of approximately 0.0125 in. Layer 1136 comprises a 30 ppi braid and has a thickness of approximately 0.002 in. by 0.0065 in. Layer 1137 comprises 40D polymer and has a thickness of approximately 0.006 in. Layer 1138 comprises a 40D polymer layer and has a thickness of approximately 0.0035 in. And finally, layer 1139 comprises a 55D liner. In addition, coiled steering lumens are included for approximately 0.0105 in. diameter pullwires 1120. And, central lumen 1163 is of sufficient size for passage of devices. Referring to FIG. 65I, layer 1140 comprises a 40D polymer, layer 1141 comprises a 35D polymer, layer 1142 comprises a braid and layer 1143 comprises a liner. In addition, coiled steering lumens 1144 are included for pullwires. And, central lumen 1163 is of sufficient size for passage of devices.

Figure 66A:
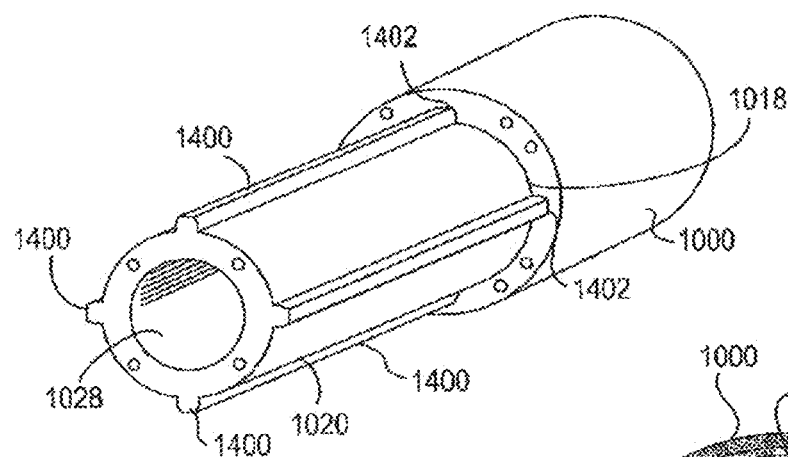
FIGS. 66A-66C illustrate a keying feature of the present invention.
Figure 66B:
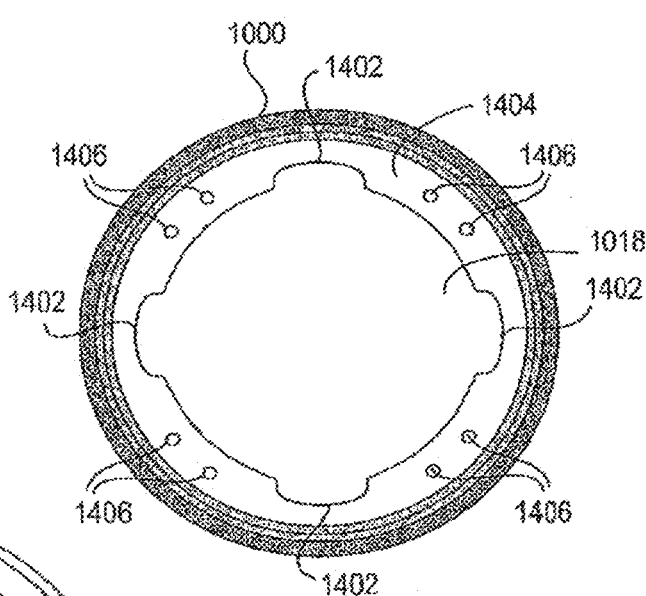
Figure 66C:
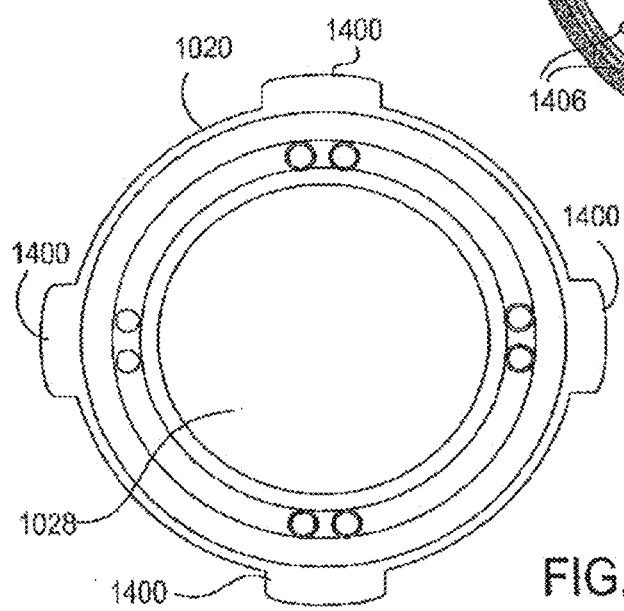

FIGS. 66A-66C illustrate an embodiment of a keying feature which may be incorporated into the catheter shafts. The keying feature is used to maintain relationship between the inner and outer guide catheters to assist in steering capabilities. As shown in FIG. 66A, the inner guide catheter 1020 includes one or more protrusions 1400 which extend radially outwardly. In this example, four protrusions 1400 are present, equally spaced around the exterior of the catheter 1020. Likewise, the outer guide catheter 1000 includes corresponding notches 1402 which align with the protrusions 1400. Thus, in this example, the catheter 1000 includes four notches equally spaced around its central lumen 1018.

Thus, the inner guide catheter 1020 is able to be translated within the outer guide catheter 1000, however rotation of the inner guide catheter 1020 within the outer guide catheter 1000 is prevented by the keying feature, i.e. the interlocking protrusions 1400 and notches 1402. Such keying helps maintain a known correlation of position between the inner guide catheter 1020 and outer guide catheter 1000. Since the inner and outer guide catheters 1020, 1000 form curvatures in different directions, such keying is beneficial to ensure that the compound curvature formed by the separate curvatures in the inner and outer guide catheters 1020, 1000 is the compound curvature that is anticipated. Keying may also increase stability wherein the curvatures remain in position reducing the possibility of compensating for each other.

FIG. 66B illustrates a cross-sectional view of the outer guiding catheter 1000 of FIG. 66A. Here, the catheter 1000 includes a notched layer 1404 along the inner surface of central lumen 1018. The notched layer 1404 includes notches 1402 in any size, shape, arrangement and number. Optionally, the notched layer 1404 may include lumens 1406, typically for passage of pullwires 1120. However, the lumens 1406 may alternatively or in addition be used for other uses. It may also be appreciated that the notched layer 1404 may be incorporated into the wall of the catheter 1000, such as by extrusion, or may be a separate layer positioned within the catheter 1000. Further, it may be appreciated that the notched layer 1404 may extend the entire length of the catheter 1000 or one or more portions of the length of the catheter 1000, including simply a small strip at a designated location along the length of the catheter 1000.

FIG. 66C illustrates a cross-sectional view of the inner guiding catheter 1020 of FIG. 66A. Here, the catheter 1020 includes protrusions 1400 along the outer surface of the catheter 1020. The protrusions 1400 may be of any size, shape, arrangement and number. It may be appreciated that the protrusions 1400 may be incorporated into the wall of the catheter 1020, such as by extrusion, may be included in a separate cylindrical layer on the outer surface of the catheter 1020, or the protrusions 1400 may be individually adhered to the outer surface of the catheter 1020. Further, it may be appreciated that the protrusions 1400 may extend the entire length of the catheter 1000 or one or more portions of the length of the catheter 1020, including simply a small strip at a designated location along the length of the catheter 1020.

Thus, the keying feature may be present along one or more specific portions of the catheters 1000, 1020 or may extend along the entire length of the catheters 1000, 1020. Likewise, the notches 1402 may extend along the entire length of the outer guiding catheter 1020 while the protrusions 1400 extend along discrete portions of the inner guiding catheter 1000 and vice versa. It may further be appreciated that the protrusions 1400 may be present on the inner surface of the outer guiding catheter 1000 while the notches 1402 are present along the outer surface of the inner guiding catheter 1020.

Figure 67A:
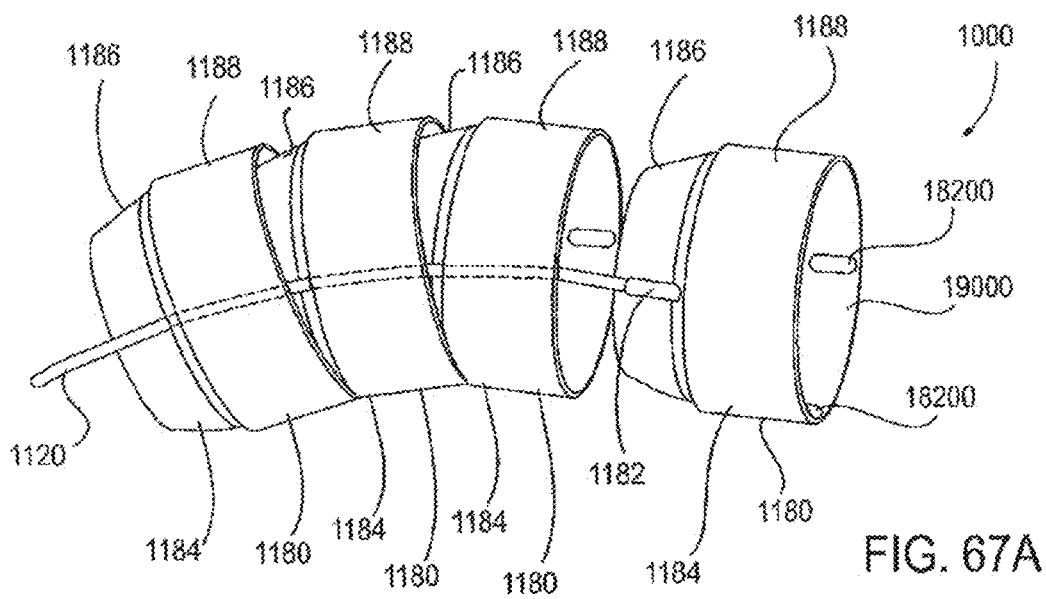
FIGS. 67A-67B are perspective views of a guide catheter including a series of articulating members.
Figure 67B:
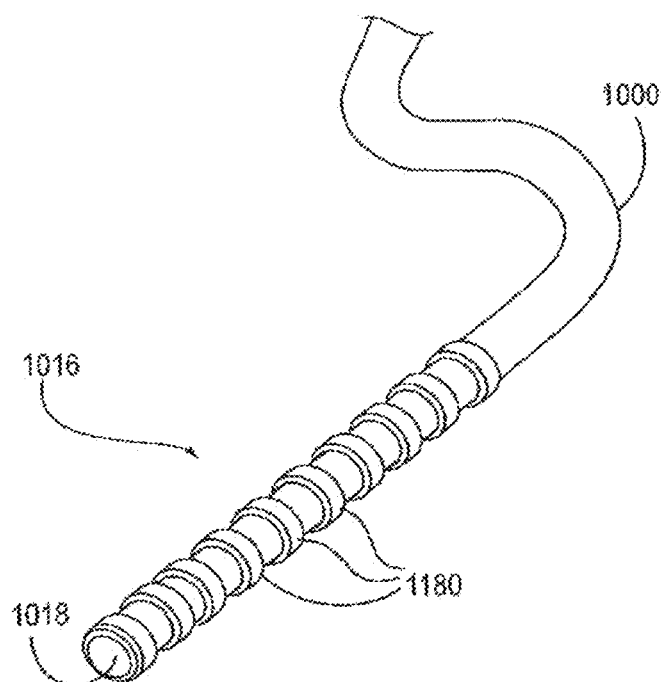

Alternatively or in addition, one or more steerable portions of the catheter 1000 may comprise a series of articulating members 1180 as illustrated in FIG. 67A. Exemplary embodiments of steerable portions of catheters comprising such articulating members 1180 are described in U.S. patent application Ser. No. 10/441,753 incorporated herein by reference for all purposes. FIG. 67B illustrates the outer guide catheter 1000 having a steerable portion comprising articulating members 1180 at its distal end 1016.

Briefly, referring to FIG. 67A, each articulating member 1180 may have any shape, particularly a shape which allows interfitting or nesting as shown. In addition, it is desired that each member 1180 have the capability of independently rotating against an adjacent articulating member 1180. In this embodiment, the articulating members 1180 comprise interfitting domed rings 1184. The domed rings 1184 each include a base 1188 and a dome 1186. The base 1188 and dome 1186 have a hollow interior which, when the domed rings 1184 are interfit in a series, forms a central lumen 1190. In addition, the dome 1186 allows each articulating member 1180 to mate against an inner surface of an adjacent domed ring 1184.

The interfitting domed rings 1184 are connected by at least one pullwire 1120. Such pullwires typically extend through the length of the catheter 1000 and at least one of the interfitting domed rings 1184 to a fixation point where the pullwire 1120 is fixedly attached. By applying tension to the pullwire 1120, the pullwire 1120 arcs the series of interfitting domed rings 1184 proximal to the attachment point to form a curve. Thus, pulling or applying tension on at least one pullwire, steers or deflects the catheter 1000 in the direction of that pullwire 1120. By positioning various pullwires 1120 throughout the circumference of the domed rings 1184, the catheter 1000 may be directed in any number of directions.

Also shown in FIG. 67A, each interfitting domed ring 1184 may comprise one or more pullwire lumens 1182 through which the pullwires 1120 are threaded. Alternatively, the pullwires 1120 may be threaded through the central lumen 1190. In any case, the pullwires are attached to the catheter 1000 at a position where a desired curve is to be formed. The pullwires 1120 may be fixed in place by any suitable method, such as soldering, gluing, tying, welding or potting, to name a few. Such fixation method is typically dependent upon the materials used. The articulating members 1180 may be comprised of any suitable material including stainless steel, various metals, various polymers or co-polymers. Likewise the pullwires 1120 may be comprised of any suitable material such as fibers, sutures, metal wires, metal braids, or polymer braids.

E. Handles

Figure 68:
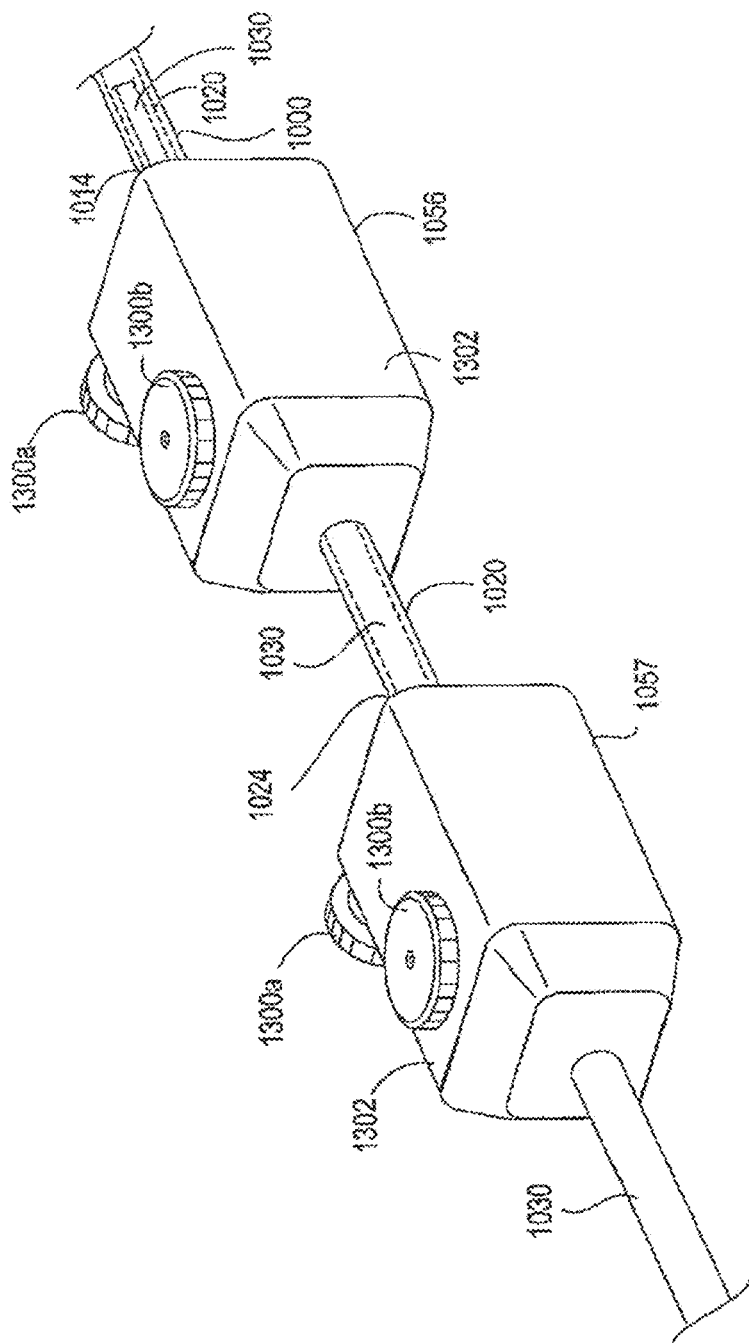
FIG. 68 illustrates embodiments of the handles.

As mentioned previously, manipulation of the guide catheters 1000, 1020 is achieved with the use of handles 1056, 1057 attached to the proximal ends of the catheters 1000, 1020. FIG. 68 illustrates a preferred embodiment of handles 1056, 1057. As shown, handle 1056 is attached to the proximal end 1014 of outer guide catheter 1000 and handle 1057 is attached to the proximal end 1024 of inner guide catheter 1020. Inner guide catheter 1020 is inserted through handle 1056 and is positioned coaxially within outer guide catheter 1000. In this embodiment, the handles 1056, 1057 are not linked together as shown in the embodiment illustrated in FIG. 60. It may be appreciated that such handles 1056, 1057 may alternatively be connected by external connecting rods, bars or plates or by an additional external stabilizing base. An embodiment of a stabilizing base will be described in a later section. Referring back to FIG. 68, interventional catheter is inserted through handle 1057 and is positioned coaxially within inner guide catheter 1020 and outer guide catheter 1000.

Each handle 1056, 1057 includes two steering knobs 1300a, 1300b emerging from a handle housing 1302 for manipulation by a user. Steering knobs 1300a are disposed on a side of the housing 1302 and steering knobs 1300b are disposed on a face of the housing 1302. However, it may be appreciated that such placement may vary based on a variety of factors including type of steering mechanism, size and shape of handle, type and arrangement of parts within handle, and ergonomics to name a few.

Figure 69:
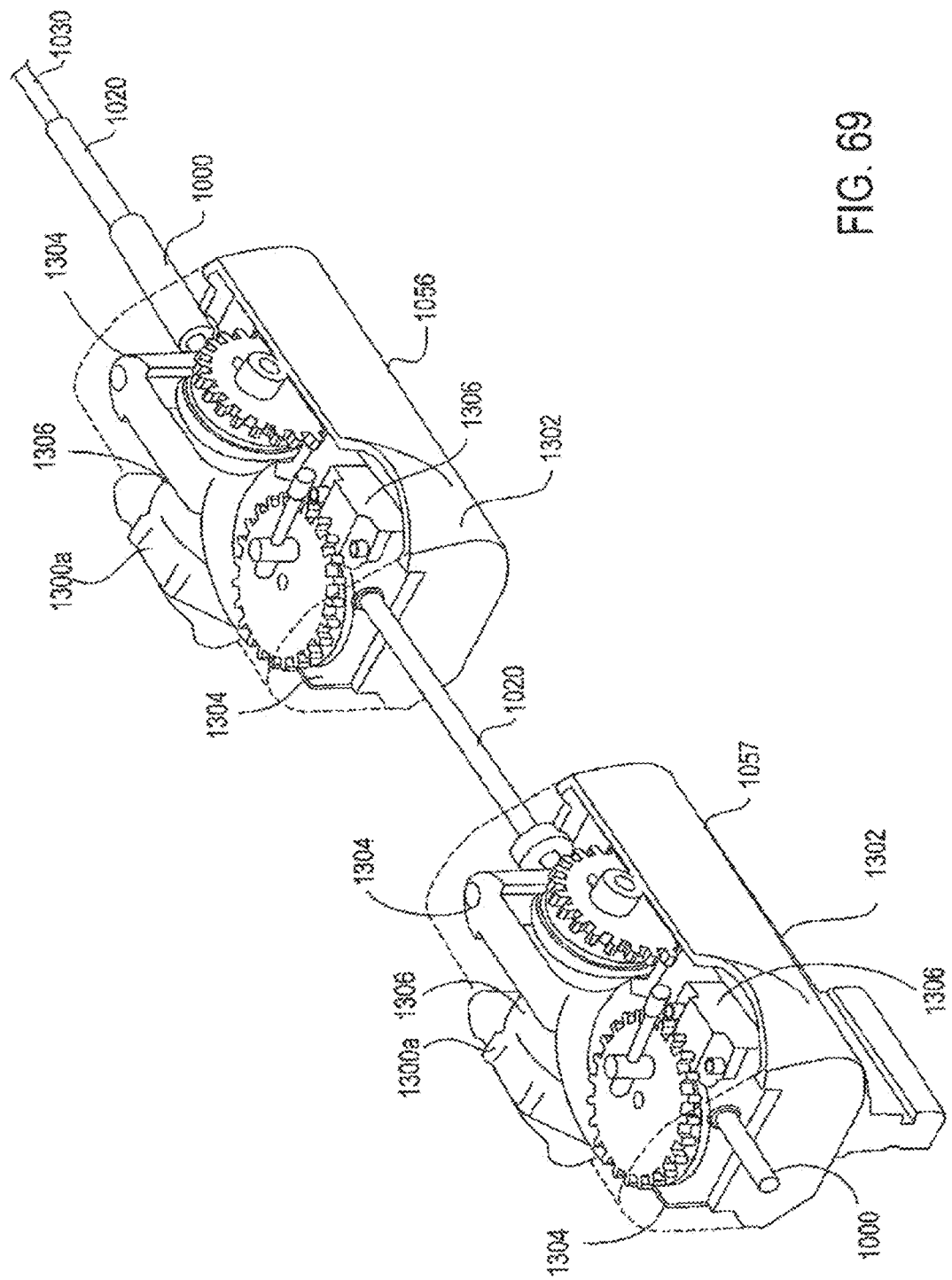
FIG. 69 illustrates the handles of FIG. 68 with a portion of the housing removed.

FIG. 69 illustrates the handles 1056, 1057 of FIG. 68 with a portion of the housing 1302 removed to reveal the assemblies of the handles. Each knob 1300a, 1300b controls a steering mechanism which is used to form a curvature in the attached catheter. Each steering mechanism includes a hard stop gear assembly 1304 and a friction assembly 1306. Tension is applied to one or more pullwires by action of the hard stop gear assembly to form a curve in a catheter. Tension is maintained by the friction assembly. When tension is released from the one or more pullwires the catheter returns to a straightened position.

Figure 70:
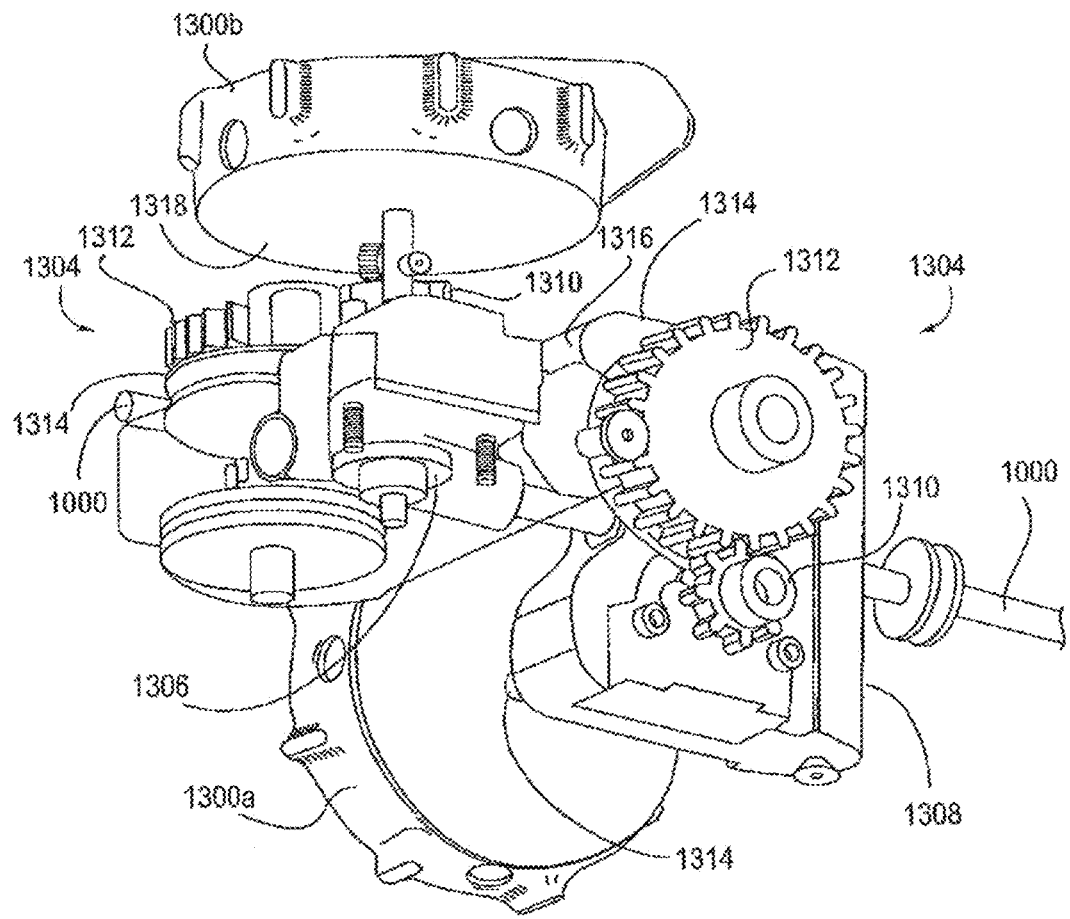
FIG. 70 illustrates steering mechanisms within a handle.

FIG. 70 illustrates steering mechanisms within a handle wherein the housing 1302 is removed for clarity. Here, steering knob 1300a is attached to a hard stop gear assembly 1304 and a friction assembly (not in view) and steering knob 1300b is attached to a separate hard stop gear assembly 1304 and friction assembly 1306. Steering knob 1300a is attached to a knob post 1318 which passes through a base 1308, terminating in a knob gear wheel 1310. The knob gear wheel 1310 actuates the hard stop gear assembly 1304, thereby applying tension to one or more pullwires 1120.

Figure 71:
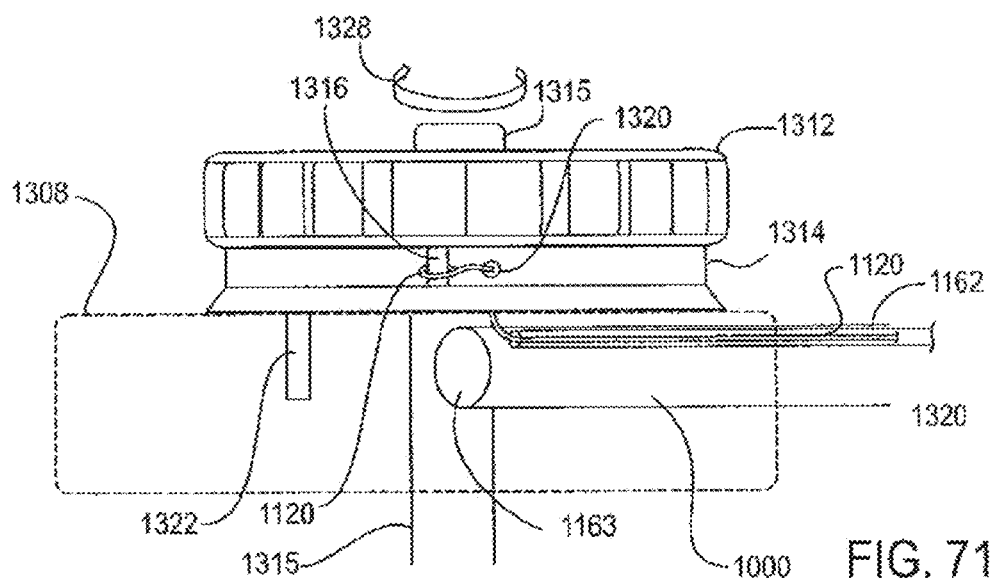
FIG. 71 illustrates attachment of a pullwire to a disk.

The knob gear wheel 1310 is a toothed wheel that engages a disk gear wheel 1312. Rotation of the steering knob 1300a rotates the knob post 1318 and knob gear wheel 1310 which in turn rotates the disk gear wheel 1312. Rotation of the disk gear wheel 1312 applies tension to one or more pullwires extending through the attached catheter, in this example the outer guiding catheter 1000. As shown, the outer guiding catheter 1000 passes through the base 1308, wherein one or more pullwires 1120 extending through the catheter 1000 are attached to the disk 1314. Such attachment is schematically illustrated in FIG. 71. Catheter 1000 is shown passing through base 1308. A pullwire 1120 passing through a steering lumen 1162 in the catheter 1000 emerges from the wall of the catheter 1000, passes through an aperture 1320 in the disk 1314 and is attached to an anchor peg 1316 on the disk 1314. Rotation of the disk 1314 (indicated by arrow 1328) around disk post 1315 by action of the disk gear wheel 1312, applies tension to the pullwire 1120 by drawing the pullwire 1120 through the aperture 1320 and wrapping the pullwire 1120 around the disk 1314 as it rotates. Additional rotation of the disk 1314 applies increasing tension to the pullwire 1120. To limit the amount of tension applied to the pullwire 1120, to limit curvature of the catheter and/or to avoid possible breakage of the pullwire 1120, the rotation of the disk 1314 may be restricted by hard stop peg 1322 which is attached to the disk 1314 and extends into the base 1308.

Figures 72A, 72B:
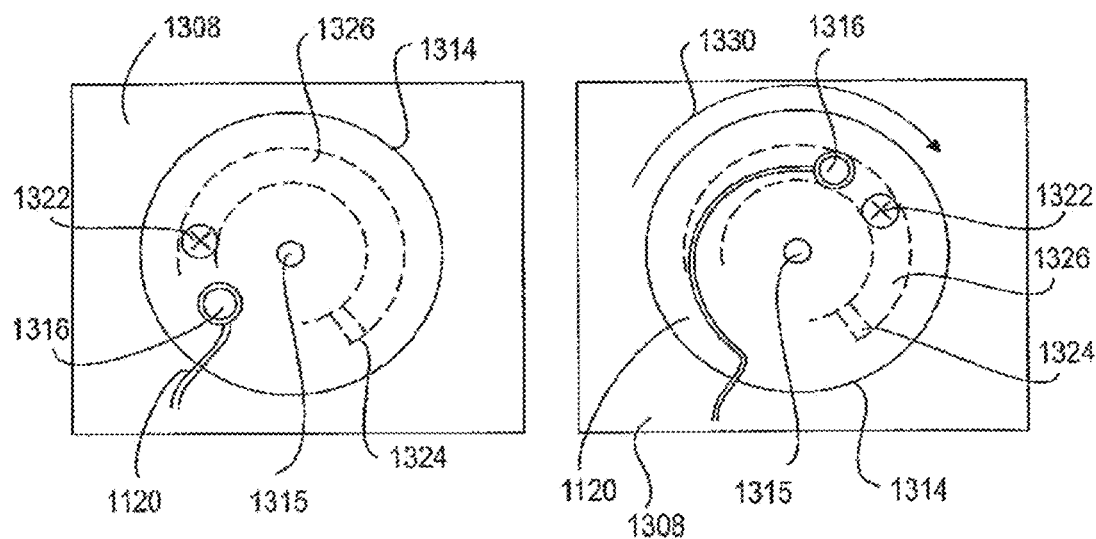
FIGS. 72A-72B illustrate a hard stop peg restricting rotation of a disk.

FIGS. 72A-72B illustrate how the hard stop peg 1322 is used to restrict rotation of disk 1314. FIGS. 72A-72B provide a top view, wherein the disk 1314 is disposed on the base 1308. The anchor peg 1316 is shown with the pullwire 1120 there attached. A groove 1326 is formed in the base 1308 beneath the disk 1314 and forms an arc shape. The hard stop peg 1322 extends from the disk 1314 into the groove 1326 in the base 1308. Referring now to FIG. 72B, rotation of the disk 1314 around knob post 1318, indicated by arrow 1330, draws the pullwire 1120 through the aperture 1320 as previously described, wrapping the pullwire 1120 around the disk 1314. As the disk 1314 rotates, the hard stop peg 1322 follows along the groove 1326, as shown. The disk 1314 continues rotating until the hard stop peg 1322 reaches a hard stop 1324. The hard stop 1324 is positioned in the groove 1326 and prevents further passage of the hard stop peg 1322. Thus, disk 1314 rotation may be restricted to any degree of rotation less than or equal to 360 degrees by positioning of the hard stop 1324.

Figure 73A:
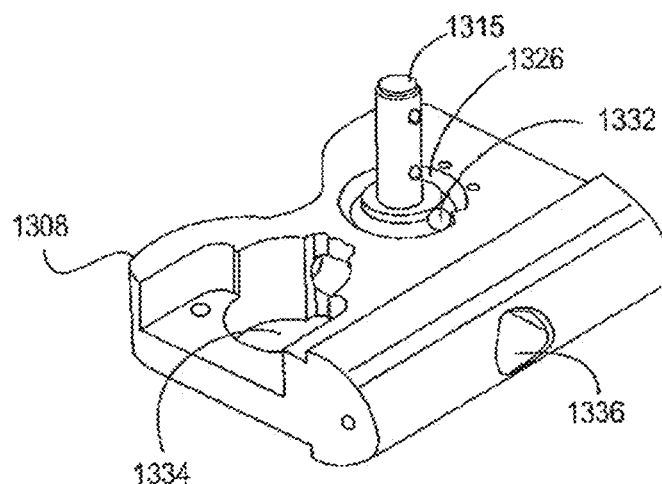
FIGS. 73A-73C illustrates a portion of a hard stop gear assembly.
Figure 73B:
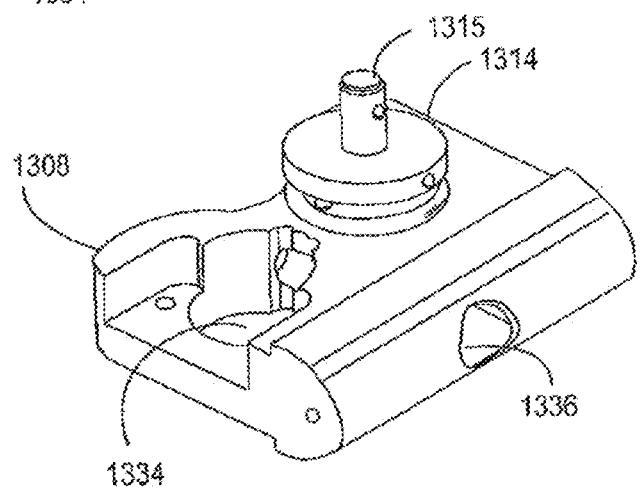
Figure 73C:
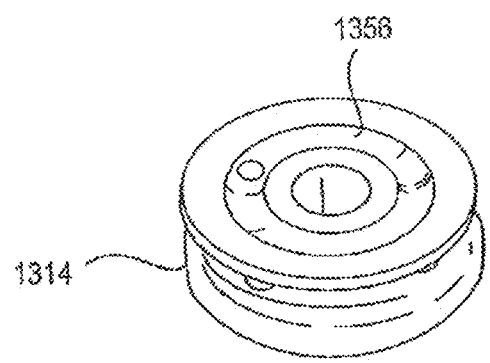

In some instances, it is desired to restrict rotation of the disk 1314 to a degree of rotation which is more than 360 degrees. This may be achieved with another embodiment of the hard stop gear assembly 1304. Referring now to FIGS. 73A-73B, a portion of such a hard stop gear assembly 1304 is shown. FIG. 73A illustrates the base 1308 and the disk post 1315 positioned therethrough. Also shown in the base 1308 is an aperture 1334 through which the knob post 1318, knob gear wheel 1310 and friction assembly 1306 pass, and a passageway 1336 through which the catheter 1000 passes. In this embodiment of the hard stop gear assembly 1304, a groove 1326 is also present in an arc shape around the disk post 1315, however a ball 1332 is positioned in the groove 1326 rather than a hard stop peg 1322. Disk 1314 is positioned over the groove 1326 and the ball 1332 as shown in FIG. 73B. The disk 1314, illustrated in FIG. 73C, has a groove 1356 in its surface which is positioned adjacent to the base 1308, the groove 1356 having an arc shape similar to the groove 1326 in the base 1308. The ball 1332 is not fixedly attached to the base 1308 or the disk 1314 and is therefore free to move along the channel formed by the groove 1326 in the base 1308 and the groove in the disk 1314.

FIGS. 74A-74F illustrate how rotation of the disk 1314 may be restricted by the ball 1332 to a degree of rotation which is more than 360 degrees. FIGS. 74A-74F illustrate the groove 1326 in the base 1308 wherein the groove 1326 has an arc shape around disk post 1315. The groove 1326 does not form a complete circle; a first groove end 1350a and a second groove end 1350b form a wall which prevent passage of the ball 1332. It may be appreciated that the groove ends 1350a, 1350b may be any distance apart, shortening the length of the groove 1326 by any amount, and allowing the ball 1332 movement, and hence catheter deflection, to be adjusted to any desired amount. To begin, referring to FIG. 74A, the ball 1332 is positioned within the groove 1326 near the first groove end 1350a. The disk 1314 has a matching groove 1352 (shape illustrated in dashed line) including a first groove end 1354a and a second groove end 1354b. The disk 1314 is positioned over the ball 1332 so that the ball 1332 is near the second groove end 1354b.

Referring now to FIG. 74B, the disk 1314 may be rotated while the ball 1332 remains in place. Here, the disk 1314 has rotated 90 degrees, as indicated by arrow 36000 and the position of the groove ends 1354a, 1354b. Referring now to FIG. 74C, the disk 1314 may be further rotated while the ball 1332 remains in place. Here, the disk 1314 has rotated 270 degrees, as indicated by arrow 36000 and the position of the groove ends 1354a, 1354b. The disk 1314 may continue rotating to 360 degrees, as shown in FIG. 74D, indicated by arrow 36000. Here, the first groove end 1354a in the disk 1314 has contacted the ball 1332 and pushes the ball 1332 along groove 1326 in the base. Referring now to FIG. 74E, the disk 1314 may be further rotated while the ball 1332 is pushed along the groove 1326 in the base 1308 by the first groove end 1354a in the disk 1314. Here, the disk 1314 is shown to have rotated 540 degrees. Referring to FIG. 74F, the disk 1314 rotates until the ball 1332 reaches the second groove end 1350b of the base 1308, providing a hard stop. In this position, the ball 1332 is held between the first groove end 1354a of the disk 1314 and the second groove end 1350b of the base 1308 and further rotation of the disk 1314 is prevented. Thus, the disk 1314 was rotated approximately 660 degrees in this example. Any maximum degree of rotation may be set by positioning of groove ends 1350a, 1350b and/or groove ends 1354a, 1354b. Additionally, in some embodiments, rotation can be limited by adding more than one ball 1332 to the groove 1326, for example, two, three, four, five, six, seven, eight, nine, ten or more balls may be used to limit travel and hence curvature.

It may be appreciated that one or more pullwires 1120 are attached to the disk 1314 in a manner similar to that illustrated in FIG. 71. Therefore, as the disk 1314 rotates, around disk post 1315 by action of the disk gear wheel 1312, tension is applied to the pullwire 1120 by drawing the pullwire 1120 through the aperture 1320 and wrapping the pullwire 1120 around the disk 1314 as it rotates. Additional rotation of the disk 1314 applies increasing tension to the pullwire 1120. Restriction of rotation as described above limits the amount of tension applied to the pullwire 1120, to limit curvature of the catheter and/or to avoid possible breakage of the pullwire 1120.

Figure 75:
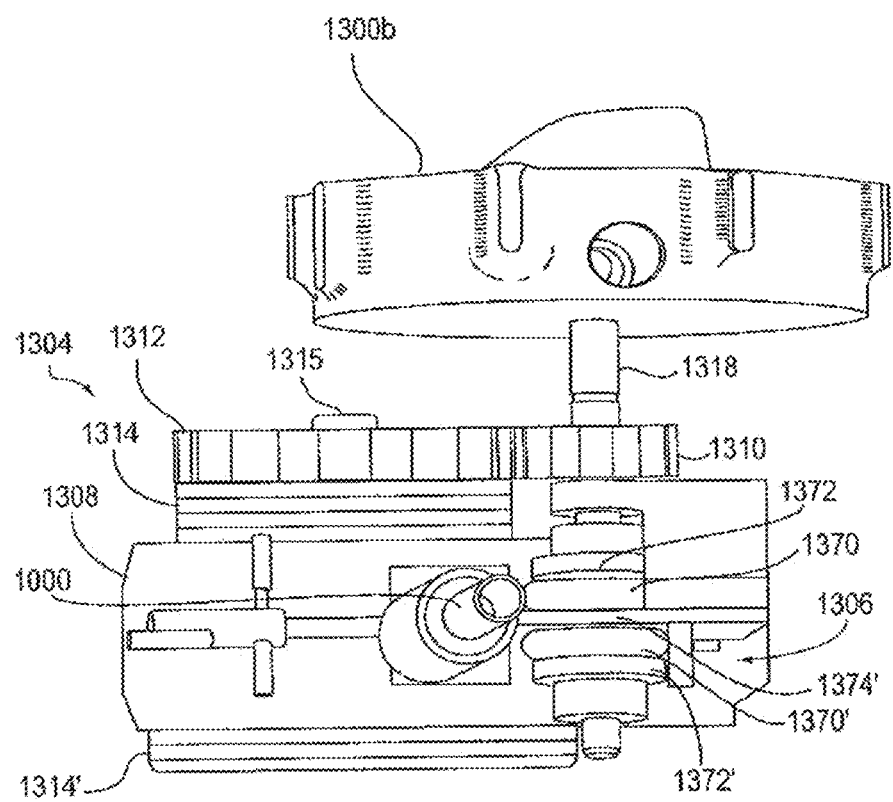
FIG. 75 illustrates an embodiment of a friction assembly.

As mentioned, each steering mechanism includes at least a hard stop gear assembly 1304 and a friction assembly 1306. As described above, tension is applied to one or more pullwires by action of the hard stop gear assembly to form a curve in a catheter. Tension is maintained by the friction assembly. FIG. 75 illustrates an embodiment of a friction assembly 1306. The friction assembly 1306 essentially holds a steering knob, in this example steering knob 1300*b*, and the associated knob post 1318 in a rotated position. Here, rotation of the knob 1300*b* and post 1318 rotates attached knob gear wheel 1310. The knob gear wheel 1310 actuates the hard stop gear assembly 1304, thereby applying tension to one or more pullwires 1120. The knob gear wheel 1310 is a toothed wheel that engages a disk gear wheel 1312. Rotation of the steering knob 1300*b* rotates the knob post 1318 and knob gear wheel 1310 which in turn rotates the disk gear wheel 1312. Rotation of the disk gear wheel 1312 applies tension to one or more pullwires extending through the attached catheter, in this example the outer guiding catheter 1000.

The steering knob 1300*b* and knob post 1318 are held in a rotated position by friction provided by a frictional pad 1370. The frictional pad 1370 is positioned between ring 1372 attached to the knob post 1318 and a plate 1374 attached to the base 1308. The knob post 1318 extends from the knob 1300*b* through the ring 1372, the frictional pad 1370 and then the plate 1374. The plate 1374 has internal threads which mate with threads on the knob post 1318. As the knob post 1318 rotates, the threads on the post 1318 advance through the threads on the plate 1374. This draws the ring 1372 closer to the plate 1374, compressing the frictional pad 1370 therebetween. Frictional pad 1370 may be comprised of any O-ring or sheet material with desirable frictional and compressibility characteristics, such as silicone rubber, natural rubber or synthetic rubbers, to name a few. In preferred embodiments, an EPDM rubber O-ring is used. Reverse rotation of the knob post 1318 is resisted by friction of the frictional pad 1370 against the ring 1372. The higher the compression of the frictional pad 1370 the stronger the frictional hold. Therefore, as the steering knob 1300*b* is rotated and increasing amounts of tension are applied to the pullwires 1120, increasing amounts of friction are applied to the ring 1372 to hold the knob 1300*b* in place.

Manual reverse rotation of the steering knob 1300*b* releases tension on the pullwires 1120 and draws the ring 1372 away from the plate 1374 thereby reducing the frictional load. When tension is released from the pullwires 1120 the catheter 1000 returns toward a straightened position.

It may be appreciated that each handle 1056, 1057 includes a steering mechanism for each curve to be formed in the attached catheter. Thus, as shown in FIG. 69, handle 1056 includes a steering mechanism to form the primary curve 1100 in outer guiding catheter 1000 and a steering mechanism to form the additional curve 1110. Likewise, handle 1057 includes a steering mechanism to form the secondary curve 1104 in inner guiding catheter 1020 and a steering mechanism to form the angle theta 1070.

Some curves, such as the primary curve 1100, secondary curve 1104 and additional curve 1110 each typically vary in curvature between a straight configuration and a curved configuration in a single direction. Such movement may be achieved with single set of a hard stop gear assembly 1304 and a friction assembly 1306. However, other curves, such as the angle theta 1070, may be formed in two directions as shown in FIGS. 61C-61D. Such movement is achieved with two sets of the hard stop gear assembly 1304 and the friction assembly 1306, each set controlling curvature in a single direction.

FIG. 75 illustrates the presence of an additional set of the friction assembly 1306'. One or more pullwires 1120', such as an opposing set as illustrated in FIG. 64D, extending within the wall of the catheter 1000 are attached to the disk 1314' in the same manner as pullwires 1120 are attached to disk 1314. The disks 1314, 1314' are arranged so that rotation of steering knob 1300*b* in one direction applies tension to the pullwires 1120 via disk 1314 and rotation of steering knob 1300*b* in the opposite direction applies tension to the pullwires 1120' via disk 1314'. Likewise, the additional friction assembly 1306' is shown having a ring 1372' attached to the knob post 1318 and a frictional pad 1370' disposed between the ring 1372' and the opposite side of the plate 1374. Therefore, as rotation of the steering knob 1300*b* in the opposite direction applies tension to the pullwires 1120' via disk 1314', the frictional pad 1370' applies tension to the ring 1372' holding the knob post 1318' in place.

It may be appreciated that various other mechanisms may be used for tensioning and holding pullwires 1120 in place. Example mechanisms that may alternatively be used include clutches, ratchets, levers, knobs, rack and pinions, and deformable handles, to name a few.

F. Interventional System

Figure 76:
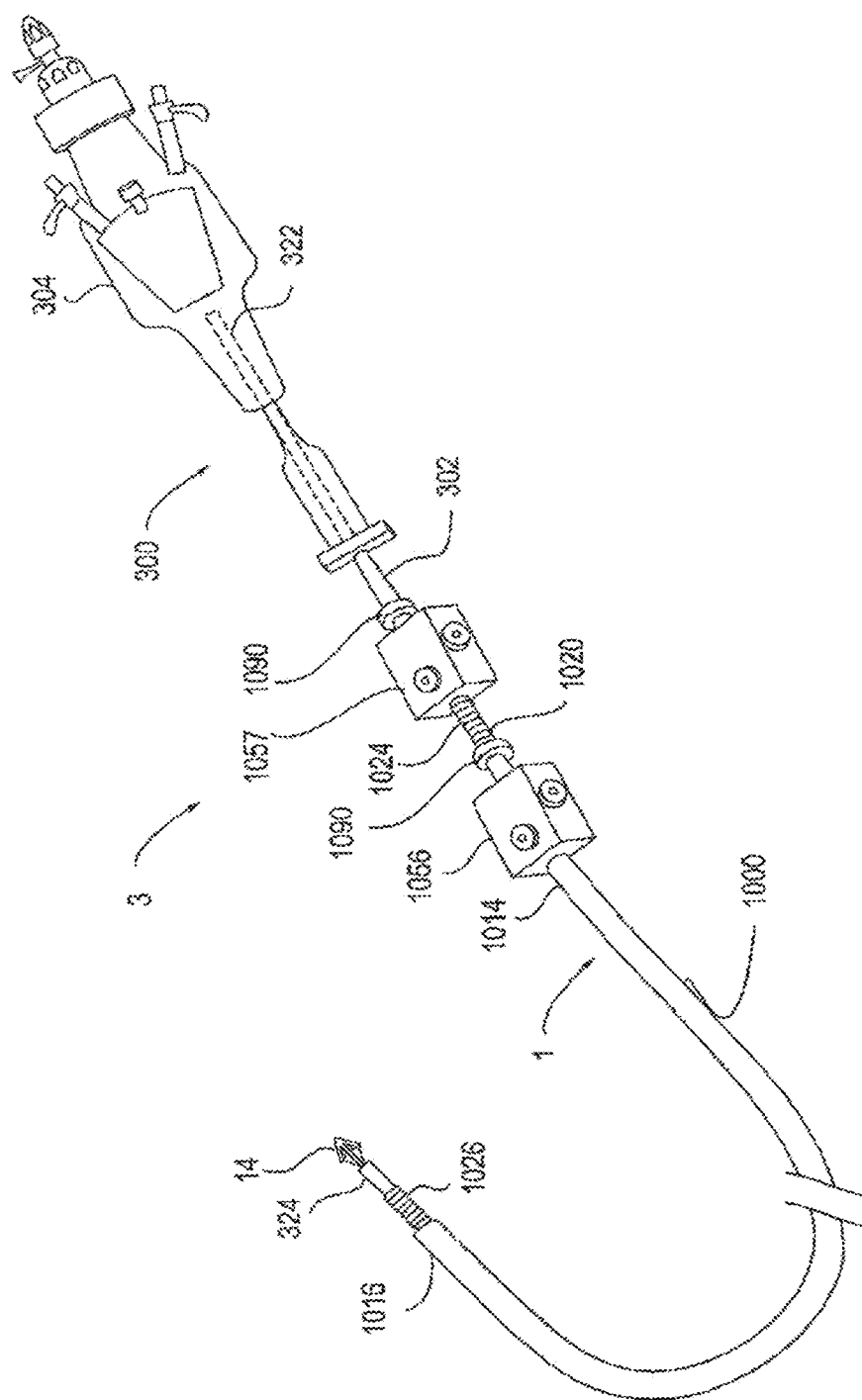
FIG. 76 illustrates an embodiment of an interventional system of the present invention.
Figure 76A:
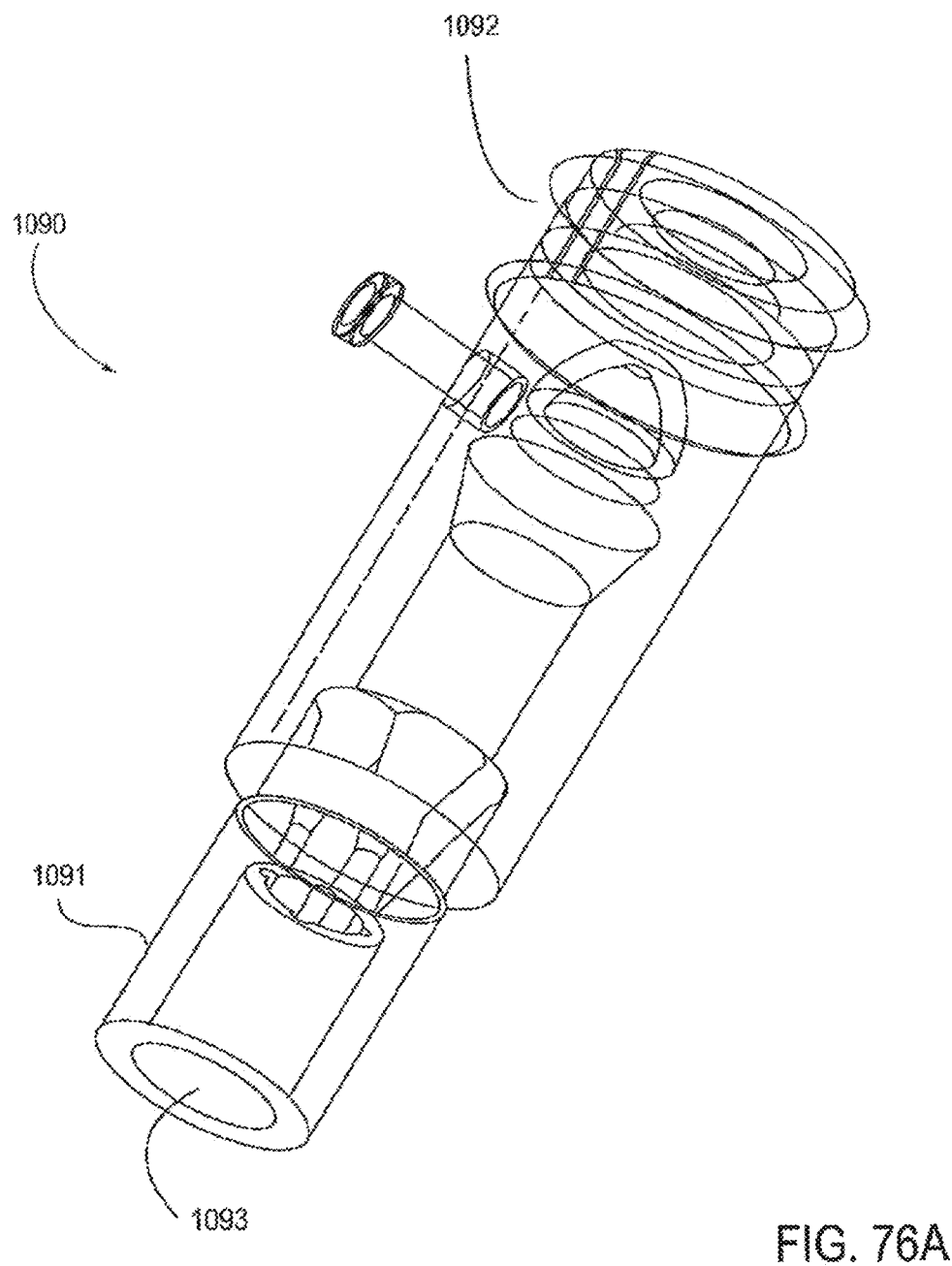
FIG. 76A illustrates an embodiment of a hemostatic valve for use with the present invention.

FIG. 76 illustrates an embodiment of an interventional system 3 of the present invention. An embodiment of the multi-catheter guiding system 1 of the present invention is shown comprising an outer guide catheter 1000, having a proximal end 1014 and a distal end 1016, and an inner guide catheter 1020, having a proximal end 1024 and a distal end 1026, wherein the inner guide catheter 1020 is positioned coaxially within the outer guide catheter 1000, as shown. In addition, a hemostatic valve 1090 is disposed within handle 1056 or external to handle 1056 as shown to provide leak-free sealing with or without the inner guide catheter 1020 in place. The valve 1090 also prevents back bleeding and reduces the possibility of air introduction when inserting the inner guide catheter 1020 through the outer guide catheter 1000. An example of a hemostatic valve 1090 is illustrated in FIG. 76A, however any suitable valve or hemostatic valve may be used to provide similar functions. In FIG. 76A, the valve 1090 has a first end 1091, a second end 1092 and a lumen 1093 therethrough. The inner wall of lumen 1093 is preferably tapered toward end 1091 and may further include a plurality of tapered axial channels configured to receive the protrusions 1400 on the inner guide catheter 1020. The first end 1091 is attached to the outer guide catheter 1000 and the second end 1092 is free. Referring now back to FIG. 76, the distal ends 1016, 1026 of catheters 1000, 1020, respectively, are sized to be passable to a body cavity, typically through a body lumen such as a vascular lumen.

Figure 76B:
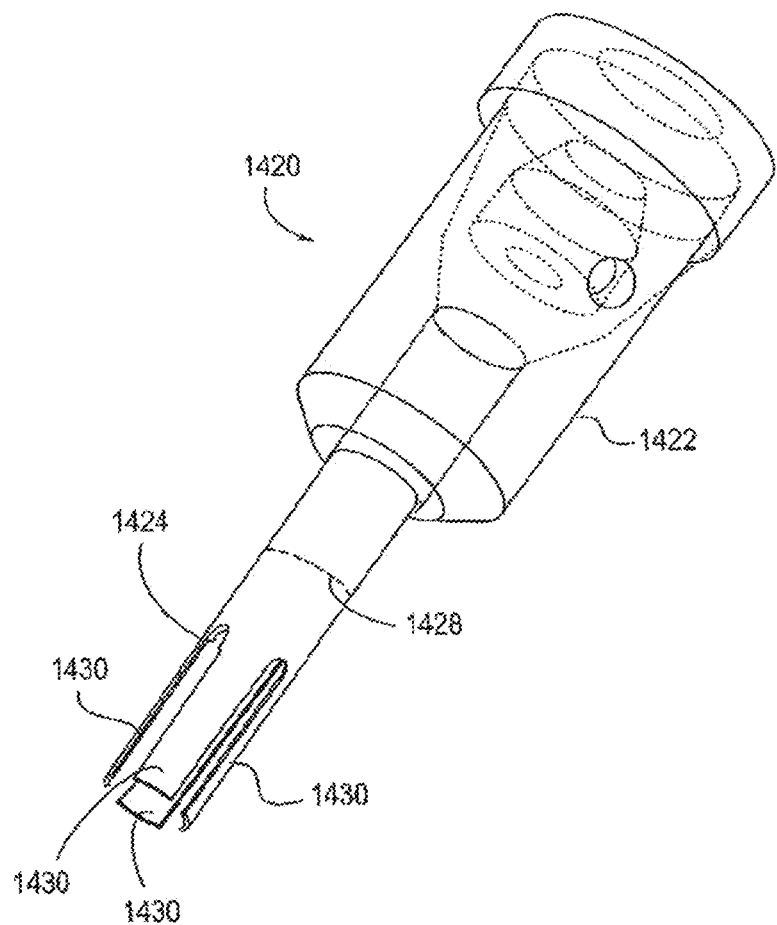
FIG. 76B illustrates an embodiment of a fixation device introducer.

To assist in inserting the fixation device 14 through a hemostatic valve 1090, a fixation device introducer may be used. For example, when the fixation device 14 is loaded on a delivery catheter 300 and an inner guide catheter 1020, insertion of the fixation device 14, delivery catheter 300 and inner guide catheter 1020 through an outer guide catheter 1000 involves passing the fixation device 14 through a hemostatic valve 1090 on the outer guide catheter 1000. To reduce any trauma to the fixation device 14 by the hemostatic valve 1090, a fixation device introducer may be used. An embodiment of a fixation device introducer 1420 is illustrated in FIG. 76B. The introducer 1420 includes a loading body 1422 and an insertion endpiece 1424. The fixation device 14 is loaded into the loading body 1422 and into the insertion endpiece 1424 to approximately the dashed line 1428. The insertion endpiece 1424 has a split end creating individual split sections 1430, in this embodiment, four split sections 1430. By compressing the split sections 1430, the endpiece 1424 forms a taper. Such a taper is then inserted through a hemostatic valve 1090, so that the insertion endpiece 1424 creates a smooth passageway through the valve for the fixation device 14. Once the insertion endpiece 1424 is inserted through the valve 1090, the fixation device 14, and attached delivery catheter 300 and inner guide catheter 1020, may then be advanced through the fixation device introducer 1420. The fixation device introducer 1420 also includes a hemostatic valve within the loading body 1422 to prevent any backbleeding or leakage through the introducer 1420.

Manipulation of the guide catheters 1000, 1020 is achieved with the use of handles 1056, 1057 attached to the proximal ends of the catheters 1000, 1020. As shown, handle 1056 is attached to the proximal end 1014 of outer guide catheter 1000 and handle 1057 is attached to the proximal end 1024 of inner guide catheter 1020. Inner guide catheter 1020 is inserted through handle 1056 and is positioned coaxially within outer guide catheter 1000.

An embodiment of the delivery catheter 300 of the present invention is inserted through handle 1057 and is positioned coaxially within inner guide catheter 1020 and outer guide catheter 1000. Therefore, a hemostatic valve 1090 is disposed within handle 1057 or external to handle 1057 as shown to provide leak-free sealing with or without the delivery catheter 300 in place. The valve 1090 functions as described above. The delivery catheter 300 includes a shaft 302, having a proximal end 322 and a distal end 324, and a handle 304 attached to the proximal end 322. A fixation device 14 is removably coupled to the distal end 324 for delivery to a site within the body.

The outer guide catheter 1000 and/or the inner guide catheter 1020 are precurved and/or have steering mechanisms to position the distal ends 1016, 1026 in desired directions. Precurvature or steering of the outer guide catheter 1000 directs the distal end 1016 in a first direction to create a primary curve while precurvature and/or steering of the inner guide catheter 1020 directs distal end 1026 in a second direction, differing from the first, to create a secondary curve. Together, the primary and secondary curves form a compound curve. Advancement of the delivery catheter 300 through the coaxial guide catheters 1000, 1020 guides the delivery catheter 300 through the compound curve toward a desired direction, usually in a direction which will position the fixation device 14 in a desired location within the body.

Figure 77:
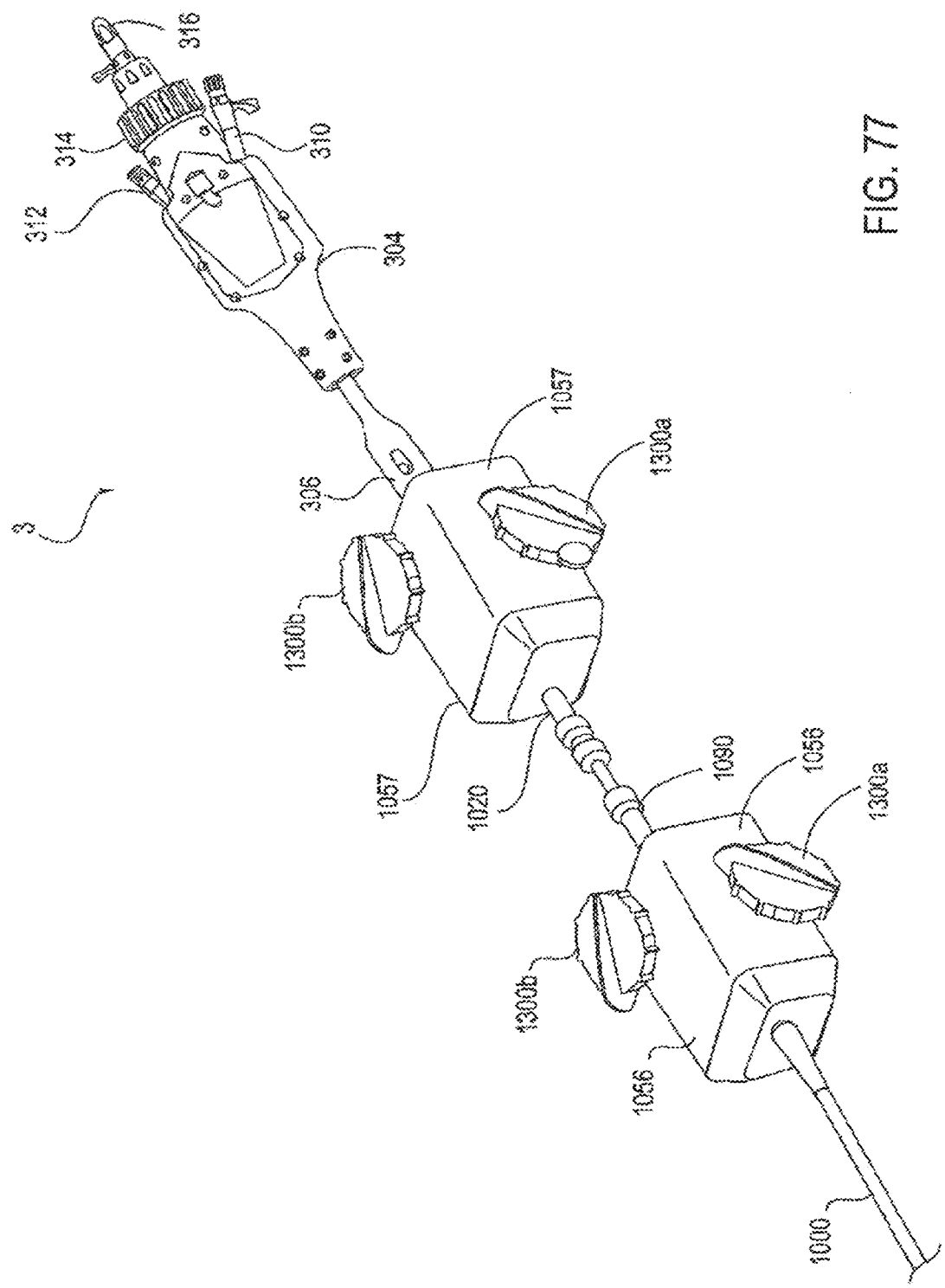
FIG. 77 illustrates another embodiment of an interventional system of the present invention.

FIG. 77 illustrates portions of another embodiment of an interventional system 3 of the present invention. Handles 1056, 1057 of the multi-catheter guiding system 1 of the present invention are shown. Each handle 1056, 1057 includes a set of steering knobs 1300a, 1300b, as shown. Manipulation of the guide catheters 1000, 1020 is achieved with the use of the steering knobs 1300a, 1300b attached to the proximal ends of the catheters 1000, 1020. Handle 304 of the delivery catheter 300 is also shown, including the proximal element line handle 312, the lock line handle 310, the actuator rod control 314 and the actuator rod handle 316, among other features. The handle 304 is supported by the support base 306 which is connected to the handle 1057.

It may be appreciated the above described systems 3 are not intended to limit the scope of the present invention. The systems 3 may include any or all of the components of the described invention. In addition, the multi-catheter guiding system 1 of the present invention may be used to introduce other delivery catheters, interventional catheters or other devices. Likewise, the delivery catheter 300 may be introduced through other introducers or guiding systems. Also, the delivery catheter 300 may be used to deliver other types of devices to a target location within the body, including endoscopic staplers, devices for electrophysiology mapping or ablation, septal defect repair devices, heart valves, annuloplasty rings and others.

In addition, many of the components of the system 3 may include one or more hydrophilic coatings. Hydrophilic coatings become slippery when wet, eliminate the need for separate lubricants. Thus, such coatings may be present on the multi-catheter guiding system, delivery catheter, and fixation device, including the proximal elements and distal elements, to name a few.

Figure 78:
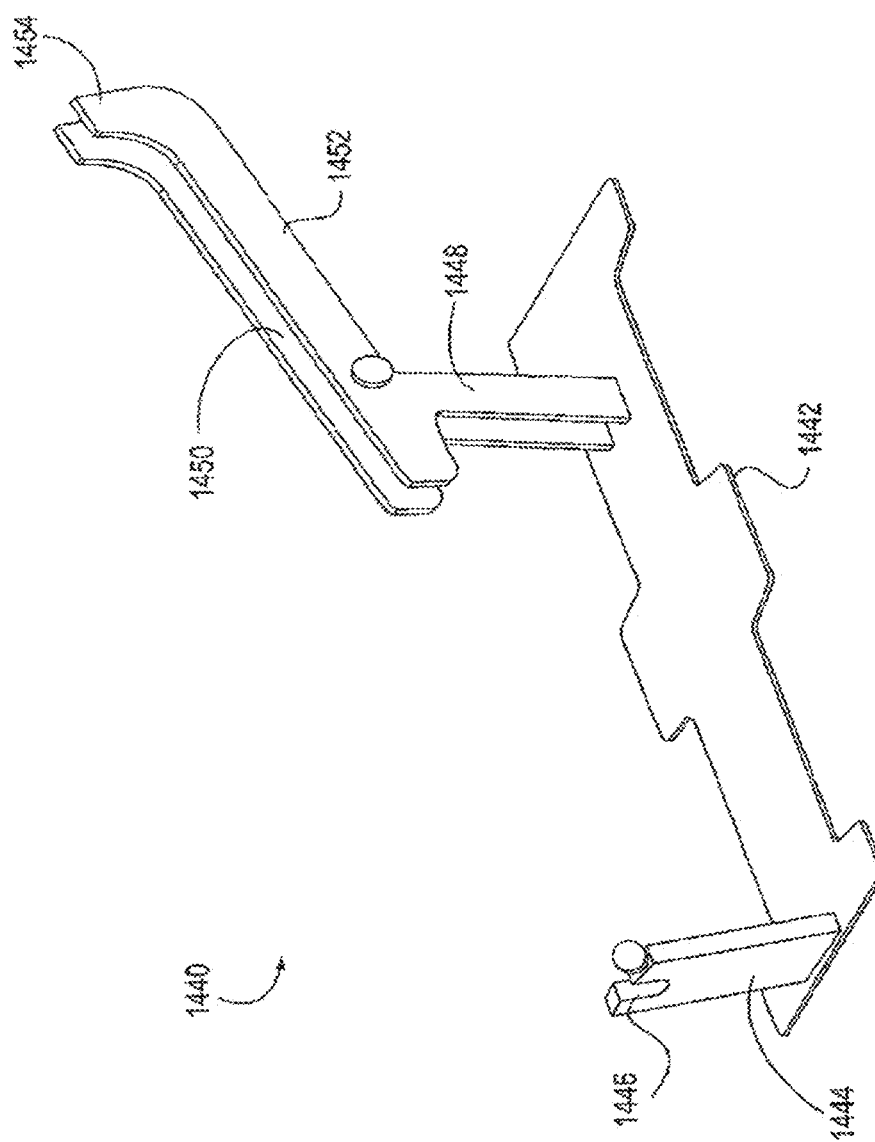
FIGS. 78-80 illustrate an embodiment of a stabilizer base for use with the present invention.
Figure 79:
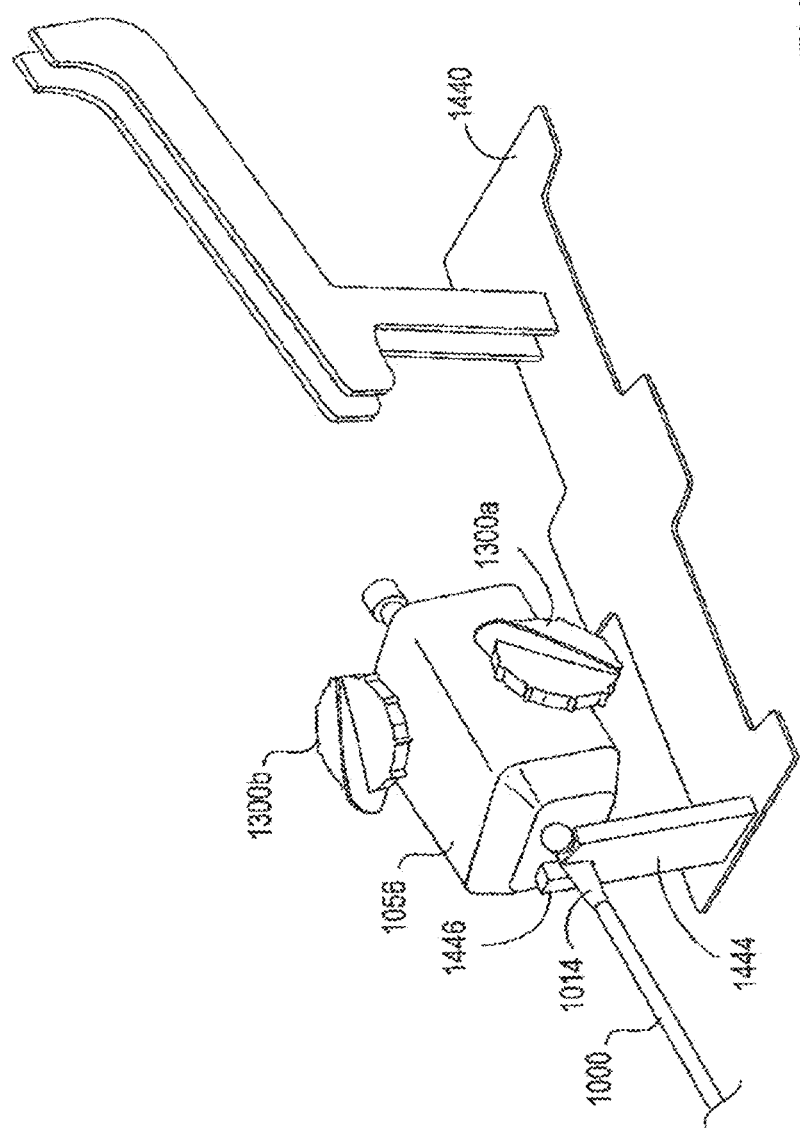
Figure 80:
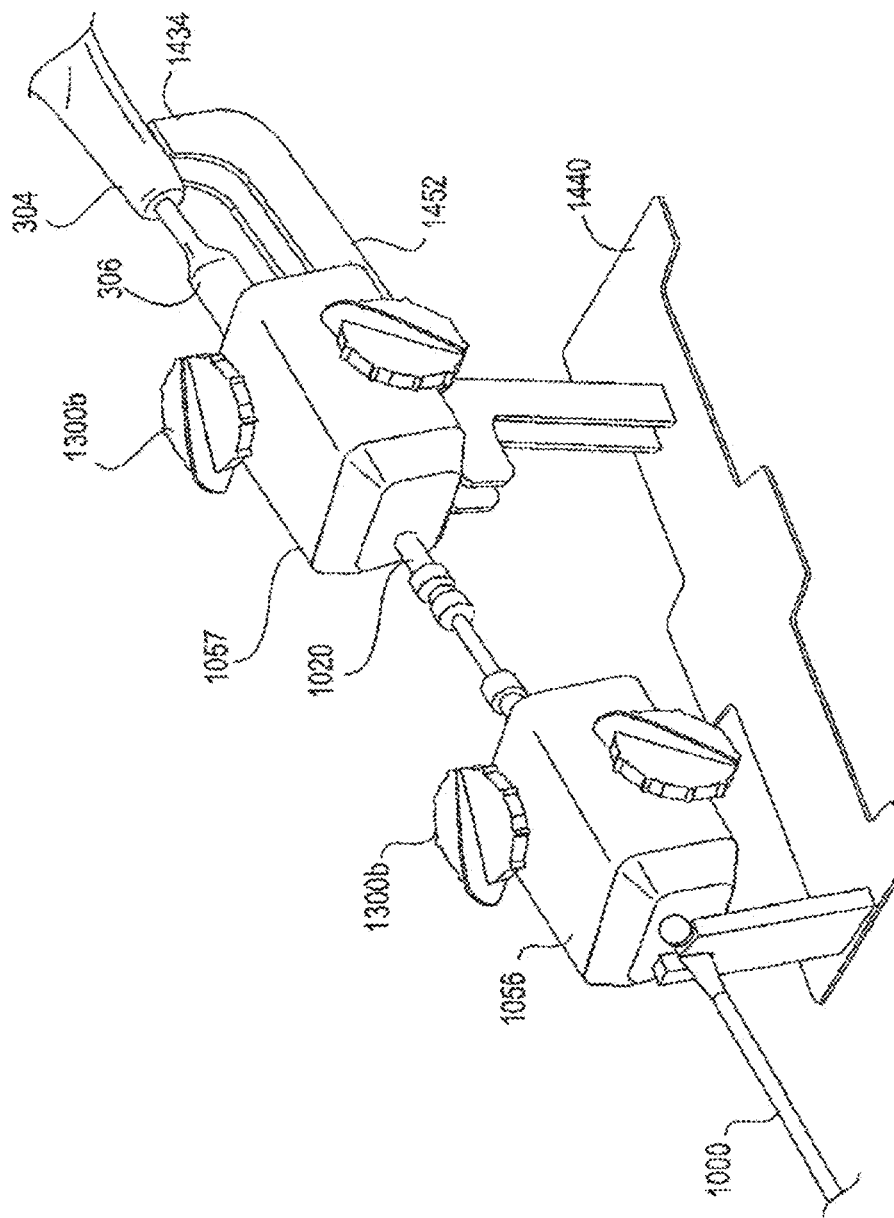

Further, the system 3 may be supported by an external stabilizer base 1440, an embodiment of which is illustrated in FIG. 78. Stabilizer base 1440 maintains the relative positions of the outer guide, inner guide and delivery catheter during a procedure. In this embodiment, the base 1440 comprises a platform 1442 having a planar shape for positioning on or against a flat surface, such as a table or benchtop. The base 1440 further includes a pair of handle holders 1444, 1448, each attached to the platform 1442 and extending upwardly from the platform 1442, either angularly or perpendicularly. Handle holder 1444 includes a notch 1446 for holding the outer guiding catheter 1000, as illustrated in FIG. 79, thereby supporting the handle 1056. FIG. 79 shows the handle 1056 attached to the outer guiding catheter 1000 positioned so that the proximal end 1014 of the outer guiding catheter 1000 rests in the notch 1446. Referring back to FIG. 78, handle holder 1448 includes an elongate portion 1452 having a trough 1450 and a hooked end 1454. As shown in FIG. 80, handle 1057 rests on the elongate portion 1452 and the handle 304 rests on hooked end 1454 so that the inner guiding catheter 1020 extends from the handle 1057 to the handle 1056 and continues on within outer guiding catheter 1000. The handle 304 is additionally supported by support base 306, as shown.

It may be appreciated that the stabilizer base 1440 may take a variety of forms and may include differences in structural design to accommodate various types, shapes, arrangements and numbers of handles.

G. Kits

Figure 81:
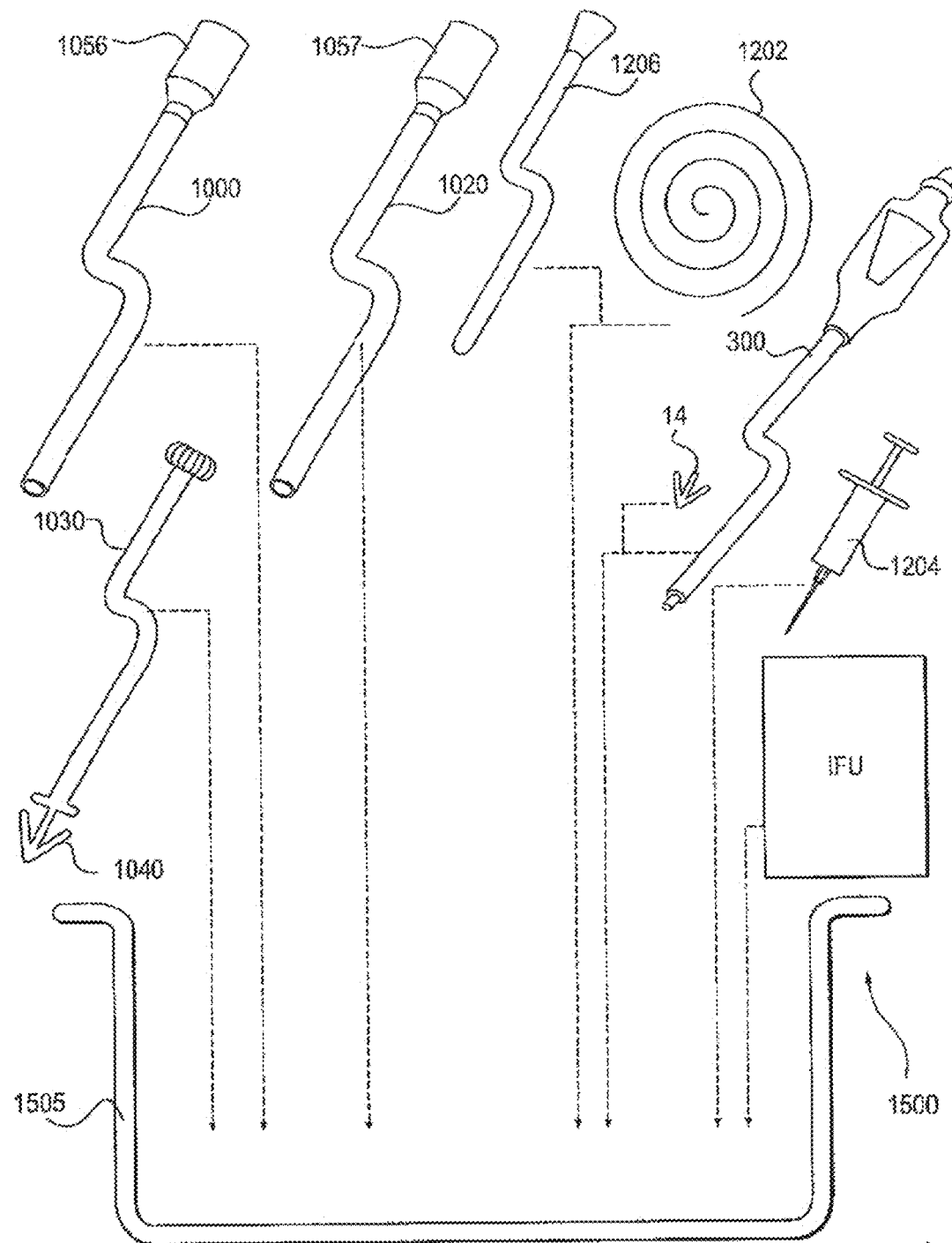
FIG. 81 illustrates a kit constructed in accordance with the principles of the present invention

Referring now to FIG. 81, kits 1500 according to the present invention comprise any of the components described in relation to the present invention. The kits 1500 may include any of the components described above, such as the outer guide catheter 1000 including handle 1056, the inner guide catheter 1020 including handle 1057, the delivery catheter 300 and the fixation device 14 and instructions for use IFU. Optionally, any of the kits may further include any other system components described above, such as various interventional tools 1040, or components associated with positioning a device in a body lumen, such as a guidewire 1202, dilator 1206 or needle 1204. The instructions for use IFU will set forth any of the methods as described above, and all kit components will usually be packaged together in a pouch 1505 or other conventional medical device packaging. Usually, those kit components which will be used in performing the procedure on the patient will be sterilized and maintained within the kit. Optionally, separate pouches, bags, trays or other packaging may be provided within a larger package, where the smaller packs may be opened separately to separately maintain the components in a sterile fashion.

While the foregoing is a complete description of the preferred embodiments of the invention, various alternatives, substitutions, additions, modifications, and equivalents are possible without departing from the scope of the invention. For example, in many of the above-described embodiments, the invention is described in the context of approaching a valve structure from the upstream side—that is, the atrial side in the case of a mitral valve. It should be understood that any of the foregoing embodiments may be utilized in other approaches as well, including from the ventricular or downstream side of the valve, as well as using surgical approaches through a wall of the heart. Moreover, the invention may be used in the treatment of a variety of other tissue structures besides heart valves, and will find usefulness in a variety of tissue approximation, attachment, closure, clamping and ligation applications, some endovascular, some endoscopic, and some open surgical.

Again, although the foregoing invention has been described in some detail by way of illustration and example, for purposes of clarity of understanding, it will be obvious that various alternatives, modifications and equivalents may be used and the above description should not be taken as limiting in scope of the invention which is defined by the appended claims.

What is claimed is:

1. A system for fixation of native leaflets of a heart valve comprising:
    a delivery catheter having an elongated shaft, a proximal end portion and a distal end portion configured to be positioned proximate native leaflets of a heart valve from a remote vascular access point, the delivery catheter further comprising an actuator rod; and
    a fixation device releasably coupled to the delivery catheter, the fixation device comprising:
        a first arm moveable between a closed position and an open position by the actuator rod, wherein the first arm is configured to engage a ventricular side of a first native leaflet of the native leaflets;
        a second arm moveable between a closed position and an open position by the actuator rod, wherein the second arm is configured to engage a ventricular side of a second native leaflet of the native leaflets;
        a first gripping element movable relative to the first arm in the open position, the first gripping element biased toward the first arm on an atrial side of the first native leaflet to capture the first native leaflet of the heart valve therebetween;
        a second gripping element movable relative to the second arm in the open position, the second gripping element biased toward the second arm on an atrial side of the first native leaflet to capture the second native leaflet of the heart valve therebetween,
    wherein the first gripping element and the second gripping element each comprises a plurality of barbs extending therefrom, the plurality of barbs aligned in at least one row transversely with the respective first and second gripping element; and
    a covering disposed on each of the first gripping element and the second gripping element, wherein the plurality of barbs of the first gripping element and the second gripping element, respectively, protrude through the covering.

2. The system of claim 1, wherein a first suture line is coupled with the first gripping element to raise and lower the first gripping element, and a second suture line is coupled with the second gripping element to raise and lower the second gripping element.

3. The system of claim 1, wherein at least a portion of each of the first gripping element and the second gripping element comprises Nitinol.

4. The system of claim 1, wherein the covering comprises a biocompatible fabric material.

5. The system of claim 1, wherein the covering comprises polyethylene terephthalate.

6. The system of claim 1, wherein the fixation device is configured to capture the first native leaflet of the heart valve between the first gripping element and the first arm, and separately to capture the second native leaflet of the heart valve between the second gripping element and the second arm.

7. The system of claim 1, wherein the fixation device further comprises a central member disposed between the first arm and second arm when in the closed position.

8. The system of claim 7, wherein the first arm and the second arm are each configured to flex relative the central member when in the closed position.

9. The system of claim 1, wherein the actuator rod extends between the proximal end portion and the distal end portion, wherein the fixation device is released from the delivery catheter by axial movement of the actuator rod.

10. The system of claim 9, wherein the delivery catheter further comprises an actuator rod handle coupled to the actuator rod.

11. The system of claim 1, further comprising a steerable guide catheter configured to receive the delivery catheter therethrough.

12. The system of claim 1, further comprising a steerable guide catheter configured to receive the delivery catheter therethrough.

13. A system for fixation of leaflets of a heart valve comprising:
    a delivery catheter having an elongated shaft, a proximal end portion and a distal end portion configured to be positioned proximate native leaflets of a heart valve from a remote vascular access point; and
    a fixation device releasably coupled to the delivery catheter, the fixation device comprising:
        a first arm moveable between a closed position and an open position;
        a second arm moveable between a closed position and an open position;
        a gripping arrangement consisting essentially of:
            a first gripping element movable relative to the first arm in the open position, the first gripping element biased toward the first arm to capture a first leaflet of the heart valve therebetween;

a second gripping element movable relative to the second arm in the open position, the second gripping element biased toward the second arm to capture a second leaflet of the heart valve therebetween, wherein the first gripping element and the second gripping element each comprises a plurality of barbs extending therefrom, the plurality of barbs aligned in at least one row transversely with the respective first and second gripping element; and a covering disposed on each of the first gripping element and the second gripping element, wherein the plurality of barbs of the first gripping element and the second gripping element, respectively, protrude through the covering.

14. The system of claim 13, wherein a first suture line is coupled with the first gripping element to raise and lower the first gripping element, and a second suture line is coupled with the second gripping element to raise and lower the second gripping element.

15. The system of claim 13, wherein at least a portion of each of the first gripping element and the second gripping element comprises Nitinol.

16. The system of claim 13, wherein the fixation device is configured to capture the first leaflet of the heart valve between the first gripping element and the first arm, and separately to capture the second leaflet of the heart valve between the second gripping element and the second arm.

17. The system of claim 13, wherein the fixation device further comprises a central member disposed between the first arm and second arm when in the closed position and wherein the first arm and the second arm are each configured to flex relative the central member when in the closed position.

18. The system of claim 13, wherein the delivery catheter further comprises an actuator rod extending between the proximal end portion and the distal end portion, wherein the fixation device is released from the delivery catheter by axial movement of the actuator rod, wherein the delivery catheter further comprises an actuator rod handle coupled to the actuator rod.

* * * * *